OTHER PUBLICATIONS

United States Patent [19]
Alitalo et al.
[11] Patent Number: 6,130,071
[45

Claesson–Welsh et al., "cDNA Cloning and Expression of the Human A–type Platelet–Derived Growth Factor (PDGF) Receptor Establishes Structural Similarity to the B–type PDGF Receptor," *Proc. Nat'l Acad. Sci., USA,* 86(13):4917–4921 (Jul., 1989).

Claesson–Welsh et al., "cDNA Cloning and Expression of a Human Platelet–Derived Growth Factor (PDGF) Receptor Specific for B–Chain–Containing PDGF Molecules," *Mol. Cell Biol.,* 8(8):3476–3486 (Aug., 1988).

Coffin et al., "Angioblast Differentiation and Morphogenesis of the Vascular Endothelium in the Mouse Embryo," *Devel. Biol.,* 148:51–62 (1991).

Collins et al., "Cultured Human Endothelial Cells Express Platelet–Derived Growth Factor B Chain: cDNA Cloning and Structural Analysis," *Nature,* 316:748–750 (Aug., 1985).

Curran and Franza, "Fos and Jun: The AP–1 Connection," *Cell,* 55:395–397 (Nov. 4, 1988).

De Vries et al., "The fms–Like Tyrosine Kinase, a Receptor for Vascular Endothelial Growth Factor," *Science,* 255:989–991 (Feb. 21, 1992).

Dignam et al., "Balbiani Ring 3 in *Chironomus tentans* Encodes a 185–kDa Secretory Protein Which is Synthesized Throughout the Fourth Larval Instar," *Gene,* 88:133–140 (1990).

DiSalvo et al., "Purification and Characterization of a Naturally Occurring Vascular Endothelial Growth Factor: Placenta Growth Factor Heterodimer," *J. Biol. Chem.,* 270(13):7717–7723 (Mar. 31, 1995).

Don et al., "'Touchdown' PCR to Circumvent Spurious Priming During Gene Amplification," *Nucl. Acids Res.,* 19:4008 (1991).

Dumont et al., "Dominant–negative and Targeted Null Mutations in the Endothelial Receptor Tyrosine Kinase, tek, Reveal a Critical Role in Vasculogenesis of the Embryo," *Genes Dev.,* 8:1897–1909 (1994).

Dumont et al., "Vascularization of the Mouse Embryo: A Study of flk–1, tek, tie and Vascular Endothelial Growth Factor Expression During Development," *Development Dynamics,* 203:80–92 (1995).

Dvorak et al., "Review: Vascular Permeability Factor/Vascular Endothelial Growth Factor, Microvascular Hyperpermeability, and Angiogenesis," *Amer. J. Path.,* 146:1029–1039 (1995).

Eichmann et al., "Two Molecules Related to the VEGF Receptor are Expressed in Early Endothelial Cells During Avian Embryonic Development," *Mech. Dev.,* 42:33–48 (1993).

Ferrara et al., "Molecular and Biological Properties of the Vascular Endothelial Growth Factor Family of Proteins," *Endocrine Rev.,* 13(1):18–32 (1992).

Finnerty et al., "Molecular Cloning of Murine FLT and FLT4," *Oncogene,* 8(11):2293–2298 (1993).

Flamme et al., "Vascular Endothelial Growth Factor (VEGF) and VEGF–Receptor 2 (flk–1) are Expressed During Vasculogenesis and Vascular Differentiation in the Quail Embryo," *Devel. Biol.,* 169:699–712 (1995).

Flanagan and Leder, "The kit Ligand: A Cell Surface Molecule Altered in Steel Mutant Fibroblasts," *Cell,* 63:185–194 (Oct. 5, 1990).

Folkman, "Angiogenesis in Cancer, Vascular, Rheumatoid and Other Disease," *Nature Med.,* 1(1):27–31 (1995).

Folkman et al., "Angiogenesis," *J. Biol. Chem.,* 267(16):10931–10934 (Jun. 5, 1992).

Folkman et al., "Long–term Culture of Capillary Endothelial Cells," *Proc. Nat'l Acad. Sci., USA,* 76(10):5217–5221 (Oct., 1979).

Fong et al., "Role of the Flt–1 Receptor Tyrosine Kinase in Regulating the Assembly of Vascular Endothelium," *Nature,* 376:66–70 (Jul. 6, 1995).

Fossum et al., "Lymphedema Etiopathogenesis," *J. Vet. Int. Med.,* 6:283–293 (1992).

Fournier et al., "Mutation of Tyrosine Residue 1337 Abrogates Ligand–Dependent Transforming Capacity of the FLT4 Receptor," *Oncogene,* 11(5):921–931 (Sep. 7, 1995).

Friesel et al., "Molecular Mechanisms of Angiogenesis: Fibroblast Growth Factor Signal Transduction," *FASEB J.,* 9:919–25 (1995).

Fukumura et al., "Tumor Necrosis Factor α–induced Leukocyte Adhesion in Normal and Tumor Vessels: Effect of Tumor Type, Transplantation Site, and Host Strain," *Cancer Research,* 55:4824–4829 (Nov. 1, 1995).

Galland et al., "The Flt4 Gene Encodes a Transmembrane Tyrosine Kinase Related to the Vascular Endothelial Growth Factor Receptor," *Oncogene,* 8:1233–1240 (1993).

Genbank M22734, "Human Platelet–derived Growth Factor A Type Receptor mRNA, Complete cds.," Deposited by Claesson–Welsh et al., Dated Jan. 7, 1995.

Genbank M21616, "Human Platelet–derived Growth Factor (PDGF) Receptor mRNA, Complete cds." Deposited by Claesson–Welsh et al., Dated Sep. 28, 1992.

Genbank M32977, "Human Heparin–binding Vascular Endothelial Growth Factor (VEGF) mRNA, Complete cds." Deposited by Leung et al., Dated Feb. 28, 1991.

Genbank S66407, "FLT4 Receptor Tyrosine Kinase Isoform FLT4 Long (3' Region, Alternatively Spliced) [Human, mRNA Partial, 216 nt].," Deposited by Pajusola et al., Dated Dec. 17, 1993.

Genbank U48800, "Mus Musculus Vascular Endothelial Growth Factor B Precursor (VEGF–B) MRNA, Complete Cds.," Deposited by Olofsson et al., Dated Aug. 19, 1996.

Genbank U48801, "Human Vascular Endothelial Growth Factor B Precursor (VEGF–B) mRNA, Complete cds." Deposted by Olofsson et al., Dated Aug. 19, 1996.

Genbank X02811, "Human mRNA for Platelet–derived Growth Factor B Chain (PDGF–B)," Deposited by Collins et al., Dated Mar. 27, 1995.

Genbank X15997, "Human Vascular Permeability Factor mRNA, Complete Cds.," Deposited by Keck et al., Dated Jun. 15, 1990.

Genbank X54936, "H. sapiens mRNA for Placenta Growth Factor (PlGF)" Deposited by Persico, M.G., Dated Nov. 12, 1991.

Genbank X60280, "Vector Plasmid pLTRpoly DNA.," Deposited by Maekelae, T.P., Dated Jul. 16, 1996.

Genbank X68203, "H. sapiens mRNA for FLT4, Class III Receptor Tyrosine Kinase.," Deposited by Aprelikova, O., Dated Nov., 30, 1993.

Genbank X94216, "Homo sapiens mRNA for VEGF–C protein," Deposited by Joukov et al., Dated Feb. 6, 1996.

Harlow et al., *Antibodies, a Laboratory Manual,* Cold Spring Harbor Laboratory Press, pp. 72–137, 141–157, 287 & 321–358 (1988).

Heldin et al., "Structure of Platelet–Derived Growth Factor: Implications for Functional Properties," *Growth Factors,* 8:245–252 (1993).

Hillier et al., "The WashU–Merck EST Project," EMBL Database entry HS991157. Accession No. H07991, Jul. 2, 1995.

Hillier et al., y185b08.21 Homo sapiens cDNA clone 44993 5'. EST–STS Accession No. H05177 (Jun. 21, 1995).

Hillier et al., y186g06.r1 Homo sapiens cDNA clone 45138 5'. EST–STS Accession No. H07991 (Jun. 23, 1995).

Hillier et al., yd29f07.r1 Homo sapiens cDNA clone 109669 5' similar to SP:BAR3_CHITE Q03376 Balbiani Ring Protein 3. EST–STS Accession No. T81690 (Mar. 15, 1995).

Joukov et al., "A Novel Vascular Endothelial Growth Factor, VEGF–C, Is a Ligand for the Flt4 (VEGFR–3) and KDR (VEGFR–2) Receptor Tyrosine Kinases," *EMBO J.*, 15(2):290–298 (1996).

Kaipainen et al., "Expression of the FMS–Like Tyrosine Kinase 4 Gene Becomes Restricted to Lymphatic Endothelium During Development," *Proc. Nat'l Acad. Sci., USA*, 92:3566–3570 (Apr., 1995).

Kaipainen et al., "The Related FLT4, FLT1 and KDR Receptor Tyrosine Kinases Show Distinct Expression Patterns in Human Fetal Endothelial Cells," *J. Exp. Med.*, 178:2077–2988 (Dec., 1993).

Kaipainen et al., "Enhanced Expression of the Tie Receptor Tyrosine Kinase Messenger RNA in the Vascular Endothelium of Metastatic Melanomas," *Cancer Res.*, 54:6571–6577 (Dec. 15, 1994).

Keyt et al., "Identification of Vascular Endothelial Growth Factor Determinants for Binding KDR and FLT–1 Receptors," *J. Biol. Chem.*, 271(10):5638–5646 (Mar. 8, 1996).

Kim et al., "The Vascular Endothelial Growth Factor Proteins: Identification of Biologically Relevant Regions by Neutralizing Monoclonal Antibodies," *Growth Factors*, 7(1):53–64 (1992).

Korhonen et al., "The Mouse Tie Receptor Tyrosine Kinase Gene: Expression During Embryonic Angiogenesis," *Oncogene*, 9:395–403 (1994).

Kozak, "An Analysis of 5'–Non–Coding Sequences from 699 Vertebrate Messenger RNAs," *Nucl. Acids Res. 15:* 8125–8148 (1987).

Kukk et al., "VEGF–C Receptor Binding and Pattern of Expression with VEGFR–3 Suggests a Role in Lymphatic Vascular Development," *Development*, 122:3829–3837 (1996).

Leak, L.V., "Electron Microscopic Observations on Lymphatic Capillaries and the Structural Components of the Connective Tissue–Lymph Interface," *Microvasc. Res.*, 2:361–391 (1970).

Lee et al., "Vascular Endothelial Growth Factor–Related Protein: A Ligand and Specific Activator of the Tyrosine Kinase Receptor Flt4," *Proc. Nat'l Acad. Sci., USA*, 93:1988–1992 (Mar., 1996).

Leu et al., "Flow Velocity in the Superficial Lymphatic Network of the Mouse Tail," *Am. J. Physiol.*, 267:H1507–H1513 (1994).

Leung et al., "Vascular Endothelial Growth Factor Is a Secreted Angiogenic Mitogen," *Science*, 246:1306–1309 (Dec. 8, 1989).

Levy et al., "Post–transcriptional Regulation of Vascular Endothelial Growth Factor by Hypoxia," *J. Biol. Chem.*, 271(5):2746–2753 (Feb. 2, 1996).

Levy et al., "Transcriptional Regulation of the Rat Vascular Endothelial Growth Factor Gene by Hypoxia," *J. Biol. Chem.*, 270(22):13333–13340 (Jun. 2, 1995).

Lyman et al., "Molecular Cloning of a Ligand for the flt3/ftk–2 Tyrosine Kinase Receptor: A Proliferative Factor for Primitive Hematopoietic Cells," *Cell*, 75:1157–1167 (Dec. 17, 1993).

Maglione et al., "Isolation of a Human Placenta cDNA Coding for a Protein Related to the Vascular Permeability Factor," *Proc. Nat'l Acad. Sci., USA*, 88:9267–9271 (Oct., 1991).

Maglione et al., "Two Alternative mRNAs Coding for the Angiogenic Factor, Placenta Growth Factor (PlGF) are Transcribed from a Single Gene of Chromosome 14," *Oncogene*, 8:925–931 (1993).

Mäkelä et al., "Plasmid pLTRpoly: A Versatile High–Efficiency Mammalian Expression Vector," *Gene*, 118:293–294 (1992).

Matthews et al., "A Receptor Tyrosine Kinase cDNA Isolated from a Population of Enriched Primitive Hematopoietic Cells and Exhibiting Close Genetic Linkage to c–kit," *Proc. Nat'l Acad. Sci., USA*, 88:9026–9030 (Oct., 1991).

Metzelaar et al., "CD63 Antigen," *J. of Biol. Chem.*, 266(5):3239–3245 (Feb. 15, 1991).

Millauer et al., "Glioblastoma Growth Inhibited in vivo by a Dominant–Negative Flk–1 Mutant," *Nature*, 367:576–579 (Feb. 10, 1994).

Bowie et al., "Deciphering the Message in Protein Sequences: tolerance to amino acid substitutions," *Science*, 247:1306–1310 (Mar. 16, 1990).

Millauer et al., "High Affinity VEGF Binding and Developmental Expression Suggest Flk–1 as a Major Regulator of Vasculogenesis and Angiogenesis," *Cell*, 72:835–846 (Mar. 26, 1993).

Miles et al., "Vascular Reactions to Histamine, Histamine–Liberator and Leukotaxine in the Skin of Guinea–Pigs," *J. Physiol.*, 118:228–257 (1952).

Mitchell et al., "Transcription Factor AP–2 is Expressed in Neural Crest Cell Lineages During Mouse Embryogenesis," *Genes and Dev.*, 5:105–119 (1991).

Morgenstern et al., "Advanced Mammalian Gene Transfer: High Titre Retroviral Vectors With Multiple Drug Selection Markers and a Complementary Helper–Free Packaging Cell Line," *Nucl. Acids Res.*, 18(12):3587–3595 (1990).

Mount, S.M., "A Catalogue of Splice Junction Sequences," *Nucl. Acids Res.*, 10(2):459–472 (1982).

Muragaki et al., "Mouse Col18a1 is expressed in a tissue specific manner as three alternative variants and is localized in basement membrane zones," *Proc. Nat'l Acad. Sci., USA*, 92:8763–8776 (Sep., 1995).

Mustonen et al., "Endothelial Receptor Tyrosine Kinases Involved in Angiogenesis," *J. Cell Biol.*, 129:895–898 (May, 1995).

Nelson and Sun, "The 50– and 59–kdalton Keratin Classes as Molecular Markers for Stratified Squamous Epithelia: Cell Culture Studies," *J. Cell Biol.*, 97:244–251 (Jul., 1983).

Neufeld et al., "Vascular Endothelial Growth Factor and Its Receptors," *Prog. Growth Fact. Res.*, 5:89–97 (1994).

Oefner et al., "Crystal Structure of Human Platelet–derived Growth Factor BB," *EMBO J.*, 11(11):3921–3926 (1992).

Oelrichs et al., "NYK/FLK–1: A Putative Receptor Tyrosine Kinase Isolated from E10 Embryonic Neuroepithelium is Expressed in Endothelial Cells of the Developing Embryo," *Oncogene*, 8:11–18 (1993).

Olofsson et al., "Vascular Endothelial Growth Factor B, A Novel Growth Factor for Endothelial Cells," *Proc. Nat'l Acad. Sci., USA*, 93:2576–2581 (Mar., 1996).

Orlandini et al., "Identification of a c–fos–induced gene that is related to the platelet–derived growth factor/vascular endothelial growth factor family," *Proc. Nat'l Acad. Sci., USA*, 93(21):11675–11680 (Oct., 1996).

Paavonen et al., "Chromosomal Localization and Regulation of Human Vascular Endothelial Growth Factors B and C (VEGF–B and VEGF–C)," IX International Vascular Biology Meeting, Seattle, Washington, Sep. 4–8, 1996, p. 76 (Abstract 299).

Paavonen et al., "Novel Human Vascular Endothelial Growth Factor Genes VEGF–B and VEGF–C Localize to Chromosomes 11q13 and 4q34, Respectively," *Circulation* 93(6):1079–1082 (Mar. 15, 1996).

Pajusola, "Cloning and Characterization of a New Endothelial Receptor Tyrosine Kinase Flt4 and Two Novel VEGF–Like Growth Factors VEGF–B and VEFG–C," *Academic Dissertation, Molecular/Cancer Biology Laboratory and Department of Pathology*, Haartman Institute and Department of Biosciences, Division of Genetics, University of Helsinki, (Jan. 26, 1996).

Pajusola et al., "FLT4 Receptor Tyrosine Kinase Contains Seven Immunoglobulin–Like Loops and Is Expressed in Multiple Human Tissues and Cell Lines," *Cancer Res.*, 52:5738–5743 (Oct. 15, 1992).

Pajusola et al., "Signalling Properties of FLT4, a Proteolytically Processed Receptor Tyrosine Kinase Related to Two VEGF Receptors," *Oncogene*, 9:3545–3555 (1994).

Pajusola et al., "Two Human FLT4 Receptor Tyrosine Kinase Isoforms With Distinct Carboxy Terminal Tails are Produced by Alternative Processing of Primary Transcripts," *Oncogene*, 8:2931–2937 (1993).

Park et al., "Placenta Growth Factor, Potentiation of Vascular Endothelial Growth Factor Bioactivity In vitro and In vivo, and High Affinity Binding to Flt–1 but not to Flk–1/KDR," *J. Biol. Chem.*, 269(41):25646–25654 (Oct. 14, 1994).

Partanen et al., "A Novel Endothelial Cell Surface Receptor Tyrosine Kinase with Extracellular Epidermal Growth Factor Homology Domains," *Mol. & Cell. Biol.*, 12(4):1698–1707 (Apr., 1992).

Partanen et al., "Putative Tyrosine Kinases Expressed in K–562 Human Leukemia Cells," *Proc. Nat'l Acad. Sci., USA*, 87:8913–8917 (Nov., 1990).

Paulsson et al., "The Balbiani Ring 3 Gene in *Chironomus tentans* has a Diverged Repetitive Structure Split by Many Introns," *J. Mol. Biol.*, 211:331–349 (1990).

Pear et al., "Production of High–titer Helper–free Retroviruses by Transient Transfection," *Proc. Nat'l Acad. Sci., USA*, 90:8392–8396 (Sep., 1993).

Pertovaara et al., "Vascular Endothelial Growth Factor Is Induced in Response to Transforming Growth Factor–$\beta$ in Fibroblastic and Epithelial Cells," *J. Biol. Chem.*, 269(9):6271–6274 (Mar. 4, 1994).

Peters et al., "Vascular Endothelial Growth Factor Receptor Expression during Embryogenesis and Tissue Repair Suggests a Role in Endothelial Differentiation and Blood Vessel Growth," *Proc. Nat'l Acad. Sci., USA*, 90:8915–8918 (Oct., 1993).

Pötgens et al., "Covalent Dimerization of Vascular Permeability Factor/Vascular Endothelial Growth Factor Is Essential for Its Biological Activity," *J. Biol. Chem.*, 269(52):32879–32885 (Dec. 30, 1994).

Puri et al., "The Receptor Tyrosine Kinase Tie is Required for Integrity and Survival of Vascular Endothelial Cells," *EMBO J.*, 14:5884–5891 (1995).

Quinn et al., "Fetal Liver Kinase 1 is a Receptor for Vascular Endothelial Growth Factor and is Selectively Expressed in Vascular Endothelium," *Proc. Nat'l Acad. Sci., USA*, 90:7533–7537 (Aug., 1993).

Risau et al., "Changes on the Vascular Extracellular Matrix During Embryonic Vasculogenesis and Angiogenesis," *Devel. Biol.*, 125:441–450 (1988).

Risau et al., "Platelet–Derived Growth factor is Angiogenic In Vivo," *Growth Factors*, 7:261–266 (1992).

Risau, W., "Differentiation of Endothelium," *FASEB J.*, 9:926–933 (1995).

Sabin, F.R., "The Lymphatic System in Human Embryos, With A Consideration of the Morphology of the System as a Whole," *Am. J. Anat.*, 9(1):43–91 (1909).

Saksela et al., "Cell–Associated Plasminogen Activation: Regulation and Physiological Function," *Ann. Rev. Cell Biol.*, 4:93–126 (1988).

Sambrook et al., *Molecular Cloning: a Laboratory Manual*, Second Edition, Cold Spring Harbor, New York: Cold Spring Harbor Laboratory (1989), pp. 2.60–2.79, 4.21–4.32, 7.3–7.36, and 9.47–9.51.

Sato et al., "Distinct Roles of the Receptor Tyrosine Kinases Tie–1 and Tie–2 in Blood Vessel Formation," *Nature*, 376:70–74 (Jul. 6, 1995).

Schmelz et al., "*Complexus adhaerentes*, A New Group of Desmoplakin–containing Junctions in Endothelial Cells: II. Different Types of Lymphatic Vessels," *Differentiation*, 57:97–117 (1994).

Schneider et al., "A One–step Purification of Membrane Proteins Using a High Efficiency Immunomatrix," *J. Biol. Chem.*, 257(18):10766–70769 (Sep. 25, 1982).

Seetharam et al., "A Unique Signal Transduction from FLT Tyrosine Kinase, a Receptor for Vascular Endothelial Growth Factor VEGF," *Oncogene*, 10:135–147 (1995).

Senger et al., "Tumor Cells Secrete a Vascular Permeability Factor That Promotes Accumulation of Ascites Fluid," *Science*, 219:983–985 (Feb. 25, 1983).

Shalaby et al., "Failure of Blood–Island Formation and Vasculogenesis in Flk–1–deficient Mice," *Nature*, 376:62–66 (Jul. 6, 1995).

Shibuya et al., "Nucleotide Sequence and Expression of a Novel Human Receptor–Type Tyrosine Kinase Gene (flt) Closely Related to the fms Family," *Oncogene*, 5:519–524 (1990).

Shibuya, M., "Role of VEGF–FLT Receptor System in Normal and Tumor Angiogenesis," *Adv. Cancer Res.*, 67:281–316 (1995).

Shweiki et al., "Patterns of Expression of Vascular Endothelial Growth Factor (VEGF) and VEGF Receptors in Mice Suggest a Role in Hormonally Regulated Angiogenesis," *J. Clin. Invest.*, 91:2235–2243 (May, 1993).

Sitaras et al., "Constitutive Production of Platelet–Derived Growth Factor–Like Proteins by Human Prostate Carcinoma Cell Lines," *Cancer Research*, 48(7):1930–1935 (Apr. 1, 1988).

Southern and Berg, "Transformation of Mammalian Cells to Antibiotic Resistance with a Bacterial Gene Under Control of the SV40 Early Region Promoter," *J. Mol. Appl. Genet.*, 1:327–341 (1982).

Swartz et al., "Transport in Lymphatic Capillaries. I. Macroscopic measurements using residence time distribution theory," *Am. J. Physiol.*, 270:H324–H329 (1996).

Terman et al., "Identification of New Endothelial Cell Growth Factor Receptor Tyrosine Kinase," *Oncogene*, 6:1677–1683 (1991).

Terman et al., "Identification of the KDR Tyrosine Kinase as a Receptor for Vascular Endothelial Cell Growth Factor," *Biochem. Biophys. Res. Commun.*, 187:1579–1586 (Sep. 30, 1992).

Terman et al., "VEGF Receptor Subtype KDR and FLT1 Show Different Sensitivities to Heparin and Placenta Growth Factor," *Growth Factors*, 11(3):187–195 (1994).

Tessier et al., "Enhanced Secretion From Insect Cells of a Foreign Protein Fused to the Honeybee Melittin Signal Peptide," *Gene*, 98:177–183 (1991).

Tischer et al., "The Human Gene for Vascular Endothelial Growth Factor. Multiple Protein Forms are Encoded Through Alternative Exon Splicing," *J. Biol. Chem.*, 266(18):11947–11954 (Jun. 25, 1991).

Udaka et al., "Simple Method for Quantitation of Enhanced Vascular Permeability," *Proc. Soc. Exp. Biol. Med.*, 133:1384–1387 (1970).

Van der Geer et al., "Receptor Protein–Tyrosine Kinases and Their Signal Transduction Pathways," *Ann. Rev. Cell Biol.*, 10:251–337 (1994).

Vassar et al., "Tissue–specific and Differentiation –specific Expression of a Human K14 Keratin Gene in Transgenic Mice," *Proc. Nat'l Acad,. Sci., USA*, 86:1563–1567 (Mar., 1989).

Vassar et al., "Transgenic Mice Provide New Insights Into the Role of TGF–α During Epidermal Development and Differentiation," *Genes & Dev.*, 5:714–727 (1991).

Vassbotn et al., "Reversion of Autocrine Transformation by a Dominant Negative Platelet–Derived Growth Factor Mutant," *Mol. Cell. Biol.*, 13(7):4066–4076 (Jul., 1993).

Västrik et al., "Expression of the Mad Gene During Cell Differentiation In Vivo and Its Inhibition of Cell Growth In Vitro," *J. Cell. Biol.*, 128(6):1197–1208 (Mar., 1995).

von Heijne, G., "A New Method for Predicting Signal Sequence Cleavage Sites," *Nucleic Acids Res.*, 14(11):4683–4690 (1986).

Waltenberger et al., "Different Signal Transduction Properties of KDR and Flt1, Two Receptors for Vascular Endothelial Growth Factor," *J. Biol. Chem*, 269(43):26988–26995 (Oct. 28, 1994).

Wanaka et al., "Expression of FGF Receptor Gene in Rat Development," *Development*, 111:455–468 (1991).

Wells, "Additivity of Mutational Effects in Proteins," *Biochemistry*, 29(37):8509–8517 (Sep. 17, 1990).

Wen et al., "New Differentiation Factor: A Transmembrane Glycoprotein Containing an EGF Domain and an Immunoglobulin Homology Unit," *Cell 69:*559–572 (May 1, 1992).

Yamane et al., "A New Communication System Between Hepatocytes and Sinusoidal Endothelial Cells in Liver Through Vascular Endothelial Growth Factor and Flt Tyrosine Kinase Receptor Family (Flt–1 and KDR/Flk–1)," *Oncogene*, 9:2683–2690 (1994).

Achen, M.G. et al., "Vascular Endothelial Growth Factor D (VEGF–D) is a Ligand for the Tyrosine Kinases VEGF Receptor 2 (Flk1) and VEGF Receptor 3 (Flt4)," Proceedings of the National Academy of Science, USA, 95:548–553 (Jan., 1998).

Adams, M.D. et al., "Initial assessment of human gene diversity and expression patterns based upon 83 million nucleotides of cDNA sequence," *Nature*, 377(6547 Supplement):3–174 (Sep., 1995).

Cohen, T. et al., "VEGF$_{121}$, A Vascular Endothelial Growth Factor (VEGF) Isoform Lacking Heparin Binding Ability, Requires Cell–Surface Heparan Sulfates for Efficient Binding to the VEGF Receptors of Human Melanoma Cells," *Journal of Biological Chemistry*, 270(19):11322–11326 (May 12, 1995).

Genbank AA151613, "z127h03.s1 Soares pregnant uterus NbHPU Homo sapiens cDNA clone 503189 3'," Hillier, L. et al., Dated May 14, 1997.

Genbank AA425486, "zw46b06.r1 Soares total fetus Nb2HF8 9w Homo sapiens cDNA clone 773075 5' similar to SW: VEGF_Mouse Q00731 Vascular Endothelial Growth Factor Precursor," Deposited by Hillier, L. et al. Dated Oct. 16, 1997.

Genbank N31713, "yy15b12.s1 Homo sapiens cDNA clone 271295 3'," Deposited by Hillier, L. et al. Dated Jan. 10, 1996.

Genbank N31720, "yy15d12.s1 Homo sapiens cDNA clone 271319 3'," Deposited by Hillier, L. et al. Dated Jan. 10, 1996.

Genbank AA406492, "zv12g06.r1 Soars NhHMPu S1 Homo sapiens cDNA clone 75366 5'," Deposited by Hillier, L. et al. Dated May 17, 1997.

Genbank N50972, "yy94b08.s1 Homo sapiens cDNA clone 281175 3'," Deposited by Hillier, L. et al. Dated Feb. 14, 1996.

Genbank AA421713, "zu24b03.s1 Soares NhHMPu S1 Homo sapiens cDNA clone 738893 3'," Deposited by Hillier, L. et al. Dated Oct. 16, 1997.

Genbank N31713, "yy15b12.s1 Homo sapiens cDNA clone 271295 3'," Deposited by Hillier, L. et al. Dated Jan. 10, 1996.

Genbank N94399, "zb76f04.s1 Soares senescent fibroblasts NbHSF Homo sapiens cDNA clone 309535 3'," Deposited by Hillier, L. et al. Dated Aug. 20, 1996.

Genbank H05177, "y185b08.r1 Homo sapiens cDNA clone 44993 5'," Deposited by Hillier, L. et al. Dated Jun. 21, 1995.

Genbank AA479987, "zv18h12.s1 Soares NhHMPu S1 Homo sapiens cDNA clone 754055 3'," Deposited by Hillier, L. et al. Dated Aug. 8, 1997.

Genbank H05134, "y185b08.s1 Homo sapiens cDNA clone 44993 3'," Deposited by Hillier, L. et al. Dated Jun. 21, 1995.

Genbank, AA298182 "EST113866 Bone VII Homo sapiens cDNA 5' end," Deposited by Adams, M.D. et al. Dated Apr. 18, 1997.

Genbank AA298283, "EST113896 Bone VII Homo sapiens cDNA 5' end similar to similar to vascular endothlial growth factor," Deposited by Adams, M.D. et al. Dated Apr. 18, 1997.

Genbank T81481, "Yd29f07.s1 Homo sapiens cDNA clone 109669 3'," Deposited by Hillier, L. et al. Dated Mar. 15, 1995.

Genbank AA425303, "zw46b06.s1 Soares total fetus Nb2HF8 9w Homo sapiens cDNA clone 773075 3', mRNA sequence," Deposited by Hillier, L. et al. Dated Oct. 16, 1997.

Genbank Z40230, "H. sapiens partial cDNA sequence; clone c–1wf11," Deposited by Genexpress. Dated Sep. 21, 1995.

Genbank Z44272, "H. sapiens partial cDNA sequence; clone c–1wf11," Deposited by Genexpress. Dated Sep. 21, 1995.

Genbank AA478766, "zv18h12.r1 Soares NhHMPu S1 Homo sapiens cDNA clone 754055 5'," Deposited by Hillier, L. et al. Dated Aug. 8, 1997.

Genbank H96876, "yw04b12.s1 Soares melanocyte 2NbHM Homo sapiens cDNA clone 251231 3'," Deposited by Hillier, L. et al. Dated Nov. 25, 1996.

Genbank H96533, "yw04b12.r1 Soares melanocyte 2NbHM Homo sapiens cDNA clone 251231 5'," Deposited by Hillier, L. et al. Dated Nov. 25, 1996.

Genbank T81690, "yd29f07.r1 Homo sapiens cDNA clone 109669 5' similar to SP:BAR3_CHITE Q03376 Balbiani Ring Protein 3," Deposited by Hillier, L. et al. Dated Mar. 15, 1995.

Genbank T84377, "yd37h08.r1 Homo sapiens cDNA clone 110463 5' similar to SP:BAR3_CHITE Q03376 Balbiani Ring Protein 3," Deposited by Hillier, L. et al. Dated Mar. 16, 1995.

Genbank N42368, "yy15b11.r1 Homo sapiens cDNA clone 271293 5'," Deposited by Hillier, L. et al. Dated Jan. 25, 1996.

Genbank N42374, "yy15d11.r1 Homo sapiens cDNA clone 271317 5'," Deposited by Hillier, L. et al. Dated Jan. 25, 1996.

Genbank H81868, "yv83d09.s1 Homo sapiens cDNA clone 249329 3'," Deposited by Hillier, L. et al. Dated Nov. 9, 1995.

Genbank H81867, "yv83d09.r1 Homo sapiens cDNA clone 249329 5'," Deposited by Hillier, L. et al. Dated Nov. 9, 1995.

Genbank AA149461, "z127h03.r1 Soares pregnant uterus NbHPU Homo sapiens cDNA clone 503189 5' similar to SW:BAR3_CHITE Q03376 Balbiani Ring Protein 3 Precursor," Deposited by Hillier, L. et al. Dated May 14, 1997.

Genbank R77495, "yi79e04.s1 Homo sapiens cDNA clone 145470 3'," Deposited by Hillier, L. et al. Dated Jun. 7, 1995.

Genbank H07899, "yl86g06.s1 Homo sapiens cDNA clone 45138 3'," Deposited by Hillier, L. et al. Dated Jun. 23, 1995.

Genbank T89295, "yd37h08.s1 Homo sapiens cDNA clone 110463 3'," Deposited by Hillier, L. et al. Dated Mar. 20, 1995.

Genbank C21512, "HUMGS0010510, Human Gene Signature, 3'–directed cDNA sequence," Deposited by Okubo, K. Dated Oct. 1, 1996.

Genbank N82975, "TgESTzy53h10.r1 TgRH Tachyzoite cDNA Toxoplasma gondii cDNA clone tgzy53h10.r1 5'," Deposited by Hehl, A. et al. Dated Sep. 10, 1997.

Genbank AA285997, "vb99h06.r1 Soares mouse 3NbMS Mus musculus CDNA clone 764123 5'," Deposited by Marra, M. et al. Dated Apr. 9, 1997.

Genbank AA549856, "0929m3 gmbPfHB3.1, G. Roman Reddy Plasmodium falciparum genomic clone 0920m," Deposited by Dame, J.B. et al. Dated Aug. 11, 1997.

Jeltsch, M. et al., "Hyperplasia of Lymphatic Vessels in VEGF–C Transgenic Mice," *Science*, 276:1423–1425 (May, 1997).

Joukov, V. et al., "Proteolytic Processing Regulates Receptor Specificity and Activity of VEGF–C," *EMBO Journal*, 16(13):3898–3911 (Jun., 1997).

Joukov, V. et al., "A Recombinant Mutant Vascular Endothelial Growth Factor–C that has Lost Endothelial Growth Factor Receptor–2 Binding, Activation, and Vascular Permeability Activities," *Journal of Biological Chemistry*, 273(12):6599–6602 (Mar. 20, 1998).

Lee, J. et al., "Vascular Endothelial Growth Factor Related Protein (vrp): A Ligand and Specific Activator of the Tyrosine Kinase Receptor Flt4," EMBL Sequence Data Library, XP002066361, accession No. U4142. Dated Jan. 10, 1996.

```
            1                                                           50
PDGF-A      ..........  ..........  ..........  ..........  .MRTLACLLL
PDGF-B      ..........  ..........  ..........  ..........  MNRCWA.LFL
PlGF-1      ..........  ..........  ..........  ..........  ..........
VEGF165     ..........  ..........  ..........  ..........  ..........
VEGF-B167   ..........  ..........  ..........  ..........  ..........
VEGF-C      MHLLGFFSVA  CSLLAAALLP  GPREAPAAAA  AFESGLDLSD  AEPDAGEATA 51                                                          100
PDGF-A      LGCGYLAHVL  AEEAEIPREV  IERLARSQIH  SIRDLQRLLE  IDSVGSEDSL
PDGF-B      SLCCYLRLVS  AEGDPIPEEL  YEMLSDHSIR  SFDDLQRLLH  GDP.GEEDGA
PlGF-1      ..........  ..MPVM      RLFPC..FLQ  LLAGLAL...  PAVPPQQW..
VEGF165     ..........  ......M     NFLLS..WVH  WSLALLLYLH  HAKWSQAA..
VEGF-B167   ..........  ......M     SPLLR..RLL  LAALLQLAPA  QAPVSQP...
VEGF-C      YASKDLEEQL  RSVSSVDELM  TVLYPEYWKM  YKCQLRKGGW  QHNREQANLN 101                                                         150
PDGF-A      DTSLRAHGVH  ATKHVPEKRP  LPIRRKRSI.  .....EEAVP  AVCKTRTVIY
PDGF-B      ELDLNMTRSH  SGGELES...  .LARGRRSLG  SLTIAEPAMI  AECKTRTEVF
PlGF-1      .ALSAG      NGSSEVEVVP  FQE.VWGR..  ..........  SYCRALERLV
VEGF165     .PMAEG      GGQNHHEVVK  FMD.VYQR..  ..........  SYCHPIETLV
VEGF-B167   .......D    APGHQRKVVS  WID.VYTR..  ..........  ATCQPREVVV
VEGF-C      SRTEETIKFA  AAHYNTEILK  SIDNEWRK..  ..........  TQCMPREVCI 151                                                         200
PDGF-A      EIPRSQVDPT  SANFLIWPPC  VEVKRCTGCC  NTSSVKCQPS  RVHHRSVKVA
PDGF-B      EISRRLIDRT  NANFLVWPPC  VEVQRCSGCC  NNRNVQCRPT  QVQLRPVQVR
PlGF-1      DVVSEYPSEV  ..EHMFSPSC  VSLLRCTGCC  GDENLHCVPV  ETANVTMQLL
VEGF165     DIFQEYPDEI  ..EYIFKPSC  VPLMRCGGCC  NDEGLECVPT  EESNITMQIM
VEGF-B167   PLTVELMGTV  ..AKQLVPSC  VTVQRCGGCC  PDDGLECVPT  GQHQVRMQIL
VEGF-C      DVGKEFGVAT  ..NTFFKPPC  VSVYRCGGCC  NSEGLQCMNT  STSYLSKTLF
```

FIGURE 2A

```
         201                                                                      250
PDGF-A   KVEYVRKKPK LKEVQVRLEE HLECACAT.. .......... .......... TSLNPDYREE
PDGF-B   KIEIVRKKPI FKKATVTLED HLACKCETVA AARPVTRSPG GSQEQRAKTP
P1GF-1   KIRSG..DRP .SYVELTFSQ HVRCECRPLR EK........ ..........
VEGF165  RIKPH..QGQ .HIGEMSFLQ HNKCECRPKK DR........ ..........
VEGF-B167 MIRYP..SSQ ..LGEMSLEE HSQCECRPKK KD........ ..........
VEGF-C   EITVPLSQGP .KPVTISFAN HTSCRCMSKL DVYRQVHSII RRSLPATLPQ 251                                                                      300
PDGF-A   DTDVR..... .......... .......... .......... ..........
PDGF-B   QTRVTIRTVR VRRPPKGKHR KFKHTHDKTA LKETLGA... ..........
P1GF-1   .......... .......... .......... .MKPERCGDA VPRR......
VEGF165  .......... .......... .......... .ARQENPCGP CSERRKHLFV
VEGF-B167 .......... .......... .......S AVKPDSPRPL CPRCTQHHQR
VEGF-C   CQAANKTCPT NYMWNNHICR CLAQEDFMFS SDAGDDSTDG FHDICGPNKE 301                                                                      350
PDGF-A   .......... .......... .......... .......... ..........
PDGF-B   .......... .......... .......... .......... ..........
P1GF-1   .......... .......... .......... .......... ..........
VEGF165  QDPQTCKCSC KNTDS.RCKA RQLELNERTC RCDKPRR... ..........
VEGF-B167 PDPRTCRCRC RRRSFLRCQG RGLELNPDTC RCRKLRR... ..........
VEGF-C   LDEETCQCVC RAGLRPASCG PHKELDRNSC QCVCKNKLFP SQCGANREFD
```

FIGURE 2B

```
              351                                                                400
PDGF-A        ..........  ..........  ..........  ..........  ..........
PDGF-B        ..........  ..........  ..........  ..........  ..........
PlGF-1        ..........  ..........  ..........  ..........  ..........
VEGF165       ..........  ..........  ..........  ..........  ..........
VEGF-B167     ..........  ..........  ..........  ..........  ..........
VEGF-C        ENTCQCVCKR  TCPRNQPLNP  GKCACECTES  PQKCLLKGKK  FHHQTCSCYR 401              434
PDGF-A        ..........  ....
PDGF-B        ..........  ....
PlGF-1        ..........  ....
VEGF165       ..........  ....
VEGF-B167     ..........  ....
VEGF-C        RPCTNRQKAC  EPGFSYSEEV  CRCVPSYWKR  PQMS
```

FIGURE 2C

VEGF-C alignment

```
       1                                                                    50
Hum    HMLLGFFSVA  CSLLAAALLP  GPREAPAAAA  AFESGLDLSD  AEPDAGEATA
Mou    MHLLCFLSLA  CSLLAAALIP  SPREAPATVA  AFESGLGFSE  AEPDGGEVKA
Qua    MHLLEMLSLG  CCLAAGAVLL  GPRQPPVA.A  AYESGHGYYE  EEPGAGEPKA 51                                                                  100
Hum    YASKDLEEQL  RSVSSVDELM  TVLYPEYWKM  YKCQLRKGGW  QHNREQANLN
Mou    FEGKDLEEQL  RSVSSVDELM  SVLYPDYWKM  YKCQLRKGGW  Q....QPTLN
Qua    HASKDLEEQL  RSVSSVDELM  TVLYPEYWKM  FKCQLRKGGW  QHNREHSSSD 101                                                                 150
Hum    SRTEETIKFA  AAHYNTEILK  SIDNEWRKTQ  CMPREVCIDV  GKEFGVATNT
Mou    TRTGDSVKFA  AAHYNTEILK  SIDNEWRKTQ  CMPREVCIDV  GKEFGAATNT
Qua    TRSDDSLKFA  AAHYNAEILK  SIDTEWRKTQ  GMPREVCVDL  GKEFGATTNT 151                                                                 200
Hum    FFKPPCVSVY  RCGGCCNSEG  LQCMNTSTSY  LSKTLFEITV  PLSQGPKPVT
Mou    FFKPPCVSVY  RCGGCCNSEG  LQCMNTSTGY  LSKTLFEITV  PLSQGPKPVT
Qua    FFKPPCVSIY  RCGGCCNSEG  LQCMNISTNY  ISKTLFEITV  PLSHGPKPVT 201                                                                 250
Hum    ISFANHTSCR  CMSKLDVYRQ  VHSIIRRSLP  ATLPQCQAAN  KTCPTNYMWN
Mou    ISFANHTSCR  CMSKLDVYRQ  VHSIIRRSLP  ATLPQCQAAN  KTCPTNYVWN
Qua    VSFANHTSCR  CMSKLDVYRQ  VHSIIRRSLP  ATQTQCHVAN  KTCPKNHVWN 251                                                                 300
Hum    NHICRCLAQE  DFMFSSDAGD  DSTDGFHDIC  GPNKELDEET  CQCVCRAGLR
Mou    NYMCRCLAQQ  DFIFYSNVED  DSTNGFHDVC  GPNKELDEDT  CQCVCKGGLR
Qua    NQICRCLAQH  DFGFSSHLGD  SDTSEGFHIC  GPNKELDEET  CQCVCKGGVR 301                                                                 350
Hum    PASCGPHKEL  DRNSCQCVCK  NKLFPSQCGA  NREFDENTCQ  CVCKRTCPRN
Mou    PSSCGPHKEL  DRDSCQCVCK  NKLFPNSCGA  NREFDENTCQ  CVCKRTCPRN
Qua    PISCGPHKEL  DRASCQCMCK  NKLLPSSCGP  NKEFDEEKCQ  CVCKKTCPKH 351                                                                 400
Hum    QPLNPGKCAC  ECTESPQKCL  LKGKKFHHQT  CSCYRRPCTN  RQKACEPGFS
Mou    QPLNPGKCAC  ECTENTQKCF  LKGKKFHHQT  CSCYRRPCAN  RLKHCDPGLS
Qua    HPLNPAKCIC  ECTESPNKCF  LKGKRFHHQT  CSCYRPPCTV  RTKRCDAGFL 401            420
Hum    YSEEVCRCVP  SYWKRPQMS*
Mou    FSEEVCRCVP  SYWKRPHLN.
Qua    LAEEVCRCVR  TSWKRPLMN*
```

FIGURE 5

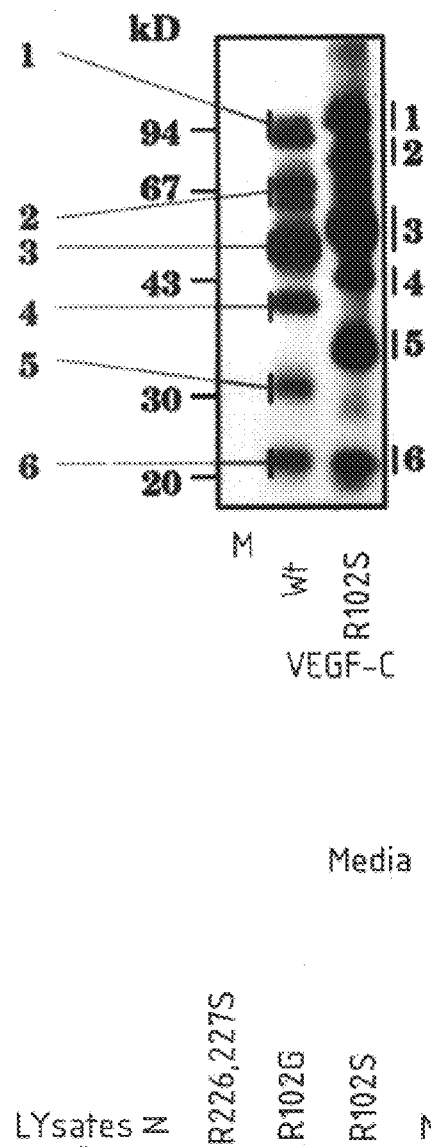
FIGURA 6B
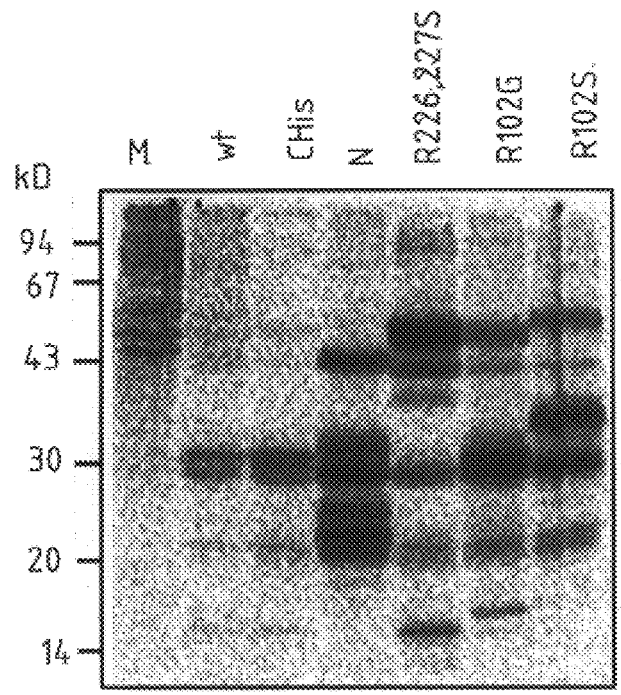
FIGURA 7A
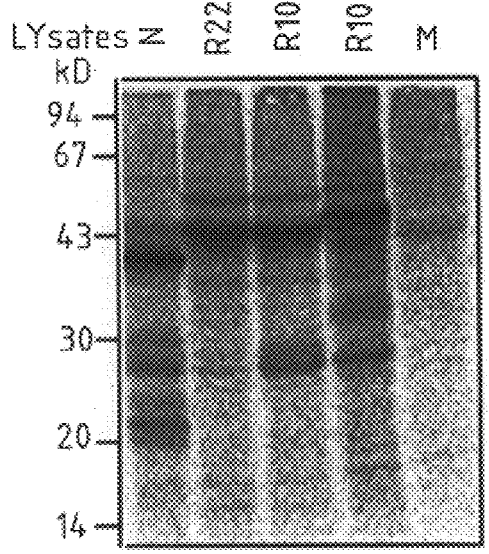
FIGURA 7B

FIGURE 10

```
              Signal sequence          ▼      N-terminal propeptide
         1                         31    32                                                    98
mouse    MHLLCFLSLACLLAAALIPSREAPATVAA    FESGLGFSEAEPDGGEVKAFEGKNLEEQLRSVSSVDELMSVLYPDYWKMYKCQLRKGGWQ...QPTLNTR
human    ....G.F.V......L.G......AA..    .....DL.D...A..AT.YAS.D.............T...E.........HNRE.AN..S.

VEGF homology
                    C                        C...RC..CC.....C                          C..C                   222
99  TGDSVKFAAAHYNTEILKSIDNEWRKTQCMPREVCIDVGKEFGAATNTFFKPPCVSVYRCGGCCNSEGLQCMNTSTGYLSKTLFEITVPLSQGPKPVTISFANHTSCRCMSKLDVYRQVHSIIR
    .EETI......................................V.....................S.............................................

BR3P homology
                              C           C C  C
223  RSLPATLQCQAANKTCPTNYVWNNYMCRC LAQQDFIFYSNVEDDSTNGFHDV GPNKELDEDTCQCVC KGGLRPSS
     ...............SP...L........    ..E..M.S.DAG...D...I..   .E.........RA..A.

CGPHKELDRDSCQCVC KNKLFPNS
                                                          .............N..    ..SQ

CGANREFDENTCQCVC KRT
                                                          .R..............

CPRNQPLNPGKCACEC
                                                          ................
                                                                                        415
     ....TENTQKCFLKGKKFHHQTCSCYRRP
     .....SP..L..................

....CANRLKHCDPGLSFSEEVCRC VPSYWKRPHLN           QMS
     ....T.Q.A.E..GF.Y.......
```

FIGURE 13A

| HUMAN Exon length | Donor site | Intron length | Acceptor site |
|---|---|---|---|
| | ...G...E...A...T(49)........ | | ...A...Y...A...S. |
| E1.......GGC.GAG.GCC.ACG.gtaggtctgcgt...>10.kb..TTTCTTTGACAG.GCT.TAT.GCA.AGC |
| | ...E...I...L...K(116)....... | | ...S...I...D...N. |
| E2.214.bp..GAG.ATC.TTG.AAA.Agtaagtatggg...1.6.kb....atgacttgacagGT.ATT.GAT.AAT |
| | ...L...S...K...T(180)....... | | ...L...F...E...I. |
| E3.191.bp..CTC.AGC.AAG.ACG.gtgggtattgt....9.kb..ccctctcttgtag.TTA.TTT.GAA.ATT |
| | ...T...L...P...Q(231)....... | | ...C...Q...A...A. |
| E4.152.bp..ACA.CTA.CCA.CAgtgagtatgaattaaa..>10.kb..ttcttccaaagG.TGT.CAG.GCA.GCG |
| | ...A...G...D...(266)......... | | ...D...S...T...D. |
| E5.107.bp..GCT.GGA.GAT.Ggtagcagaatg.....301.bp....ctattgtctagAC.TCA.ACA.GAT |
| | ...Q...T...C...S(378)........ | | ...C...Y...R...R. |
| E6.334.bp..CAA.ACA.TGC.AGgtaagagatcc.....>10.kb..tgttcctcctagC.TGT.TAC.AGA.CGG |
| | ...Q...M...S(419)Stop........ | | |
| E7.(501).bp..CAA.ATG.AGC.TAA.GTATGTACTGTT..ATTGTATTAT | | | |

MOUSE

| Exon length | Donor site | Intron length | Acceptor site |
|---|---|---|---|
| | ...G...E...V...K(49)............ | ............................. | ....A...F...E...G. |
| E1 | GGC.GAG.GTC.AAG.gtaggtgcaagg. | >10.kb.attgtcttgacag. | GCT.TTT.TGA.AGG |
| | ...E...I...L...K(116)........... | ............................. | .......S...I...D...N. |
| E2 201.bp | GAG.ATC.CTG.AAA.Agtaagtag..... | ....4.kb....tgtgactcgacagGT. | ATT.GAT.AAT |
| | ...L...S...K...T(180)........... | ............................. | ......L...F...E...I. |
| E3 191.bp | CTC.AGC.AAG.ACG.gtaggtat...... | ....9.kb..ttgtcccttgtag. | TTG.TTT.GAA.ATT |
| | ...T...L...P...Q(231)........... | ............................. | ......C...Q...A...A. |
| E4 152.bp | ACA.TTA.CCA.CAgtgagtatg....... | ...10.kb.gtctcccaaaagG. | TGT.CAG.GCA.GCT |
| | ...N...V...E...D(266)........... | ............................. | ......D...S...T...N. |
| E5 107.bp | AAT.GTT.GAA.GAT.Ggtaagtaaaa... | .350.bp.................tctagAC. | TCA.ACC.AAT |
| | ...Q...T...C...S(378)........... | ............................. | ......C...Y...R...R. |
| E6 334.bp | CAA.ACA.TGC.AGgtaaggagtgt..... | ....6.kb..ttttcccctagT. | TGT.TAC.AGA.AGA |
| | ...H...L...N(415)Stop........... | ............polyA............ | |
| E7 506.bp | CAT.CTG.AAC.TAA.GATCATACC... | ATTGTATTATAAgctgtgaag | |

FIGURE 13B

VASCULAR ENDOTHELIAL GROWTH FACTOR C (VEGF-C) ΔCYS$_{156}$ PROTEIN AND GENE, AND USES THEREOF

FIELD OF THE INVENTION

The present invention generally relates to the field of genetic engineering and more particularly to growth factors for endothelial cells and growth factor genes.

BACKGROUND OF THE INVENTION

Developmental growth, the remodeling and regeneration of adult tissues, as well as solid tumor growth, can only occur when accompanied by blood vessel formation. Angioblasts and hematopoietic precursor cells differentiate from the mesoderm and form the blood islands of the yolk sac and the primary vascular system of the embryo. The development of blood vessels from these early (in situ) differentiating endothelial cells is termed vasculogenesis. Major embryonic blood vessels are believed to arise via vasculogenesis, whereas the formation of the rest of the vascular tree is thought to occur as a result of vascular sprouting from pre-existing vessels, a process called angiogenesis, Risau et al., *Devel. Biol.,* 125:441–450 (1988).

Endothelial cells give rise to several types of functionally and morphologically distinct vessels. When organs differentiate and begin to perform their specific functions, the phenotypic heterogeneity of endothelial cells increases. Upon angiogenic stimulation, endothelial cells may re-enter the cell cycle, migrate, withdraw from the cell cycle and subsequently differentiate again to form new vessels that are functionally adapted to their tissue environment. Endothelial cells undergoing angiogenesis degrade the underlying basement membrane and migrate, forming capillary sprouts that project into the perivascular stroma. Ausprunk et al., *Microvasc. Rev.,* 14:51–65 (1977). Angiogenesis during tissue development and regeneration depends on the tightly controlled processes of endothelial cell proliferation, migration, differentiation, and survival. Dysfunction of the endothelial cell regulatory system is a key feature of many diseases. Most significantly, tumor growth and metastasis have been shown to be angiogenesis dependent. Folkman et al., *J. Biol. Chem.,* 267:10931–10934 (1992).

Key signals regulating cell growth and differentiation are mediated by polypeptide growth factors and their transmembrane receptors, many of which are tyrosine kinases. Autophosphorylated peptides within the tyrosine kinase insert and carboxyl-terminal sequences of activated receptors are commonly recognized by kinase substrates involved in signal transduction for the readjustment of gene expression in responding cells. Several families of receptor tyrosine kinases have been characterized. Van der Geer et al., *Ann. Rev. Cell Biol.,* 10:251–337 (1994). The major growth factors and receptors transducing angiogenic stimuli are schematically shown in FIG. 1.

Fibroblast growth factors are also known to be involved in the regulation of angiogenesis. They have been shown to be mitogenic and chemotactic for cultured endothelial cells. Fibroblast growth factors also stimulate the production of proteases, such as collagenases and plasminogen activators, and induce tube formation by endothelial cells. Saksela et al., *Ann. Rev. Cell Biol.,* 4:93–126 (1988). There are two general classes of fibroblast growth factors, FGF-1 and FGF-2, both of which lack conventional signal peptides. Both types have an affinity for heparin and FGF-2 is bound to heparin sulfate proteoglycans in the subendothelial extracellular matrix from which it may be released after injury. Heparin potentiates the stimulation of endothelial cell proliferation by angiogenic FGFs, both by protecting against denaturation and degradation and dimerizing the FGFs. Cultured endothelial cells express the FGF-1 receptor but no significant levels of other high-affinity fibroblast growth factor receptors.

Among other ligands for receptor tyrosine kinases, the platelet derived growth factor, PDGF-BB, has been shown to be weakly angiogenic in the chick chorioallantoic membrane. Risau et al., *Growth Factors,* 7:261–266 (1992). Transforming growth factor α (TGFα) is an angiogenic factor secreted by several tumor cell types and by macrophages. Hepatocyte growth factor (HGF), the ligand of the c-met proto-oncogene-encoded receptor, also is strongly angiogenic.

Recent evidence shows that there are endothelial cell specific growth factors and receptors that may be primarily responsible for the stimulation of endothelial cell growth, differentiation and certain differentiated functions. The best studied of these is vascular endothelial growth factor (VEGF), a member of the PDGF family. Vascular endothelial growth factor is a dimeric glycoprotein of disulfide-linked 23 kD subunits. Other reported effects of VEGF include the mobilization of intracellular calcium, the induction of plasminogen activator and plasminogen activator inhibitor-1 synthesis, stimulation of hexose transport in endothelial cells, and promotion of monocyte migration in vitro. Four VEGF isoforms, encoded by distinct mRNA splice variants, appear to be equally capable of stimulating mitogenesis in endothelial cells. However, each isoform has a different affinity for cell surface proteoglycans, which behave as low affinity receptors for VEGF. The 121 and 165 amino acid isoforms of VEGF (VEGF121 and VEGF165) are secreted in a soluble form, whereas the isoforms of 189 and 206 amino acid residues remain cell surface-associated and have a strong affinity for heparin. VEGF was originally purified from several sources on the basis of its mitogenic activity toward endothelial cells, and also by its ability to induce microvascular permeability, hence it is also called vascular permeability factor (VPF).

The pattern of VEGF expression suggests its involvement in the development and maintenance of the normal vascular system and in tumor angiogenesis. During murine development, the entire 7.5 day post-coital (p.c.) endoderm expresses VEGF and the ventricular neuroectoderm produces VEGF at the capillary ingrowth stage. See Breier et al., *Development,* 114:521–523 (1992). On day two of quail development, the vascularized area of the yolk sac as well as the whole embryo show expression of VEGF. In addition, epithelial cells next to fenestrated endothelia in adult mice show persistent VEGF expression, suggesting a role in the maintenance of this specific endothelial phenotype and function.

Two high affinity receptors for VEGF have been characterized. These are VEGFR-1/Flt-1 (fms-like tyrosine kinase-1) and VEGFR-2/Kdr/Flk-1 (kinase insert domain containing receptor/fetal liver kinase-1). Those receptors are classified in the PDGF-receptor family, but they have seven rather than five immunoglobulin-like loops in their extracellular domain (see FIG. 1) and they possess a longer kinase insert than normally observed in this family. The expression of VEGF receptors occurs mainly in vascular endothelial cells, although some may be present on hematopoietic progenitor cells, monocytes, and melanoma cells. Only endothelial cells have been reported to proliferate in response to VEGF, and endothelial cells from different sources show different responses. Thus, the signals mediated through VEGFR-1 and VEGFR-2 appear to be cell type specific. The VEGF-related placenta growth factor (PlGF) was recently shown to bind to VEGFR-1 with high affinity. PlGF was able to enhance the growth factor activity of VEGF, but it did not stimulate endothelial cells on its own. Naturally occurring VEGF/PlGF heterodimers were nearly as potent mitogens as VEGF homodimers for endothelial cells. Cao et al., *J. Biol. Chem.*, 271:3154–62 (1996).

The Flt4 receptor tyrosine kinase (VEGFR-3) is closely related in structure to the products of the VEGFR-1 and VEGFR-2 genes. Despite this similarity, the mature form of Flt4 differs from the VEGF receptors in that it is proteolytically cleaved in the extracellular domain into two disulfide-linked polypeptides. Pajusola et al., *Cancer Res.*, 52:5738–5743 (1992). The 4.5 and 5.8 kb Flt4 mRNAs encode polypeptides which differ in their C-termini due to the use of alternative 3' exons. Isoforms of VEGF or PlGF do not show specific binding to Flt4 or induce its autophosphorylation.

Expression of Flt4 appears to be more restricted than the expression of VEGFR-1 or VEGFR-2. The expression of Flt4 first becomes detectable by in situ hybridization in the angioblasts of head mesenchyme, the cardinal vein, and extraembryonically in the allantois of 8.5 day p.c. mouse embryos. In 12.5 day p.c. embryos, the Flt4 signal is observed in developing venous and presumptive lymphatic endothelia, but arterial endothelia appear negative. During later stages of development, Flt4 mRNA becomes restricted to developing lymphatic vessels. The lymphatic endothelia and some high endothelial venules express Flt4 mRNA in adult human tissues and increased expression occurs in lymphatic sinuses in metastatic lymph nodes and in lymphangioma. These results support the theory of the venous origin of lymphatic vessels.

Five endothelial cell specific receptor tyrosine kinases, Flt-1 (VEGFR-1), KDR/Flk-1 (VEGFR-2), Flt4 (VEGFR-3), Tie, and Tek/Tie-2 have so far been described, which possess the intrinsic tyrosine kinase activity essential for signal transduction. Targeted mutations inactivating Flt-1, Flk-1, Tie, and Tek in mouse embryos have indicated their essential and specific roles in vasculogenesis and angiogenesis at the molecular level. VEGFR-1 and VEGFR-2 bind VEGF with high affinity ($K_d$ 16 pM and 760 pM, respectively) and VEGFR-1 also binds the related placenta growth factor (PlGF; $K_d$ about 200 pM). A ligand for Tek is reported in PCT patent publication WO 96/11269.

SUMMARY OF THE INVENTION

The present invention provides a ligand, designated VEGF-C, for the Flt4 receptor tyrosine kinase (VEGFR-3). Thus, the invention provides a purified and isolated polypeptide which is capable of binding to the Flt4 receptor tyrosine kinase. Preferably, an Flt4 ligand of the invention is capable of stimulating tyrosine phosphorylation of Flt4 receptor tyrosine kinase in a host cell expressing the Flt4 receptor tyrosine kinase. Preferred ligands of the invention are mammalian polypeptides. Highly preferred ligands are human polypeptides. As explained in detail below, dimers and multimers comprising polypeptides of the invention linked to each other or to other polypeptides are specifically contemplated as ligands of the invention.

In one embodiment, an Flt4 ligand polypeptide has a molecular weight of approximately 23 kD as determined by SDS-PAGE under reducing conditions. For example, the invention includes a ligand composed of one or more polypeptides of approximately 23 kD which is purifyable from conditioned media from a PC-3 prostatic adenocarcinoma cell line, the cell line having ATCC Acc. No. CRL 1435. Amino acid sequencing of this PC-3 cell-derived ligand polypeptide revealed that the ligand polypeptide comprises an amino terminal amino acid sequence set forth in SEQ ID NO: 5. A conditioned medium comprising an Flt4 ligand is itself an aspect of the invention. The present invention also provides a new use for the PC-3 prostatic adenocarcinoma cell line which produces an Flt4 ligand. In a preferred embodiment, the ligand may be purified and isolated directly from the PC-3 cell culture medium.

In a highly preferred embodiment, the ligand polypeptide comprises a fragment of the amino acid sequence shown in SEQ ID NO: 8 which specifically binds to the human Flt4 receptor tyrosine kinase. Exemplary fragments include: a polypeptide comprising an amino acid sequence set forth in SEQ ID NO: 8 from about residue 112 to about residue 213; a polypeptide comprising an amino acid sequence from about residue 104 to about residue 227 of SEQ ID NO: 8; and a polypeptide comprising an amino acid sequence from about residue 112 to about residue 227 of SEQ ID NO: 8. Other exemplary fragments include polypeptides comprising amino acid sequences of SEQ ID NO: 8 that span, approximately, the following residues: 31-213, 31-227, 32-227, 103-217, 103-225, 104-213, 113-213, 103-227, 113-227, 131-211, 161-211, 103-225, 227-419, 228-419, 31-419, and 1-419, as described in greater detail below.

The present invention also provides one or more polypeptide precursors of an Flt4 ligand, wherein one such precursor (designated "prepro-VEGF-C") comprises the complete amino acid sequence (amino acid residues 1 to 419) shown in SEQ ID NO: 8. Thus, the invention includes a purified and isolated polypeptide having the amino acid sequence of residues 1 to 419 shown in SEQ ID NO: 8. Ligand precursors according to the invention, when expressed in an appropriate host cell, produce, via cleavage, a polypeptide which binds specifically to the Flt4 receptor tyrosine kinase. A putative 102 amino acid leader (prepro) peptide has been identified in the amino acid sequence shown in SEQ ID NO: 8. Thus, in a related aspect, the invention includes a purified and isolated polypeptide having the amino acid sequence of residues 103-419 shown in SEQ ID NO: 8.

In one embodiment, an expressed Flt4 ligand polypeptide precursor is proteolytically cleaved upon expression to produce an approximately 23 kD Flt4 ligand polypeptide. Thus, an Flt4 ligand polypeptide is provided which is the cleavage product of the precursor polypeptide shown in SEQ ID NO: 8 and which has a molecular weight of approximately 23 kD under reducing conditions.

Putative VEGF-C precursors/processing products consisting of polypeptides with molecular weights of about 29 and 32 kD also are considered aspects of the invention.

In another embodiment, an expressed Flt4 ligand polypeptide precursor is proteolytically cleaved upon expression to produce an approximately 21 kD VEGF-C polypeptide. Sequence analysis has indicated that an observed 21 kD form has an amino terminus approximately 9 amino acids downstream from the amino terminus of the 23 kD form, suggesting that alternative cleavage sites exist.

From the foregoing, it will be apparent that an aspect of the invention includes a fragment of the purified and isolated polypeptide having the amino acid sequence of residues 1 to 419 shown in SEQ ID NO: 8, the fragment being capable of specifically binding to Flt4 receptor tyrosine kinase. Preferred embodiments include fragments having an apparent molecular weight of approximately 21/23 kD and 29/32 kD as assessed by SDS-PAGE under reducing conditions. More generally, the invention includes a purified and isolated polypeptide according to claim 1 that is a VEGF-C of vertebrate origin, wherein the VEGF-C has a molecular weight of about 21–23 kD, as assessed by SDS-PAGE under reducing conditions, and wherein the VEGF-C is capable of binding to Flt4 receptor tyrosine kinase (VEGFR-3).

Evidence suggests that the amino acids essential for retaining Flt4 ligand activity are contained within approximately amino acids 103/112–226/227 of SEQ ID NO: 8, and that a carboxy-terminal proteolytic cleavage to produce a mature, naturally-occurring Flt4 ligand occurs at the approximate position of amino acids 226–227 of SEQ ID NO: 8. Accordingly, a preferred Flt4 ligand comprises approximately amino acids 103–227 of SEQ ID NO: 8.

VEGF-C mutational analysis described herein indicates that a naturally occurring VEGF-C polypeptide spanning amino acids 103–227 of SEQ ID NO: 8, produced by a natural processing cleavage that defines the C-terminus, exists and is biologically active as an Flt4 ligand. A polypeptide fragment consisting of residues 104-213 of SEQ ID NO: 8 has been shown to retain VEGF-C biological activity. Additional mutational analyses indicate that a polypeptide spanning only amino acids 113–213 of SEQ ID NO: 8 retains Flt4 ligand activity. Accordingly, preferred polypeptides comprise sequences spanning, approximately, amino acid residues 103-227, 104-213, or 113-213, of SEQ ID NO: 8.

Moreover, sequence comparisons of members of the VEGF family of polypeptides provide an indication that still smaller fragments will retain biological activity, and such smaller fragments are intended as aspects of the invention. In particular, eight highly conserved cysteine residues of the VEGF family of polypeptides define a region from residue 131 to residue 211 of SEQ ID NO: 8 (see FIGS. 10 & 32); therefore, a polypeptide spanning from about residue 131 to about residue 211 is expected to retain VEGF-C biological activity. In fact, a polypeptide comprising approximately residues 161-211, which retains an evolutionarily-conserved RCXXCC motif, is postulated to retain VEGF-C activity, and therefore is intended as an aspect of the invention.

In addition to binding Flt4, VEGF-C polypeptides are shown herein to bind and activate kdr/flk-1 receptor tyrosine kinase (VEGFR-2). Thus, the invention includes a purified and isolated polypeptide that is capable of binding to at least one of kdr receptor tyrosine kinase (VEGFR-2) and Flt4 receptor tyrosine kinase (VEGFR-3), the polypeptide comprising a portion of the amino acid sequence in SEQ ID NO: 8 effective to permit such binding. In one preferred embodiment, the portion of the amino acid sequence in SEQ ID NO: 8 is a continuous portion having as its amino terminal residue an amino acid between residues 102 and 161 of SEQ ID NO: 8 and having as its carboxy terminal residue an amino acid between residues 210 and 228 of SEQ ID NO: 8. In a highly preferred embodiment, the portion has, as its amino terminal residue, an amino acid between residues 102 and 131 of SEQ ID NO: 8. In a very highly preferred embodiment, the portion of the amino acid sequence in SEQ ID NO: 8 is a continuous portion having as its amino terminal residue an amino acid between residues 102 and 114 of SEQ ID NO: 8 and having as its carboxy terminal residue an amino acid between residues 212 and 228 of SEQ ID NO: 8. Polypeptides of the invention which bind to and activate a receptor (e.g., VEGFR-2 or VEGFR-3) are useful for stimulating VEGF-C biological activities that are mediated through the receptor. Polypeptides of the invention which bind to but do not activate a receptor are useful for inhibiting VEGF-C activities mediated through that receptor.

The definition of polypeptides of the invention is intended to include within its scope variants thereof. The polypeptide variants contemplated include purified and isolated polypeptides having amino acid sequences that differ from the exact amino acid sequences of such polypeptides (e.g., VEGF-C, VEGF-C precursors and VEGF-C fragments) by conservative substitutions, as recognized by those of skill in the art, that are compatible with the retention of at least one VEGF-C biological activity or VEGF-C-inhibitory activity of the polypeptide. The term "variants," when used to refer to polypeptides, also is intended to include polypeptides having amino acid additions, including but not limited to additions of a methionine and/or leader sequence to promote translation and/or secretion; additions of peptide sequences to facilitate purification (e.g., polyhistidine sequences and/or epitopes for antibody purification); and additions of polypeptide-encoding sequences to produce fusion proteins with VEGF-C. The term "variants" also is intended to include polypeptides having amino acid deletions at the amino terminus, the carboxy terminus, or internally of amino acids that are non-conserved amongst the human, mouse, and quail VEGF-C sequences taught herein, and that are compatible with the retention of the VEGF-C or VEGF-C-inhibitory activity of the polypeptide to which the deletions have been made.

The term "variant" also is intended to include polypeptides having modifications to one or more amino acid residues that are compatible with retaining VEGF-C or VEGF-C inhibitory activity of the polypeptide. Such modifications include glycosylations (identical or different to glycosylations of native VEGF-C); and the addition of other substituents (e.g., labels, compounds to increase serum half-life (e.g., polyethylene glycol), and the like.

Additional polypeptides of the invention include certain fragments that have been observed to result from the processing of prepro-VEGF-C into mature VEGF-C. For example, the invention includes a purified and isolated polypeptide having a molecular weight of about 29 kD as assessed by SDS-PAGE under reducing conditions and having an amino acid sequence consisting essentially of a portion of SEQ ID NO: 8 having residue 228 of SEQ ID NO: 8 as its amino terminal amino acid residue; and a purified and isolated polypeptide having a molecular weight of about 15 kD as assessed by SDS-PAGE under reducing conditions and having an amino acid sequence consisting essentially of a portion of SEQ ID NO: 8 having residue 32 of SEQ ID NO: 8 as its amino terminal amino acid residue. Such polypeptides are expected to modulate VEGF-C biological activity through their interactions with VEGF-C receptors and/or interactions with biologically active VEGF-C.

Some of the conserved cysteine residues in VEGF-C participate in interchain disulfide bonding to make homo- and heterodimers of the various naturally occurring VEGF-C polypeptides. Beyond the preceding considerations, evidence exists that VEGF-C polypeptides lacking interchain disulfide bonds retain VEGF-C biological activity. Consequently, the materials and methods of the invention include all VEGF-C fragments that retain at least one biological activity of VEGF-C, regardless of the presence or absence of interchain disulfide bonds. The invention also includes multimers (including dimers) comprising such fragments linked to each other or to other polypeptides. Fragment linkage may be by way of covalent bonding (e.g., disulfide bonding) or non-covalent bonding of polypeptide chains (e.g, hydrogen bonding, bonding due to stable or induced dipole-dipole interactions, bonding due to hydrophobic or hydrophilic interactions, combinations of these bonding mechanisms, and the like). Thus, the invention includes a purified and isolated polypeptide multimer, wherein at least one monomer thereof is a polypeptide that is capable of binding to VEGFR-2 and/or VEGFR-3, the polypeptide comprising a portion of the amino acid sequence in SEQ ID NO: 8 effective to permit such binding, and wherein the multimer itself is capable of binding to VEGFR-2 and/or VEGFR-3. In a preferred embodiment, the multimer has at least one VEGF-C biological activity as taught herein.

In one embodiment, at least one monomer of the multimer is a polypeptide from another member of the PDGF/VEGF family of proteins, e.g., a vascular endothelial growth factor (VEGF) polypeptide, a vascular endothelial growth factor B (VEGF-B) polypeptide, a platelet derived growth factor A (PDGF-A) polypeptide, a platelet derived growth factor B (PDGF-B) polypeptide, a c-fos induced growth factor (FIGF) polypeptide, or a placental growth factor (PlGF) polypeptide.

In a highly preferred embodiment, the multimer of the invention is a dimer of two monomer polypeptides. For example, the invention includes a dimer wherein each monomer thereof is capable of binding to at least one of VEGFR-2 and VEGFR-3 and has an amino acid sequence comprising a portion of SEQ ID NO: 8 effective to permit such binding. Dimers having covalent attachments and dimers wherein the two monomers are free of covalent attachments to each other are contemplated.

In yet another aspect, the invention includes analogs of the polypeptides of the invention. The term "analog" refers to polypeptides having alterations involving one or more amino acid insertions, internal amino acid deletions, and/or non-conservative amino acid substitutions (replacements). The definition of analog is intended to include within its scope variants of analog polypeptides embodying such alterations. The term "mutant," when used with respect to polypeptides herein, is intended to refer generically to VEGF-C variants, VEGF-C analogs, and variants of VEGF-C analogs.

For example, in one embodiment, the invention includes a polypeptide analog of a VEGF-C of vertebrate origin that is capable of binding to VEGFR-3 (e.g., an analog of a vertebrate VEGF-C of about 21–23 kD as assessed by SDS-PAGE under reducing conditions), wherein an evolutionarily conserved cysteine residue in the VEGF-C has been deleted or replaced, and wherein the analog is capable of binding to VEGFR-3 and has reduced VEGFR-2 binding affinity relative to the wildtype VEGF-C. For analogs according to this embodiment of the invention, the determination that a residue is "evolutionarily conserved" is made solely by reference to the alignment of human, mouse, and quail VEGF-C sequences provided herein and aligned to show similarity in FIG. 5. The presence of the same residue in all three sequences indicates that the residue is evolutionarily conserved, notwithstanding the fact that VEGF-C from other species may lack the residue. In a preferred embodiment, the conserved cysteine residue corresponds to the cysteine at position 156 of SEQ ID NO: 8. "Correspondence to the cysteine at position 156" is readily determined from an analysis of the vertebrate VEGF-C sequence of interest, since the cysteine at position 156 of SEQ ID NO: 8 (human VEGF-C) falls within an evolutionarily conserved portion of VEGF-C (see FIG. 5, comparing human, mouse, and quail VEGF-C polypeptides). Alignment of human VEGF-C allelic variants, other mammalian VEGF-C polypeptides, and the like with the three VEGF-C forms in FIG. 5 will identify that cysteine which corresponds to the cysteine at position 156 of SEQ ID NO: 8, even if the allelic variant has greater or fewer than exactly 155 residues preceding the cysteine of interest.

In another embodiment, the invention includes a purified polypeptide that is an analog of human VEGF-C and that is capable of binding to at least one of flt-1 receptor tyrosine kinase (VEGFR-1), kdr receptor tyrosine kinase (VEGFR-2), and Flt4 receptor tyrosine kinase (VEGFR-3).

Specifically contemplated is an analog of human VEGF-C that binds VEGFR-3 but has reduced VEGFR-2 binding affinity, as compared to the VEGFR-2 binding affinity of a wildtype human VEGF-C (e.g., as compared to the VEGFR-2 binding affinity of a human VEGF-C having an amino acid sequence consisting essentially of amino acids 103–227 of SEQ ID NO: 8). One such family of human VEGF-C analogs are VEGF-C $\Delta_{156}$ polypeptides. By "VEGF-C $\Delta C_{156}$ polypeptide" is meant an analog wherein the cysteine at position 156 of SEQ ID NO: 8 has been deleted or replaced by another amino acid. A VEGF-C $\Delta C_{156}$ polypeptide analog can be made from any VEGF-C polypeptide of the invention that comprises all of SEQ ID NO: 8 or a portion thereof that includes position 156 of SEQ ID NO: 8. Preferably, the VEGF-C $\Delta C_{156}$ polypeptide analog comprises a portion of SEQ ID NO: 8 effective to permit binding to VEGFR-3.

For example, the invention includes a VEGF-C $\Delta C_{156}$ polypeptide that binds VEGFR-3, has reduced VEGFR-2 binding affinity, and has an amino acid sequence which includes amino acids 131 to 211 of SEQ ID NO: 8, wherein the cysteine residue at position 156 of SEQ ID NO: 8 has been deleted or replaced. In a preferred embodiment, the VEGF-C $\Delta C_{156}$ polypeptide comprises a continuous portion of SEQ ID NO: 8, the portion having as its amino terminal residue an amino acid between residues 102 and 114 of SEQ ID NO: 8, and having as its carboxy terminal residue an amino acid between residues 212 and 228 of SEQ ID NO: 8, wherein the cysteine residue at position 156 of SEQ ID NO: 8 has been deleted or replaced. In an embodiment exemplified herein, the cysteine residue at position 156 of SEQ ID NO: 8 has been replaced by a serine residue.

A second family of human VEGF-C analogs that bind VEGFR-3 but have reduced VEGFR-2 binding affinity are VEGF-C $\Delta R_{226} \Delta R_{227}$ polypeptides. By "VEGF-C $\Delta R_{226} \Delta R_{227}$ polypeptide" is meant an analog wherein the arginine residues at positions 226 and 227 of SEQ ID NO: 8 have been deleted or replaced by other amino acids, for the purpose of eliminating a proteolytic processing site of the carboxy terminal pro-peptide of VEGF-C. Preferably, the VEGF-C $\Delta R_{226} \Delta R_{227}$ polypeptide comprises a portion of SEQ ID NO: 8 effective to permit binding of VEGFR-3. For example, the invention includes a VEGF-C $\Delta R_{226} \Delta R_{227}$ polypeptide having an amino acid sequence comprising amino acids 112–419 of SEQ ID NO: 8, wherein the arginine residues at positions 226 and 227 of SEQ ID NO: 8 have been deleted or replaced. Specifically exemplified herein is a VEGF-C $\Delta R_{226} \Delta R_{227}$ polypeptide wherein the arginine residues at positions 226 and 227 of SEQ ID NO: 8 have been replaced by serine residues.

Another family of VEGF-C analogs of the invention are human VEGF-C$^{basic}$ polypeptides. By "VEGF-C$^{basic}$ polypeptide" is meant a VEGF-C analog wherein at least one amino acid having a basic side chain has been introduced into the VEGF-C coding sequence, to emulate one or more basic residues in VEGF (e.g., residues $Arg_{108}$, $Lys_{110}$, and $His_{112}$ in the VEGF165 precursor shown in FIG. 2.) that have been implicated in VEGF receptor binding. Preferably, two or three basic residues are introduced into VEGF-C. Based on the VEGF/VEGF-C polypeptide alignment provided herein, positions 187, 189, and 191 of SEQ ID NO: 8 are preferred positions to introduce basic residues. For example, the invention includes a VEGF-C$^{basic}$ polypeptide that is capable of binding to at least one of VEGFR-1, VEGFR-2, and VEGFR-3, and that has an amino acid sequence comprising residues 131 to 211 of SEQ ID NO: 8, wherein the glutamic acid residue at position 187, the threonine residue at position 189, and the proline residue at position 191 of SEQ ID NO: 8 have been replaced by an arginine residue, a lysine residue, and a histidine residue, respectively.

In yet another aspect of the invention, VEGF-C structural information is employed to create useful analogs of VEGF. For example, mature VEGF-C contains an unpaired cysteine (position 137 of SEQ ID NO: 8) and is able to form non-covalently bonded polypeptide dimers. In one embodiment, a VEGF analog is created wherein this unpaired cysteine residue from mature VEGF-C is introduced at an analogous position of VEGF (e.g., introduced in place of Leu$_{58}$ of the human VEGF165 precursor (FIG. 2, Genbank Acc. No. M32977). Such VEGF analogs are termed VEGF$^{+cys}$ polypeptides. Thus, the invention includes a human VEGF analog wherein a cysteine residue is introduced in the VEGF amino acid sequence at a position selected from residues 53 to 63 of the human VEGF165 precursor having the amino acid sequence set forth in SEQ ID NO: 56. At least four naturally occurring VEGF isoforms have been described, and VEGF$^{+cys}$ polypeptide analogs of each isoform are contemplated. Most preferably, the cysteine is introduced at a position in a VEGF isoform which corresponds to position 58 of the VEGF165 precursor having the amino acid sequence set forth in SEQ ID NO: 56.

The present invention also provides purified and isolated polynucleotides (i.e., nucleic acids) encoding all of the polypeptides of the invention, including but not limited to cDNAs and genomic DNAs encoding VEGF-C precursors, VEGF-C, and biologically active fragments thereof, and DNAs encoding VEGF-C variants and VEGF-C analogs. A preferred nucleic acid of the invention comprises a DNA encoding amino acid residues 1 to 419 of SEQ ID NO: 8 or one of the aforementioned fragments or analogs thereof. Due to the degeneracy of the genetic code, numerous such coding sequences are possible, each having in common the coding of the amino acid sequence shown in SEQ ID NO: 8 or the fragment or analog thereof. Distinct polynucleotides encoding any polypeptide of the invention by virtue of the degeneracy of the genetic code are within the scope of the invention.

A preferred polynucleotide according to the invention comprises the human VEGF-C cDNA sequence set forth in SEQ ID NO: 7 from nucleotide 352 to 1611. Other polynucleotides according to the invention encode a VEGF-C polypeptide from, e.g., mammals other than humans, birds (e.g., avian quails), and others. Still other polynucleotides of the invention comprise a coding sequence for a VEGF-C fragment, and allelic variants of those DNAs encoding part or all of VEGF-C. Still other polynucleotides of the invention comprise a coding sequence for a VEGF-C variant or a VEGF-C analog.

The invention further comprises polynucleotides that hybridize to the aforementioned polynucleotides under standard stringent hybridization conditions. Exemplary stringent hybridization conditions are as follows: hybridization at 42° C. in 50% formamide, 5×SSC, 20 mM Na.PO$_4$, pH 6.8 and washing in 0.2×SSC at 55° C. It is understood by those of skill in the art that variation in these conditions occurs based on the length and GC nucleotide content of the sequences to be hybridized. Formulas standard in the art are appropriate for determining appropriate hybridization conditions. See Sambrook et al., *Molecular Cloning: A Laboratory Manual* (Second ed., Cold Spring Harbor Laboratory Press, 1989) §§ 9.47–9.51. These polynucleotides, capable of hybridizing to polynucleotides encoding VEGF-C, VEGF-C fragments, or VEGF-C analogs, are useful as nucleic acid probes for identifying, purifying and isolating polynucleotides encoding other (non-human) mammalian forms of VEGF-C and human VEGF-C allelic variants. Additionally, these polynucleotides are useful in screening methods of the invention, as described below.

Preferred nucleic acids useful as probes of the invention comprise nucleic acid sequences of at least about 16 continuous nucleotides of SEQ ID NO: 7. More preferably, these nucleic acid probes would have at least about 20 continuous nucleotides found in SEQ ID NO: 7. In using these nucleic acids as probes, it is preferred that the nucleic acids specifically hybridize to a portion of the sequence set forth in SEQ ID NO: 7. Specific hybridization is herein defined as hybridization under standard stringent hybridization conditions. To identify and isolate other mammalian VEGF-C genes specifically, nucleic acid probes preferably are selected such that they fail to hybridize to genes related to VEGF-C (e.g., fail to hybridize to human VEGF or to human VEGF-B genes).

Thus, the invention comprehends polynucleotides comprising at least about 16 nucleotides wherein the polynucleotides are capable of specifically hybridizing to a gene encoding VEGF-C, e.g., a human gene. The specificity of hybridization ensures that a polynucleotide of the invention is able to hybridize to a nucleic acid encoding a VEGF-C under hybridization conditions that do not support hybridization of the polynucleotide to nucleic acids encoding, e.g., VEGF or VEGF-B. In one embodiment, polynucleotides of at least about 16 nucleotides, and preferably at least about 20 nucleotides, are selected as continuous nucleotide sequences found in SEQ ID NO: 7 or the complement of the nucleotide sequence set forth in SEQ ID NO: 7.

In another embodiment, the invention includes polynucleotides having at least 90 percent (preferably at least 95 percent, and more preferably at least 97, 98, or 99 percent) nucleotide sequence identity with a nucleotide sequence encoding a polypeptide of the invention. In a highly preferred embodiment, the polynucleotides have at least 95 percent sequence identity with a nucleotide sequence encoding a human VEGF-C precursor (such as the VEGF-C precursor in SEQ ID NO: 8 and allelic variants thereof), human VEGF-C, or biologically active VEGF-C fragments.

Additional aspects of the invention include vectors which comprise nucleic acids of the invention; and host cells transformed or transfected with nucleic acids or vectors of the invention. Preferred vectors of the invention are expression vectors wherein nucleic acids of the invention are operatively connected to appropriate promoters and other control sequences that regulate transcription and/or subsequent translation, such that appropriate prokaryotic or eukaryotic host cells transformed or transfected with the vectors are capable of expressing the polypeptide encoded thereby (e.g., the VEGF-C, VEGF-C fragment, VEGF-C variant, or VEGF-C analog encoded thereby). A preferred vector of the invention is plasmid pFLT4-L, having ATCC accession no. 97231. Such vectors and host cells are useful for recombinantly producing polypeptides of the invention, including VEGF-C, and fragments, variants, and analogs thereof.

In a related aspect of the invention, host cells such as procaryotic and eukaryotic cells, especially unicellular host cells, are modified to express polypeptides of the invention. Host cells may be stably transformed or transfected with isolated DNAs of the invention in a manner allowing expression of polypeptides of the invention therein. Thus, the invention further includes a method of making polypeptides of the invention. In a preferred method, a nucleic acid or vector of the invention is expressed in a host cell, and a polypeptide of the invention is purified from the host cell or the host cell's growth medium.

Similarly, the invention includes a method of making a polypeptide capable of specifically binding to VEGFR-1, VEGFR-2 and/or VEGFR-3, comprising the steps of: (a) transforming or transfecting a host cell with a nucleic acid of the invention; (b) cultivating the host cell to express the nucleic acid; and (c) purifying a polypeptide capable of specifically binding to VEGFR-1, VEGFR-2, and/or VEGFR-3 from the host cell or from the host cell's growth media. The invention also includes purified and isolated polypeptides produced by methods of the invention. In one preferred embodiment, the invention includes a human VEGF-C polypeptide or biologically active fragment, variant, or analog thereof that is substantially free of other human polypeptides.

Alternatively, host cells may be modified by activating an endogenous VEGF-C gene that is not normally expressed in the host cells or that is expressed at a lower rate than is desired. Such host cells are modified (e.g., by homologous recombination) to express the VEGF-C by replacing, in whole or in part, the naturally-occurring VEGF-C promoter with part or all of a heterologous promoter so that the host cells express VEGF-C. In such host cells, the heterologous promoter DNA is operatively linked to the VEGF-C coding sequences, i.e., controls transcription of the VEGF-C coding sequences. See, for example, PCT International Publication No. WO 94/12650; PCT International Publication No. WO 92/20808; and PCT International Publication No. WO 91/09955. The invention also contemplates that, in addition to heterologous promoter DNA, amplifiable marker DNA (e.g., ada, dhfr, and the multifunctional CAD gene which encodes carbamyl phosphate synthase, aspartate transcarbamylase, and dihydro-orotase) and/or intron DNA may be recombined along with the heterologous promoter DNA into the host cells. If linked to the VEGF-C coding sequences, amplification of the marker DNA by standard selection methods results in co-amplification of the VEGF-C coding sequences in such host cells. Thus, the invention includes, for example, a cell comprising a nucleic acid having a sequence encoding human VEGF-C and further comprising a non-VEGF-C promoter sequence (i.e., a heterologous promoter sequence) or other non-VEGF-C control sequence that increases RNA transcription in the cell of the sequence encoding human VEGF-C.

The DNA sequence information provided by the present invention also makes possible the development, by homologous recombination or "knockout" strategies [see, Capecchi, Science, 244: 1288–1292 (1989)], of rodents that fail to express functional VEGF-C or that express a VEGF-C fragment, variant, or analog. Such rodents are useful as models for studying the activities of VEGF-C and VEGF-C modulators in vivo.

In another aspect, the invention includes an antibody which is specifically reactive with one or more polypeptides of the invention, and/or is reactive with polypeptide multimers of the invention. Antibodies, both monoclonal and polyclonal, may be made against a polypeptide of the invention according to standard techniques in the art. See, e.g., Harlow and Lane, *Antibodies: A Laboratory Manual* (Cold Spring Harbor Laboratory Press, Cold Spring Harbor, N.Y. (1988)). Standard protein manipulation techniques and recombinant techniques also may be employed to generate humanized antibodies and antigen-binding antibody fragments and other chimeric antibody polypeptides, all of which are considered antibodies of the invention. The invention further includes hybridoma cells that produce antibodies of the invention or other cell types that have been genetically engineered to express antibody polypeptides of the invention. Antibodies of the invention may be used in diagnostic applications to monitor angiogenesis, vascularization, lymphatic vessels and their disease states, wound healing, or certain tumor cells, hematopoietic, or leukemia cells. The antibodies also may be used to block the ligand from activating its receptors; to purify polypeptides of the invention; and to assay fluids for the presence of polypeptides of the invention. The invention further includes immunological assays (including radio-immuno assays, enzyme linked immunosorbent assays, sandwich assays and the like) which employ antibodies of the invention.

Ligands according to the invention may be labeled with a detectable label and used to identify their corresponding receptors in situ. Labeled Flt4 ligand and anti-Flt4 ligand antibodies may be used as imaging agents in the detection of lymphatic vessels, high endothelial venules and their disease states, and Flt4 receptors expressed in histochemical tissue sections. The ligand or antibody may be covalently or non-covalently coupled to a suitable supermagnetic, paramagnetic, electron dense, echogenic, or radioactive agent for imaging. Other, non-radioactive labels, such as biotin and avidin, may also be used.

A related aspect of the invention is a method for the detection of specific cells, e.g., endothelial cells. These cells may be found in vivo, or in ex vivo biological tissue samples. The method of detection comprises the steps of contacting a biological tissue comprising, e.g., endothelial cells, with a polypeptide according to the invention which is capable of binding to VEGFR-2 and/or VEGFR-3, under conditions wherein the polypeptide binds to the cells, optionally washing the biological tissue, and detecting the polypeptide bound to the cells in the biological tissue, thereby detecting the cells. It will be apparent that certain polypeptides of the invention are useful for detecting and/or imaging cells that express both VEGFR-2 and VEGFR-3, whereas other polypeptides (e.g., VEGF-C $\Delta C_{156}$ polypeptides) are useful for imaging specifically those cells which express VEGFR-3.

The many biological activities described herein for VEGF-C (including but not limited to affecting growth and migration of vascular endothelial cells; promoting growth of lymphatic endothelial cells and lymphatic vessels; increasing vascular permeability; and affecting myelopoiesis (e.g., growth of neutrophilic granulocytes)) support numerous diagnostic and in vitro and in vivo clinical utilities for polypeptides and antibodies of the invention, for modulating (stimulating or inhibiting) these biological activities. Generally, VEGF-C and precursor, fragment, variant, and analog polypeptides that retain one or more VEGF-C biological activities are useful agonists for stimulating the desired biological activity; whereas precursor, fragment, variant, and analog polypeptides that are capable of binding to VEGFR-2 and/or VEGFR-3 (either alone or as a homo- or hetero-dimer with other polypeptides) without stimulating receptor-mediated VEGF-C activity (i.e., without activating the receptor) are useful as antagonists (inhibitors) of VEGF-C. Similarly, antibodies of the invention that bind biologically active VEGF-C forms and thereby interfere with VEGF-C-receptor interactions are useful as inhibitors of VEGF-C. Antisense oligonucleotides comprising a portion of the VEGF-C coding sequence and/or its complement also are contemplated as inhibitors of the invention. Both biologically active polypeptides and inhibitor polypeptides of the invention have utilities in various imaging applications.

For example, the biological effects of VEGF-C on vascular endothelial cells indicate in vivo uses for polypeptides of the invention for stimulating angiogenesis (e.g., during wound healing, in tissue transplantation, in eye diseases, in the formation of collateral vessels around arterial stenoses and into injured tissues after infarction) and for inhibiting angiogenesis (e.g., to inhibit tumor growth and/or metastatic cancer). The biological effects on vascular endothelial cells indicate in vitro uses for biologically active forms of VEGF-C to promote the growth of cultured vascular endothelial cells.

The biological effects of VEGF-C on lymphatic endothelia indicate in vivo uses for polypeptides of the invention for stimulating lymphangiogenesis (e.g., to promote re-growth or permeability of lymphatic vessels in, for example, organ transplant patients; to mitigate the loss of axillary lymphatic vessels following surgical interventions in the treatment of cancer (e.g., breast cancer); to treat aplasia of the lymphatic vessels or lymphatic obstructions) and for inhibiting it (e.g., to treat lymphangiomas). Additional in vivo uses for polypeptides of the invention include the treatment or prevention of inflammation, edema, elephantiasis, and Milroy's disease. The biological effects on lymphatic endothelial cells indicate in vitro uses for biologically active forms of VEGF-C to promote the growth of cultured lymphatic endothelial cells.

Thus, the invention includes a method of modulating (stimulating/increasing or inhibiting/decreasing) the growth of vertebrate endothelial cells comprising contacting such endothelial cells with a polypeptide or antibody (or antigen-binding portion thereof) of the invention, in an amount effective to modulate the growth of the endothelial cells. Mammalian endothelial cells are preferred. Human endothelial cells are highly preferred. In one embodiment, the endothelial cells are lymphatic endothelial cells. In another embodiment, the cells are vascular endothelial cells. The method may be an in vitro method (e.g., for cultured endothelial cells) or an in vivo method. For in vivo methods, it is highly preferable to administer a pharmaceutical composition (comprising the polypeptide formulated in a pharmaceutically acceptable diluent, adjuvant, excipient, carrier, or the like) to the subject, in an amount effective to modulate the growth of lymphatic endothelial cells in vivo.

In one preferred embodiment, the endothelial cells are lymphatic endothelial cells, and the polypeptide is one that has reduced effect on the permeability of mammalian blood vessels compared to a wildtype VEGF-C polypeptide (e.g., compared with VEGF-C having an amino acid sequence set forth in SEQ ID NO: 8 from residue 103 to residue 227). VEGF-C $\Delta C_{156}$ polypeptides are contemplated for use in this embodiment.

In modulating the growth of endothelial cells in vivo, the invention contemplates the modulation of endothelial cell-related disorders. Endothelial cell disorders contemplated by the invention include, but are not limited to, physical loss of lymphatic vessels (e.g., surgical removal of axillary lymph tissue), lymphatic vessel occlusion (e.g., elephantiasis), and lymphangiomas. In a preferred embodiment, the subject, and endothelial cells, are human. The endothelial cells may be provided in vitro or in vivo, and they may be contained in a tissue graft. An effective amount of a polypeptide is defined herein as that amount of polypeptide empirically determined to be necessary to achieve a reproducible change in cell growth rate (as determined by microscopic or macroscopic visualization and estimation of cell doubling time, or nucleic acid synthesis assays), as would be understood by one of ordinary skill in the art.

Polypeptides of the invention may be used to stimulate lymphocyte production and maturation, and to promote or inhibit trafficking of leukocytes between tissues and lymphatic vessels or to affect migration in and out of the thymus.

The biological effects of VEGF-C on myelopoiesis indicate in vivo and in vitro uses for polypeptides of the invention for stimulating myelopoiesis (especially growth of neutrophilic granuloctyes) or inhibiting it. Thus, the invention includes a method for modulating myelopoiesis in a mammalian subject comprising administering to a mammalian subject in need of modulation of myelopoiesis an amount of a polypeptide or antibody (or antigen-binding portion thereof) of the invention that is effective to modulate myelopoiesis. In one embodiment, a mammalian subject suffering from granulocytopenia is selected, and the method comprises administering to the subject an amount of a polypeptide effective to stimulate myelopoiesis. In particular, a polypeptide of the invention is administered in an amount effective to increase the neutrophil count in blood of the subject. Preferred subjects are human subjects. An effective amount of a polypeptide is an amount of polypeptide empirically determined to be necessary to achieve a reproducible change in the production of neutrophilic granulocytes (as determined by microscopic or macroscopic visualization and estimation of cell doubling time, or nucleic acid synthesis assays), as would be understood by one of ordinary skill in the art.

In a related embodiment, the invention includes a method of increasing the number of neutrophils in the blood of a mammalian subject comprising the step of expressing in a cell in a subject in need of an increased number of blood neutrophils a DNA encoding a VEGF-C protein, the DNA operatively linked to a non-VEGF-C promoter or other non-VEGF-C control sequence that promotes expression of the DNA in the cell.

Similarly, the invention includes a method of modulating the growth of neutrophilic granulocytes in vitro or in vivo comprising the step of contacting mammalian stem cells with a polypeptide or antibody of the invention in an amount effective to modulate the growth of mammalian endothelial cells.

For methods which involve the in vivo administration of polypeptides or antibodies of the invention, it is contemplated that the polypeptides or antibodies will be administered in any suitable manner using an appropriate pharmaceutically-acceptable vehicle, e.g., a pharmaceutically-acceptable diluent, adjuvant, excipient or carrier. Thus, the invention further includes compositions, e.g., pharmaceutical compositions, comprising one or more polypeptides or antibodies of the invention. By pharmaceutical composition is meant a composition that may be administered to a mammalian host, e.g., orally, topically, parenterally (including subcutaneous injections, intravenous, intramuscular, intracisternal injection or infusion techniques), by inhalation spray, or rectally, in unit dosage formulations containing conventional non-toxic carriers, diluents (e.g., calcium carbonate, sodium carbonate, lactose, calcium phosphate, sodium phosphate, kaolin, water), adjuvants, vehicles, and the like, including but not limited to flavoring agents, preserving agents; granulating and disintegrating agents; binding agents; time delay materials; oils; suspending agents; dispersing or wetting agents; anti-oxidants; emulsifiers, etc.

The invention further provides a method of using a polypeptide of the invention for the manufacture of a medicament for use in any of the foregoing methods. Similarly, the invention further provides a method of using a polypeptide of the invention for the manufacture of a medicament for the treatment of any of the foregoing indicated conditions and disease states. Such methods optionally involve the use of additional biologically active ingredients (e.g., VEGF, PlGF, G-CSF, etc.) for the manufacture of the medicament.

Effective amounts of polypeptides for the foregoing methods are empirically determined using standard in vitro and in vivo dose-response assays. In addition, experimental data provided herein provide guidance as to amounts of polypeptides of the invention that are effective for achieving a desired biological response. For example, the dissociation constants determined for one form of mature VEGF-C ($K_D$=135 pM for VEGFR-3 and $K_D$=410 pM for VEGFR-2) provide an indication as to the concentration of VEGF-C necessary to achieve biological effects, because such dissociation constants represent concentrations at which half of the VEGF-C polypeptide is bound to the receptors through which VEGF-C biological effects are mediated. Results from in vivo Miles assays, wherein 0–8 picomoles of VEGF-C was injected intradermally, provide an indication that picomole quantities of mature VEGF-C are sufficient to induce localized biological effects. In vitro analysis of $^3$H-thymidine incorporation into bovine capillary endothelial cells treated with a mature VEGF-C form showed increasing VEGF-C effects on cell proliferation at concentrations of 10–1000 pM. Collectively, this data suggests that localized concentrations of 100–1000 pM of fully-processed VEGF-C have VEGF-C biological activity in vivo. Effective concentrations of other polypeptides of the invention are generally expected to correlate with the dissociation constant of the polypeptides for the relevant receptors. Pharmacokinetic and pharmacological analyses reveals the preferred dosages, dosage formulations, and methods of administration to achieve the desired local or systemic concentration of a polypeptide of the invention.

Polypeptides of the invention also may be used to quantify future metastatic risk by assaying biopsy material for the presence of active receptors or ligands in a binding assay. Such a binding assay may involve the use of a detectably labeled polypeptide of the invention or of an unlabeled polypeptide in conjunction with a labeled antibody, for example. Kits comprising such substances are included within the scope of the invention.

The present invention also provides methods for using the claimed nucleic acids (i.e., polynucleotides) in screening for endothelial cell disorders. In a preferred embodiment, the invention provides a method for screening an endothelial cell disorder in a mammalian subject comprising the steps of providing a sample of endothelial cell nucleic acids from the subject, contacting the sample of endothelial cell nucleic acids with a polynucleotide of the invention which is capable of hybridizing to a gene encoding VEGF-C (and preferably capable of hybridizing to VEGF-C mRNA), determining the level of hybridization between the endothelial cell nucleic acids and the polynucleotide, and correlating the level of hybridization with a disorder. A preferred mammalian subject, and source of endothelial cell nucleic acids, is a human. The disorders contemplated by the method of screening with polynucleotides include, but are not limited to, vessel disorders such as the aforementioned lymphatic vessel disorders, and hypoxia.

Purified and isolated polynucleotides encoding other (non-human) VEGF-C forms also are aspects of the invention, as are the polypeptides encoded thereby, and antibodies that are specifically immunoreactive with the non-human VEGF-C forms. Preferred non-human forms of VEGF-C are forms derived from other vertebrate species, including avian and mammalian species. Mammalian forms are highly preferred. Thus, the invention includes a purified and isolated mammalian VEGF-C polypeptide, and also a purified and isolated polynucleotide encoding such a polypeptide.

In one embodiment, the invention includes a purified and isolated polypeptide having the amino acid sequence of residues 1 to 415 of SEQ ID NO: 11, which sequence corresponds to a putative mouse VEGF-C precursor. The putative mouse VEGF-C precursor is believed to be processed into a mature mouse VEGF-C in a manner analogous to the processing of the human prepro-polypeptide. Thus, in a related aspect, the invention includes a purified and isolated polypeptide capable of specifically binding to an Flt4 receptor tyrosine kinase (e.g., a human or mouse Flt-4 receptor tyrosine kinase), the polypeptide comprising a fragment of the purified and isolated polypeptide having the amino acid sequence of residues 1 to 415 of SEQ ID NO: 11, the fragment being capable of specifically binding to the Flt4 receptor tyrosine kinase. The invention further includes multimers of the foregoing polypeptides and purified and isolated nucleic acids encoding the foregoing polypeptides, such as a nucleic acid comprising all or a portion of the sequence shown in SEQ ID NO: 10.

In another embodiment, the invention includes a purified and isolated quail VEGF-C polypeptide, biologically active fragments and multimers thereof, and polynucleotides encoding the foregoing polypeptides.

It is also contemplated that VEGF-C polypeptides from other species may be altered in the manner described herein with respect to human VEGF-C variants, in order to alter biological properties of the wildtype protein. For example, elimination of the cysteine at position 152 of SEQ ID NO: 11 or position 155 of SEQ ID NO: 13 is expected to alter VEGFR-2 binding properties in the manner described below for human VEGF-C $\Delta C_{156}$ mutants.

In yet another embodiment, the invention includes a DNA comprising a VEGF-C promoter, that is capable of promoting expression of a VEGF-C gene or another operatively-linked, protein-encoding gene in native host cells, under conditions wherein VEGF-C is expressed in such cells. Thus, the invention includes a purified nucleic acid comprising a VEGF-C promoter sequence. Genomic clone lambda 5 described herein comprises more than 5 kb of human genomic DNA upstream of the VEGF-C translation initiation codon, and contains promoter DNA of the invention. Approximately 2.4 kb of this upstream sequence is set forth in SEQ ID NO: 48. Thus, in one embodiment, the invention includes a purified nucleic acid comprising a portion of SEQ ID NO: 48, wherein the portion is capable of promoting expression of a protein encoding gene operatively linked thereto under conditions wherein VEGF-C is expressed in native host cells. Similarly, the invention includes a chimeric nucleic acid comprising a VEGF-C promoter nucleic acid according to the invention operatively connected to a sequence encoding a protein other than a human VEGF-C.

Additional aspects and embodiments of the invention will be apparent from the detailed description which follows.

BRIEF DESCRIPTION OF THE DRAWINGS

FIGS. 2A, 2B, and 2C show a comparison of the deduced amino acid sequences of PDGF-A (SEQ ID NO: 53), PDGF-B (SEQ ID NO: 54), PlGF-1 (SEQ ID NO: 55), VEGF-B$_{167}$ (SEQ ID NO: 56), VEGF165 (SEQ ID NO: 57), and Flt4 ligand (VEGF-C, (SEQ ID NO: 8)).

FIG. 5 depicts the amino acid sequences of human (SEQ ID NO: 8), murine (SEQ ID NO: 11), and quail (SEQ ID NO: 13) VEGF-C polypeptides, aligned to show similarity. Residues conserved in all three species are depicted in bold.

FIGS. 6A–C depict electrophoretic fractionations of the various forms of recombinant VEGF-C produced by transfected 293 EBNA cells. FIG. 6B depicts the electrophoretic fractionation, under non-reducing conditions, of polypeptides produced from mock (M) transfected cells, cells transfected with wild type (wt) VEGF-C cDNA, and cells transfected with a cDNA encoding the VEGF-C mutant VEGF-C-R102S. Each of the bands identified in FIG. 6B was excised and electrophoretically fractionated in a separate lane under reducing conditions. Fractionation of bands corresponding to wt VEGF-C are depicted in FIG. 6A; fractionation of bands corresponding to the R102S mutant are depicted in FIG. 6C.

FIGS. 7A–B depict the forms and sizes of wild type and mutant recombinant VEGF-Cs, as revealed by non-reducing gel electrophoresis. FIG. 7A shows the VEGF-C forms secreted into the media; FIG. 7B shows the VEGF-C forms retained by the cells. Mock (M) transfected cells served as a control.

FIG. 10 presents a comparison of the human and mouse VEGF-C amino acid sequences. The amino acid sequence of mouse VEGF-C is presented on the top line and differences in the human sequence are marked below it. An arrow indicates the putative cleavage site for the signal peptidase; BR3P motifs, as well as a CR/SC motif, are boxed; and conserved cysteine residues are marked in bold above the sequence. Arginine residue 158 is also marked in bold. The numbering refers to mouse VEGF-C residues.

FIGS. 13A and 13B depict the genomic structure of the human (13A) and murine (13B) VEGF-C genes. Sequences of exon-intron junctions are depicted together with exon and intron lengths. Intron sequences are depicted in lower case letters. Nucleotides of the open reading frame observed in VEGF-C cDNAs are indicated as upper case letters in triplets (corresponding to the codons encoded at the junctions).

DETAILED DESCRIPTION OF THE INVENTION

Figure 1:
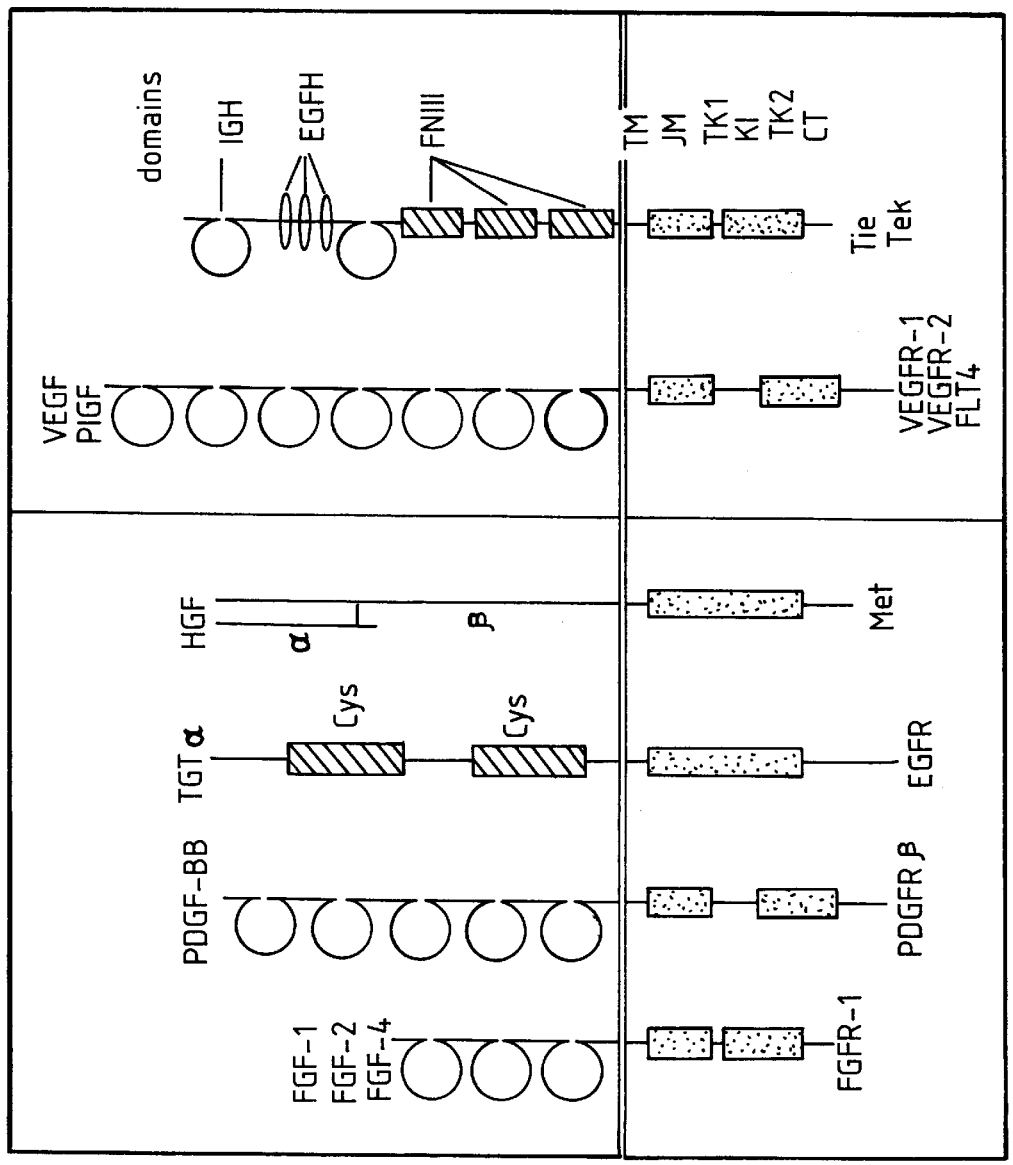
FIG. 1 schematically depicts major endothelial cell receptor tyrosine kinases and growth factors involved in vasculogenesis and angiogenesis. Major structural domains are depicted, including immunoglobulin-like domains (IGH), epidermal growth factor homology domains (EGFH), fibronectin type III domains (FNIII), transmembrane (TM) and juxtamembrane (JM) domains, tyrosine kinase (TK1, TK2) domains, kinase insert domains (KI), and carboxy-terminal domains (CT).

Described herein is the isolation of a novel vascular endothelial growth factor and the cloning of a DNA encoding this novel growth factor from a cDNA library prepared from the human prostatic adenocarcinoma cell line PC-3. The isolated cDNA encodes a protein which is proteolytically processed and secreted to cell culture medium. The processing is described in detail below. The secreted protein, designated VEGF-C, binds to the extracellular domain and induces tyrosine autophosphorylation of both Flt4 (VEGFR-3) and kdr/flk-1 (VEGFR-2). In contrast, neither VEGF nor PlGF showed specific binding to VEGFR-3 or induced its autophosphorylation. VEGF-C also stimulates the migration of endothelial cells in collagen gel and induces vascular permeability in vivo. In transgenic mice, VEGF-C induces proliferation of the lymphatic endothelium and an causes an increase in neutrophilic granulocytes. Based on studies of VEGF-C variants and analogs and studies of VEGF precursors, it is anticipated that one or more VEGF-C precursors (the largest putative native VEGF-C precursor, excluding signal peptide, having the complete amino acid sequence from residue 32 to residue 419 of SEQ ID NO: 8) is capable of stimulating VEGFR-3.

In addition to providing a cDNA sequence encoding prepro-VEGF-C, the present application also provides significant guidance concerning portions of the VEGF-C amino acid sequence which are necessary for biological activity and portions (of one or more amino acids) which, when altered, will modulate (up-regulate or inhibit) VEGF-C biological activities. Such alterations are readily achieved through recombinant DNA and protein techniques, such as site-directed mutagenesis of a VEGF-C encoding cDNA and recombinant expression of the resultant modified cDNA. The skilled artisan also understands that, in recombinant production of proteins, additional sequence may be expressed along with a sequence encoding a polypeptide having a desired biological activity, while retaining a desired biological activity of the protein. For example, additional amino acids may be added at the amino terminus, at the carboxy-terminus, or as an insertion into the polypeptide sequence. Similarly, deletion variants of a protein with a desired biological activity can be recombinantly expressed that lack certain residues of the endogenous/natural protein, while retaining a desired biological activity. Moreover, it is well-known that recombinant protein variants may be produced having conservative amino acid replacements (including but not limited to substitution of one or more amino acids for other amino acids having similar chemical side-chains (acidic, basic, aliphatic, aliphatic hydroxyl, aromatic, amide, etc.)) which do not eliminate the desired biological activity of the protein. Accordingly, it is anticipated that such alterations of VEGF-C are VEGF-C equivalents within the scope of the invention.

As set forth in greater detail below, the putative prepro-VEGF-C has a deduced molecular mass of 46,883; a putative prepro-VEGF-C processing intermediate has an observed molecular weight of about 32 kD; and mature VEGF-C isolated from conditioned media has a molecular weight of about 23 kD as assessed by SDS-PAGE under reducing conditions. A major part of the difference in the observed molecular mass of the purified and recombinant VEGF-C and the deduced molecular mass of the prepro-VEGF-C encoded by the VEGF-C open reading frame (ORF) is attributable to proteolytic removal of sequences at the amino-terminal and carboxyl-terminal regions of the prepro-VEGF-C polypeptide. Extrapolation from studies of the structure of PDGF (Heldin et al., *Growth Factors*, 8:245–52 (1993)) suggests that the region critical for receptor binding and activation by VEGF-C is contained within amino acids residues 104-213, which are found in the secreted form of the VEGF-C protein (i.e., the form lacking the putative prepro leader sequence and some carboxyterminal sequences). The 23 kD polypeptide binding VEGFR-3 corresponds to a VEGF-homologous domain of VEGF-C. After biosynthesis, the nascent VEGF-C polypeptide may be glycosylated at three putative N-linked glycosylation sites identified in the deduced VEGF-C amino acid sequence. Polypeptides containing modifications, such as N-linked glycosylations, are intended as aspects of the invention.

The carboxyl terminal amino acid sequences, which increase the length of the VEGF-C polypeptide in comparison with other ligands of this family, show a pattern of spacing of cysteine residues reminiscent of the Balbiani ring 3 protein (BR3P) sequence (Dignam et al., *Gene*, 88:133–40 (1990); Paulsson et al., *J. Mol. Biol.*, 211:331–49 (1990)). This novel C-terminal silk protein-like structural motif of VEGF-C may fold into an independent domain, which is cleaved off after biosynthesis. Interestingly, at least one cysteine motif of the BR3P type is also found in the carboxyl terminus of VEGF. As explained in detail below, putative precursors and putative fully-processed VEGF-C were both detected in the cell culture media, suggesting cleavage by cellular proteases. The determination of amino-terminal and carboxy-terminal sequences of VEGF-C isolates was performed to identify the proteolytic processing sites. Antibodies generated against different parts of the pro-VEGF-C molecule were used to determine the precursor-product relationship and ratio, their cellular distribution, and the kinetics of processing and secretion.

Figure 9:
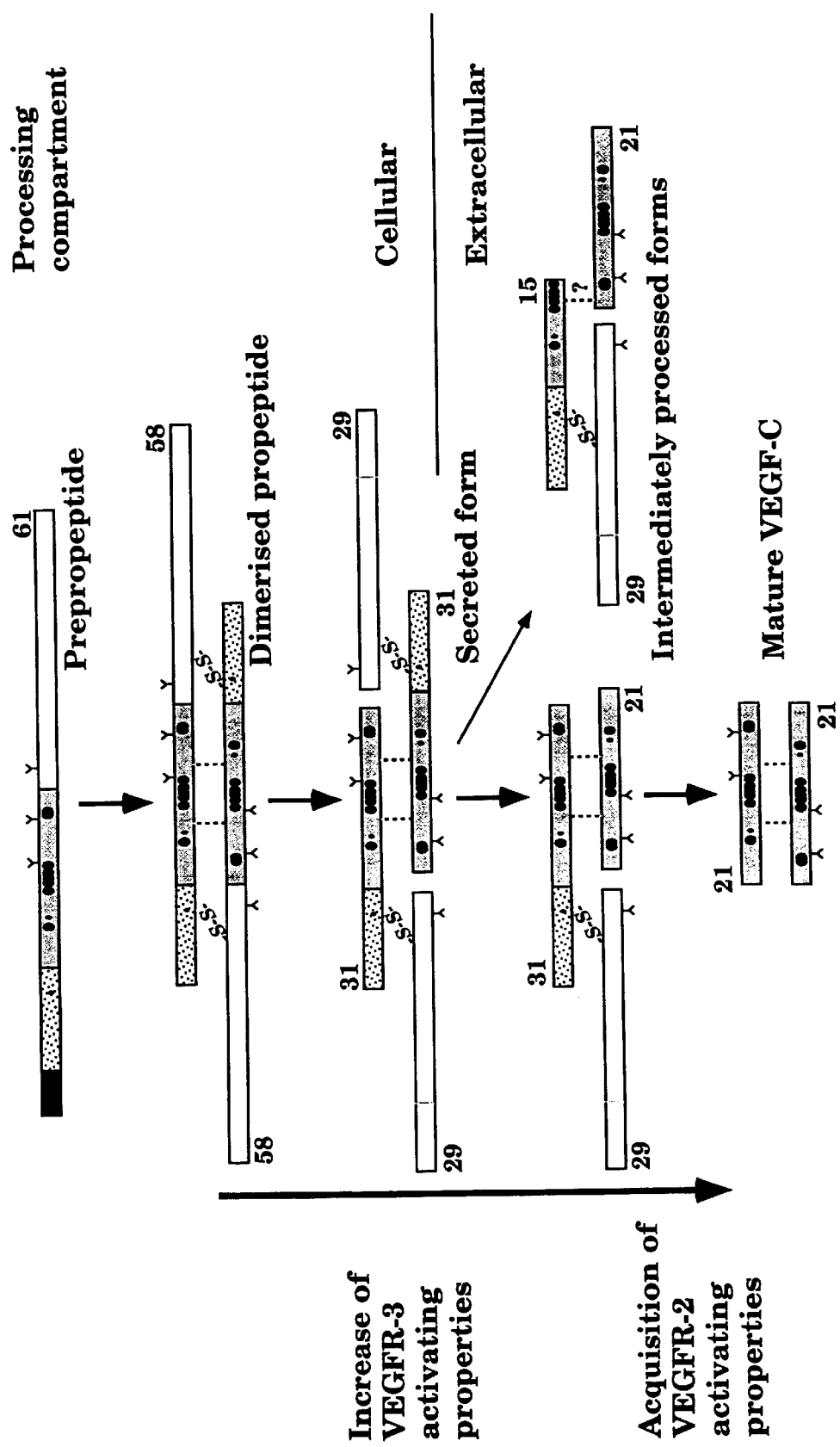
FIG. 9 is a schematic model of the proteolytic processing of VEGF-C. The regions of the VEGF-C polypeptide are depicted as follows: signal sequence=dark shaded box; VEGF-homology domain=medium shaded box; N-terminal and C-terminal propeptides=dotted and open boxes, respectively. Conserved cysteine residues in the VEGF-homology domain are depicted with dots (for clarity, cysteine residues in the C-terminal propeptide are not marked). Putative sites of N-linked glycosylation are shown with Y symbols. Numbers indicate approximate molecular mass (kDa) of the corresponding polypeptide as measured by SDS-PAGE in reducing conditions. Disulfide bonds are marked as —S—S—; non-covalent bonds are depicted as dotted lines. A question mark indicates the presence of a possible non-covalent bond. The proteolytic generation of a small fraction of disulfide-linked 21 kDa forms is not indicated in the figure. Several intermediate forms also are omitted to simplify the scheme. Particularly, only one precursor polypeptide is cleaved initially. The figure is not intended to suggest that other intermediate forms, for example 21 kDa+31 kDa, 31 kDa+31 kDa+29 kDa, do not exist.

VEGF-C has a conserved pattern of eight cysteine residues, which may participate in the formation of intra- and interchain disulfide bonds, creating an antiparallel, dimeric, biologically active molecule, similar to PDGF. Mutational analysis of the cysteine residues involved in the interchain disulfide bridges has shown that, in contrast to PDGF, VEGF dimers need to be held together by these covalent interactions in order to maintain biological activity. Disulfide linking of the VEGF-C polypeptide chains was evident in the analysis of VEGF-C in nonreducing conditions, although recombinant protein also contained "fully processed" ligand-active VEGF-C forms which lacked disulfide bonds between the polypeptides. (See FIG. 9.).

VEGFR-3, which distinguishes between VEGF and VEGF-C, is closely related in structure to VEGFR-1 and VEGFR-2. Finnerty et al., *Oncogene*, 8:2293–98 (1993); Galland et al., *Oncogene*, 8:1233–40 (1993); Pajusola et al., *Cancer Res.*, 52:5738–43 (1992). Besides VEGFR-3, VEGFR-2 tyrosine kinase also is activated in response to VEGF-C. VEGFR-2 mediated signals cause striking changes in the morphology, actin reorganization and membrane ruffling of porcine aortic endothelial cells overexpressing this receptor. In these cells, VEGFR-2 also mediated ligand-induced chemotaxis and mitogenicity. Waltenberger et al., *J. Biol. Chem.*, 269:26988–95 (1994). Similarly, the receptor chimera CSF-1R/VEGFR-3 was mitogenic when ectopically expressed in NIH 3T3 fibroblastic cells, but not in porcine aortic endothelial cells (Pajusola et al., 1994). Consistent with such results, the bovine capillary endothelial (BCE) cells, which express VEGFR-2 mRNA but very little or no VEGFR-1 or VEGFR-3 mRNAs, showed enhanced migration when stimulated with VEGF-C. Light microscopy of the BCE cell cultures in collagen gel also suggested that VEGF-C stimulated the proliferation of these cells. The data thus indicate that the VEGF family of ligands and receptors show a great specificity in their signalling, which may be cell-type-dependent.

The expression pattern of the VEGFR-3 (Kaipainen et al., *Proc. Natl. Acad. Sci. (USA)*, 92:3566–70 (1995)) suggests that VEGF-C may function in the formation of the venous and lymphatic vascular systems during embryogenesis. Constitutive expression of VEGF-C in adult tissues shown herein further suggests that this gene product also is involved in the maintenance of the differentiated functions of the lymphatic and certain venous endothelia where VEGFR-3 is expressed (Kaipainen et al., 1995). Lymphatic capillaries do not have well-formed basal laminae and an interesting possibility exists that the silk-like BR3P motif is involved in producing a supramolecular structure which could regulate the availability of VEGF-C in tissues. However, as shown here, VEGF-C also activates VEGFR-2, which is abundant in proliferating endothelial cells of vascular sprouts and branching vessels of embryonic tissues, but not so abundant in adult tissues. Millauer et al., *Nature*, 367:576–78 (1993). These data have suggested that VEGFR-2 is a major regulator of vasculogenesis and angiogenesis. VEGF-C may thus have a unique effect on lymphatic endothelium and a more redundant function, shared with VEGF, in angiogenesis and possibly in regulating the permeability of several types of endothelia. Because VEGF-C stimulates VEGFR-2 and promotes endothelial migration, VEGF-C may be useful as an inducer of angiogenesis of blood and lymphatic vessels in wound healing, in tissue transplantation, in eye diseases, and in the formation of collateral vessels around arterial stenoses and into injured tissues after infarction.

Previously-identified growth factors that promote angiogenesis include the fibroblast growth factors, hepatocyte growth factor/scatter factor, PDGF and TGF-α. (See e.g., Folkman, *Nature Med.*, 1:27–31 (1995); Friesel et al., *FASEB J.*, 9:919–25 (1995); Mustonen et al., *J. Cell. Biol.*, 129:895–98 (1995). However, VEGF has been the only growth factor relatively specific for endothelial cells. The newly identified factors VEGF-B [Olofsson et al., *Proc. Natl. Acad. Sci.*, 93:2578–81 (1996)] and VEGF-C thus increase our understanding of the complexity of the specific and redundant positive signals for endothelial cells involved in vasculogenesis, angiogenesis, permeability, and perhaps also other endothelial functions. Expression studies using Northern blotting show abundant VEGF-C expression in heart and skeletal muscle; other tissues, such as placenta, ovary, small intestine, thyroid gland, kidney, prostate, spleen, testis and large intestine also express this gene. Whereas PlGF is predominantly expressed in the placenta, the expression patterns of VEGF, VEGF-B and VEGF-C overlap in many tissues, which suggests that members of the VEGF family may form heterodimers and interact to exert their physiological functions.

Targeted mutagenesis leading to inactivation of the VEGF receptor loci in the mouse genome has shown that VEGFR-1 is necessary for the proper organization of endothelial cells forming the vascular endothelium, while VEGFR-2 is necessary for the generation of both endothelial and hematopoietic cells. This suggests that the four genes of the VEGF family can be targets for mutations leading to vascular malformations or cardiovascular diseases.

The following Examples illustrate preferred embodiments of the invention, wherein the isolation, characterization, and function of VEGF-C, VEGF-C variants and analogs, VEGF-C-encoding nucleic acids, and anti-VEGF-C antibodies according to the invention are shown.

EXAMPLE 1

Production of pLTRFlt41 Expression Vector

The identification and isolation of two forms of Flt4 receptor tyrosine kinase (VEGFR-3) CDNA (Flt4 short form (Flt4s), Genbank Accession No. X68203, SEQ ID NO: 1; and Flt4 long form, (Flt4l), Genbank Accession Nos. X68203 and S66407, SEQ ID NO: 2) was reported in U.S. patent application Ser. No. 08/340,011, filed Nov. 14, 1994, incorportated by reference herein. An Flt4 expression vector designated pLTRFlt4l (encoding the long form of Flt4) was constructed using the pLTRpoly expression vector reported in Mäkelä et al., *Gene*, 118: 293–294 (1992) (Genbank accession number X60280, SEQ ID NO: 3) and the Flt4 cDNAs, in the manner described in commonly-owned PCT patent application PCT/FI96/00427, filed Aug. 1, 1996, and commonly-owned U.S. patent application Ser. Nos. 08/671,573, filed Jun. 28, 1996; 08/601,132, filed Feb. 14, 1996; 08/585,895, filed Jan. 12, 1996; and 08/510,133, filed Aug. 1, 1995, all of which are incorporated by reference in their entirety.

EXAMPLE 2

Production and Analysis of Flt4l Transfected Cells

NIH 3T3 cells (60% confluent) were co-transfected with 5 micrograms of the pLTRFlt4l construct and 0.25 micrograms of the pSV2neo vector containing the neomycin phosphotransferase gene (Southern et al., *J. Mol. Appl. Genet.*, 1:327 (1982)), using the DOTAP liposome-based transfection reagents (Boehringer-Mannheim, Mannheim, Germany). One day after transfection, the cells were transferred into selection media containing 0.5 mg/ml geneticin (GIBCO, Grand Island, N.Y.). Colonies of geneticin-resistant cells were isolated and analyzed for expression of the Flt4 proteins. Cells were lysed in boiling lysis buffer containing 3.3% SDS and 125 mM Tris, pH 6.8. Protein concentrations of the samples were measured by the BCA method (Pierce, Rockford, Ill.). About 50 micrograms of protein from each lysate were analyzed for the presence of Flt4 by 6% SDS-polyacrylamide gel electrophoresis (SDS-PAGE) and immunoblotting using antisera against the carboxyl terminus of Flt4. Signals on Western blots were revealed using the ECL method (Amersham).

For production of anti-Flt4 antiserum, the Flt4 cDNA fragment encoding the 40 carboxy-terminal amino acid residues of the Flt4 short form: NH2-PMTPTTYKG SVD-NQTDSGM VLASEEFEQI ESRHRQESGFR-COOH (SEQ ID NO: 4) was cloned as a 657 bp EcoRI-fragment into the pGEX-1λT bacterial expression vector (Pharmacia-LKB, Inc., Uppsala, Sweden) in frame with the glutathione-S-transferase coding region. The resultant GST-Flt4S fusion protein was produced in *E. coli* and purified by affinity chromatography using a glutathione-Sepharose 4B column.

The purified protein was lyophilized, dissolved in phosphate-buffered saline (PBS), mixed with Freund's adjuvant and used for immunization of rabbits at bi-weekly intervals using methods standard in the art (Harlow et al., *Antibodies: A Laboratory Manual* (Cold Spring Harbor Laboratory Press, 1988)). Antisera were used, after the fourth booster immunization, for immunoprecipitation of Flt4 from transfected cells. Cell clones expressing Flt4 were also used for ligand stimulation analysis.

EXAMPLE 3

Construction of a Flt4 EC Baculovirus Vector and Expression and Purification of its Product Using the pVTBac plasmid described in Tessier et al., *Gene* 98:177–183 (1991), and the Flt4 cDNAs described in Example 1, a baculovirus expression vector was constructed to facilitate expression of the extracellular domain of Flt4 (Flt4 EC), as described in commonly-owned PCT patent application PCT/FI96/00427, filed Aug. 1, 1996, and commonly-owned U.S. patent application Ser. Nos. 08/671,573, filed Jun. 28, 1996; 08/601,132, filed Feb. 14, 1996; 08/585,895, filed Jan. 12, 1996; and 08/510,133, filed Aug. 1, 1995, all of which are incorporated by reference herein. A nucleotide sequence encoding a 6×His tag was operatively connected to the Flt4 EC coding sequence to facilitate purification.

The Flt4EC construct was transfected together with baculovirus genomic DNA into SF-9 cells by lipofection. Recombinant virus was purified, amplified and used for infection of High-Five cells (Invitrogen, San Diego, Calif.) using methods standard in the art. The Flt4 extracellular domain (Flt4EC) was purified from the culture medium of the infected High-Five cells using Ni-NTA affinity chromatography according to manufacturer's instructions (Qiagen) for binding and elution of the 6×His tag encoded in the COOH-terminus of the recombinant Flt4 extracellular domain.

EXAMPLE 4

Isolation of an Flt4 Ligand from Conditioned Media

A human Flt4 ligand according to the invention was isolated from media conditioned by a PC-3 prostatic adenocarcinoma cell line (ATCC CRL 1435) in serum-free Ham's F-12 Nutrient mixture (GIBCO) (containing 7% fetal calf serum (FCS)). Cells were reseeded and grown in this medium, which was subsequently changed to serum-free medium. The preparation of the conditioned media, and the identification of a component therein which stimulated Flt4 tyrosine phosphorylation, are described in detail in commonly-owned PCT patent application PCT/FI96/00427, filed Aug. 1, 1996, and commonly-owned U.S. patent application Ser. Nos. 08/671,573, filed Jun. 28, 1996; 08/601,132, filed Feb. 14, 1996; 08/585,895, filed Jan. 12, 1996; 08/510,133, filed Aug. 1, 1995; and 08/340,011, filed Nov. 14, 1994 now U.S. Pat. No 5,726,755, all of which are incorporated by reference herein in their entirety. The ability of the conditioned medium to stimulate Flt4 phosyphorylation was considerably increased when the PC-3 conditioned medium was concentrated four-fold using a Centricon-10 concentrator (Amicon). Pretreatment of the concentrated PC-3 conditioned medium with 50 microliters of Flt4 extracellular domain coupled to CNBr-activated sepharose CL-4B (Pharmacia; about 1mg of Flt4EC domain/ml sepharose resin) completely abolished Flt4 tyrosine phosphorylation. Similar pretreatment of the conditioned medium with unsubstituted sepharose CL-4B did not affect stimulatory activity. Also, the flow through obtained after concentration, which contained proteins of less than 10,000 molecular weight, did not stimulate Flt4 phosphorylation.

In another experiment, a comparison of Flt4 autophosphorylation in transformed NIH 3T3 cells expressing LTRFlt41 was conducted, using unconditioned medium, medium from PC-3 cells expressing the Flt4 ligand, or unconditioned medium containing either 50 ng/ml of VEGF165 or 50 ng/ml of PlGF-1. The cells were lysed, immunoprecipitated using anti-Flt4 antiserum and analyzed by Western blotting using anti-phosphotyrosine antibodies. Only the PC-3 conditioned medium expressing the Flt4 ligand (lane Flt-4L) stimulated Flt4 autophosphorylation.

These experiments showed that PC-3 cells produce a ligand which binds to the extracellular domain of Flt4 and activates this receptor.

EXAMPLE 5

Purification of the Flt4 Ligand

The ligand expressed by human PC-3 cells as characterized in Example 4 was purified and isolated using a recombinantly-produced Flt4 extracellular domain (Flt4EC) in affinity chromatography.

Two harvests of serum-free conditioned medium, comprising a total of 8 liters, were collected from 500 confluent 15 cm diameter culture dishes containing confluent layers of PC-3 cells. The conditioned medium was clarified by centrifugation at 10,000×g and concentrated 80-fold using an Ultrasette Tangential Flow Device (Filtron, Northborough, Mass.) with a 10 kD cutoff Omega Ultrafiltration membrane according to the manufacturer's instructions. Recombinant Flt4 extracellular domain was expressed in a recombinant baculovirus cell system and purified by affinity chromatography on Ni-agarose (Ni-NTA affinity column obtained from Qiagen). The purified extracellular domain was coupled to CNBr-activated Sepharose CL-4B at a concentration of 5 mg/ml and used as an affinity matrix for ligand affinity chromatography.

Concentrated conditioned medium was incubated with 2 ml of the recombinant Flt4 extracellular domain-Sepharose affinity matrix in a rolling tube at room temperature for 3 hours. All subsequent purification steps were at +4° C. The affinity matrix was then transferred to a column with an inner diameter of 15 mm and washed successively with 100 ml of PBS and 50 ml of 10 mM Na-phosphate buffer (pH 6.8). Bound material was eluted step-wise with 100 mM glycine-HCl, successive 6 ml elutions having pHs of 4.0, 2.4, and 1.9. Several 2 ml fractions of the eluate were collected in tubes containing 0.5 ml 1 M Na-phosphate (pH 8.0). Fractions were mixed immediately and dialyzed in 1 mM Tris-HCl (pH 7.5). Aliquots of 75 µl each were analyzed for their ability to stimulate tyrosine phosphorylation of Flt4. The ultrafiltrate, 100 µl aliquots of the concentrated conditioned medium before and after ligand affinity chromatography, as well as 15-fold concentrated fractions of material released from the Flt4 extracellular domain-Sepharose matrix during the washings were also analyzed for their ability to stimulate Flt4 tyrosine phosphorylation.

The concentrated conditioned medium induced prominent tyrosine phosphorylation of Flt4 in transfected NIH 3T3 cells overexpressing Flt4. This activity was not observed in conditioned medium taken after medium was exposed to the Flt4 Sepharose affinity matrix. The specifically-bound Flt4-stimulating material was retained on the affinity matrix after washing in PBS, 10 mM Na-phosphate buffer (pH 6.8), and at pH 4.0. It was eluted in the first two 2 ml aliquots at pH 2.4. A further decrease of the pH of the elution buffer did not cause release of additional Flt4-stimulating material. No Flt4 phosphorylation was observed in a control wherein Flt4-expressing cells were treated with unconditioned medium; similarly, no phosphorylation was observed following treatment of Flt4-expressing cells with the ultrafiltrate fraction of conditioned medium containing polypeptides of less than 10 kD molecular weight.

Small aliquots of the chromatographic fractions were concentrated in a SpeedVac concentrator (Savant, Farmingdale, N.Y.) and subjected to SDS-PAGE under reducing conditions with subsequent silver staining of the gel, a standard technique in the art. The major polypeptide, having a molecular weight of approximately 23 kD (reducing conditions), was detected in the fractions containing Flt4 stimulating activity. That polypeptide was not found in the other chromatographic fractions. On the other hand, besides these bands and a very faint band having a 32 kD mobility, all other components detected in the two active fractions were also distributed in the starting material and in small amounts in the other washing and eluting steps after their concentration. Similar results were obtained in three independent affinity purifications, indicating that the 23 kD polypeptide specifically binds to Flt4 and induces tyrosine phosphorylation of Flt4.

Fractions containing the 23 kD polypeptide were combined, dried in a SpeedVac concentrator and subjected to SDS-PAGE in a 12.5% gel. The proteins from the gel were then electroblotted to Immobilon-P (PVDF) transfer membrane (Millipore, Marlborough, Mass.) and visualized by staining of the blot with Coomassie Blue R-250. The region containing only the stained 23 kD band was cut from the blot and subjected to N-terminal amino acid sequence analysis in a Prosite Protein Sequencing System (Applied Biosystems, Foster City, Calif.). The data were analyzed using a 610A Data Analysis System (Applied Biosystems). Analysis revealed a single N-terminal sequence of $NH_2$—XEETIKFAAAHYNTEILK—COOH (SEQ ID NO: 5).

EXAMPLE 6

Construction of PC-3 Cell cDNA Library in a Eukaryotic Expression Vector

Human poly(A)$^+$ RNA was isolated from five 15 cm diameter dishes of confluent PC-3 cells by a single step method using oligo(dT) (Type III, Collaborative Biomedical Products, Becton-Dickinson Labware, Bedford, Mass.) cellulose affinity chromatography (Sambrook et al., 1989). The yield was 70 micrograms. Six micrograms of the Poly(A)$^+$ RNA were used to prepare an oligo(dT)-primed cDNA library in the mammalian expression vector pcDNA I and the Librarian kit of Invitrogen according to the instructions included in the kit. The library was estimated to contain about $10^6$ independent recombinants with an average insert size of approximately 1.8 kb.

EXAMPLES 7–9

Amplification of a CDNA Encoding the Flt4 Ligand Amino Terminus

The procedures used to isolate a cDNA encoding the Flt4 ligand are described in detail in commonly-owned PCT patent application PCT/FI96/00427, filed Aug. 1, 1996, and commonly-owned U.S. patent application Ser. Nos. 08/671,573, filed Jun. 28, 1996; 08/601,132, filed Feb. 14, 1996; 08/585,895, filed Jan. 12, 1996; and 08/510,133, filed Aug. 1, 1995, all of which are incorporated by reference herein. Initially, degenerate oligonucleotides were designed based on the N-terminal amino acid sequence of the isolated human Flt4 ligand and were used as primers in a polymerase chain reaction (PCR) to amplify a partial cDNA encoding the (fully-processed) Flt4 ligand amino terminus from the PC-3 cDNA library. The amplified cDNA fragment was cloned into a pCR II vector (Invitrogen) using the TA cloning kit (Invitrogen) and sequenced using the radioactive dideoxynucleotide sequencing method of Sanger. Six clones were analyzed and all six clones contained the sequence encoding the expected peptide (amino acid residues 104-120 of the Flt4 ligand precursor, SEQ ID NO: 8). Nucleotide sequence spanning the region from the third nucleotide of codon 6 to the third nucleotide of codon 13 (the extension region between the PCR primers) was identical in all six clones and thus represented an amplified product from the unique sequence encoding part of the amino terminus of the Flt4 ligand.

Based on the unique nucleotide sequence encoding the N-terminus of the isolated human Flt4 ligand, two pairs of nested primers were designed to amplify, in two nested PCR reactions, the complete 5'-end of the corresponding cDNAs from one microgram of DNA of the above-described PC-3 cDNA library. One major product of about 220 bp and three minor products of about 270 bp, 150 bp, and 100 bp were obtained.

The amplified fragment of approximately 220 bp was excised from an agarose gel, cloned into a pCRII vector using the TA cloning kit, and sequenced. Three recombinant clones were analyzed and they contained the sequence 5'-TCACTATAGGGAGACCCAAGCTTGGTACCGAG-CTCGGATCCACTAGTAACGGCCGCC AGTGTGGTG-GAATTCGAC<u>GAACTCATGA-CTGTACTCTACCCAGAATATTGGAAAATG TACAAGTGTCAGCTAAGGCAAGGAGGCTGG CAACATAACAGAGAACAGGCCAACCTC AACTCAAGGACAGAAGAGACTATAAAA TTCGCTGCAGCACACTACAAC</u>-3' (SEQ ID NO: 6). The beginning of the sequence represents the vector and the underlined sequence represents the amplified product of the 5'-end of the cDNA insert.

Based upon the amplified 5'-sequence of the clones encoding the amino terminus of the 23 kD human Flt4 ligand, two pairs of non-overlapping nested primers were designed to amplify the 3'-portion of the Flt4-ligand-encoding cDNA clones via PCR. Two DNA fragments were obtained, having sizes of 1350 bp and 570 bp. Those fragments were cloned into a pCRII vector and the inserts of the clones were sequenced. Both of these fragments were found to contain sequences encoding an amino acid sequence homologous to the VEGF sequence.

EXAMPLE 10

Screening the PC-3 Cell CDNA Library Using the 5' PCR Fragment of Flt4 Ligand CDNA A 153 bp fragment encoding the 5' end of the Flt4 ligand was labeled with [$^{32}$P]-dCTP using the Klenow fragment of E. coli DNA polymerase I (Boehringer Mannheim). That fragment was used as a probe for hybridization screening of the amplified PC-3 cell cDNA library.

Filter replicas of the library were hybridized with the radioactively labeled probe at 42° C. for 20 hours in a solution containing 50% formamide, 5×SSPE, 5×Denhardt's solution, 0.1% SDS and 0.1 mg/ml denatured salmon sperm DNA. Filters were washed twice in 1×SSC, 0.1% SDS for 30 minutes at room temperature, then twice for 30 minutes at 65° C. and exposed overnight.

On the basis of autoradiography, 10 positive recombinant bacterial colonies hybridizing with the probe were chosen from the library. Plasmid DNA was purified from these colonies and analyzed by EcoRI and NotI digestion and agarose gel electrophoresis followed by ethidium bromide staining. The ten plasmid clones were divided into three groups on the basis of the presence of insert sizes of approximately 1.7, 1.9 and 2.1 kb, respectively. Inserts of plasmids from each group were sequenced using the T7 oligonucleotide as a primer and walking primers for subsequent sequencing reactions.

Sequence analysis showed that all clones contain the open reading frame encoding the NH2-terminal sequence of the 23 kD human Flt4 ligand. Dideoxy sequencing was continued using walking primers in the downstream direction. A complete human cDNA sequence and deduced amino acid sequence from a 2 kb clone is set forth in SEQ ID NOs: 7 and 8, respectively. A putative cleavage site of a "prepro" leader sequence is located between residues 102 and 103 of SEQ ID NO: 8. When compared with sequences in the GenBank Database, the predicted protein product of this reading frame was found to be homologous with the predicted amino acid sequences of the PDGF/VEGF family of growth factors, as shown in FIGS. 2A, 2B and 2C.

Plasmid pFLT4-L, containing the 2.1 kb human cDNA clone in pcDNAI vector, has been deposited with the American Type Culture Collection, 12301 Parklawn Drive, Rockville, Md. 20852 as accession number 97231.

EXAMPLE 11

Stimulation of Flt4 Autophosphorylation by the Protein Product of the Flt4 Ligand Vector The 2.1 kb human cDNA insert of plasmid pFlt4-L, which contains the open reading frame encoding the sequence shown in SEQ ID NOs: 7 and 8; human prepro-VEGF-C, see below), was cut out from the pcDNAI vector using HindIII and NotI restriction enzymes, isolated from a preparative agarose gel, and ligated to the corresponding sites in the pREP7 expression vector (Invitrogen). The pREP7 vector containing the pFlt4-L insert was transfected into 293-EBNA cells (Invitrogen) using the calcium phosphate transfection method (Sambrook et al., 1989). About 48 hours after transfection the medium of the transfected cells was changed to DMEM medium lacking fetal calf serum and incubated for 36 h. The conditioned medium was then collected, centrifuged at 5000×g for 20 minutes, the supernatant was concentrated 5-fold using Centriprep 10 (Amicon) and used to stimulate NIH 3T3 cells expressing LTRFlt4l (the Flt4 receptor) as in Example 4. The cells were lysed, immunoprecipitated using anti-Flt4 antiserum and analyzed by Western blotting using anti-phosphotyrosine antibodies.

The conditioned medium from two different dishes of the transfected cells stimulated Flt4 autophosphorylation in comparison with the medium from mock-transfected cells, which gave only background levels of phosphorylation of the Flt4 receptor. When the concentrated conditioned medium was pre-absorbed with 20 microliters of a slurry of Flt4EC domain coupled to Sepharose (see example 4), no phosphorylation was obtained, showing that the activity responsible for Flt4 autophosphorylation was indeed the Flt4 ligand. Thus, these results demonstrate that an expression vector having an approximately 2.1 kb insert and containing an open reading frame as shown in SEQ ID NO: 7 is expressed as a biologically active Flt4 ligand (VEGF-C) in transfected cells. The sequence encoded by that open reading frame is shown in SEQ ID NO: 8.

The deduced molecular weight of a polypeptide consisting of the complete amino acid sequence in SEQ ID NO: 8 (residues 1 to 419) is 46,883. The deduced molecular weight of a polypeptide consisting of amino acid residues 103 to 419 of SEQ ID NO: 8 is 35,881. The Flt4 ligand purified from PC-3 cultures had an observed molecular weight of about 23 kD as assessed by SDS-PAGE under reducing conditions. Thus, it appeared that the Flt4 ligand mRNA was translated into a precursor polypeptide, from which the mature ligand was derived by proteolytic cleavage. Also, the Flt4 ligand may be glycosylated at three putative N-linked glycosylation sites conforming to the consensus which can be identified in the deduced Flt4 ligand amino acid sequence (N-residues underlined in FIGS. 2A, 2B and 2C).

The carboxyl terminal amino acid sequences, which increase the predicted molecular weight of the Flt4 ligand subunit in comparison with other ligands of this family, show a pattern of spacing of cysteine residues reminiscent of the Balbiani ring 3 protein (BR3P) sequence (Dignam et al., Gene, 88:133–140 (1990)). Such a sequence may encode an independently folded domain present in a Flt4 ligand precursor and it may be involved, for example, in the regulation of secretion, solubility, stability, cell surface localization or activity of the Flt4 ligand. Interestingly, at least one cysteine motif of the BR3P type is also found in the VEGF carboxy terminal amino acid sequences.

Thus, the Flt4 ligand MRNA appears first to be translated into a precursor from the MRNA corresponding to the cDNA insert of plasmid FLT4-L, from which the mature ligand is derived by proteolytic cleavage. To define the mature Flt4 ligand polypeptide, one first expresses the cDNA clone (which is deposited in the pcDNAI expression vector) in cells, such as COS cells. One uses antibodies generated against encoded polypeptides, fragments thereof, or bacterial Flt4 fusion proteins, such as a GST-fusion protein, to raise antibodies against the VEGF-homologous domain and the amino- and carboxyl-terminal propeptides of Flt4 ligand. One then follows the biosynthesis and processing of the Flt4 ligand in the transfected cells by pulse-chase analysis using radioactive cysteine for labelling of the cells, immunoprecipitation, and gel electrophoresis. Using antibodies against the three domains of the product encoded by the cDNA insert of plasmid FLT4-L, material for radioactive or nonradioactive amino-terminal sequence analysis is isolated. The determination of the amino-terminal sequence of the mature VEGF-C polypeptide allows for identification of the amino-terminal proteolytic processing site. The determination of the amino-terminal sequence of the carboxyl-terminal propeptide will give the carboxyl-terminal processing site. This is confirmed by site-directed mutagenesis of the amino acid residues adjacent to the cleavage sites, which would prevent the cleavage.

The Flt4 ligand is further characterizeable by progressive 3' deletions in the 3' coding sequences of the Flt4 ligand precursor clone, introducing a stop codon resulting in carboxy-terminal truncations of its protein product. The activities of such truncated forms are assayed by, for example, studying Flt4 autophosphorylation induced by the truncated proteins when applied to cultures of cells, such as NIH 3T3 cells expressing LTRFlt4l. By extrapolation from studies of the structure of the related platelet derived growth factor (PDGF, Heldin et al., *Growth Factors,* 8:245–252 (1993)) one determines that the region critical for receptor activation by the Flt4 ligand is contained within the first approximately 180 amino acid residues of the secreted VEGF-C protein lacking the putative 102 amino acid prepro leader (SEQ ID NO: 8, residues 103–282), and apparently within the first approximately 120 amino acid residues (SEQ ID NO: 8, residues 103–223).

On the other hand, the difference between the molecular weights observed for the purified ligand and deduced from the open reading frame of the Flt4 ligand clone may be due to the fact that the soluble ligand was produced from an alternatively spliced MRNA which would also be present in the PC-3 cells, from which the isolated ligand was derived. To isolate such alternative cDNA clones one uses cDNA fragments of the deposited clone and PCR primers made according to the sequence provided as well as techniques standard in the art to isolate or amplify alternative cDNAs from the PC-3 cell cDNA library. One may also amplify using reverse transcription (RT)-PCR directly from the PC-3 MRNA using the primers provided in the sequence of the CDNA insert of plasmid FLT4-L. Alternative cDNA sequences are determined from the resulting cDNA clones. One can also isolate genomic clones corresponding to the Flt4 ligand MRNA transcript from a human genomic DNA library using methods standard in the art and sequence such clones or their subcloned fragments to reveal the corresponding exons. Alternative exons can then be identified by a number of methods standard in the art, such as heteroduplex analysis of CDNA and genomic DNA, which are subsequently characterized.

EXAMPLE 12

Expression of the Gene Encoding VEGF-C in Human Tumor Cell Lines

Expression of transcripts corresponding to the Flt4 ligand (VEGF-C) was analyzed by hybridization of Northern blots containing isolated poly(A)$^+$ RNA from HT-1080 and PC-3 human tumor cell lines. The probe was the radioactively labelled insert of the 2.1 kb cDNA clone (pFlt4-L/VEGF-C, specific activity $10^8$–$10^9$ cpm/mg of DNA). The blot was hybridized overnight at 42° C. using 50% formamide, 5×SSPE buffer, 2% SDS, 10×Denhardt's solution, 100 mg/ml salmon sperm DNA and 1×10$^6$ cpm of the labelled probe/ml. The blot was washed at room temperature for 2×30 minutes in 2×SSC containing 0.05% SDS, and then for 2×20 minutes at 52° C. in 0.1×SSC containing 0.1% SDS. The blot was then exposed at −70° C. for three days using intensifying screens and Kodak XAR film. Both cell lines expressed an Flt4 ligand mRNA of about 2.4 kb, as well as VEGF and VEGF-B mRNAs.

EXAMPLE 13

VEGF-C Chains Are Proteolytically Processed After Biosynthesis and Disulfide Linked The predicted molecular mass of a secreted human VEGF-C polypeptide, as deduced from the VEGF-C open reading frame, is 46,883 kD, suggesting that VEGF-C mRNA may be first translated into a precursor, from which the observed ligands of 21/23 kD and 29/32 kD are derived by proteolytic cleavage.

This possibility was explored by metabolic labelling of 293 EBNA cells expressing VEGF-C. Initially, 293 EBNA cells were transfected with the VEGF-C cDNA construct. Expression products were labeled by the addition of 100 μCi/ml of Pro-mix™ L-[$^{35}$S] in vitro cell labelling mix ((containing $^{35}$S-methionine and $^{35}$S-cysteine) Amersham, Buckinghamshire, England) to the culture medium devoid of cysteine and methionine. After two hours, the cell layers were washed twice with PBS and the medium was then replaced with DMEM-0.2% BSA. After 1, 3, 6, 12 and 24 hours of subsequent incubation, the culture medium was collected, clarified by centrifugation, and concentrated, and human VEGF-C was bound to 30 μl of a slurry of Flt4EC-Sepharose overnight at +4° C., followed by three washes in PBS, two washes in 20 mM Tris-HCl (pH 7.5), alkylation, SDS-PAGE and autoradiography. Alkylation was carried out by treatment of the samples with 10 mM 1,4 Dithiothreitol (Boehringer-Mannheim, Mannheim, Germany) for one hour at 25° C., and subsequently with 30 mM iodoacetamide (Fluka, Buchs, Switzerland).

Figure 3A:
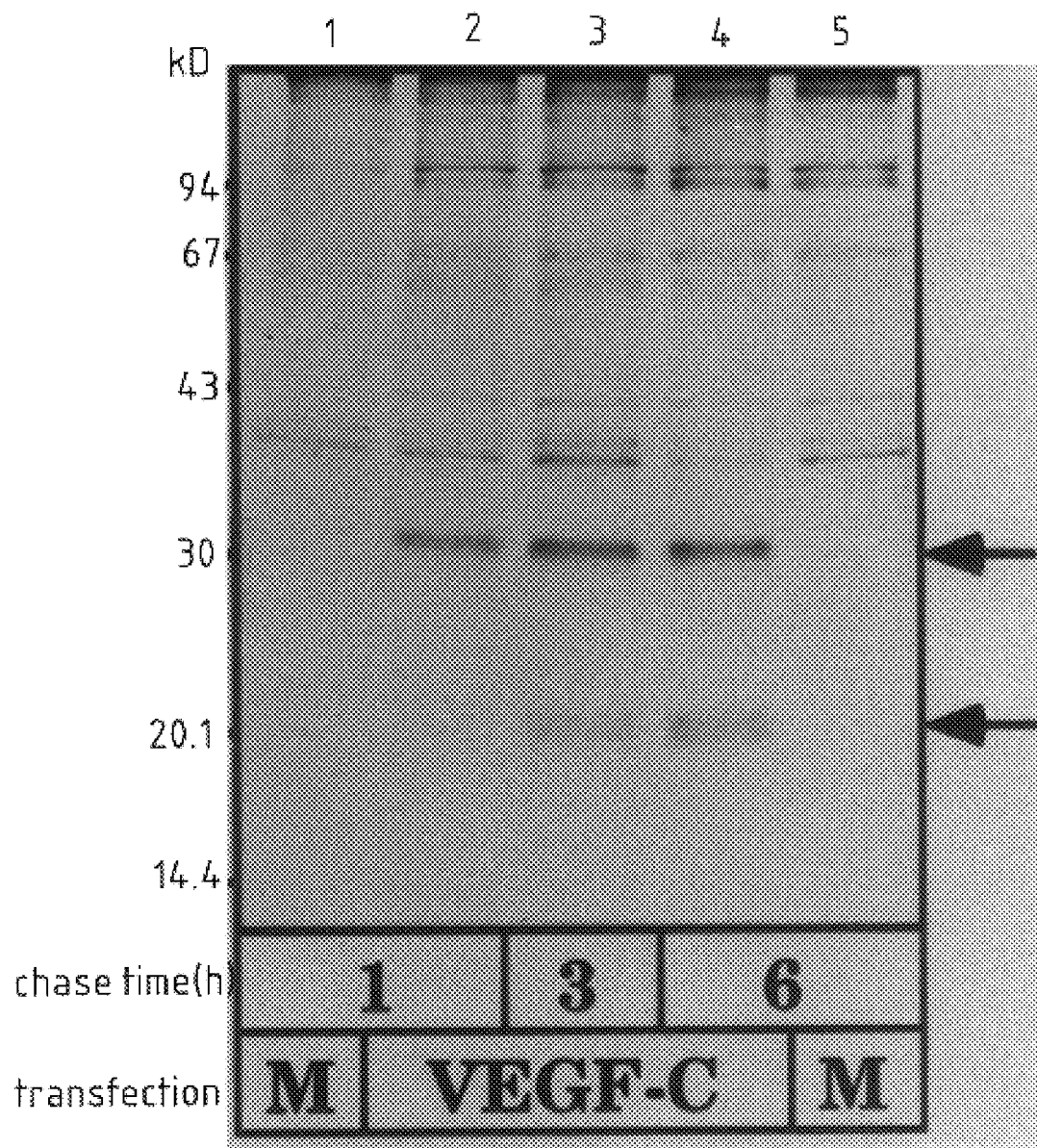
FIG. 3A is an autoradiograph showing recombinant VEGF-C isolated following a pulse-chase experiment and electrophoresed via SDS-PAGE under reducing conditions.

These experiments demonstrated that a putative precursor polypeptide of 32 kD apparent molecular mass was bound to the Flt4EC affinity matrix from the conditioned medium of metabolically labelled cells transfected with the human VEGF-C expression vector (FIG. 3A), but not from mock (M) transfected cells. Increased amounts of a 23 kD receptor binding polypeptide accumulated in the culture medium of VEGF-C transfected cells during a subsequent chase period of three hours, but not thereafter (lanes 2–4 and data not shown), suggesting that the 23 kD form is produced by proteolytic processing, which is incomplete, at least in the transiently transfected cells. The arrows in FIG. 3A indicate the 32 kD and 23 kD polypeptides of secreted VEGF-C. Subsequent experiments showed that the 32 kD VEGF-C form contains two components migrating in the absence of alkylation as polypeptides of 29 and 32 kD (FIGS. 6–8).

Figure 3B:
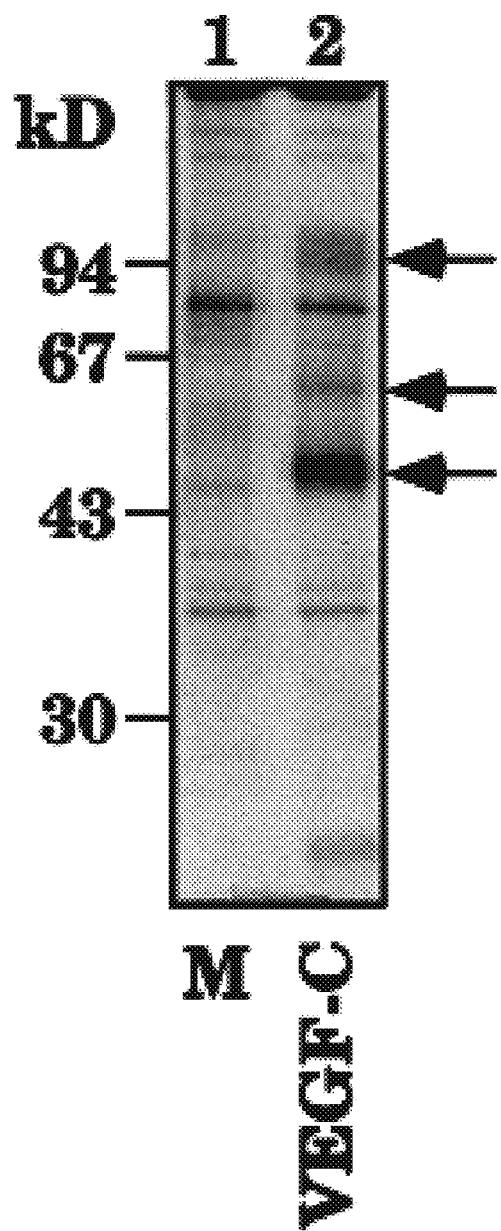
FIG. 3B is a photograph of polyacrylamide gel showing that recombinant VEGF-C forms are disulfide-linked in nonreducing conditions.

In a related experiment, human VEGF-C isolated using Flt4EC-Sepharose after a 4 h continuous metabolic labelling was analyzed by polyacrylamide gel electrophoresis in non-reducing conditions (FIG. 3B). Higher molecular mass forms were observed under nonreducing conditions, suggesting that the VEGF-C polypeptides can form disulfide-linked dimers and/or multimers (arrows in FIG. 3B).

Additional experiments have shown that higher molecular mass forms of VEGF-C (about 58 kD and about 43 kD) are observed under reducing conditions as well. (See below and FIGS. 6A and 14A.)

EXAMPLE 14

Stimiulation Of VEGPR-2 Autophosphorylation By VEGF-C

Conditioned medium (CM) from 293 EBNA cells transfected with the human VEGF-C vector also was used to stimulate porcine aortic endothelial (PAE) cells expressing VEGFR-2 (Kdr). Pajusola et al., *Oncogene,* 9:3545–55 (1994); Waltenberger et al., *J. Biol. Chem.,* 269:26988–26995 (1994). The cells were lysed and immunoprecipitated using VEGFR-2-specific antiserum (Waltenberger et al., 1994).

PAE-KDR cells (Waltenberger et al., 1994) were grown in Ham's F12 medium-10% fetal calf serum (FCS). Confluent NIH 3T3-Flt4 cells or PAE-KDR cells were starved overnight in DMEM or Ham's F12 medium, respectively, supplemented with 0.2% bovine serum albumin (BSA), and then incubated for 5 minutes with the analyzed media. Recombinant human VEGF (R&D Systems) and PDGF-BB, functional as stimulating agents, were used as controls. The cells were washed twice with ice-cold Tris-Buffered Saline (TBS) containing 100 mM sodium orthovanadate and lysed in RIPA buffer containing 1 mM phenylmethylsulfonyl fluoride (PMSF), 0.1 U/ml aprotinin and 1 mM sodium orthovanadate. The lysates were sonicated, clarified by centrifugation at 16,000×g for 20 minutes and incubated for 3–6 hours on ice with 3–5 µl of antisera specific for Flt4 (Pajusola et al., 1993), VEGFR-2 or PDGFR-β (Claesson-Welsh et al., J. Biol. Chem., 264:1742–1747 (1989); Waltenberger et al., 1994). Immunoprecipitates were bound to protein A-Sepharose, washed three times with RIPA buffer containing 1 mM PMSF, 1 mM sodium orthovanadate, washed twice with 10 mM Tris-HCl (pH 7.4), and subjected to SDS-PAGE using a 7% gel. Polypeptides were transferred to nitrocellulose by Western blotting and analyzed using PY20 phosphotyrosine-specific monoclonal antibodies (Transduction Laboratories) or receptor-specific antiserum and the ECL detection method (Amersham Corp.).

PAE cells expressing VEGFR-2 were treated with 10- or 2-fold concentrated medium from mock-transfected 293-EBNA cells, or with 2-, 5- or 10-fold concentrated medium from 293-EBNA cell cultures expressing the recombinant VEGF-C. VEGFR-2 was immunoprecipitated with specific antibodies and analyzed by SDS-PAGE and Western blotting using phosphotyrosine antibodies. For comparison, the treatments were also carried out with non-conditioned medium containing 50 ng/ml of purified recombinant VEGF. Additional cells were also treated with VEGF-C- or VEGF-containing media pretreated with Flt4EC.

The results of this experiment were as follows. A basal level of tyrosine phosphorylation of VEGFR-2 was detected in cells stimulated by CM from the mock-transfected cells. A further concentration of this medium resulted in only a slight enhancement of VEGFR-2 phosphorylation. CM containing recombinant VEGF-C stimulated tyrosine autophosphorylation of VEGFR-2 and the intensity of the autophosphorylated polypeptide band was increased upon concentration of the VEGF-C CM. Furthermore, the stimulating effect was abolished after pretreatment of the medium with the Flt4EC affinity matrix. The maximal effect of VEGF-C in this assay was comparable to the effect of recombinant VEGF added to unconditioned medium at concentration of 50 ng/ml. Pretreatment of the medium containing VEGF with Flt4EC did not abolish its stimulating effect on VEGFR-2. These results suggest that the VEGF-C expression vector encodes a ligand not only for Flt4 (VEGFR-3), but also for Kdr/Flk-1 (VEGFR-2).

In order to further confirm that the stimulating effect of VEGF-C on tyrosine phosphorylation of VEGFR-3 and VEGFR-2 was receptor-specific, we analyzed the effect of VEGF-C on tyrosine phosphorylation of PDGF receptor β (PDGFR-β) which is abundantly expressed on fibroblastic cells. PDGFR-β-expressing NIH 3T3 cells were treated with non-conditioned medium, 5-fold concentrated CM from mock-transfected or VEGF-C-transfected cells, or with non-conditioned medium containing 50 ng/ml of recombinant human PDGF-BB. Medium containing VEGF-C was also pretreated with recombinant Flt4EC (lane 4). PDGFR-β was immunoprecipitated with specific antibodies and analyzed by SDS-PAGE and Western blotting using phosphotyrosine antibodies with subsequent stripping and reprobing of the membrane with antibodies specific for PDGFR-β. A weak tyrosine phosphorylation of PDGFR-β was detected upon stimulation of Flt4-expressing NIH 3T3 cells with CM from the mock-transfected cells. A similar low level of PDGFR-β phosphorylation was observed when the cells were incubated with CM from the VEGF-C transfected cells, with or without prior treatment with Flt4EC. In contrast, the addition of 50 ng/ml of PDGF-BB induced a prominent tyrosine autophosphorylation of PDGFR-β.

EXAMPLE 15

VEGF-C Stimulates Endothelial Cell Migration In Collagen Gel

Conditioned media (CM) from cell cultures transfected with the VEGF-C expression vector was placed in a well made in collagen gel and used to stimulate the migration of bovine capillary endothelial (BCE) cells in the three-dimensional collagen gel as follows.

BCE cells (Folkman et al., Proc. Natl. Acad. Sci. (USA), 76:5217–5221 (1979)) were cultured as described in Pertovaara et al., J. Biol. Chem., 269:6271–74 (1994). The collagen gels were prepared by mixing type I collagen stock solution (5 mg/ml in 1 mM HCl) with an equal volume of 2×MEM and 2 volumes of MEM containing 10% newborn calf serum to give a final collagen concentration of 1.25 mg/ml. The tissue culture plates (5 cm diameter) were coated with about 1 mm thick layer of the solution, which was allowed to polymerize at 37° C. BCE cells were seeded on top of this layer. For the migration assays, the cells were allowed to attach inside a plastic ring (1 cm diameter) placed on top of the first collagen layer. After 30 minutes, the ring was removed and unattached cells were rinsed away. A second layer of collagen and a layer of growth medium (5% newborn calf serum (NCS)), solidified by 0.75% low melting point agar (FMC BioProducts, Rockland, Me.), were added. A well (3 mm diameter) was punched through all the layers on both sides of the cell spot at a distance of 4 mm, and the sample or control media were pipetted daily into the wells. Photomicrographs of the cells migrating out from the spot edge were taken after six days through an Olympus CK 2 inverted microscope equipped with phase-contrast optics. The migrating cells were counted after nuclear staining with the fluorescent dye bisbenzimide (1 mg/ml, Hoechst 33258, Sigma).

Figure 4:
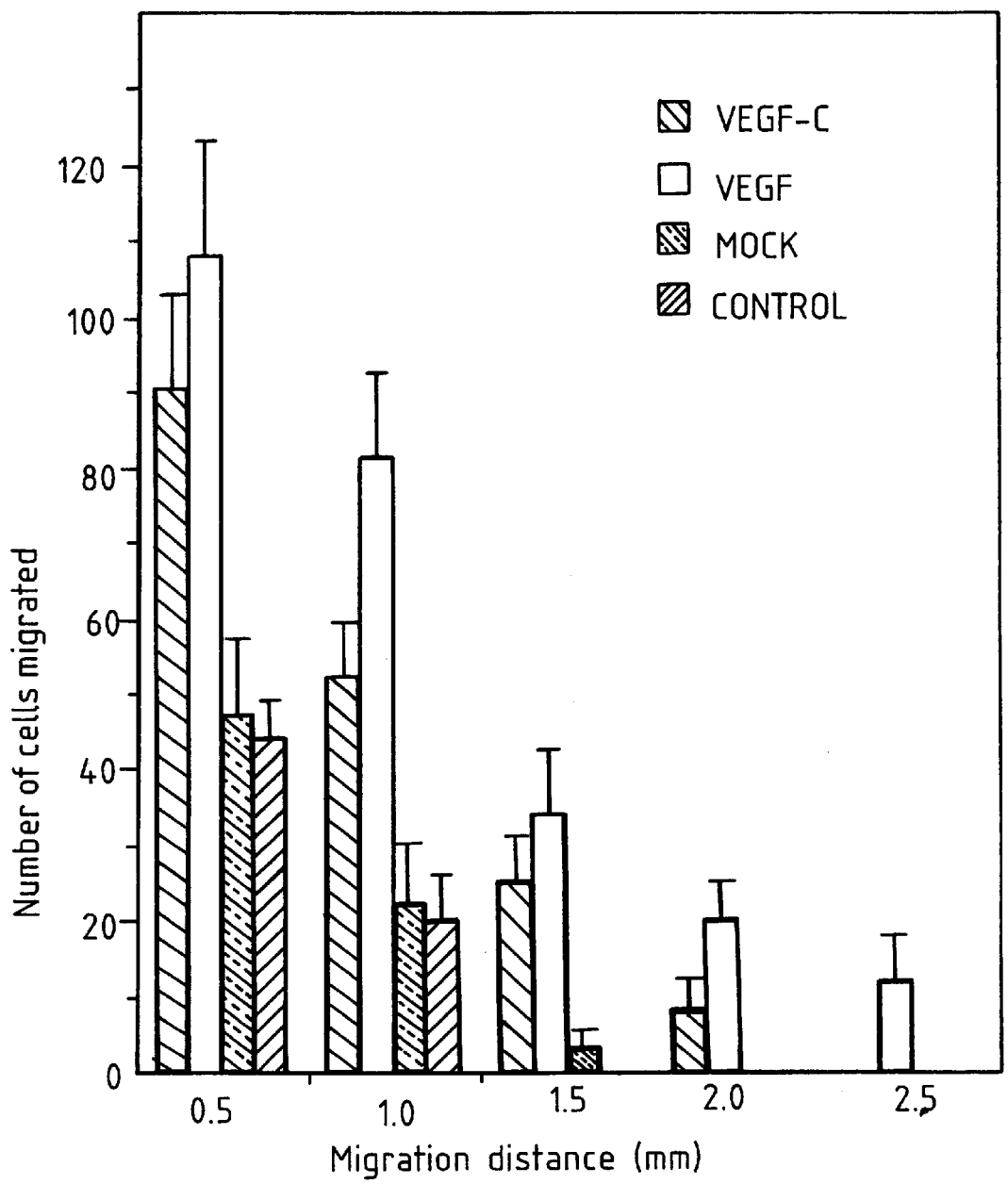
FIG. 4 shows that VEGF-C stimulates endothelial cell migration in a three-dimensional collagen gel assay.

FIG. 4 depicts a comparison of the number of cells migrating at different distances from the original area of attachment towards wells containing media conditioned by the non-transfected (control) or transfected (mock; VEGF-C; VEGF) cells, 6 days after addition of the media. The number of cells migrating out from the original ring of attachment was counted in five adjacent 0.5 mm×0.5 mm squares using a microscope ocular lens grid and 10× magnification with a fluorescence microscope. Cells migrating further than 0.5 mm were counted in a similar way by moving the grid in 0.5 mm steps. The experiments were carried out twice with similar results, and medium values from the one of the experiments are presented with standard error bars. As can be seen from the columns, VEGF-C-containing CM stimulated cell migration more than medium conditioned by the non-transfected or mock-transfected cells but less than medium from cells transfected with a VEGF expression vector. Daily addition of 1 ng of FGF2 into the wells resulted in the migration of approximately twice the number of cells when compared to the stimulation by CM from VEGF-transfected cells.

In related experiments, a "recombinantly-matured" VEGF-C polypeptide (VEGF-C ΔNΔCHis, described below) was shown to stimulate the incorporation of $^3$H-thymidine into the DNA of BCE cells in a dose dependent manner (VEGF-C concentrations of 0, 10, 100, and 1000 pM tested). This data tends to confirm the observation, under light microscopy, that VEGF-C stimulates proliferation of these cells.

EXAMPLE 16

VEGF-C Is Expressed In Multiple Tissues

Northern blots containing 2 micrograms of isolated poly (A)+ RNA from multiple human tissues (blot from Clontech Laboratories, Inc., Palo Alto, Calif.) were probed with radioactively labelled insert of the 2.1 kb VEGF-C cDNA clone. Northern blotting and hybridization analysis showed that the 2.4 kb RNA and smaller amounts of a 2.0 kb mRNA are expressed in multiple human tissues, most prominently in the heart, placenta, muscle, ovary and small intestine, and less prominently in prostate, colon, lung, pancreas, and spleen. Very little VEGF-C RNA was seen in the brain, liver, kidney, testis, or thymus and peripheral blood leukocytes (PBL) appeared negative. A similar analysis of RNA from human fetal brain, lung, liver, and kidney tissues showed that VEGF-C is highly expressed in the kidney and lung and to a lesser degree in the liver, while essentially no expression is detected in the brain. Interestingly, VEGF expression correlates with VEGF-C expression in these tissues, whereas VEGF-B is highly expressed in all four fetal tissues analyzed.

EXAMPLE 17

The VEGF-C Gene Localizes To Chromosome 4q34

A DNA panel of 24 interspecies somatic cell hybrids, which had retained one or two human chromosomes, was used for the chromosomal localization of the VEGF-C gene (Bios Laboratories, Inc., New Haven, Conn.). The procedures employed are described in detail in commonly-owned PCT patent application PCT/FI96/00427, filed Aug. 1, 1996, and commonly-owned U.S. patent application Ser. Nos. 08/671,573, filed Jun. 28, 1996; 08/601,132, filed Feb. 14, 1996; and 08/585,895, filed Jan. 12, 1996, all of which are incorporated by reference herein.

In order to determine the chromosomal localization of the human VEGF-C gene, DNAs from human rodent somatic cell hybrids containing defined sets of human chromosomes were analyzed by Southern blotting and hybridization with a VEGF-C cDNA probe. Among 24 DNA samples on the hybrid panel, representing different human chromosomes, human-specific signals were observed only in hybrids which contained human chromosome 4. The results were confirmed by PCR of somatic cell hybrid DNAs using VEGF-C specific primers, where amplified bands were obtained only from DNAs containing human chromosome 4.

A genomic P1 plasmid for VEGF-C was isolated using specific primers and PCR and verified by Southern blotting and hybridization using a VEGF-C specific cDNA probe. The chromosomal localization of VEGF-C was further studied using metaphase FISH. Using the P1 probe for VEGF-C in FISH a specific hybridization to the 4q34 chromosomal band was detected in 40 out of 44 metaphases. Double-fluorochrome hybridization using a cosmid probe specific for the aspartylglucosaminidase (AGA) gene showed that VEGF-C is located just proximal to the AGA gene previously mapped to the 4q34–35 chromosomal band.

Biotin labelled VEGF-C P1 and digoxigenin labeled AGA cosmid probes were hybridized simultaneously to metaphase chromosomes. This experiment demonstrated that the AGA gene is more telomerically located than the VEGF-C gene. The foregoing example demonstrates the utility of polynucleotides of the invention as chromosomal markers and for the presence or absence of the VEGF-C gene region in normal or diseased cells. The VEGF-C locus at 4q34 is a candidate target for mutations leading to vascular malformations or cardiovascular diseases.

EXAMPLE 18

Effect of Glucose Concentration and Hypoxia on VEGF, VEGF-B and VEGF-C mRNA Levels in C6 Glioblastoma Cells Confluent cultures of C6 cells (ATCC CCL 107) were grown on 10 cm diameter tissue culture plates containing 2.5 ml of DMEM and 5% fetal calf serum plus antibiotics. The cultures were exposed for 16 hours to normoxia in a normal cell culture incubator containing 5% $CO_2$ or hypoxia by closing the culture plates in an airtight glass chamber and burning a piece of wood inside until the flame was extinguished due to lack of oxygen. Polyadenylated RNA was isolated (as in the other examples), and 8 micrograms of the RNA was electrophoresed and blot-hybridized with a mixture of the VEGF, VEGF-B and VEGF-C probes. The results show that hypoxia strongly induces VEGF mRNA expression, both in low and high glucose, but has no significant effect on the VEGF-B mRNA levels. The VEGF-C MRNA isolated from hypoxic cells runs slightly faster in gel electrophoresis and an extra band of faster mobility can be seen below the upper MRNA band. This observation suggests that hypoxia affects VEGF-C RNA processing. One explanation for this observation is that VEGF-C MRNA splicing is altered, affecting the VEGF-C open reading frame and resulting in an alternative VEGF-C protein being produced by hypoxic cells. Such alternative forms of VEGF-C and VEGF-C-encoding polynucleotides are contemplated as an aspect of the invention. This data indicates screening and diagnostic utilities for polynucleotides and polypeptides of the invention, such as methods whereby a biological sample is screened for the hypoxia-induced form of VEGF-C and/or VEGF-C MRNA. The data further suggests a therapeutic indication for antibodies and/ or other inhibitors of the hypoxia-induced form of VEGF-C or the normal form of VEGF-C.

EXAMPLE 19

Pulse-Chase Labeling and Immunoprecipitation of VEGF-C Polypeptides From 293 EBNA Cells Transfected With VEGF-C Expression Vector.

The following VEGF-C branched amino-terminal peptide, designated PAM126, was synthesized for production of anti-VEGF-C antiserum:

$NH_2$-E-E-T-I-K-F-A-A-A-H-Y-N-T-E-I-L-K-COOH (SEQ ID NO: 9).

In particular, PAM126 was synthesized as a branched polylysine structure K3PA4 having four peptide acid (PA) chains attached to two available lysine (K) residues. The synthesis was performed on a 433A Peptide Synthesizer (Applied Biosystems) using Fmoc-chemistry and TentaGel S MAP RAM10 resin mix (RAPP Polymere GmbH, Tubingen, Germany), yielding both cleavable and resin-bound peptides. The cleavable peptide was purified via reverse phase HPLC and was used together with the resin-bound peptide in immunizations. The correctness of the synthesis products were confirmed using mass-spectroscopy (Lasermatt).

The PAM126 peptide was dissolved in phosphate buffered saline (PBS), mixed with Freund's adjuvant, and used for immunization of rabbits at bi-weekly intervals using methods standard in the art (Harlow and Lane, *Antibodies, a laboratory manual*, Cold Spring Harbor Laboratory Press (1988)). Antisera obtained after the fourth booster immunization was used for immunoprecipitation of VEGF-C in pulse-chase experiments, as described below.

For pulse-chase analysis, 293 EBNA cells transfected with a VEGF-C expression vector (i.e., the FLT4-L CDNA inserted into the pREP7 expression vector as described above) were incubated for 30 minutes in methionine-free, cysteine-free, serum-free DMEM culture medium at 37° C. The medium was then changed, and 200 µCi of Pro-mix™ (Amersham), was added. The cell layers were incubated in this labeling medium for two hours, washed with PBS, and incubated for 0, 15, 30, 60, 90, 120, or 180 minutes in serum-free DMEM (chase). After the various chase periods, the medium was collected, the cells were again washed two times in PBS, and lysed in immunoprecipitation buffer. The VEGF-C polypeptides were analyzed from both the culture medium and from the cell lysates by immunoprecipitation, using the VEGF-C-specific antiserum raised against the $NH_2$-terminal peptide (PAM126) of the 23 kD VEGF-C form. Immunoprecipitated polypeptides were analyzed via SDS-PAGE followed by autoradiography.

The resultant autoradiograms demonstrated that immediately after a 2 hour labeling (chase time 0), the VEGF-C vector-transfected cells contained a radioactive polypeptide band of about 58 kD (originally estimated to be about 55 kD, and re-evaluated to be about 58 kD using different size standards), which was not observed in mock-transfected cells (M). Most of this ~58 kD precursor undergoes dimerization. This ~58 kD polypeptide band gradually diminished in intensity with increasing chase periods. A 32 kD polypeptide band also is observed in VEGF-C transfected cells (but not mock-transfected cells). This 32 kD band disappears from cells with similar kinetics to that of the ~58 kD band. Additional analysis indicated that the 32 kD band was a doublet of 29 kD and 31–32 kD forms, held together by disulfide bonds. Simultaneously, increasing amounts of 32 kD and subsequently 23 kD and 14–15 kD polypeptides appeared in the medium.

Collectively, the data from the pulse-chase experiments indicate that the ~58 kD intracellular polypeptide represents a pro-VEGF-C polypeptide, which is proteolytically cleaved either intracellularly or at the cell surface into the 29 kD and 31–32 kD polypeptides. The 29/31 kD form is secreted and simultaneously further processed by proteolysis into the 23 kD and 14–15 kD forms. In additional experiments, disulfide linked dimers of the 29 kD and 15 kD forms were observed. Without intending to be limited to a particular theory, it is believed that processing of the VEGF-C precursor occurs as removal of a signal sequence, removal of the COOH-terminal domain (BR3P), and removal of an amino terminal polypeptide, resulting in a VEGF-C polypeptide having the TEE . . . amino terminus.

At high resolution, the 23 kD polypeptide band appears as a closely-spaced polypeptide doublet, suggesting heterogeneity in cleavage or glycosylation.

EXAMPLE 20

Isolation of Mouse and Quail CDNA Clones Encoding VEGF-C

To clone a murine VEGF-C, approximately $1 \times 10^6$ bacteriophage lambda clones of a commercially-available 12 day mouse embryonal cDNA library (lambda EXlox library, Novagen, catalog number 69632-1) were screened with a radiolabeled fragment of human VEGF-C CDNA containing nucleotides 495 to 1661 of SEQ ID NO: 7. One positive clone was isolated.

A 1323 bp EcoRI/HindIII fragment of the insert of the isolated mouse cDNA clone was subcloned into the corresponding sites of the pBluescript SK+ vector (Stratagene) and sequenced. The cDNA sequence of this clone was homologous to the human VEGF-C sequence reported herein, except that about 710 bp of 5'-end sequence present in the human clone was not present in the mouse clone.

For further screening of mouse cDNA libraries, a HindIII-BstXI (HindIII site is from the pBluescript SK+ polylinker) fragment of 881 bp from the coding region of the mouse cDNA clone was radiolabeled and used as a probe to screen two additional mouse cDNA libraries. Two additional cDNA clones from an adult mouse heart ZAP II cDNA library (Stratagene, catalog number 936306) were identified. Three additional clones also were isolated from a mouse heart 5'-stretch-plus cDNA library in λgt11 (Clontech Laboratories, Inc., catalog number ML5002b). Of the latter three clones, one was found to contain an insert of about 1.9 kb. The insert of this cDNA clone was subcloned into EcoRI sites of pBluescript SK+ vector and both strands of this clone were completely sequenced, resulting in the nucleotide and deduced amino acid sequences shown in SEQ ID NOs: 10 and 11.

It is contemplated that the polypeptide corresponding to SEQ ID NO: 11 is processed into a mature mouse VEGF-C protein, in a manner analogous to the processing of the human VEGF-C prepropeptide. Putative cleavage sites for the mouse protein are identified using procedures outlined above for identification of cleavage sites for the human VEGF-C polypeptide.

The foregoing results demonsof polynucleotity of polynucleotides of the invention for identifying and isolating polynucleotides encoding other non-human mammalian VEGF-C proteins. Such identified and isolated polynucleotides, in turn, can be expressed (using procedures similar to those described in preceding examples) to produce recombinant polypeptides corresponding to non-human mammalian forms of VEGF-C.

The mouse and human VEGF-C sequences were used to design probes for isolating a quail VEGF-C cDNA from a quail cDNA library. A fragment of the human VEGF-C cDNA comprising nucleotides 495–1670 of SEQ ID NO: 7 was obtained by PCR amplification, cloned into the pCRII vector (Invitrogen) according to the manufacturer's instructions, and amplified. The insert was isolated by Eco RI digestion and preparative gel electrophoresis and then labelled using radioactive dCTP and random priming. A cDNA library made from quail embryos of stage E-4 in pcDNA-1 vector (Invitrogen) was then screened using this probe. About 200,000 colonies were plated and filter replicas were hybridized with the radioactive probe. Nine positive clones were identified and secondarily plated. Two of the nine clones hybridized in secondary screening. The purified clones (clones 1 and 14) had approximately 2.7 kb Eco RI inserts. Both clones were amplified and then sequenced using the T7 and SP6 primers (annealing to the vector). In addition, an internal Sph I restriction endonuclease cleavage site was identified about 1.9 kb from the T7 primer side of the vector and used for subcloning 5'- and 3'- Sph I fragments, followed by sequencing from the Sph I end of the subclones. The sequences obtained were identical from both clones and showed a high degree of similarity to the human VEGF-C coding region. Subsequently, walking primers were made in both directions and double-stranded sequencing was completed for 1743 base pairs, including the full-length open reading frame.

The cDNA sequence obtained includes a long open reading frame and 5' untranslated region. The DNA and deduced amino acid sequences for the quail CDNA are set forth in SEQ ID NOs: 12 and 13, respectively. Studies performed with the putative quail VEGF-C cDNA have shown that its protein product is secreted from transfected cells and interacts with avian VEGFR-3 and VEGFR-2, further confirming the conclusion that the cDNA encodes a quail VEGF-C protein. As shown in FIG. 5, the human, murine, and avian (quail) VEGF-C precursor amino acid sequences share a significant degree of conservation. This high degree of homology permits the isolation of VEGF-C encoding sequences from other species, especially vertebrate species, and more particularly mammalian and avian species, using polynucleotides of the present invention as probes and using standard molecular biological techniques such as those described herein.

EXAMPLE 21

N-terminal Peptide Sequence Analyses of Recombinant VEGF-C

Figure 6A:
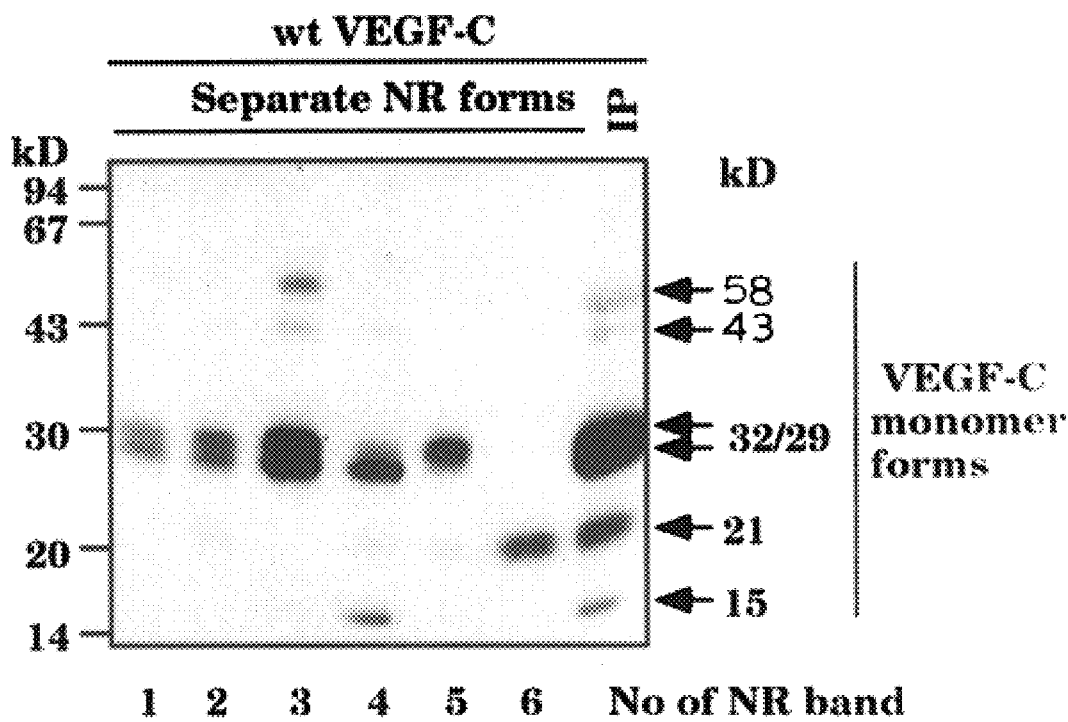

Cells (293 EBNA) transfected with VEGF-C CDNA (see Example 13) secrete several forms of recombinant VEGF-C (FIG. 6A, lane IP). In the absence of alkylation, the three major, proteolytically-processed forms of VEGF-C migrate in SDS-PAGE as proteins with apparent molecular masses of 32/29 kD (doublet), 21 kD and 15 kD. Two minor polypeptides exhibit approximate molecular masses of 63 and 52 kD, respectively. More precise size measurements (using SDS-PAGE under reducing conditions) revealed that the molecular masses of the VEGF-C forms that were initially estimated as 63, 52, 32, 23, and 14 kD (using SDS-PAGE under reducing conditions and a different set of size standards) are approximately 58, 43, 31, 29, 21, and 15 kD, respectfully (the initial measurements in most cases falling within acceptable 10% error of the more precise measurements). One of these polypeptides is presumably a glycosylated and non-processed form; the other polypeptide is presumably glycosylated and partially processed.

To determine sites of proteolytic cleavage of the VEGF-C precursor, an immunoaffinity column was used to purify VEGF-C polypeptides from the conditioned medium of 293 EBNA cells transfected with VEGF-C cDNA. To prepare the immunoaffinity column, a rabbit was immunized with a synthetic peptide corresponding to amino acids 104–120 of SEQ ID NO: 8: $H_2$N-EETIKFAAAHYNTEILK (see PAM126 in Example 19). The IgG fraction was isolated from the serum of the immunized rabbit using protein A Sepharose (Pharmacia). The isolated IgG fraction was covalently bound to CNBr-activated Sepharose CL-4B (Pharmacia) using standard techniques at a concentration of 5 mg IgG/ml of Sepharose. This immunoaffinity matrix was used to isolate processed VEGF-C from 1.2 liters of the conditioned medium (CM).

The purified material eluted from the column was analyzed by gel electrophoresis and Western blotting. Fractions containing VEGF-C polypeptides were combined, dialyzed against 10 mM Tris HCl, vacuum-dried, electrotransferred to Immobilon-P (polyvinylidene difluoride or PVDF) transfer membrane (Millipore, Marlborough, Mass.) and subjected to N-terminal amino acid sequence analysis.

The polypeptide band of 32 kD yielded two distinct sequences: $NH_2$-FESGLDLSDA . . . and $NH_2$- AVVMTQTPAS . . . (SEQ ID NO: 14), the former corresponding to the N-terminal part of VEGF-C after cleavage of the signal peptide, starting from amino acid 32 (SEQ ID NO: 8), and the latter corresponding to the kappa-chain of IgG, which was present in the purified material due to "leakage" of the affinity matrix during the elution procedure.

In order to obtain the N-terminal peptide sequence of the 29 kD form of VEGF-C, a construct (VEGF-C NHis) encoding a VEGF-C mutant was generated. In particular, the construct encoded a VEGF-C mutant that fused a 6×His tag to the N-terminus of the secreted precursor (i.e., between amino acids 31 and 33 in SEQ ID NO: 8). The phenylalanine at position 32 was removed to prevent possible cleavage of the tag sequence during secretion of VEGF-C. The VEGF-C NHis construct was cloned into pREP7 as a vector; the construction is described more fully in Example 28, below.

Figure 11A:
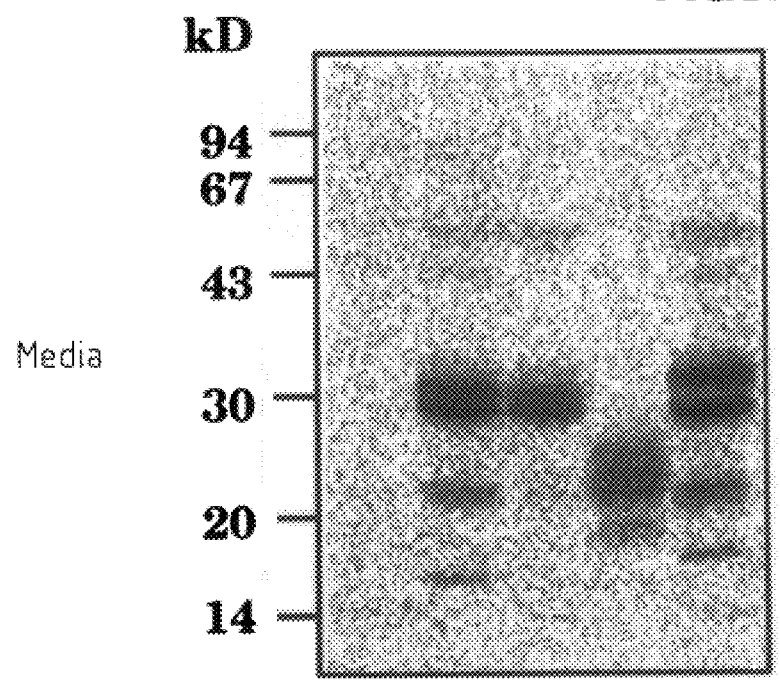
FIGS. 11A–B present gel electrophoretograms of human VEGF-C (wt) and VEGF-C mutants secreted (FIG. 11A) or retained (FIG. 11B) by the host 293 EBNA cells. Mock (M) transfected cells served as a control. Molecular weight markers are indicated on the left in kilodaltons (kD).
Figure 11B:
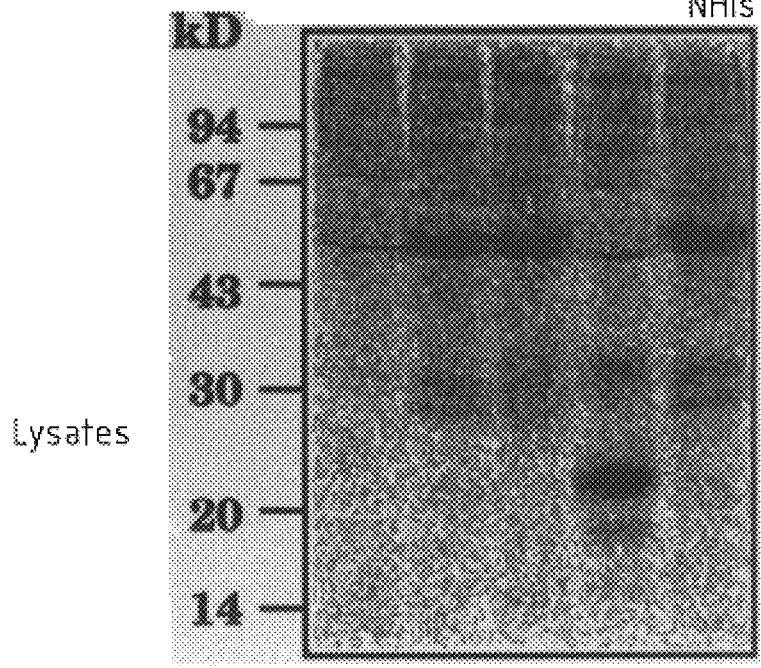

The calcium phosphate co-precipitation technique was used to transfect VEGF-C NHis into 293 EBNA cells. Cells were incubated in DMEM/10% fetal calf serum in 15 cm cell culture dishes (a total of 25 plates). The following day, the cells were reseeded into fresh culture dishes (75 plates) containing the same medium and incubated for 48 hours. Cell layers were then washed once with PBS and DMEM medium lacking FCS was added. Cells were incubated in this medium for 48 hours and the medium was collected, cleared by centrifugation at 5000×g and concentrated 500× using an Ultrasette Tangential Flow Device (Filtron, Northborough, Mass.), as described in Example 5 above. VEGF-C NHis was purified from the concentrated conditioned medium using TALON™ Metal Affinity Resin (Clontech Laboratories, Inc.) and the manufacturer's protocol for native protein purification using imidazole-containing buffers. The protein was eluted with a solution containing 20 mM Tris-HCl (pH 8.0), 100 mM NaCl, and 200 mM imidazole. The eluted fractions containing purified VEGF-C NHis were detected by immunoblotting with Antiserum 882 (antiserum from rabbit 882, immunized with the PAM-126 polypeptide). Fractions containing VEGF-C NHis were combined, dialyzed and vacuum-dried. As can be seen in FIG. 11, due to the presence of the 6×His tag at the N-terminus of this form of VEGF-C, the upper component of the major doublet of the VEGF-CNHis migrates slightly slower than the 32 kD form of wild type VEGF-C, thereby improving the separation of the VEGF-CNHis 32 kD mutant from the 29 kD band using SDS-PAGE. Approximately 15 μg of the purified VEGF-C were subjected to SDS-PAGE under reducing conditions, electrotransferred to Immobilon-P (PVDF) transfer membrane (Millipore, Inc., Marlborough, Mass.) and the band at 29 kD was subjected to N-terminal amino acid sequence analysis. This sequence analysis revealed an N-terminal sequence of $H_2$N-SLPAT . . . , corresponding to amino acids 228–232 of VEGF-C (SEQ ID NO: 8).

The polypeptide band of 21 kD yielded the sequence $H_2$N-AHYNTEILKS . . . , corresponding to an amino-terminus starting at amino acid 112 of SEQ ID NO: 8. Thus, the proteolytic processing site which results in the 21 kD form of VEGF-C produced by transfected 293 EBNA cells apparently occurs nine amino acid residues downstream of the cleavage site which results in the 23 kD form of VEGF-C secreted by PC-3 cells.

The N-terminus of the 15 kD form was identical to the N-terminus of the 32 kD form ($NH_2$-FESGLDLSDA . . . ). The 15 kD form was not detected when recombinant VEGF-C was produced by COS cells. This suggests that production of this form is cell lineage specific.

EXAMPLE 22

Dimeric and Monomeric Formis of VEGF-C

The composition of VEGF-C dimers was analyzed as follows. Cells (293 EBNA cells), transfected with the pREP7 VEGF-C vector as described in Example 11, were metabolically labelled with Pro-mix L- [$^{35}$S] labelling mix (Amersham Corp.) to a final concentration of 100 µCi/ml.

In parallel, a VEGF-C mutant, designated "R102S", was prepared and analyzed. To prepare the DNA encoding VEGF-C-R102S, the arginine codon at position 102 of SEQ ID NO: 8 was replaced with a serine codon. This VEGF-C-R102S-encoding DNA, in a PREP7 vector, was transfected into 293 EBNA cells and expressed as described above. VEGF-C polypeptides were immunoprecipitated using antisera 882 (obtained by immunization of a rabbit with a polypeptide corresponding to residues 104–120 of SEQ ID NO: 8 (see previous Example)) and antisera 905 (obtained by immunization of a rabbit with a polypeptide corresponding to a portion of the prepro- VEGF-C leader: H$_2$N-ESGLDLSDAEPDAGEATAYASK (residues 33 to 54 of SEQ ID NO: 8).

The immunoprecipitates from each cell culture were subjected to SDS-PAGE under non-denaturing conditions (FIG. 6B). Bands 1–6 were cut out from the gel, soaked for 30 minutes in 1×gel-loading buffer containing 200 mM β-mercaptoethanol, and individually subjected to SDS-PAGE under denaturing conditions (FIGS. 6A and 6C, lanes 1–6).

Figure 6C:
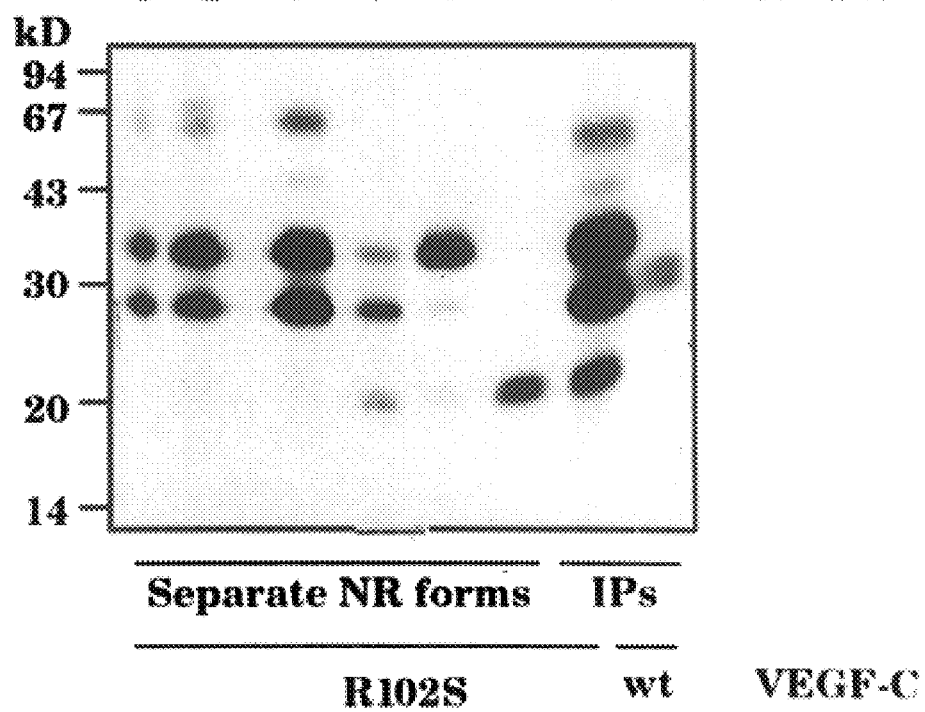

As can be seen from FIGS. 6A–C, each high molecular weight form of VEGF-C (FIG. 6B, bands 1–4) consists of at least two monomers bound by disulfide bonds (Compare FIGS. 6A and 6C, lanes 1–4, in the reducing gels). The main component of bands 1–3 is the doublet of 32/29 kD, where both proteins are present in an equimolar ratio. The main fraction of the 21 kD form is secreted as either a monomer or as a homodimer connected by means other than disulfide bonds (bands 6 and lanes 6 in FIGS. 6A–C).

The R102S mutation creates an additional site for N-linked glycosylation in VEGF-C at the asparagine residue at position 100 in SEQ ID NO: 8. Glycosylation at this additional glycosylation site increases the apparent molecular weight of polypeptides containing the site, as confirmed in FIGS. 6A–C and FIGS. 7A–B. The additional glycosylation lowers the mobility of forms of VEGF-C-R102S that contain the additional glycosylation site, when compared to polypeptides of similar primary structure corresponding to VEGF-C. FIGS. 6A–C and FIGS. 7A–B reveal that the VEGF-C-R102S polypeptides corresponding to the 32 kD and 15 kD forms of wt VEGF-C exhibit increased apparent molecular weights, indicating that each of these polypeptides contains the newly introduced glycosylation site. In particular, the VEGF-C-R102S polypeptide corresponding to the 15 kD polypeptide from VEGF-C comigrates on a gel with the 21 kD form of the wild type (wt) VEGF-C, reflecting a shift on the gel to a position corresponding to a greater apparent molecular weight. (Compare lanes 4 in FIGS. 6A and 6C). The mobility of the 58 kD form of VEGF-C was slowed to 64 kD by the R102S mutation, indicating that this form contains the appropriate N-terminal peptide of VEGF-C. The mobilities of the 21, 29, and 43 kD forms were unaffected by the R102S mutation, suggesting that these polypeptides contain peptide sequences located C-terminally of R$_{102}$.

In a related experiment, another VEGF-C mutant, designated "R226,227S," was prepared and analyzed. To prepare a DNA encoding VEGF-C-R226,227S, the arginine codons at positions 226 and 227 of SEQ ID NO: 8 were replaced with serine codons by site-directed mutagenesis. The resultant DNA was transfected into 293 EBNA cells as described above and expressed and analyzed under the same conditions as described for VEGF-C and VEGF-C-R102S. In the conditioned medium from the cells expressing VEGF-C-R226,227S, no 32 kD form of VEGF-C was detected. These results indicate that a C-terminal cleavage site of wild-type VEGF-C is adjacent to residues 226 and 227 of SEQ ID NO: 8, and is destroyed by the mutation of the arginines to serines. Again, the mobility of the 29 kD component of the doublet was unchanged (FIGS. 7A–B).

Taken together, these data indicate that the major form of the processed VEGF-C is a heterodimer consisting of (1) a polypeptide of 32 kD containing amino acids 32–227 of the prepro-VEGF-C (amino acids 32 to 227 in SEQ ID NO: 8) attached by disulfide bonds to (2) a polypeptide of 29 kD beginning with amino acid 228 in SEQ ID NO: 8. These data are also supported by a comparison of the pattern of immunoprecipitated, labelled VEGF-C forms using antisera 882 and antisera 905.

Figure 8A:
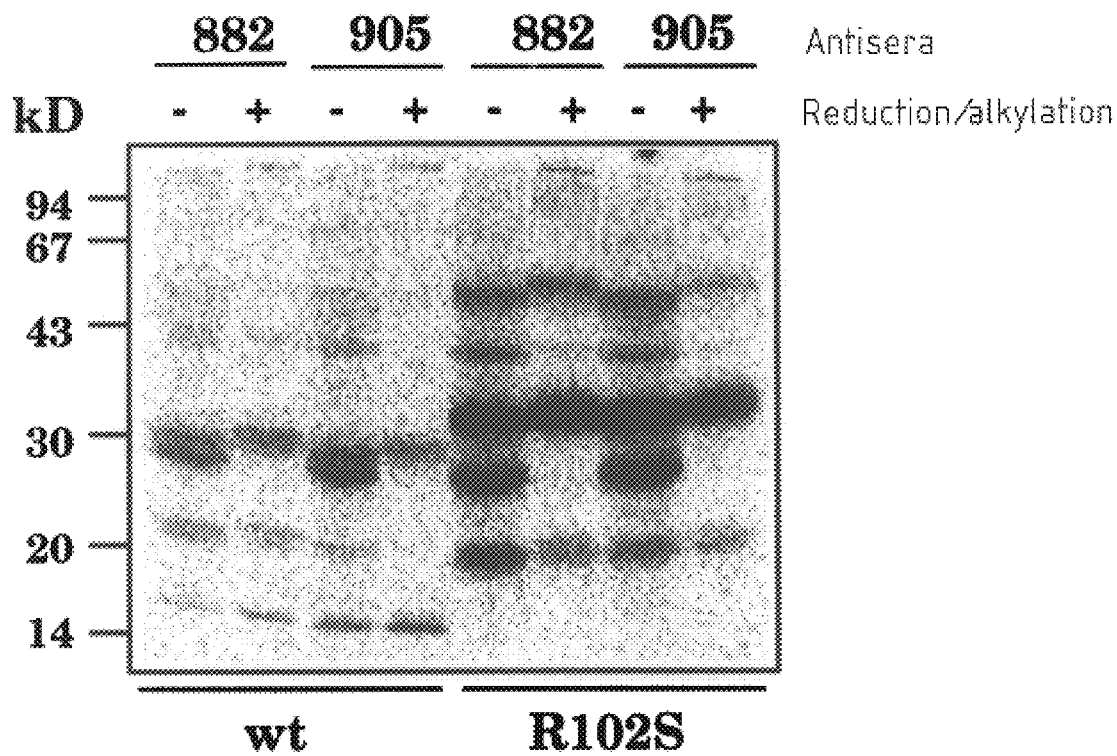
FIGS. 8A–B present a comparison of the pattern of immunoprecipitated, labelled VEGF-C forms using antisera 882 and antisera 905. Adjacent lanes contain immunoprecipitates that were (lanes marked +) or were not (lanes marked –) subjected to reduction and alkylation.
Figure 8B:
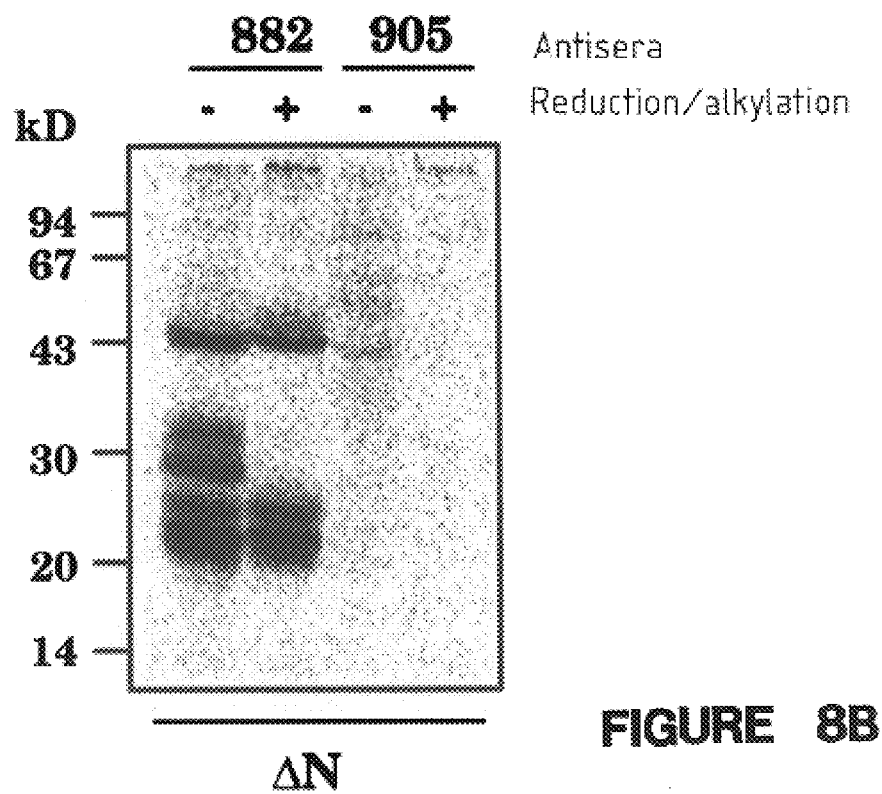

When VEGF-C immunoprecipitation was carried out using conditioned medium, both antisera (882 and 905) recognized some or all of the three major processed forms of VEGF-C (32/29 kD, 21 kD and 15 kD). When the conditioned medium was reduced by incubation in the presence of 10 mM dithiothreitol for two hours at room temperature with subsequent alkylation by additional incubation with 25 mM iodoacetamide for 20 minutes at room temperature, neither antibody precipitated the 29 kD component, although antibody 882 still recognized polypeptides of 32 kD, 21 kD and 15 kD. In subsequent experiments it was observed that neither antibody was capable of immunoprecipitating the 43 kD form. These results are consistent with the nature of the oligopeptide antigen used to elicit the antibodies contained in antisera 882, an oligopeptide containing amino acid residues 104–120 of SEQ ID NO: 8. On the other hand, antisera 905 recognized only the 32 kD and 15 kD polypeptides, which include sequence of the oligopeptide (amino acids 33 to 54 of SEQ ID NO: 8) used for immunization to obtain antisera 905. Taking into account the mobility shift of the 32 kD and 15 kD forms, the immunoprecipitation results with the R102S mutant were similar (FIGS. 8A–B). The specificity of antibody 905 is confirmed by the fact that it did not recognize a VEGF-C ΔN form wherein the N-terminal propeptide spanning residues 32–102 of the unprocessed polypeptide had been deleted (FIG. 8B).

The results of these experiments also demonstrate that the 21 kD polypeptide is found (1) in heterodimers with other molecular forms (see FIGS. 6A–C and FIGS. 7A–B), and (2) secreted as a monomer or a homodimer held by bonds other than disulfide bonds (FIGS. 6A and 6B, lanes 6).

The experiments disclosed in this example demonstrate that several forms of VEGF-C exist. A variety of VEGF-C monomers were observed and these monomers can vary depending on the level and pattern of glycosylation. In addition, VEGF-C was observed as a multimer, for example a homodimer or a heterodimer. The processing of VEGF-C is schematically presented in FIG. 9 (disulfide bonds not shown). All forms of VEGF-C are within the scope of the present invention.

EXAMPLE 23

In Situ Hybridization of Mouse Embryos

To analyze VEGF-C mRNA distribution in different cells and tissues, sections of 12.5 and 14.5-day post-coitus (p.c.) mouse embryos were prepared and analyzed via in situ hybridization using labeled VEGF-C probes. In situ hybridization of tissue sections was performed as described in Vastrik et al., *J. Cell Biol.*, 128:1197–1208 (1995). A mouse VEGF-C antisense RNA probe was generated from linearized pBluescript II SK+ plasmid (Stratagene Inc., La Jolla, Calif.), containing a CDNA fragment corresponding to nucleotides 499–979 of a mouse VEGF-C CDNA (SEQ ID NO: 10). Radiolabeled RNA was synthesized using T7 polymerase and [$^{35}$S]-UTP (Amersham). Mouse VEGF-B antisense and sense RNA probes were synthesized in a similar manner from linearized PCRII plasmid containing the mouse VEGF-B CDNA insert as described Olofsson et al., *Proc. Natl. Acad. Sci. (USA)*, 93:2576–2581 (1996). The high stringency wash was for 45 minutes at 65° C. in a solution containing 30 mM dithiothreitol (DTT) and 4×SSC. The slides were exposed for 28 days, developed and stained with hematoxylin. For comparison, similar sections were hybridized with a VEGFR-3 probe and the 12.5-day p.c. embryos were also probed for VEGF-B MRNA.

Darkfield and lightfield photomicrographs from these experiments are presented in commonly-owned PCT patent application PCT/FI96/00427, filed Aug. 01, 1996, incorporated by reference herein. Observations from the photomicrographs are summarized below. In a 12.5 day p.c. embryo, a parasagittal section revealed that VEGF-C mRNA was particularly prominent in the mesenchyme around the vessels surrounding the developing metanephros. In addition, hybridization signals were observed between the developing vertebrae, in the developing lung mesenchyme, in the neck region and developing forehead. The specificity of these signals was evident from the comparison with VEGF-B expression in an adjacent section, where the myocardium gave a very strong signal and lower levels of VEGF-B mRNA were detected in several other tissues. Both genes appear to be expressed in between the developing vertebrae, in the developing lung, and forehead. Hybridization of the VEGF-C sense probe showed no specific expression within these structures.

Studies also were conducted of the expression patterns of VEGF-C and VEGFR-3 in 12.5 day p.c. mouse embryos in the jugular region, where the developing dorsal aorta and cardinal vein are located. This is the area where the first lymphatic vessels sprout from venous sac-like structures according to the long-standing theory of Sabin, *Am. J. Anat.*, 9:43–91 (1909). An intense VEGF-C signal was detected in the mesenchyme surrounding the developing venous sacs which also were positive for VEGFR-3.

The mesenterium supplies the developing gut with blood and contains developing lymphatic vessels. The developing 14.5 day p.c. mesenterium is positive for VEGF-C mRNA, with particularly high expression in connective tissue surrounding certain vessels. The adjacent mesenterial VEGFR-3 signals that were observed originate from small capillaries of the mesenterium. Therefore, there appears to be a paracrine relationship between the production of the mRNAs for VEGF-C and its receptor. This data indicates that VEGF-C is expressed in a variety of tissues. Moreover, the pattern of expression is consistent with a role for VEGF-C in venous and lymphatic vessel development. Further, the data reveals that VEGF-C is expressed in non-human animals.

EXAMPLE 24

Analysis of VEGF, VEGF-B, and VEGF-C mRNA Expression in Fetal and Adult Tissues

A human fetal tissue Northern blot containing 2 μg of polyadenylated RNAs from brain, lung, liver and kidney (Clontech Inc.) was hybridized with a pool of the following probes: a human full-length VEGF-C CDNA insert (Genbank Acc. No. X94216), a human VEGF-B$_{167}$ cDNA fragment (nucleotides 1-382, Genbank Acc. No. U48800) obtained by PCR amplification; and a human VEGF 581 bp cDNA fragment covering base pairs 57–638 (Genbank Acc. No. X15997). Blots were washed under stringent conditions, using techniques standard in the art.

Mouse embryo multiple tissue Northern blot (Clontech Inc.) containing 2 μg of polyadenylated RNAs from 7, 11, 15 and 17 day postcoital (p.c.) embryos was hybridized with mouse VEGF-C cDNA fragment (base pairs 499–656). A mouse adult tissue Northern blot was hybridized with the probes for human VEGF, VEGF-B$_{167}$, VEGF-C and with a VEGFR-3 CDNA fragment (nucleotides 1-595; Genbank Acc. No. X68203).

In adult mouse tissues, both 2.4 kb and 2.0 kb MRNA signals were observed with the VEGF-C probe, at an approximately 4:1 ratio. The most conspicuous signals were obtained from lung and heart RNA, while kidney, liver, brain, and skeletal muscle had lower levels, and spleen and testis had barely visible levels. As in the human tissues, VEGF mRNA expression in adult mice was most abundant in lung and heart RNA, whereas the other samples showed less coordinate regulation with VEGF-C expression. Skeletal muscle and heart tissues gave the highest VEGF-B MRNA levels from adult mice, as previously reported Olofsson et al., *Proc. Natl. Acad. Sci. (USA)*, 93:2576–2581 (1996). Comparison with VEGFR-3 expression showed that the tissues where VEGF-C is expressed also contain MRNA for its cognate receptor tyrosine kinase, although in the adult liver VEGFR-3 MRNA was disproportionally abundant.

To provide a better insight into the regulation of the VEGF-C mRNA during embryonic development, polyadenylated RNA isolated from mouse embryos of various gestational ages (7, 11, 15, and 17 day p.c.) was hybridized with the mouse VEGF-C probe. These analyses showed that the amount of 2.4 kb VEGF-C MRNA is relatively constant throughout the gestational period.

EXAMPLE 25

Regulation of mRNAs for VEGF Family Members by Serum, Interleukin-1 and Dexamethasone in Human Fibroblasts in Culture Human IMR-90 fibroblasts were grown in DMEM medium containing 10% FCS and antibiotics. The cells were grown to 80% confluence, then starved for 48 hours in 0.5% FCS in DMEM. Thereafter, the growth medium was changed to DMEM containing 5% FCS, with or without 10 ng/ml interleukin-1 (IL-1) and with or without 1 mM dexamethasone. The culture plates were incubated with these additions for the times indicated, and total cellular RNA was isolated using the TRIZOL kit (GIBCO-BRL). About 20 μg of total RNA from each sample was electrophoresed in 1.5% formaldehyde-agarose gels as described in Sambrook et al., supra (1989). The gel was used for Northern blotting and hybridization with radiolabeled insert DNA from the human VEGF clone (a 581 bp cDNA covering bps 57–638, Genbank Acc. No. 15997) and a human VEGF-B$_{167}$ cDNA fragment (nucleotides 1-382, Genbank Acc. No. U48800). Subsequently, the Northern blots were probed with radiolabelled insert from the VEGF-C cDNA plasmid. Primers were labelled using a standard technique involving enzymatic extension reactions of random primers, as would be understood by one of ordinary skill in the art.

The Northern blot analyses revealed that very low levels of VEGF-C and VEGF are expressed by the starved IMR-90 cells as well as cells after 1 hour of stimulation. In contrast, abundant VEGF-B mRNA signal was visible under these conditions. After 4 hours of serum stimulation, there was a strong induction of VEGF-C and VEGF mRNAs, which were further increased in the IL-1 treated sample. The effect of IL-1 seemed to be abolished in the presence of dexamethasone. A similar pattern of enhancement was observed in the 8 hour sample, but a gradual down-regulation of all signals was observed for both RNAs in the 24 hour and 48 hour samples. In contrast, VEGF-B mRNA levels remained constant and thus showed remarkable stability throughout the time period. The results are useful in guiding efforts to use VEGF-C and its fragments, its antagonists, and anti-VEGF-C antibodies in methods for treating a variety of disorders.

EXAMPLE 26

Expression and Analysis of Recombinant Murine VEGF-C

The mouse VEGF-C CDNA was expressed as a recombinant protein and the secreted protein was analyzed for its receptor binding properties. The binding of mouse VEGF-C to the human VEGFR-3 extracellular domain was studied by using media from Bosc23 cells transfected with mouse VEGF-C cDNA in a retroviral expression vector.

The 1.8 kb mouse VEGF-C cDNA was cloned as an EcoRI fragment into the retroviral expression vector pBabe-puro containing the SV40 early promoter region [Morgenstern et al., Nucl. Acids Res., 18:3587–3595 (1990)], and transfected into the Bosc23 packaging cell line [Pearet et al., Proc. Natl. Acad. Sci. (USA), 90:8392–8396 (1994)] by the calcium-phosphate precipitation method. For comparison, Bosc23 cells also were transfected with the previously-described human VEGF-C construct in the pREP7 expression vector. The transfected cells were cultured for 48 hours prior to metabolic labelling. Cells were changed into DMEM medium devoid of cysteine and methionine, and, after 45 minutes of preincubation and medium change, Pro-mix™ L- [$^{35}$S] in vitro cell labelling mix (Amersham Corp.), in the same medium, was added to a final concentration of about 120 $\mu$Ci/ml. After 6 hours of incubation, the culture medium was collected and clarified by centrifugation.

For immunoprecipitation, 1 ml aliquots of the media from metabolically-labelled Bosc23 cells transfected with empty vector or mouse or human recombinant VEGF-C, respectively, were incubated overnight on ice with 2 $\mu$l of rabbit polyclonal antiserum raised against an N-terminal 17 amino acid oligopeptide of mature human VEGF-C (H$_2$N-EETIKFAAAHYNTEILK) (SEQ ID NO: 8, residues 104–120). Thereafter, the samples were incubated with protein A sepharose for 40 minutes at 4° C. with gentle agitation. The sepharose beads were then washed twice with immunoprecipitation buffer and four times with 20 mM Tris-HCl, pH 7.4. Samples were boiled in Laemmli buffer and analyzed by 12.59 sodium dodecyl sulfate polyacrylamide gel electrophoresis (SDS-PAGE).

Immunoprecipitation of VEGF-C from media of transfected and metabolically-labelled cells revealed bands of approximately 30–32×10$^3$ M$_T$ (a doublet) and 22–23×10$^3$ M$_T$ in 12.5% SDS-PAGE. These bands were not detected in samples from nontransfected or mock-transfected cells. These results show that antibodies raised against human VEGF-C recognize the corresponding mouse ligand.

For receptor binding experiments, 1 ml aliquots of media from metabolically-labelled Bosc23 cells were incubated with VEGFR-3 extracellular domain (see Example 3), covalently coupled to sepharose, for 4 hours at 4° C. with gentle mixing. The sepharose beads were washed four times with ice-cold phosphate buffered saline (PBS), and the samples were analyzed by gel electrophoresis as described in Joukov et al., EMBO J., 15:290–298 (1996).

Similar 30–32×10$^3$ M$_T$ doublet and 22–23×10$^3$ M$_T$ polypeptide bands were obtained in the receptor binding assay as compared to the immunoprecipitation assay. Thus, mouse VEGF-C binds to human VEGFR-3. The slightly faster mobility of the mouse VEGF-C polypeptides that was observed may be caused by the four amino acid residue difference observed in sequence analysis (residues H88–E91, FIG. 10).

The capacity of mouse recombinant VEGF-C to induce VEGFR-3 autophosphorylation was also investigated. For the VEGFR-3 receptor stimulation experiments, subconfluent NIH 3T3-Flt4 cells, Pajusola et al., Oncogene, 9:3545–3555 (1994), were starved overnight in serum-free medium containing 0.2% BSA. In general, the cells were stimulated with the conditioned medium from VEGF-C vector-transfected cells for 5 minutes, washed three times with cold PBS containing 200 $\mu$M vanadate, and lysed in RIPA buffer for immunoprecipitation analysis. The lysates were centrifuged for 25 minutes at 16000×g and the resulting supernatants were incubated for 2 hours on ice with the specific antisera, followed by immunoprecipitation using protein A-sepharose and analysis in 7% SDS-PAGE. Polypeptides were transferred to nitrocellulose and analyzed by immunoblotting using anti-phosphotyrosine (Transduction Laboratories) and anti-receptor antibodies, as described by Pajusola et al., Oncogene, 9:3545–3555 (1994). Filter stripping was carried out at 50° C. for 30 minutes in 100 mM 2-mercaptoethanol, 2% SDS, 62.5 mM Tris-HCl, pH 6.7, with occasional agitation. The results of the experiment demonstrated that culture medium containing mouse VEGF-C stimulates the autophosphorylation of VEGFR-3 to a similar extent as human baculoviral VEGF-C or the tyrosyl phosphatase inhibitor pervanadate.

Mouse VEGF-C appeared to be a potent inducer of VEGFR-3 autophosphorylation, with the 195×10$^3$ M$_T$ precursor and proteolytically-cleaved 125×10$^3$ M$_T$ tyrosine kinase polypeptides of the receptor (Pajusola et al., Oncogene, 9:3545–3555 (1994)), being phosphorylated.

VEGFR-2 stimulation was studied in subconfluent porcine aortic endothelial (PAE) cells expressing Kdr (VEGFR-2) (PAE-VEGFR-2) [Waltenberger et al., J. Biol. Chem., 269:26988–26995 (1994)], which were starved overnight in serum-free medium containing 0.2% BSA. Stimulation was carried out and the lysates prepared as described above. For receptor immunoprecipitation, specific antiserum for VEGFR-2 [Waltenberger et al., J. Biol. Chem., 269:26988–26995 (1994)] was used. The immunoprecipitates were analyzed as described for VEGFR-3 in 7% SDS-PAGE followed by Western blotting with anti-phosphotyrosine antibodies, stripping of the filter, and re-probing it with anti-VEGFR-2 antibodies (Santa Cruz). VEGFR-2 stimulation was first tried with unconcentrated medium from cells expressing recombinant VEGF-C, but immunoblotting analysis did not reveal any receptor autophosphorylation.

To further determine whether mouse recombinant VEGF-C can also induce VEGFR-2 autophosphorylation as observed for human VEGF-C, PAE cells expressing VEGFR-2 were stimulated with tenfold concentrated medium from cultures transfected with mouse VEGF-C expression vector and autophosphorylation was analyzed. For comparison, cells treated with tenfold concentrated medium containing human recombinant VEGF-C (Joukov et al., (1996)), unconcentrated medium from human VEGF-C baculovirus infected insect cells, or pervanadate (a tyrosyl phosphatase inhibitor) were used. In response to human baculoviral VEGF-C as well as pervanadate treatment, VEGFR-2 was prominently phosphorylated, whereas human and mouse recombinant VEGF-C gave a weak and barely detectable enhancement of autophosphorylation, respectively. Media from cell cultures transfected with empty vector or VEGF-C cloned in the antisense orientation did not induce autophosphorylation of VEGFR-2. Therefore, mouse VEGF-C binds to VEGFR-3 and activates this receptor at a much lower concentration than needed for the activation of VEGFR-2. Nevertheless, the invention comprehends methods for using the materials of the invention to take advantage of the interaction of VEGF-C with VEGFR-2, in addition to the interaction between VEGF-C and VEGFR-3.

EXAMPLE 27

VEGF-C E104–E213 Fragment Expressed in Pichia Yeast Stimulates Autophosphorylation of Flt4 (VEGFR-3) and KDR (VEGFR-2)

A truncated form of human VEGF-C cDNA was constructed wherein (1) the sequence encoding residues of a putative mature VEGF-C amino terminus $H_2N$-E(104)ETIK (SEQ ID NO: 8, residues 104 et seq.) was fused in-frame to the yeast PHO1 signal sequence (Invitrogen Pichia Expression Kit, Catalog #K1710-01), and (2) a stop codon was introduced after amino acid 213 ($H_2N$- . . . RCMS; i.e., after codon 213 of SEQ ID NO: 7). The resultant truncated cDNA construct was then inserted into the *Pichia pastoris* expression vector pHIL-S1 (Invitrogen). For the cloning, an internal BglII site in the VEGF-C coding sequence was mutated without change of the encoded polypeptide sequence.

This VEGF-C expression vector was then transfected into Pichia cells and positive clones were identified by screening for the expression of VEGF-C protein in the culture medium by Western blotting. One positive clone was grown in a 50 ml culture, and induced with methanol for various periods of time from 0 to 60 hours. About 10 µl of medium was analyzed by gel electrophoresis, followed by Western blotting and detection with anti-VEGF-C antiserum, as described above. An approximately 24 kD polypeptide (band spreading was observed due to glycosylation) accumulated in the culture medium of cells transfected with the recombinant VEGF-C construct, but not in the medium of mock-transfected cells or cells transfected with the vector alone.

The medium containing the recombinant VEGF-C protein was concentrated by Centricon 30 kD cutoff ultrafiltration and used to stimulate NIH 3T3 cells expressing Flt4 (VEGFR-3) and porcine aortic endothelial (PAE) cells expressing KDR (VEGFR-2). The stimulated cells were lysed and immunoprecipitated using VEGFR-specific antisera and the immunoprecipitates were analyzed by Western blotting using anti-phosphotyrosine antibodies, chemiluminescence, and fluorography. As a positive control for maximal autophosphorylation of the VEGFRs, vanadate ($VO_4$) treatment of the cells for 10 minutes was used. Medium from Pichia cultures secreting the recombinant VEGF-C polypeptide induced autophosphorylation of both Flt41 polypeptides of 195 kD and 125 kD as well as the KDR polypeptide of about 200 kD. Vanadate, on the other hand, induces heavy tyrosyl phosphorylation of the receptor bands in addition to other bands probably coprecipitating with the receptors.

These results demonstrate that a VEGF-homologous domain of VEGF-C consisting of amino acid residues 104E–213S (SEQ ID NO: 8, residues 104–213) can be recombinantly produced in yeast and is capable of stimulating the autophosphorylation of Flt4 (VEGFR-3) and KDR (VEGFR-2). Recombinant VEGF-C fragments such as the fragment described herein, which are capable of stimulating Flt4 or KDR autophosphorylation are intended as aspects of the invention; methods of using these fragments are also within the scope of the invention.

EXAMPLE 28

Properties of the Differentially Processed Forms of VEGF-C

The following oligonucleotides were used to generate a set of VEGF-C variants and analogs:

5'- TCTCTTCTGTGCTTGAGTTGAG-3' (SEQ ID NO: 15), used to generate VEGF-C R102S (arginine mutated to serine at position 102 (SEQ ID NO: 8));

5'-TCTCTTCTGTCCCTGAGTTGAG-3' (SEQ ID NO: 16), used to generate VEGF-C R102G (arginine mutated to glycine at position 102 (SEQ ID NO: 8));

5'-TGTGCTGCAGCAAATTTTATAGTCTCTTCTGT-GGCGGCGGC GGCGGCGGGCGCCTCGCGAGGACC-3' (SEQ ID NO: 17), used to generate VEGF-C ΔN (deletion of N-terminal propeptide corresponding to amino acids 32–102 (SEQ ID NO: 8));

5'- CTGGCAGGGAACTGCTAATAATGGAATGAA-3' (SEQ ID NO: 18), used to generate VEGF-C R226,227S (arginine codons mutated to serines at positions 226 and 227 (SEQ ID NO: 8));

5'-GGGCTCCGCGTCCGAGAGGTCGAGTCCGGA-CTCGTGATGGT GATGGTGATGGGCGG-CGGCGGCGGCGGGCGCCTCGCGAGGACC-3' (SEQ ID NO: 19), used to generate VEGF-C NHis (this construct encodes a polypeptide with a 6×His tag fused to approximately the N-terminus of the secreted precursor, as described in Example 21 (amino acid 33 of SEQ ID NO: 8)).

Some of the foregoing VEGF-C mutant constructs were further modified to obtain additional constructs. For example, VEGF-C R102G in pALTER (Promega) and oligonucleotide 5'-GTATTATAATGTCCTCCACCAAATTTTATAG-3' (SEQ ID NO: 20) were used to generate VEGF-C 4G, which encodes a polypeptide with four point mutations: R102G, A110G, A111G, and A112G (alanines mutated to glycines at positions 110–112 (SEQ ID NO: 8). These four mutations are adjacent to predicted sites of cleavage of VEGF-C expressed in PC-3 and recombinantly expressed in 293 EBNA cells.

Another construct was created using VEGF-C ΔN and oligonucleotide 5'-GTTCGCTGCCTGACACTGTGGTAGTGTTGCTGGC GGCCGCTAGTGATGGTGATGGTGAT-GAATAATGGAATGAACTTGTCTGTAAACATCC AG-3' (SEQ ID NO: 21) to generate VEGF-C ΔNΔCHis. This construct encodes a polypeptide with a deleted N-terminal propeptide (amino acids 32–102); a deleted C-terminal propeptide (amino acids 226–419 of SEQ ID NO: 8); and an added 6×His tag at the C-terminus.

All constructs were further digested with HindIII and NotI, subcloned into HindIII/NotI digested pREP7 vector, and used to transfect 293 EBNA cells. About 48 hours after transfection, the cells were either metabolically labelled with Pro-mix™ as described above, or starved in serum-free medium for 2 days. Media were then collected and used in subsequent experiments. As can be seen from FIGS. 11A–B, wild type (wt) VEGF-C, VEGF-C NHis and VEGF-C ΔNΔCHis were expressed to similar levels in 293 EBNA cells. At the same time, expression of the VEGF-C 4G polypeptide was considerably lower, possibly due to the changed conformation and decreased stability of the translated product. However, all the above VEGF-C mutants were secreted from the cells (compare FIGS. 11A and 11B).

The conditioned media from the transfected and starved cells were concentrated 5-fold and used to assess their ability to stimulate tyrosine phosphorylation of Flt4 (VEGFR-3) expressed in NIH 3T3 cells and KDR (VEGFR-2) expressed in PAE cells. Wild type (wt) VEGF-C, as well as all three mutant polypeptides, stimulated tyrosine phosphorylation of VEGFR-3. The most prominent stimulation observed was by the short mature VEGF-C ΔNΔCHis. This mutant, as well as VEGF-C NHis, also stimulated tyrosine phosphorylation of VEGFR-2. Thus, despite the fact that a major component of secreted recombinant VEGF-C is a dimer of 32/29 kD, the active part of VEGF-C responsible for its binding to VEGFR-3 and VEGFR-2 is localized between amino acids 102 and 226 (SEQ ID NO: 8) of the VEGF-C precursor. Analysis and comparison of binding properties and biological activities of these VEGF-C proteins and mutants, using assays such as those described herein, will provide data concerning the significance of the observed major 32/29 kD and 21–23 kD VEGF-C processed forms. The data indicate that constructs encoding amino acid residues 103–225 of the VEGF-C precursor (SEQ ID NO: 8) generate a recombinant ligand that is functional for both VEGFR-3 and VEGFR-2.

The data from this and preceding examples demonstrate that numerous fragments of the VEGF-C polypeptide retain biological activity. A naturally occurring VEGF-C polypeptide spanning amino acids 103–226 (or 103–227) of SEQ ID NO: 8, produced by a natural processing cleavage defining the C-terminus, has been shown to be active. Example 27 demonstrates that a fragment with residues 104–213 of SEQ ID NO: 8 retains biological activity.

In addition, data from Example 21 demonstrates that a VEGF-C polypeptide having its amino terminus at position 112 of SEQ ID NO: 8 retains activity. Additional experiments have shown that a fragment lacking residues 1–112 of SEQ ID NO: 8 retains biological activity.

In a related experiment, a stop codon was substituted for the lysine at position 214 of SEQ ID NO: 8 (SEQ ID NO: 7, nucleotides 991–993). The resulting recombinant polypeptide still was capable of inducing Flt4 autophosphorylation, indicating that a polypeptide spanning amino acid residues 113–213 of SEQ ID NO: 8 is biologically active.

Sequence comparisons of members of the VEGF family of polypeptides provides an indication that still smaller fragments of the polypeptide depicted in SEQ ID NO: 8 will retain biological activity. In particular, eight highly conserved cysteine residues of the VEGF family of polypeptides define a region from residues 131–211 of SEQ ID NO: 8 (see FIG. 10) of evolutionary significance; therefore, a polypeptide spanning from about residue 131 to about residue 211 is expected to retain VEGF-C biological activity. In fact, a polypeptide which retains the conserved motif RCXXCC (e.g., a polypeptide comprising from about residue 161 to about residue 211 of SEQ ID NO: 8 is postulated to retain VEGF-C biological activity. To maintain native conformation of these fragments, it may be preferred to retain about 1–2 additional amino acids at the carboxy-terminus and 1–2 or more amino acids at the amino terminus.

Beyond the preceding considerations, evidence exists that smaller fragments and/or fragment analogs which lack the conserved cysteines nonetheless will retain VEGF-C biological activity. Consequently, the materials and methods of the invention include all VEGF-C fragments, variants, and analogs that retain at least one biological activity of VEGF-C, regardless of the presence or absence of members of the conserved set of cysteine residues.

EXAMPLE 29

Expression of Human VEGF-C Under the Human K14 Keratin Promoter in Transgenic Mice Induces Abundant Growth of Lymphatic Vessels in the Skin The Flt4 receptor tyrosine kinase is relatively specifically expressed in the endothelia of lymphatic vessels. Kaipainen et al., *Proc. Natl. Acad. Sci. (USA)*, 92: 3566–3570 (1995). Furthermore, the VEGF-C growth factor stimulates the Flt4 receptor, showing less activity towards the KDR receptor of blood vessels (Joukov et al., *EMBO J.*, 15: 290–298 (1996); See Example 26).

Experiments were conducted in transgenic mice to analyze the specific effects of VEGF-C overexpression in tissues. The human K14 keratin promoter is active in the basal cells of stratified squamous epithelia (Vassar et al., *Proc. Natl. Acad. Sci. (USA)*, 86:1563–1567 (1989)) and was used as the expression control element in the recombinant VEGF-C transgene. The vector containing the K14 keratin promoter is described in Vassar et al., *Genes Dev.*, 5:714–727 (1991) and Nelson et al., *J. Cell Biol.* 97:244–251 (1983).

The recombinant VEGF-C transgene was constructed using the human full length VEGF-C cDNA (GenBank Acc. No. X94216). This sequence was excised from a pCI-neo vector (Promega) with XhoI/NotI, and the resulting 2027 base pair fragment containing the open reading frame and stop codon (nucleotides 352–1611 of SEQ ID NO: 7) was isolated. The isolated fragment was then subjected to an end-filling reaction using the Klenow fragment of DNA polymerase. The blunt-ended fragment was then ligated to a similarly opened BamHI restriction site in the K14 vector. The resulting construct contained the EcoRI site derived from the polylinker of the pCI-neo vector. This EcoRI site was removed using standard techniques (a Klenow-mediated fill-in reaction following partial digestion of the recombinant intermediate with EcoRI) to facilitate the subsequent excision of the DNA fragment to be injected into fertilized mouse oocytes.

The resulting clone, designated K14-VEGF-C, is illustrated in FIG. 20 of commonly-owned PCT patent application PCT/FI96/00427, filed Aug. 01, 1996.

The EcoRI-HindIII fragment from clone K14 VEGF-C containing the K14 promoter, VEGF-C cDNA, and K14 polyadenylation signal was isolated and injected into fertilized oocytes of the FVB-NIH mouse strain. The injected zygotes were transplanted to oviducts of pseudopregnant C57BL/6×DBA/2J hybrid mice. The resulting founder mice were analyzed for the presence of the transgene by polymerase chain reaction of tail DNA using the primers: 5'-CATGTACGAACCGCCAG-3' (SEQ ID NO: 22) and 5'-AATGACCAGAGAGAGGCGAG-3' (SEQ ID NO: 23).

In addition, the tail DNAs were subjected to EcoRV digestion and subsequent Southern analysis using the EcoRI-HindIII fragment injected into the mice. Out of 8 pups analyzed at 3 weeks of age, 2 were positive, having approximately 40–50 copies and 4–6 copies of the transgene in their respective genomes.

The mouse with the high copy number transgene was small, developed more slowly than its litter mates and had difficulty eating (i.e., suckling). Further examination showed a swollen, red snout and poor fur. Although fed with a special liquid diet, it suffered from edema of the upper respiratory and digestive tracts after feeding and had breathing difficulties. This mouse died eight weeks after birth and was immediately processed for histology, immunohistochemistry, and in situ hybridization.

Histological examination showed that in comparison to the skin of littermates, the dorsal dermis of K14-VEGF-C transgenic mice was atrophic and connective tissue was replaced by large lacunae devoid of red cells, but lined with a thin endothelial layer. These distended vessel-like structures resembled those seen in human lymphangiomas. The number of skin adnexal organs and hair follicles were reduced. In the snout region, an increased number of vessels was also seen. Therefore, VEGF-C overexpression in the basal epidermis is capable of promoting the growth of extensive vessel structure in the underlying skin, including large vessel lacunae. The endothelial cells surrounding these lacunae contained abundant Flt4 MRNA in in situ hybridization (see Examples 23 and 30 for methodology). The vessel morphology indicates that VEGF-C stimulates the growth of vessels having features of lymphatic vessels. The other K14-VEGF-C transgenic mouse had a similar skin histopathology.

Nineteen additional pups were analyzed at 3 weeks of age for the presence of the VEGF-C transgene, bring the number of analyzed pups to twenty-seven. A third transgene-positive pup was identified, having approximately 20 copies of the transgene in its genome. The 20 copy mouse and the 4–6 copy mouse described above transmitted the gene to 6 out of 11 and 2 out of 40 pups, respectively. The physiology of these additional transgenic mice were further analyzed.

The adult transgenic mice were small and had slightly swollen eyelids and poorly developed fur. Histological examination showed that the epidermis was hyperplastic and the number of hair follicles was reduced; these effects were considered unspecific or secondary to other phenotypic changes. The dermis was atrophic (45% of the dermal thickness, compared to 65% in littermate controls) and its connective tissue was replaced by large dilated vessels devoid of red cells, but lined with a thin endothelial cell layer. Such abnormal vessels were confined to the dermis and resembled the dysfunctional, dilated spaces characteristic of hyperplastic lymphatic vessels. See Fossum, et al., *J. Vet. Int. Med.*, 6: 283–293 (1992). Also, the ultrastructural features were reminiscent of lymphatic vessels, which differ from blood vessels by having overlapping endothelial junctions, anchoring filaments in the vessel wall, and a discontinuous or even partially absent basement membrane. See Leak, *Microvasc. Res.*, 2: 361–391 (1970). Furthermore, antibodies against collagen types IV, XVIII [Muragaki et al., *Proc. Natl. Acad. Sci. USA*, 92: 8763–8776 (1995)] and laminin gave very weak or no staining of the vessels, while the basement membrane staining of other vessels was prominent. The endothelium was also characterized by positive staining with monoclonal antibodies against desmoplakins I and II (Progen), expressed in lymphatic, but not in vascular endothelial cells. See Schmelz et al., *Differentiation*, 57: 97–117 (1994). Collectively, these findings strongly suggested that the abnormal vessels were of lymphatic origin.

In Northern hybridization studies, abundant VEGF-C MRNA was detected in the epidermis and hair follicles of the transgenic mice, while mRNAs encoding its receptors VEGFR-3 and VEGFR-2 as well as the Tie-1 endothelial receptor tyrosine kinase [Korhonen et al., *Oncogene*, 9: 395–403 (1994)] were expressed in endothelial cells lining the abnormal vessels. In the skin of littermate control animals, VEGFR-3 could be detected only in the superficial subpapillary layer of lymphatic vessels, while VEGFR-2 was found in all endothelia, in agreement with earlier findings. See Millauer et al., *Cell*, 72: 1–20 (1993); and Kaipainen et al., *Proc. Natl. Acad. Sci. USA*, 92: 3566–3570 (1995).

The lymphatic endothelium has a great capacity to distend in order to adapt to its functional demands. To determine whether vessel dilation was due to endothelial distension or proliferation, in vitro proliferation assays were conducted. Specifically, to measure DNA synthesis, 3mm×3mm skin biopsies from four transgenic and four control mice were incubated in D-MEM with 10 micrograms/ml BrdU for 6 hours at 37° C., fixed in 70% ethanol for 12 hours, and embedded in paraffin. After a 30 minute treatment with 0.1% pepsin in 0.1 M HCl at room temperature to denature DNA, staining was performed using mouse monoclonal anti-BrdU antibodies (Amersham). It appeared that the VEGF-C-receptor interaction in the transgenic mice transduced a mitogenic signal, because, in contrast to littermate controls, the lymphatic endothelium of the skin from young K14-VEGF-C mice showed increased DNA synthesis as demonstrated by BrdU incorporation followed by staining with anti-BrdU antibodies. This data further confirms that VEGF-C acts as a true growth factor in mammalian tissues.

In related experiments, a similar VEGF transgene did not induce lymphatic proliferation, but caused enhanced density of hyperpermeable, tortuous blood microvessels instead.

Angiogenesis is a multistep process which includes endothelial proliferation, sprouting, and migration. See Folkman et al., *J. Biol. Chem.*, 267: 10931–10934 (1992). To estimate the contribution of such processes to the transgenic phenotype, the morphology and function of the lymphatic vessels was analysed using fluorescent microlymphography using techniques known in the art. See Leu et al., *Am. J. Physiol.*, 267: 1507–1513 (1994); and Swartz et al., *Am. J. Physiol.*, 270: 324–329 (1996). Briefly, eight-week old mice were anesthetized and placed on a heating pad to maintain a 37° C. temperature. A 30-gauge needle, connected to a catheter filled with a solution of FITC-dextran 2M (8 mg/ml in PBS), was injected intradermally into the tip of the tail. The solution was infused with a constant pressure of 50 cm water (averaging roughly 0.01 microliters per minute flow rate) until the extent of network filling remained constant (approximately 2 hours). Flow rate and fluorescence intensity were monitorerd continuously throughout the experiment. In these experiments, a typical honeycomb-like network with similar mesh sizes was observed in both control and transgenic mice, but the diameter of lymphatic vessels was about twice as large in the transgenic mice, as summarized in the table below. (The intravital fluorescence microscopy of blood vessels was performed as has been described in the art. See Fukumura et al., *Cancer Res.*, 55: 4824–4829 (1995).)

Structural parameters of lymphatic and blood vessel networks

|  |  | transgenic | control | P-value** |
|---|---|---|---|---|
| lymphatic vessels* |  | (n = 4) | (n = 5) |  |
|  | diameter | 142.3 ± 26.2 | 68.2 ± 21.7 | .0143 |
|  | horizontal mesh size*** | 1003 ± 87.1 | 960.8 ± 93.1 | .2207 |
|  | Vertical mesh size | 507.3 ± 58.9 | 488.8 ± 59.9 | .5403 |
|  |  | (n = 3) | (n = 6) |  |
| blood vessels | median diameter | 8.3 ± 0.6 | 7.6 ± 1.1 | .1213 |
|  | vessel density, cm/cm$^2$ | 199.2 ± 6.6 | 216.4 ± 20.0 | .3017 | n = number of aminals
*mean ($\mu$m) ± SD
**Mann-Whitney test
***mesh size describes vessel density Some dysfunction of the abnormal vessels was indicated by the fact that it took longer for the dextran to completely fill the abnormal vessels. Injection of FITC-dextran into the tail vein, followed by fluorescence microscopy of the ear, showed that the blood vascular morphology was unaltered and leukocyte rolling and adherence appeared normal in the transgenic mice. These results suggest that the endothelial proliferation induced by VEGF-C leads to hyperplasia of the superficial lymphatic network but does not induce the sprouting of new vessels.

These effects of VEGF-C overexpression are unexpectedly specific, especially since, as described in other examples, VEGF-C is also capable of binding to and activating VEGFR-2, which is the major mitogenic receptor of blood vessel endothelial cells. In culture, high concentrations of VEGF-C stimulate the growth and migration of bovine capillary endothelial cells which express VEGFR-2, but not significant amounts of VEGFR-3. In addition, VEGF-C induces vascular permeability in the Miles assay [Miles, A. A., and Miles, E. M., *J. Physiol.*, 118:228–257 (1952); and Udaka, et al., *Proc. Soc. Exp. Biol. Med.*, 133:1384–1387 (1970)], presumably via its effect on VEGFR-2. VEGF-C is less potent than VEGF in the Miles assay, 4- to 5-fold higher concentrations of VEGF-C ΔNΔCHis being required to induce the same degree of permeability. In vivo, the specific effects of VEGF-C on lymphatic endothelial cells may reflect a requirement for the formation of VEGFR-3×VEGFR-2 heterodimers for endothelial cell proliferation at physiological concentrations of the growth factor. Such possible heterodimers may help to explain how three homologous VEGFs exert partially redundant, yet strikingly specific biological effects.

The foregoing in vivo data indicates utilities for both (i) VEGF-C polypeptides and polypeptide variants and analogs having VEGF-C biological activity, and (ii) anti-VEGF-C antibodies and VEGF-C antagonists that inhibit VEGF-C activity (e.g., by binding VEGF-C or interfering with VEGF-C/receptor interactions. For example, the data indicates a therapeutic utility for VEGF-C polypeptides in patients wherein growth of lymphatic tissue may be desirable (e.g., in patients following breast cancer or other surgery where lymphatic tissue has been removed and where lymphatic drainage has therefore been compromised, resulting in swelling; or in patients suffering from elephantiasis). The data indicates a therapeutic utility for anti-VEGF-C antibody substances and VEGF-C antagonists for conditions wherein growth-inhibition of lymphatic tissue may be desirable (e.g., treatment of lymphangiomas). Accordingly, methods of administering VEGF-C and VEGF-C variants, analogs, and antagonists are contemplated as methods and materials of the invention.

EXAMPLE 30

Expression of VEGF-C and Flt4 in the Developing Mouse

Embryos from a 16-day post-coitus pregnant mouse were prepared and fixed in 4% paraformaldehyde (PFA), embedded in paraffin, and sectioned at 6 $\mu$m. The sections were placed on silanated microscope slides and treated with xylene, rehydrated, fixed for 20 minutes in 4% PFA, treated with proteinase K (7 mg/ml; Merck, Darmstadt, Germany) for 5 minutes at room temperature, again fixed in 4% PFA and treated with acetic anhydride, dehydrated in solutions with increasing ethanol concentrations, dried and used for in situ hybridization.

In situ hybridization of sections was performed as described (Vastrik et al., *J. Cell Biol.*, 128:1197–1208 (1995)). A mouse VEGF-C antisense RNA probe was generated from linearized pBluescript II SK+plasmid (Stratagene Inc.), containing a fragment corresponding to nucleotides 499–979 of mouse VEGF-C cDNA, where the noncoding region and the BR3P repeat were removed by Exonuclease III treatment. The fragment had been cloned into the EcoRI and HindIII sites of pBluescript II SK+. Radiolabeled RNA was synthesized using T7 RNA Polymerase and [$^{35}$S]-UTP (Amersham, Little Chalfont, UK). About two million cpm of the VEGF-C probe was applied per slide. After an overnight hybridization, the slides were washed first in 2×SSC and 20–30 mM DTT for 1 hour at 50° C. Treatment continued with a high stringency wash, 4×SSC and 20 mM DTT and 50% deionized formamide for 30 minutes at 65° C. followed by RNase A treatment (20 $\mu$g/ml) for 30 minutes at 37° C. The high stringency wash was repeated for 45 minutes. Finally, the slides were dehydrated and dried for 30 minutes at room temperature. The slides were dipped into photography emulsion and exposed for 4 weeks. Slides were developed using Kodak D-16 developer, counterstained with hematoxylin and mounted with Permount (FisherChemical).

For in situ hybridizations of Flt4 sequences, a mouse Flt4 CDNA fragment covering bp 1–192 of the published sequence (Finnerty et al., *Oncogene*, 8:2293–2298 (1993)) was used, and the above-described protocol was followed, with the following exceptions. Approximately one million cpm of the Flt4 probe were applied to each slide. The stringent washes following hybridization were performed in 1×SSC and 30 mM DTT for 105 minutes.

Darkfield and lightfield photomicrographs from these experiments are presented in commonly-owned PCT patent application PCT/FI96/00427, filed Aug. 1, 1996, incorporated by reference herein. Observations from the photomicrographs are summarized below.

The most prominently Flt4-hybridizing structures appeared to correspond to the developing lymphatic and venous endothelium. A plexus-like endothelial vascular structure surrounding the developing nasopharyngeal mucous membrane was observed. The most prominent signal using the VEGF-C probe was obtained from the posterior part of the developing nasal conchae, which in higher magnification showed the epithelium surrounding loose connective tissue/forming cartilage. This structure gave a strong in situ hybridization signal for VEGF-C. With the VEGF-C probe, more weakly hybridizing areas were observed around the snout, although this signal is much more homogeneous in appearance. Thus, the expression of VEGF-C is strikingly high in the developing nasal conchae.

The conchae are surrounded with a rich vascular plexus, important in nasal physiology as a source for the mucus produced by the epithelial cells and for warming inhaled air. It is suggested that VEGF-C is important in the formation of the concheal venous plexus at the mucous membranes, and that it may also regulate the permeability of the vessels needed for the secretion of nasal mucus. Possibly, VEGF-C and its derivatives, and antagonists, could be used in the regulation of the turgor of the conchal tissue and mucous membranes and therefore the diameter of the upper respiratory tract, as well as the quantity and quality of mucus produced. These factors are of great clinical significance in inflammatory (including allergic) and infectious diseases of the upper respiratory tract. Accordingly, the invention contemplates the use of the materials of the invention, including VEGF-C, Flt4, and their derivatives, in methods of diagnosing and treating inflammatory and infectious conditions affecting the upper respiratory tract, including nasal structures.

EXAMPLE 31

Characterization of the Exon-intron Organization of the Human VEGF-C Gene

Two genomic DNA clones covering exons 1, 2, and 3 of the human VEGF-C gene were isolated from a human genomic DNA library using VEGF-C cDNA fragments as probes. In particular, a human genomic library in bacteriophage EMBL-3 lambda (Clontech) was screened using a PCR-generated fragment corresponding to nucleotides 629–746 of the human VEGF-C cDNA (SEQ ID NO: 7). One positive clone, designated "lambda 3," was identified, and the insert was subcloned as a 14 kb XhoI fragment into the pBluescript II (pBSK II) vector (Stratagene). The genomic library also was screened with a labeled 130 bp NotI-SacI fragment from the 5'-noncoding region of the VEGF-C cDNA (the NotI site is in the polylinker of the cloning vector; the SacI site corresponds to nucleotides 92–97 of SEQ ID NO: 7). Two positive clones, designated "lambda 5" and "lambda 8," were obtained. Restriction mapping analysis showed that clone lambda 3 contains exons 2 and 3, while clone lambda 5 contains exon 1 and the putative promoter region.

Three genomic fragments containing exons 4, 5, 6 and 7 were subcloned from a genomic VEGF-C P1 plasmid clone. In particular, purified DNA from a genomic P1 plasmid clone 7660 (Paavonen et al., Circulation, 93: 1079–1082 (1996)) was used. EcoRI fragments of the P1 insert DNA were ligated into pBSK II vector. Subclones of clone 7660 which contained human VEGF-C cDNA homologous sequences were identified by colony hybridization, using the full-length VEGF-C CDNA as a probe. Three different genomic fragments were identified and isolated, which contained the remaining exons 4–7.

Figure 12:
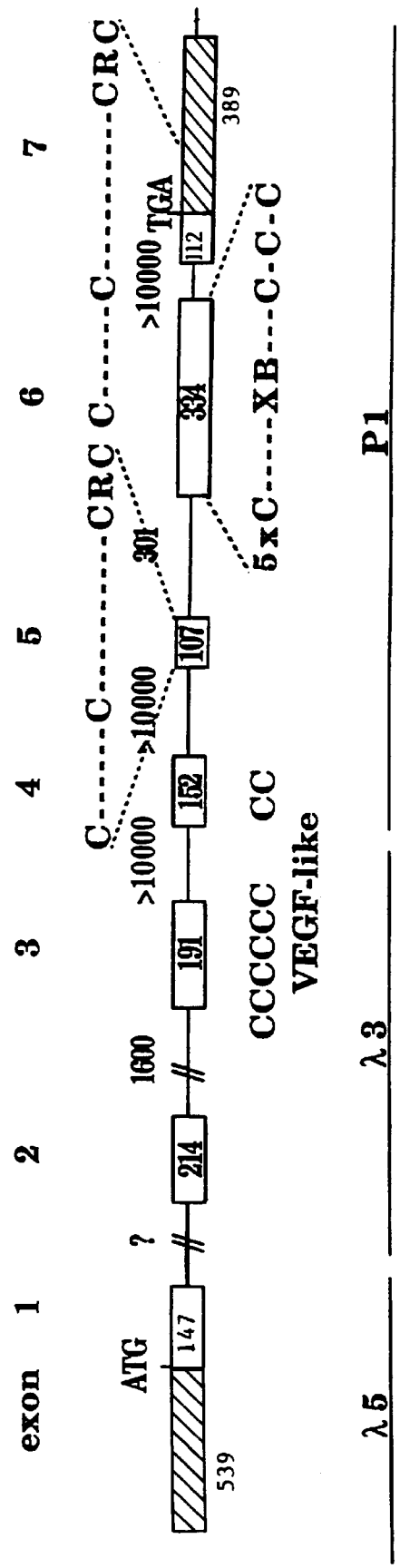
FIG. 12 depicts the exon-intron organization of the human VEGF-C gene. Seven exons are depicted as open boxes, with exon size depicted in base pairs. Introns are depicted as lines, with intron size (base pairs) depicted above the lines. 5' and 3' untranslated sequences of a putative 2.4 kb mature MRNA are depicted as shaded boxes. The location of genomic clones used to characterize the VEGF-C gene are depicted below the map of the gene.

To determine the genomic organization, the clones were mapped using restriction endonuclease cleavage. Also, the coding regions and exon-intron junctions were partially sequenced. The result of this analysis is depicted in FIGS. 12 and 13A. The sequences of all intron-exon boundaries (FIG. 13A, SEQ ID NOs: 24–35) conformed to the consensus splicing signals (Mount, Nucl. Acids Res., 10: 459–472 (1982)). The length of the intron between exon 5 and 6 was determined directly by nucleotide sequencing and found to be 301 bp. The length of the intron between exons 2 and 3 was determined by restriction mapping and Southern hybridization and was found to be about 1.6 kb. Each of the other intron is over 10 kb in length.

A similar analysis was performed for the murine genomic VEGF-C gene. The sequences of murine VEGF-C intron-exon boundaries are depicted in FIG. 13B and SEQ ID NOs: 36–47.

The restriction mapping and sequencing data indicated that the VEGF-C signal sequence and the first residues of the N-terminal propeptide are encoded by exon 1. The second exon encodes the carboxy-terminal portion of the N-terminal propeptide and the amino terminus of the VEGF homology domain. The most conserved sequences of the VEGF homology domain are distributed in exons 3 (containing 6 conserved cysteine residues) and 4 (containing 2 cys residues). The remaining exons encode cysteine-rich motifs of the type C-6X-C-10X-CRC (exons 5 and 7) and a fivefold repeated motif of type C-6X-B-3X-C-C-C, which is typical of a silk protein.

To further characterize the human VEGF-C gene promoter, the lambda 5 clone was further analyzed. Restriction mapping of this clone using a combination of single- and double-digestions and Southern hybridizations indicated that it includes: (1) an approximately 6 kb region upstream of the putative initiator ATG codon, (2) exon 1, and (3) at least 5 kb of intron I of the VEGF-C gene.

A 3.7 kb Xba I fragment of clone lambda 5, containing exon 1 and 5' and 3' flanking sequences, was subcloned and further analyzed. As reported previously, a major VEGF-C mRNA band migrates at a position of about 2.4 kb. Calculating from the VEGF-C coding sequence of 1257 bp and a 391 bp 3' noncoding sequence plus a polyA sequence of about 50–200 bp, the mRNA start site was estimated to be about 550–700 bp upstream of the translation initiation codon.

RNase protection assays were employed to obtain a more precise localization of the mRNA start site. The results of these experiments indicated that the RNA start site in the human VEGF-C gene is located 539 bp upstream of the ATG translational initiation codon.

To further characterize the promoter of the human VEGF-C gene, a genomic clone encompassing about 2.4 kb upstream of the translation initiation site was isolated, and the 5' noncoding cDNA sequence and putative promoter region were sequenced. The sequence obtained is set forth in SEQ ID NO: 48. (The beginning of the VEGF-C cDNA sequence set forth in SEQ ID NO: 7 corresponds to position 2632 of SEQ ID NO: 48; the translation initiation codon corresponds to positions 2983–2985 of SEQ ID NO: 48.) Similar to what has been observed with the VEGF gene, the VEGF-C promoter is rich in G and C residues and lacks consensus TATA and CCAAT sequences. Instead, it has numerous putative binding sites (5'-GGGCGG-3' or 5'-CCGCCC-3') for Sp1, a ubiquitous nuclear protein that can initiate transcription of TATA-less genes. See Pugh and Tjian, Genes and Dev., 5:105–119 (1991). In addition, sequences upstream of the VEGF-C translation start site were found to contain frequent consensus binding sites for the AP-2 factor (5'-GCCN$_3$GCC-3') and binding sites for the AP-1 factor (5'-TKASTCA-3'). Binding sites for regulators of tissue-specific gene expression, like NFKB and GATA, are located in the distant part of VEGF-C promoter. This suggests that the cAMP-dependent protein kinase and protein kinase C, as activators of AP-2 transcription factor [Curran and Franza, Cell, 55:395–397 (1988)], mediate VEGF-C transcriptional regulation.

The VEGF-C gene is abundantly expressed in adult human tissues, such as heart, placenta, ovary and small intestine, and is induced by a variety of factors. Indeed, several potential binding sites for regulators of tissue-specific gene expression, like NFkB (5'-GGGRNTYYC-3') and GATA, are located in the distal part of the VEGF-C promoter. For example, NFkB is known to regulate the expression of tissue factor in endothelial cells. Also, transcription factors of the GATA family are thought to regulate cell-type specific gene expression.

Unlike VEGF, the VEGF-C gene does not contain a binding site for the hypoxia-inducible factor, HIF-1 (Levy et al., *J. Biol. Chem.*, 270: 13333–13340 (1995)). This finding suggests that if the VEGF-C MRNA is regulated by hypoxia, the mechanism would be based mainly on the regulation of MRNA stability. In this regard, numerous studies have shown that the major control point for the hypoxic induction of the VEGF gene is the regulation of the steady-state level of mRNA. See Levy et al., *J. Biol. Chem.*, 271: 2746–2753 (1996). The relative rate of VEGF mRNA stability and decay is considered to be determined by the presence of specific sequence motifs in its 3' untranslated region (UTR), which have been demonstrated to regulate MRNA stability. (Chen and Shyu, *Mol. Cell Biol.*, 14: 8471–8482 (1994)). The 3'-UTR of the VEGF-C gene also contains a putative motif of this type (TTATTT), at positions 1873–1878 of SEQ ID NO: 7.

To identify DNA elements important for basal expression of VEGF-C in transfected cells, a set of luciferase reporter plasmids containing serial 5' deletions through the promoter region was constructed. Restriction fragments of genomic DNA containing 5' portions of the first exon were cloned into the polylinker of the pGL3 reporter vector (Promega) and confirmed by sequencing. About 10 μg of the individual constructs in combination with 2 μg of pSV2-β-galactosidase plasmid (used as a control of transfection efficiency) were transfected into HeLa cells using the calcium phosphate-mediated transfection method. Two days after transfection, the cells were harvested and subjected to the luciferase assay. The luciferase activity was normalized to that of the pGL3 control vector driven by SV40 promoter/enhancer.

Figure 15:
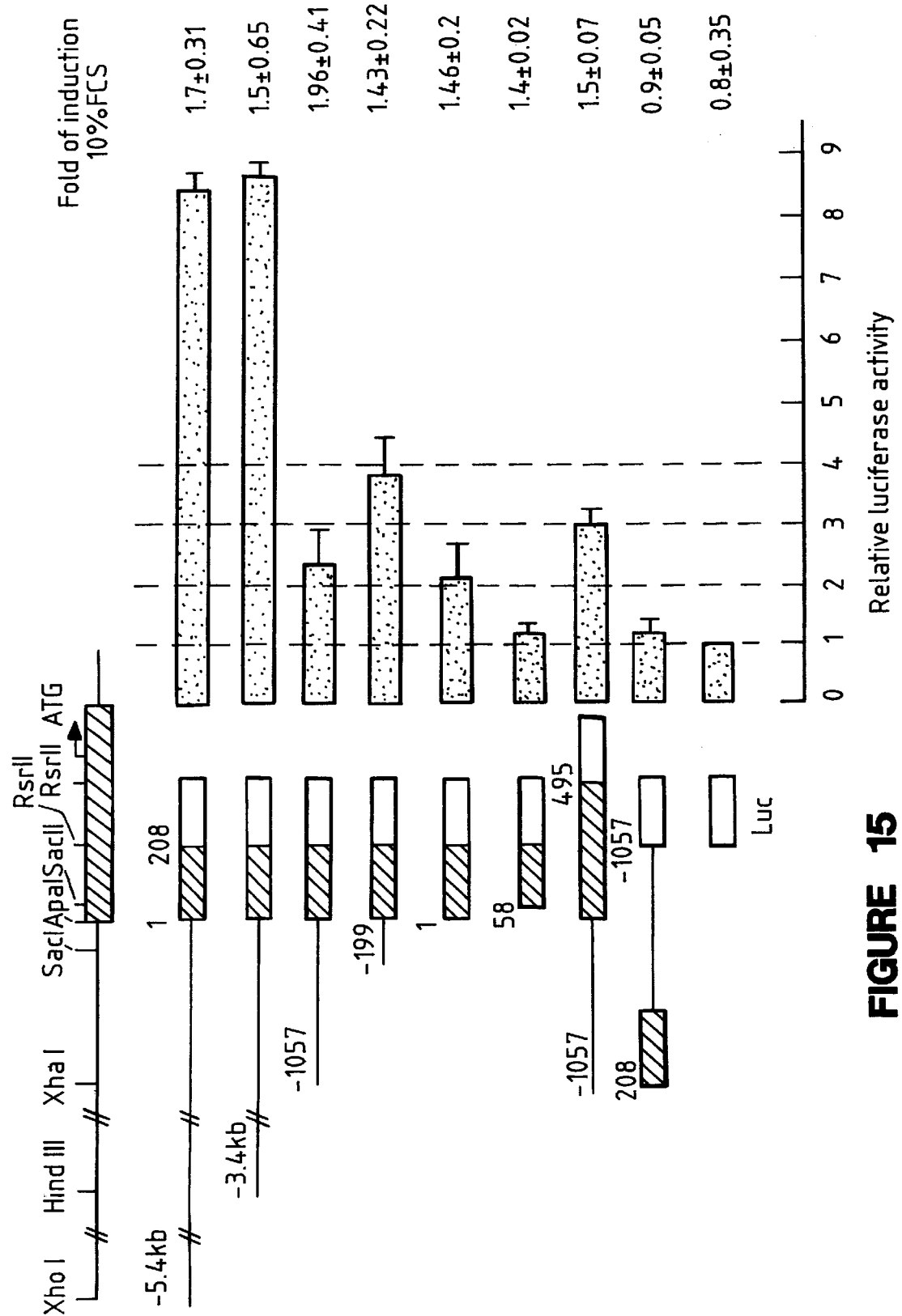
FIG. 15 schematically depicts the VEGF-C promoter-reporter constructs and their activities in transfected HeLa cells. A restriction map of a portion of a genomic clone that includes the VEGF-C initiation codon and about 6 kb of upstream sequence is depicted above the constructs. Constructs were made linking putative VEGF-C promoter to the Luciferase reporter gene in pGL3 vector (Promega) and introduced into HeLa cells by calcium phosphate-mediated transfection method. The Luciferase activity obtained was compared to the level using the promoterless pGL3basic construct to obtain a measure of relative promoter activity. Luciferase activity is expressed graphically as a ratio of activity of the constructs versus this control. Also shown are numerical ratios of Luciferase activity in experiments where the constructs were transfected into HeLa cells and cells were starved 24 hours followed by serum stimulation for four hours (Luciferase activity is expressed as a ration of activity in serum-stimulated versus serum-starved cells).

As depicted in FIG. 15, the 5.5 kb XboI-RsrII fragment of clone lambda 5 gave nearly 9-fold elevated activity when compared with a promoterless vector. Deletion of a 5' XhoI-HindIII fragment of 2 kb had no effect on the promoter activity. The activity of the 1.16 kb XbaI-RsrII fragment was about twice that of the pGL3 basic vector, while the activity of the same fragment in the reverse orientation was at background level. Further deletion of the XbaI-SacI fragment caused an increase in the promoter activity, suggesting the presence of silencer elements in the region from −1057 to −199 (i.e., 199 to 1057 bp upstream from the transcription initiation site). The shortest fragment (SacII-RsrII) yielded only background activity, which was consistent with the fact that the mRNA initiation site was not present in this construct.

S To determine whether further sequences in the first exon of human VEGF-C are important for basal expression, an RsrII fragment spanning nucleotides 214–495 (i.e., 214–495 bp downstream from the transcription initiation site) was subcloned in between of XbaI-RsrII fragment and the luciferase reporter gene. Indeed, the obtained construct showed an 50 % increase in activity when compared with the XbaI-RsrII construct.

The VEGF gene has been shown to be up-regulated by a number of stimuli including serum derived growth factors. To find out whether the VEGF-C gene also can be stimulated by serum, RNA from serum-starved and serum-stimulated HT1080 cells was subjected to primer extension analysis, which demonstrated that VEGF-C MRNA is up-regulated by serum stimulation.

Additional serum stimulation experiments indicated that the serum stimulation leads to increased VEGF-C promoter activity. Cells were transfected as described above and 24 h after transfection changed into medium containing 0.5% bovine serum albumin. Cells were then stimulated with 10% fetal calf serum for 4 hours and analyzed. The XbaI-RsrII promoter construct derived from lambda 5 yielded a twofold increased activity upon serum stimulation, while the same fragment in the reverse orientation showed no response. All other promoter constructs also showed up-regulation, ranging from 1.4 to 1.6 fold (FIG. 15).

EXAMPLE 32

Identification of a VEGF-C Splice Variant

As reported in Example 16, a major 2.4 kb VEGF-C mRNA and smaller amounts of a 2.0 kb mRNA are observable. To clarify the origin of these RNAS, several additional VEGF-C cDNAs were isolated and characterized. A human fibrosarcoma CDNA library from HT1080 cells in the lambda gt11 vector (Clontech, product #HL1048b) was screened using a 153 bp human VEGF-C cDNA fragment as a probe as described in Example 10. See also Joukov et al., *EMBO J.*, 15:290–298 (1996). Nine positive clones were picked and analyzed by PCR amplification using oligonucleotides 5'-CACGGCTTATGCAAGCAAAG-3' (SEQ ID NO: 49) and 5'-AACACAGTTTTCCATAATAG-3' (SEQ ID NO: 50) These oligonucleotides were selected to amplify the portion of the VEGF-C cDNA corresponding to nucleotides 495–1661 of SEQ ID NO: 7. PCR was performed using an annealing temperature of 55° C. and 25 cycles.

The resultant PCR products were electrophoresed on agarose gels. Five clones out of the nine analyzed generated PCR fragments of the expected length of 1147 base pairs, whereas one was slightly shorter. The shorter fragment and one of the fragments of expected length were cloned into the pCRTMII vector (Invitrogen) and analyzed by sequencing. The sequence revealed that the shorter PCR fragment had a deletion of 153 base pairs, corresponding to nucleotides 904 to 1055 of SEQ ID NO: 7. These deleted bases correspond to exon 4 of the human and mouse VEGF-C genes, schematically depicted in FIGS. 13A and 13B. Deletion of exon 4 results in a frameshift, which in turn results in a C-terminal truncation of the full-length VEGF-C precursor, with fifteen amino acid residues translated from exon 5 in a different frame than the frame used to express the full-length protein. Thus, the C-terminal amino acid sequence of the resulting truncated polypeptide would be —Leu (181)-Ser-Lys-Thr-Val-Ser-Gly-Ser-Glu-Gln-Asp-Leu-Pro-His-Glu-Leu-His-Val-Glu (199) (SEQ ID NO: 51). The polypeptide encoded by this splice variant would not contain the C-terminal cleavage site of the VEGF-C precursor. Thus, a putative alternatively spliced RNA form lacking conserved exon 4 was identified in HT-1080 fibrosarcoma cells and this form is predicted to encode a protein of 199 amino acid residues, which could be an antagonist of VEGF-C.

EXAMPLE 33

VEGF-C is Similarly Processed in Different Cell Cultures in Vitro

To study whether VEGF-C is similarly processed in different cell types, 293 EBNA cells, COS-1 cells and HT-1080 cells were transfected with wild type human VEGF-C CDNA and labelled with Pro-Mix™ as described in Example 22. The conditioned media from the cultures were collected and subjected to immunoprecipitation using antiserum 882 (described in Example 21, recognizing a peptide corresponding to amino acids 104–120 of SEQ ID NO: 8). The immunoprecipitated polypeptides were separated via SDS-PAGE, and detected via autoradiography. The major form of secreted recombinant VEGF-C observed from all cell lines tested is a 29/32 kD doublet. These two polypeptides are bound to each other by disulfide bonds, as described in Example 22. A less prominent band of approximately 21 kD also was detected in the culture media. Additionally, a non-processed VEGF-C precursor of 63 kDa was observed. This form was more prominent in the COS-1 cells, suggesting that proteolytic processing of VEGF-C in COS cells is less efficient than in 293 EBNA cells. Endogenous VEGF-C (in non-transfected cells) was not detectable under these experimental conditions in the HT-1080 cells, but was readily detected in the conditioned medium of the PC-3 cells. Analysis of the subunit polypeptide sizes and ratios in PC-3 cells and 293 EBNA cells revealed strikingly similar results: the most prominent form was a doublet of 29/32 kDa and a less prominent form the 21 kD polypeptide. The 21 kD form produced by 293 EBNA cells was not recognized by the 882 antibody in the Western blot, although it is recognized when the same antibody is used for immunoprecipitation (see data in previous examples). As reported in Example 21, cleavage of the 32 kD form in 293 EBNA cells occurs between amino acid residues 111 and 112 (SEQ ID NO: 8), downstream of the cleavage site in PC-3 cells (between residues 102 and 103). Therefore, the 21 kD form produced in 293 EBNA cells does not contain the complete N-terminal peptide used to generate antiserum 882. In a related experiment, PC-3 cells were cultured in serum-free medium for varying periods of time (1–8 days) prior to isolation of the conditioned medium. The conditioned medium was concentrated using a Centricon device (Amicon, Beverly, USA) and subjected to Western blotting analysis using antiserum 882. After one day of culturing, a prominent 32 kD band was detected. Increasing amounts of a 21–23 kD form were detected in the conditioned media from 4 day and 8 day cultures. The diffuse nature of this polypeptide band, which is simply called the 23 kD polypeptide in example 5 and several subsequent examples, is most likely due to a heterogeneous and variable amount of glycosylation. These results indicate that, initially, the cells secrete a 32 kD polypeptide, which is further processed or cleaved in the medium to yield the 21–23 kD form. The microheterogeneity of this polypeptide band would then arise from the variable glycosylation degree and, from microheterogeneity of the processing cleavage sites, such as obtained for the amino terminus in PC-3 and 293 EBNA cell cultures. The carboxyl terminal cleavage site could also vary, examples of possible cleavage sites would be between residues 225–226, 226–227 and 227–228 as well as between residues 216–217. Taken together, these data suggest the possibility that secreted cellular protease(s) are responsible for the generation of the 21–23 kD form of VEGF-C from the 32 kD polypeptide. Such proteases could be used in vitro to cleave VEGF-C precursor proteins in solution during the production of VEGF-C, or used in cell culture and in vivo to release biologically active VEGF-C.

EXAMPLE 34

Differential Binding of VEGF-C Forms by the Extracellular Domains of VEGFR-3 and VEGFR-2

In two parallel experiments, 293 EBNA cells were transfected with a construct encoding recombinant wild type VEGF-C or a construct encoding VEGF-C ΔNΔCHis (Example 28) and about 48 hours after transfection, metabolically labelled with Pro-Mix™ as described in previous examples. The media were collected from mock-transfected and transfected cells and used for receptor binding analyses.

Receptor binding was carried out in binding buffer (PBS, 0.5% BSA, 0.02% Tween 20, 1 microgram/ml heparin) containing approximately 0.2 microgram of either (a) a fusion protein comprising a VEGFR-3 extracellular domain fused to an immunoglobulin sequence (VEGFR-3-Ig) or (b) a fusion protein comprising VEGFR-2 extracellular domain fused to an alkaline phosphatase sequence (VEGF-R-2-AP; Cao et al., J. Biol. Chem. 271:3154–62 (1996)). As a control, similar aliquots of the 293 EBNA conditioned media were mixed with 2 µl of anti-VEGF-C antiserum (VEGF-C IP).

After incubation for 2 hours at room temperature, anti-VEGF-C antibodies and VEGFR-3-Ig protein were adsorbed to protein A-sepharose (PAS) and VEGFR-2-AP was immunoprecipitated using anti-AP monoclonal antibodies (Medix Biotech, Genzyme Diagnostics, San Carlos, Calif., USA) and protein G-sepharose. Complexes containing VEGF-C bound to VEGFR-3-Ig or VEGFR-2-AP were washed three times in binding buffer, twice in 20 mM Tris-HCl (pH 7.4) and VEGF-C immunoprecipitates were washed three times in RIPA buffer and twice in 20 mM tris-HCl (pH 7.4) and analyzed via SDS-PAGE under reducing and nonreducing conditions. As a control, the same media were precipitated with anti-AP and protein G-sepharose (PGS) or with PAS to control for possible nonspecific adsorption.

These experiments revealed that VEGFR-3 bound to both the 32/29 kD and 21–23 kD forms of recombinant VEGF-C, whereas VEGFR-2 bound preferentially to the 21–23 kD component from the conditioned media. In addition, small amounts of 63 kD and 52 kD VEGF-C forms were observed binding with VEGFR-3. Further analysis under nonreducing conditions indicates that a great proportion of the 21–23 kD VEGF-C bound to either receptor does not contain interchain disulfide bonds. These findings reinforce the results that VEGF-C binds VEGFR-2. This data suggests a utility for recombinant forms of VEGF-C which are active towards VEGFR-3 only or which are active towards both VEGFR-3 and VEGFR-2. On the other hand, these results, together with the results in Example 28, do not eliminate the possibility that the 32/29 kD dimer binds VEGFR-3 but does not activate it. The failure of the 32/29 kD dimer to activate VEGFR-3 could explain the finding that conditioned medium from the N-His VEGF-C transfected cells induced a less prominent tyrosine phosphorylation of VEGFR-3 than medium from VEGF-C ΔNΔCHis transfected cells, even though expression of the former polypeptide was much higher. Stable VEGF-C poly-peptide mutants that bind to a VEGF-C receptor but fail to activate the receptor are useful as VEGF-C antagonists.

EXAMPLE 35

Discovery of VEGF-C Analogs That Selectively Bind to and Activate VEGFR-3, But Not VEGFR-2

To further identify the cysteine residues of VEGF-C that are critical for retaining VEGF-C biological activities, an additional VEGF-C mutant, designated VEGF-CΔNΔCHisC156S, was synthesized, in which the cysteine residue at position 156 of the 419 amino acid VEGF-C precursor (SEQ ID NO: 8; Genbank accession number X94216) was replaced with a serine residue.

The mutagenesis procedure was carried out using the construct of VEGF-CΔNΔCHis (see Example 28), cloned in the pALTER vector, and the Altered sites II in vitro mutagenesis system of Promega. An oligonucleotide 5'-GACGGACACAGATGGAGGTTTAAAG- 3' (SEQ ID NO: 52) was used to introduce the desired mutation in the CDNA encoding VEGF-CΔNΔCHis. The resulting mutated VEGF-C cDNA fragment was subcloned into the HindIII/ NotI sites of the pREP-7 vector (Invitrogen), and the final construct was resequenced to confirm the C156S mutation. The resultant clone has an open reading frame encoding amino acids 103–225 of SEQ ID NO: 8 (with a serine codon at position 156), and further encoding a 6×His tag.

The wildtype VEGF-C cDNA and three VEGF-C mutant constructs (VEGF-C R226,227S, VEGF-C ΔNΔCHis, and VEGF-C ΔNΔCHisC156S) were used to transfect 293 EBNA cells, which were subcultured 16 hours after transfection. About 48 hours after transfection, the media were changed to DMEM/0.1% BSA, and incubation in this medium was continued for an additional 48 hours. The resultant conditioned media were concentrated 30-fold using Centriprep-10 (Amicon), and the amount of VEGF-C in the media was analyzed by Western blotting using the anti-VEGF-C antiserum 882 for immunodetection. Different amounts of the recombinant VEGF-C ΔNΔCHis, purified from a yeast expression system, were analyzed in parallel as reference samples to measure and equalize the VEGF-C concentrations in the conditioned media. The conditioned medium from mock-transfected cells was used to dilute the VEGF-C conditioned media to achieve equal concentrations.

An alliquot of the transfected cells were metabolically labelled for 6 h with 100 microcuries/ml of the PRO-MIX™ L- [$^{35}$S] in vitro cell labelling mix (Amersham). The conditioned media were collected, and binding of the radioactively labelled VEGF-C proteins to the extracellular domains of VEGFR-3 and VEGFR-2 was analyzed using recombinantly produced VEGFR-3EC-Ig and VEGFR-2EC-Ig constructs (containing seven and three Ig loops of the extracellular domains of the respective receptors, fused to an immunoglobulin heavy chain constant region).

Figure 14A:
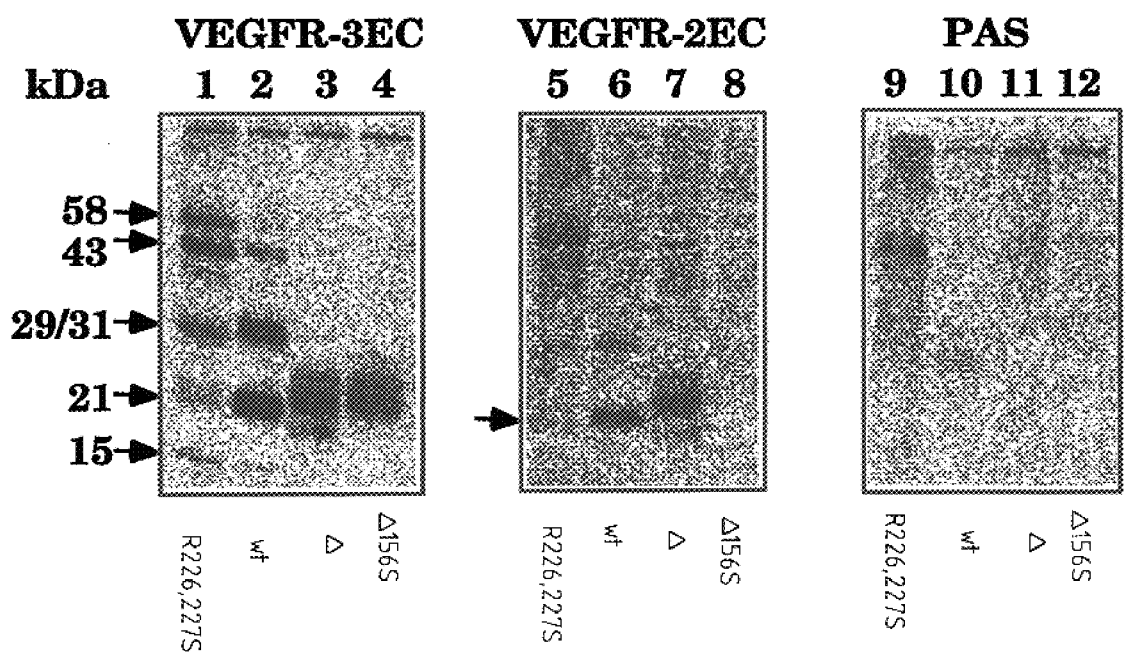
FIG. 14A depicts autoradiograms showing the binding of recombinantly produced wildtype VEGF-C (wt) and three VEGF-C mutants (VEGF-C R226,227S (R226,227S); VEGF-C ΔNΔCHis (Δ); and VEGF-C ΔNΔCHisC156S (Δ156S)) to a VEGFR-3 extracellular domain-immunoglobulin construct (left panel, VEGFR-3EC), to a VEGFR-2 extracellular domain-immunoglobulin construct (center panel, VEGFR-2EC), and to protein A sepharose (right panel, PAS).

As shown in FIG. 14A, all processed VEGF-C forms secreted to the culture medium bound to VEGFR-3EC domain, with preferential binding of the 21 kDa form (left panel). When present at high concentrations, the VEGF-C forms of 58 kDa and 29/31 kDa bound to some extent non-specifically to protein A Sepharose (PAS, right panel).

The VEGFR-2EC domain preferentially bound the mature 21 kDa form of wildtype VEGF-C and VEGF-CΔNΔCHis. Significantly, VEGF-CΔNΔCHisC156S failed to bind the VEGFR2-EC (FIG. 14A, middle panel).

Next, the ability of the above-described VEGF-C polypeptides to compete with the $^{125}$I-VEGF-CΔNΔCHis for binding to VEGFR-2 and VEGFR-3 was analyzed. Scatchard analysis using VEGF-C ΔCΔNHis provided indications of the VEGF-C binding affinity for VEGFR-3 ($K_D$= 135 pM) and VEGFR-2 ($K_D$=410 pM). Ten micrograms of the purified yeast VEGF-C ΔNΔCHis was labeled using 3 mCi of Iodine-125, carrier-free (Amersham), and an Iodo-Gen Iodination Reagent (Pierce), according to the standard protocol of Pierce. The resulting specific activity of the labeled VEGF-CΔNΔCHis was 1.25×10$^5$ cpm/ng.

To study receptor binding, PAE/VEGFR-2 and PAE/ VEGFR-3 cells were seeded into 24-well tissue culture plates (Nunclon), which had been coated with 2% gelatin in PBS. The $^{125}$-VEGF-C ΔNΔCHis (2×10$^5$ cpm) and different amounts of media containing equal concentrations of the non-labeled VEGF-C (wildtype and mutants) were added to each plate in Ham's F12 medium, containing 25 mM HEPES (pH 8.0), 0.1% BSA, and 0.1% NaN$_3$. The binding was allowed to proceed at room temperature for 90 minutes. The plates were then transferred onto ice and washed three times with ice-cold PBS containing 0.1% BSA. The cells were then lysed in 1 M NaOH, the lysates were collected, and the radioactivity was measured using a γ-counter. Binding in the presence of VEGF-C-containing conditioned medium was calculated as a percentage of binding observed in parallel control studies wherein equal volumes of medium from mock-transfected cells were used instead of VEGF-C conditioned media.

Figure 14B:
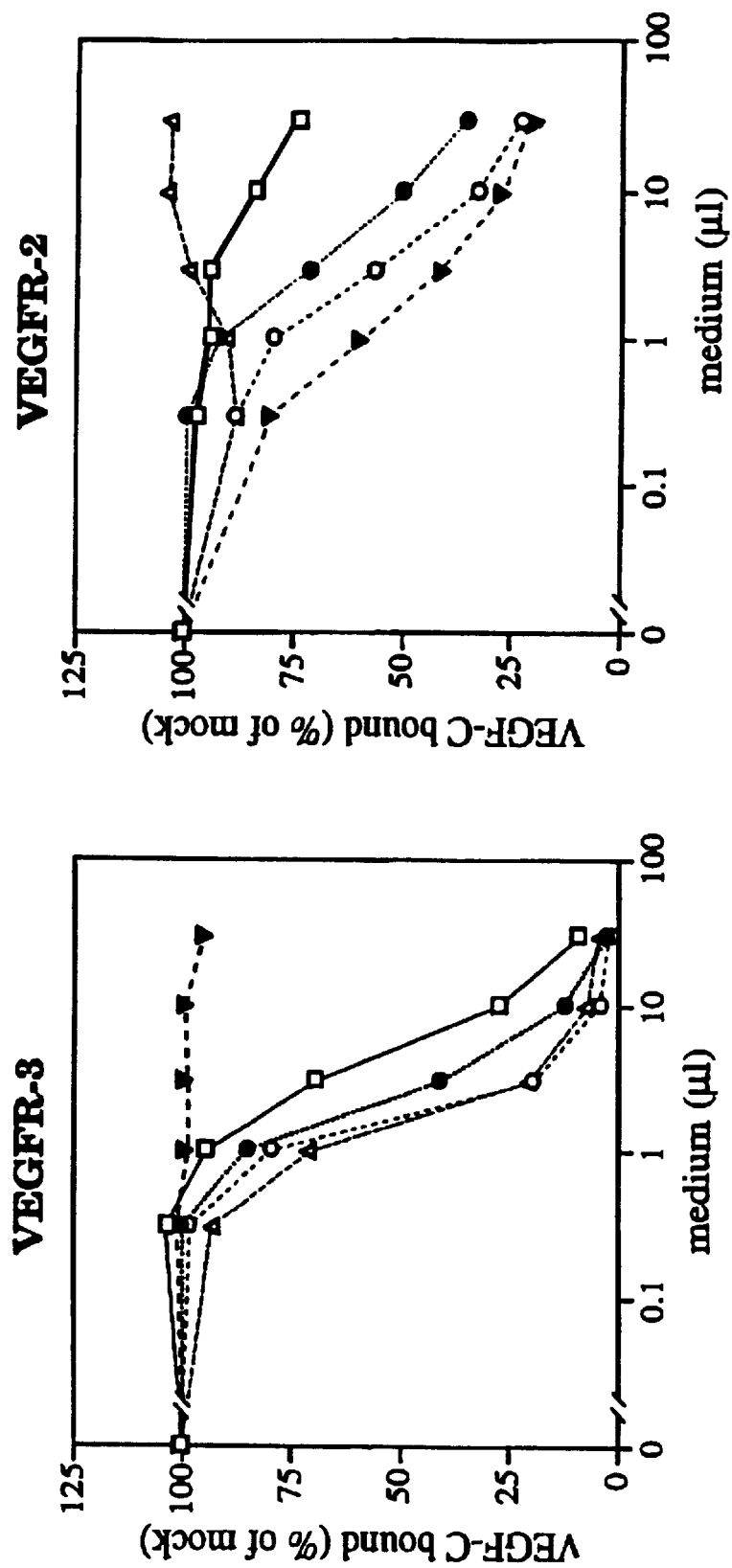
FIG. 14B graphically depicts the results of a competitive binding assay. The ability of VEGF165, wildtype VEGF-C, and various VEGF-C mutants to compete with $^{125}$I-VEGF-CΔNΔCHis for binding to VEGFR-2 and VEGFR-3 is shown.

As shown in FIG. 14B, left panel, all VEGF-C mutants displaced $^{125}$I-VEGF-CΔNΔCHis from VEGFR-3. The efficiency of displacement was as follows: VEGF-CΔNΔCHisC156S>VEGF-CΔNΔCHis>wildtype VEGF-C>VEGF-CR226,227S. These results indicate that enhanced binding to VEGFR-3 was obtained upon "recombinant maturation" of VEGF-C. Recombinant VEGF165 failed to displace VEGF-C from VEGFR-3.

VEGF, VEGF-CΔNΔCHis, and wildtype VEGF-C all efficiently displaced labeled VEGF-CΔNΔCHis from VEGFR-2, with VEGF-CΔNΔCHis being more potent when compared to wildtype VEGF-C (FIG. 1B, right panel). The non-processed VEGF-C R226,227S showed only weak competition of $^{125}$I-VEGF-CΔNΔCHis.

Surprisingly, VEGF-CΔNΔCHisR156S failed to displace VEGF-CΔNΔCHis from VEGFR-2, thus confirming the above described results obtained using a soluble extracellular domain of VEGFR-2.

The ability of the above mentioned VEGF-C forms to stimulate tyrosine phosphorylation of VEGFR-3 and VEGFR-2 was also investigated. Importantly, identical dilutions of the conditioned media were used for these experiments and for the competitive binding experiments described above. A Western blot analysis of the conditioned media using anti-VEGF-C antiserum 882 was performed to confirm the approximately equal relative amounts of the factors present.

The stimulation of VEGFR-3 and VEGFR-2 autophosphorylation by the different VEGF-C forms in general correlated with their binding properties, as well as with the degree of "recombinant processing" of VEGF-C. The VEGF-CΔNΔCHisC156S appeared to be at least as potent as VEGF-CΔNΔCHis in stimulating VEGFR-3 autophosphorylation. VEGF-CΔNΔCHis showed a higher potency when compared to wildtype VEGF-C in its ability to stimulate tyrosine autophosphorylation of both VEGFR-2 and VEGFR-3. The VEGF-CR226,227S conditioned medium possessed a considerably weaker effect on autophosphorylation of VEGFR-3, and almost no effect on VEGFR-2 autophosphorylation.

Stimulation of VEGFR-2 tyrosine phosphorylation by VEGF-CΔNΔCHisC156S did not differ from that of conditioned medium from the mock transfected cells, thus confirming the lack of VEGFR-2-binding and VEGFR-2-activating properties of this mutant.

The ability of VEGF-C ΔNΔCHisC156S to alter vascular permeability in vivo was analyzed using the Miles assay (see Example 29). The recombinant VEGF-C forms assayed (ΔNΔCHis, ΔNΔCHisC156S) were produced by 293 cells, purified from conditioned media using Ni-NTA Superflow resin (QIAGEN) as previously described, and pretreated with 15 µg/ml of anti-human VEGF neutralizing antibody (R&D systems) to neutralize residual amounts of co-purified, endogenously produced VEGF. Eight picomoles of the various VEGF-C forms, as well as 2 pmol of recombinant human VEGF165 (R&D systems) and approximately 2 pmol of VEGF165 from the conditioned medium which were either non-treated or pretreated with the above mentioned VEGF-neutralizing antibody were injected subcutaneously to the back region of a guinea pig. The area of injection was analyzed 20 minutes after injections. Both VEGF and VEGF-C ΔNΔCHis caused increases in vascular permeability, whereas ΔNΔCHisC156S did not affect vascular permeability. The neutralizing antibody completely blocked permeability activity of VEGF but did not affect VEGF-C activity. Residual permeability activity observed for the VEGF-containing conditioned medium even after its treatment with VEGF neutralizing antibody was presumably caused by permeability factors other than VEGF that are produced by 293 cells.

The Miles assay also was used to assay the ability of VEGF-C R226,227S (8 pM, pretreated with anti-VEGF antibody) to induce vascular permeability. The results indicated that the ability of VEGF-C R226,227S to induce vascular permeability was much weaker when compared to wildtype and ΔNΔCHis forms of VEGF-C. Collectively, this Miles assay data is consistent with the VEGFR-2 binding and autophosphorylation data described above, and indicates that VEGF-C effect on vascular permeability is mediated via VEGFR-2.

The foregoing data indicates that proteolytic processing of VEGF-C results in an increase in its ability to bind and to activate VEGFR-3 and VEGFR-2. Non-processed VEGF-C is a ligand and an activator of preferentially VEGFR-3, while the mature 21/23 kDa VEGF-C form is a high affinity ligand and an activator of both VEGFR-3 and VEGFR-2.

Moreover, replacement of the cysteine residue at position 156 (of prepro-VEGF-C, SEQ ID NO: 8) creates a selective ligand and activator of VEGFR-3. This alteration inactivates the ability of processed VEGF-C to bind to VEGFR-2 and to activate VEGFR-2. Importantly, it is believed that the elimination of the cysteine at position 156 is the alteration responsible for this unexpected alteration in VEGF-C selectivity, and not the substitution of a serine per se. It is expected that replacement of the cysteine at position 156 with other amino acids, or the mere deletion of this cysteine, will also result in VEGF-C analogs having selective biological activity with respect to VEGFR-3. All such replacement and deletion analogs (collectively referred to as VEGF-C $\Delta C_{156}$ polypeptides) are contemplated as aspects of the present invention.

VEGF-C polypeptides that have the C156S mutation (or functposition equivalent mutations at position 156) and that retain biological activity with respect to VEGFR-3, such as VEGF-C ΔNΔCHisC156S, are useful in all of the same manners described above for wildtype VEGF-C proteins and biologically active fragments thereof where VEGFR-3 stimulation is desired. It is contemplated that most biologically active VEGF-C fragments and processing variants, including but not limited to the biologically active fragments and variants identified in preceding examples, will retain VEGF-C biological activity (as mediated through VEGFR-3) when a $\Delta C_{156}$ mutation is introduced. All such biologically active VEGF-C $\Delta C_{156}$ polypeptides are intended as an aspect of the present invention.

Moreover, VEGF-C forms containing the C156S mutation or equivalent mutations can be used to distinguish those effects of VEGF-C mediated via VEGFR-3 and VEGFR-2 from those obtained via only VEGFR-3. The ability of such VEGF-C polypeptides to selectively stimulate VEGFR-3 are also expected to be useful in clinical practice, it being understood that selectivity of a pharmaceutical is highly desirable in many clinical contexts. For example, the selectivity of VEGF-C $\Delta C_{156}$ polypeptides for VEGFR-3 binding suggests a utility for these peptides to modulate VEGF-C biological activities mediated through VEGFR-3, without significant concomitant modulation of blood vessel permeability or other VEGF-C activities that are modulated through VEGFR-2.

The data presented herein also indicates a utility for $\Delta C_{156}$ polypeptides that are capable of binding VEGFR-3, but that do not retain biological activity mediated through VEGFR-3. Specifically, such forms are believed to be capable of competing with wildtype VEGF-C for binding to VEGFR-3, and are therefore contemplated as molecules that inhibit VEGF-C-mediated stimulation of VEGFR-3. Because of the $\Delta C_{156}$ alteration, such polypeptides (especially covalent or noncovalent dimers of such polypeptides) are not expected to bind VEGFR-2. Thus, certain $\Delta C_{156}$ polypeptides and polypeptide dimers are expected to have utility as selective inhibitors of VEGF-C biological activity mediated through VEGFR-3 (i.e., without substantially altering VEGF-C mediated stimulation of VEGFR-2).

In another embodiment of the invention, heterodimers comprising a biologically active VEGF-C polypeptide in association with a $\Delta C_{156}$ polypeptide are contemplated. It is contemplated that such heterodimers can be formed in vitro, as described below in Example 37, or formed in vivo with endogenous VEGF-C following administration of a $\Delta C_{156}$ polypeptide. Such heterodimers are contemplated as modulators of VEGF-C mediated effects in cells where the biological effects of VEGF-C are mediated through VEGFR-2/VEGFR-3 heterodimers. VEGF-C $\Delta C_{156}$ polypeptides in homodimers or in heterodimers with wt VEGF-C might selectively inhibit the ability of the latter to induce VEGF-like effects, particularly to increase the vascular permeability.

EXAMPLE 36

Utility for VEGF-C in Promoting Myelopoiesis

The effects of VEGF-C on hematopoiesis were also analyzed. Specifically, leukocytes populations were analyzed in blood samples taken from the F1 transgenic mice described in Example 29, and from their non-transgenic littermates. Leukocyte population data from these mice and from non-transgenic FVB-NIH control mice (i.e., the strain used to generate the transgenic mice) are set forth in the tables below.

| Cell Type | FVB/NIH MICE | | | | |
|---|---|---|---|---|---|
| | male 5.5 months | male 5.5 months | female 9.5 months | male 9.5 months | mean ± σ |
| Lymphocytes | 72.20% | 82.17% | 84.25% | 74.25% | 78.22 ± 5.10 |
| Neutrophils | 23.00% | 15.17% | 14.25% | 22.25% | 18.67 ± 3.98 |
| Monocytes | 0.65% | 1.00% | 0.25% | 0.50% | 0.60 ± 0.27 |
| Eosinophils | 2.15% | 1.70% | 1.25% | 3.00% | 2.03 ± 0.65 |
| Basophils | 0.00% | 0.00% | 0.00% | 0.00% | 0 ± 0 |

-continued

VEGF-C TRANSGENIC MICE

| Cell Type | male 2 months | male 3.5 months | male 7 months | mean ± σ |
|---|---|---|---|---|
| Lymphocytes | 41.3% | 41.50% | 18.70% | 33.83 ± 10.70 |
| Neutrophils | 55.3% | 53.80% | 80.17% | 63.09 ± 12.09 |
| Monocytes | 2.16% | 1.30% | 0.67% | 1.38 ± 0.61 |
| Eosinophils | 1.17% | 3.50% | .50% | 1.72 ± 1.29 |
| Basophils | 0.00% | 0.00% | 0.00% | 0 ± 0 |

VEGF-C NEGATIVE CONTROL MICE (NON-TRANSGENIC LITTERMATES OF VEGF-C TRANSGENIC MICE)

| Cell Type | male 2 months | male 2 months | male 3.5 months | male 7 months | mean ± σ |
|---|---|---|---|---|---|
| Lymphocytes | 89.00% | 67.50% | 91.00% | 71.30% | 79.7 ± 10.41 |
| Neutrophils | 7.75% | 23.00% | 7.00% | 23.75% | 15.38 ± 8.01 |
| Monocytes | 1.50% | 0.50% | 0.83% | 0.75% | 0.90 ± 0.37 |
| Eosinophils | 1.50% | 9.00% | 0.67% | 4.00% | 3.79 ± 3.25 |
| Basophils | 0.00% | 0.00% | 0.50% | 0.50% | 0.25 ± 0.25 |

As the foregoing data indicates, the overexpression of VEGF-C in the skin of the transgenic mice correlates with a distinct alteration in leukocyte populations. Notably, the measured populations of neutrophils were markedly increased in the transgenic mice. One explanation for the marked increase in neutrophils is a myelopoietic activity attributable to VEGF-C. A VEGF-C influence on leukocyte trafficking in and out of tissues also may effect observed neutrophil populations. Fluorescence-activated cell sorting analysis, performed on isolated human bone marrow and umbilical cord blood CD34-positive hematopoietic cells, demonstrated that a fraction of these cells are positive for Flt4 (VEGFR-3). Thus, the VEGF-C effect on myelopoiesis may be exerted through this VEGFR-3-positive cell population and its receptors. In any case, the foregoing data indicates a use for VEFG-C polypeptides to increase granulocyte (and, in particular, neutrophil) counts in human or non-human subjects, i.e., in order to assist the subject fight infectious diseases. The exploitation of the myelopoietic activity of VEGF-C polypeptides is contemplated both in vitro (i.e., in cell culture) and in vivo, as a sole myelopoietic agent and in combination with other effective agents (e.g., granulocyte colony stimulating factor (G-CSF)).

Additional studies of the myelopoietic effect of VEGF-C, using VEGF-C mutants (e.g., VEGF-C $\Delta C_{156}$ polypeptides, VEGF-C $\Delta N\Delta C$His, VEGF-C R226,227S) having altered VEGFR-2 binding affinities, will elucidate whether this effect is mediated through VEGFR-2, VEGFR-3, or both receptors, for example. The results of such analysis will be useful in determining which VEGF-C mutants have utility as myelopoietic agents and which have utility as agents for inhibiting myelopoiesis.

EXAMPLE 37

Generation of Heterodimers Consisting of Members of the VEGF Family of Growth Factors Both naturally-occurring and recombinantly-produced heterodimers of polypeptides of the PDGF/VEGF family of growth factors have been shown to exist in nature and possess mitogenic activities. See, e.g., Cao et al., *J. Biol. Chem.*, 271:3154–62 (1996); and DiSalvo, et al., *J. Biol. Chem.*, 270:7717–7723 (1995). Heterodimers comprising a VEGF-C polypeptide may be generated essentially as described In Cao et al. (1996), using recombinantly produced VEGF-C polypeptides, such as the VEGF-C polypeptides described in the preceding examples. Briefly, a recombinantly produced VEGF-C polypeptide is mixed at an equimolar ratio with another recombinantly produced polypeptide of interest, such as a VEGF, VEGF-B, PLGF, PDGFα, PDGFβ, or c-fos induced growth factor polypeptide. (See, e.g., Cao et al. (1990); Collins et al., *Nature*, 316:748–750 (1985) (PDGF-β, GenBank Acc. No. X02811); Claesson-Welsh et al., *Proc. Natl. Acad. Sci. USA*, 86(13):4917–4921 (1989) (PDGF-α, GenBank Acc. No. M22734); Claesson-Welsh et al., *Mol. Cell. Biol.* 8:3476–3486 (1988) (PDGF-β, GenBank Acc. No. M21616); Olofsson et al., *Proc. Natl. Acad. Sci. (USA)*, 93:2576–2581 (1996) (VEGF-B, GenBank Acc. No. U48801); Maglione et al., *Proc. Natl. Acad. Sci. (USA)*, 88(20):9267–9271 (1996) (PlGF, GenBank Acc. No. X54936); Heldin et al., *Growth Factors*, 8:245–252 (1993); Folkman, *Nature Med.*, 1:27–31 (1995); Friesel et al., *FASEB J.*, 9:919–25 (1995); Mustonen et al., *J. Cell. Biol.*, 129:895–98 (1995); Orlandini, S., *Proc. Natl. Acad. Sci. USA*, 93(21):11675–11680 (1996); and others cited elsewhere herein. The mixed polypeptides are incubated in the presence of guanidine-HCl and DTT. The thiol groups are then protected with S-sulfonation, and the protein is dialyzed overnight, initially against urea/glutathione-SH, glutathione-S-S-glutathione, and subsequently against 20 mM Tris-HCl.

In a preferred embodiment, a variety of differently processed VEGF-C forms and VEGF-C variants and analogs, such as the ones described in the preceding examples, are employed as the VEGF-C polypeptide used to generate such heterodimers. Thereafter, the heterodimers are screened to determine their binding affinity with respect to receptors of the VEGF/PDGF family (especially VEGFR-1, VEGFR-2, and VEGFR-3), and their ability to stimulate the receptors (e.g., assaying for dimer-stimulated receptor phosphorylation in cells expressing the receptor of interest on their surface). The binding assays may be competitive binding assays such as those described herein and in the art. In the initial binding assays, recombinantly produced proteins comprising the extracellular domains of receptors are employable, as described in preceding examples for VEGFR-2 and VEGFR-3. Heterodimers that bind and stimulate receptors are useful as recombinant growth factor polypeptides. Heterodimers that bind but do not stimulate receptors are useful as growth factor antagonists. Heterodimers that display agonistic or antagonistic activities in the screening assays are further screened using, e.g., endothelial cell migration assays, vascular permeability assays, and in vivo assays. It will also be apparent from the preceding examples that dimers comprising two VEGF-C polypeptides (i.e., dimers of identical VEGF-C polypeptides as well as dimers of different VEGF-C polypeptides) are advantageously screened for agonistic and antagonistic activities using the same assays.

In one preferred embodiment, VEGF-C $\Delta C_{156}$, polypeptide is employed to make the dimers. It is anticipated that agonists and antagonists comprising a VEGF-C $\Delta C_{156}$ polypeptide will have increased specificity for stimulating and inhibiting VEGFR-3, without concomitant stimulation or inhibition of VEGFR-2.

In another preferred embodiment, VEGF-C polypeptides wherein the C-terminal proteolytic cleavage site has been altered to reduce or eliminate C-terminal processing (e.g. VEGF-C R226,227S) is employed to make dimers for screening for inhibitory activity.

In yet another preferred embodiment, VEGF-C polypeptides comprising amino-terminal fragments (e.g., the VEGF-C 15 kD form described herein) of VEGF-C are employed to make dimers.

It is further contemplated that inactivation of only one polypeptide chain in a dimer could be enough to generate an inhibitory molecule, which is demonstrated e.g., by the generation of PDGF inhibitory mutant as reported in Vassbotn, *Mol. Cell. Biol.*, 13:4066–4076 (1993). Therefore, in one embodiment, inhibition is achieved by expression in vivo of a polynucleotide (e.g., a cDNA construct) encoding the heterodimerization partner which is unable to bind (or binds inefficiently) to the receptor, or by direct administration of that monomer in a pharmaceutical composition.

EXAMPLE 38

Formation and Screening of Useful Recombinant VEGF/VEGF-C Genes and Polypeptides Amino acid sequence comparison reveals that mature VEGF-C bears structural similarity to VEGF121 [Tischer et al., *J. Biol. Chem.*, 266(18):11947–54 (1991)], with certain noteworthy structural differences. For example, mature VEGF-C contains an unpaired cysteine (position 137 of SEQ ID NO: 8) and is able to form non-covalently bonded polypeptide dimers. In one embodiment of the invention, a VEGF analog is created wherein the unpaired cysteine residue from mature VEGF-C is introduced at an analogous position of VEGF (e.g., introduced at $Leu_{58}$ of the human VEGF165 precursor (FIG. 2, Genbank Acc. No. M32977) to generate a $VEGF^{+cys}$ mutant designated VEGF L58C). Such an alteration is introduced into the VEGF165 coding sequence using site-directed mutagenesis procedures known in the art, such as the procedures described above in preceding examples to generate various VEGF-C mutant forms. This $VEGF^{+cys}$ mutant is recombinantly expressed and is screened (alone and as a heterodimer with other VEGF and VEGF-C forms) for VEGFR-2 and/or VEGFR-3 binding, stimulatory, and inhibitory activities, using in vitro and in vivo activity assays as described elsewhere herein. To form another VEGF analog of the invention, a $VEGF^{+cys}$ mutant is altered to remove a conserved cysteine corresponding to cyst of the VEGF165 precursor. Elimination of this cysteine from the VEGF L58C would result in a VEGF analog resembling VEGF-CΔNΔCHisC156S. This VEGF analog is screened for its VEGF-inhibitory activities with respect to VEGFR-2 and/or VEGFR-1 and for VEGF-C like stimulatory or inhibitory activities.

Another noteworthy structural difference between VEGF and VEGF-C is the absence in VEGF-C of several basic residues found in VEGF (e.g., residues $Arg_{108}$, $Lys_{110}$ and $His_{112}$ in the VEGF165 precursor shown in FIG. 2) that have been implicated in VEGF receptor binding. See Keyt et al., *J. Biol. Chem.*, 271(10):5638–46 (1996). In another embodiment of the invention, codons for basic residues (lys, arg, his) are substituted into the VEGF-C coding sequence at one or more analogous positions by site-directed mutagenesis. For example, in a preferred embodiment, $Glu_{187}$, $Thr_{189}$, and $Pro_{191}$, in VEGF-C (SEQ ID NO: 8) are replaced with Arg, Lys, and His residues, respectively. The resultant VEGF-C analogs (collectively termed "VEGF-$C^{basic}$" polypeptides) are recombinantly expressed and screened for VEGFR-1, VEGFR-2, and VEGFR-3 stimulatory and inhibitory activity. The foregoing VEGF and VEGF-C analogs that have VEGF-like activity, VEGF-C-like activity, or that act as inhibitors of VEGF or VEGF-C, are contemplated as additional aspects of the invention. Polynucleotides encoding the analogs also are intended as aspects of the invention.

Deposit of Biological Materials: Plasmid FLT4-L has been deposited with the American Type Culture Collection (ATCC), 12301 Parklawn Dr., Rockville Md. 20952 (USA), pursuant to the provisions of the Budapest Treaty, and has been assigned a deposit date of Jul. 24, 1995 and ATCC accession number 97231.

While the present invention has been described in terms of specific embodiments, it is understood that variations and modifications will occur to those in the art. Accordingly, only such limitations as appear in the appended claims should be placed on the invention.

What is claimed is:

1. A purified and isolated VEGF-C$\Delta C_{156}$ polypeptide that binds to human Flt4 receptor tyrosine kinase (VEGFR-3) and fails to bind to human KDR receptor tyrosine (VEGFR-2), said polypeptide having an amino acid sequence comprising a portion of SEQ ID NO: 8 effective to permit binding to VEGFR-3, wherein the cysteine residue at position 156 of SEQ ID NO: 8 has been deleted or replaced by another amino acid.

2. A polypeptide according to claim 1 wherein said portion of SEQ ID NO: 8 is selected from the group consisting of:
   (a) continuous portion having as its amino terminal residue an amino acid between residues 102 and 114 of SEQ ID NO: 8 and having as its carboxy terminal residue an amino acid between residues 212 and 228 of SEQ ID NO: 8, wherein the cysteine residue at position 156 of SEQ ID NO: 8 has been deleted or replaced by another amino acid;
   (b) continuous portions that comprise an amino-terminal truncation of (a); and
   continuous portions that comprise a carboxy-terminal truncation of (a) or b).

3. A polypeptide according to claim 2, wherein said polypeptide is capable of stimulating tyrosine phosphorylation of VEGFR-3 in a host cell expressing VEGFR-3.

4. A VEGF-C $\Delta C_{156}$ polypeptide according to claim 1 comprising amino acids 113 to 213 of SEQ ID NO: 8, wherein the cysteine residue at position 156 of SEQ ID NO; 8 has been deleted or replaced.

5. A VEGF-C $\Delta C_{156}$ polypeptide according to claim 1 comprising a continuous portion of SEQ ID NO: 8, said portion having as its amino terminal residue an amino acid between residues 102 and 114 of SEQ ID NO: 8, and having as its carboxy terminal residue an amino acid between residues 212 and 228 of SEQ ID NO: 8, wherein the cysteine residue at position 156 of SEQ ID NO: 8 has been deleted or replaced.

6. A VEGF-C $\Delta C_{156}$ polypeptide according to claim 1 wherein the cysteine residue at position 156 of SEQ ID NO: 8 has been replaced by a serine residue.

7. A composition comprising a polypeptide according to claim 1 in a pharmaceutically-acceptable diluent, adjuvant, excipient, or carrier.

8. A purified and isolated polypeptide nultirner, wherein at least one monomer thereof is a polypeptide according to claim 1, and wherein said multimer is capable of binding to VEGFR-3.

9. A dimer according to claim 1.

10. A polypeptide according to claim 1 comprising amino acids 1 to 419 of SEQ ID NO: 8, wherein the cysteine residue at position 156 of SEQ ID NO: 8 has been deleted or replaced by another amino acid.

11. A method of imaging Flt4 receptor tyrosine kinase (VEGFR-3) in tissue suspected of containing VEGFR-3, comprising the steps of contacting tissue suspected of containing VEGFR-3 with a polypepude of claim 1 and imaging VEGFR-3 in the tissue by detecting the polypeptide bound to the tissue.

12. A purified and isolated nucleic acid comprising a nucleotide sequence encoding a VEGF-C $\Delta C_{156}$ polypeptide that binds to human Flt4 receptor tyrosine kinase (VEGFR-3) and fails to bind to human KDR receptor tyrosine (VEGFR-2), said polypeptide, having an amino acid sequence comprising a portion of SEQ ID NO: 8 effective to permit binding to VEGFR-3, wherein the cysteine residue at position 156 of SEQ ID NO: 8 has been deleted or replaced by another amino acid.

13. A vector comprising a nucleic acid according to claim 13.

14. A host cell transformed or transfected with a nucleic acid according to claim 12.

15. A method of making a polypeptide that binds to VEGFR-3, said method comprising the steps of:
   (a) expressing a nucleic acid according to claim 12 in a host cell; and
   (b) purifying a polypeptide that binds to VEGFR-3 from said host cell or from a growth medium of said host cell.

16. A polypeptide that binds to the extracellular domain of human Flt4 receptor tyrosine kmase (VEGFR-3),
   said polypeptide comprising a fragment of a vertebrate pepro-VEGF-C amino acid sequence that binds to human VEGFR3, with the iproviso that, in said polypeptide a conserved cysteine of the vertebrate prepro-VEGF-C has been deleted or replaced by another amino acid,
   wherein the vertebrate prepro-VEGF-C amino acid sequence comprises an amino acid sequence that is encoded by a DNA of vertebrate origin which hybridizes to a non-coding strand complementary to nucleotides 352 to 1611 of SEQ ID NO: 7 under the following hybridization conditions: hybridization at 42° C. in a hybridization solution comprising 50% formamide, 5×SSC, 20 mM Na*PO$_6$, pH 6.8; and washing in 0.2×SSC at 55° C.,
   wherein nucleotides 352 to 1611 of SEQ ID NO: 7 encode a human prepro-VEGF-C having the amino acid sequence set forth in SEQ ID NO: 8 that is characterized by eight cysteine residues at positions 131, 156, 162, 165, 166, 173, 209, and 211 of SEQ ID NO: 8 that are conserved in human vascular endothelial growth factor (VEGF), human platelet derived growth factors A and B (PDGF-A, PDGF-B), human placenta growth factor (PIGF-1), and human vascular endothelial growth factor B (VEGF-B), and
   wherein the conserved cysteine that has been deleted or replaced corresponds to position 156 of SEQ ID NO: 8.

17. A purified polypeptide according to claim 16 wherein the vertebrate is a human.

18. A polypeptide according to claim 16 wherein the vertebrate is a mouse.

19. A polypeptide according to claim 16 that binds VEGFR-3 and has reduced VEGFR-2 binding affinity relative to human VEGF-C having an amino acid sequence consisting of amino acids 103–227 of SEQ ID NO: 8.

20. A composition comprising a polypeptide according to claim 16 in a pharmaceutically-acceptable diluent, adjuvant, excipient, or carrier.

21. A polypeptide according to claim 16, wherein said polypeptide comprises an amino acid sequence selected from the group consisting of:
   (a) the amino acid sequence of SEQ ID NO: 11, wherein the cysteine residue at position 152 of SEQ ID NO: 11 has been deleted or replaced by another ammo acid;
   (b) amino-terminal trunations of (a); and
   (c) carboxyl-terminal truncations of (a) or (b).

22. A polypeptide according to claim 16, wherein said polypeptide comprises an amino acid sequence selected from the group consisting of:
   (a) the amino acid sequence of SEQ ID NO: 13, wherein the cysteine residue at position 155 of SEQ ID NO: 13 has been deleted or replaced by another amino acids;

(b) amino-terminal truncations of (a); and (c) carboxyl-terminal truncations of (a) or (b).

23. A purified and isolated nucleic acid comprising a nucteotide sequence encoding a polypeptide that binds to the extracellular domain of human Flt4 receptor trosine kiase (VEGFR-3), said polypeptide comprising a fragment of a vertebrate prepro-VEGF-C amino acid sequence that binds to human VEGFR-3, with the proviso that, in said polypeptide, a conserved cysteine of the vertebrate prepro-VEGF-C has been deleted or replaced by another amino acid, wherein the vertebrate prepro-VEGF-C amino acid sequence comprises an amino acid sequence that is encoded by a DNA of vertebrate origin which hybridizes to a non-coding strand complementary to nucleotides at 352 to 1611 of SEQ ID NO: 7 under the following hybridization condition: hybridizatin at 42° C. in a hybridization solution comprising 50% formamide, 5×SSC 20 mM Na.PO, pH 6.8; and washing in 0.2×SSC at 55° C., wherein nucleotides 352 to 1611 SEQ ID NO: 7 encoded a human prepro-VEGF-C having the amino acid sequence set forth in SEQ ID NO: 8 that is characterized by eight cysteine residues at position 131, 156, 162, 165, 166, 173, 209, and 211 of SEQ ID NO: 8 that are conserved in human vascular endothelial growth factor (VEGF), human platelet derived growth factors A, and B (PDGF-A, PDGF-B), human placenta growth factor (PlGE-1), and human vascular endothelial growth factor B (VEGR-B), and wherein the conserved cysteine that has been deleted or replaced corresponds to position 156 of SEQ ID NO: 8.

24. A vector comprising a nucleic acid according to claim 23.

25. A host cell transformed or transfected with a nucleic acid according to claim 23.

26. A method of making a polypeptide that binds to VEGFR-3, said method comprising the steps of:

(a) expressing a nucleic acid according to claim 23 in a host cell; and (b) purifying a polypeptide that binds to VEGFR-3 from said host cell or from a growth medium of said host cell.

27. A polypeptide that binds to human Flt4 receptor tyrosine kinase (VEGFR-3), said polypeptide comprising an amino acid sequence selected from the group consisting of:

(a) the amino acid sequence of SEQ ID NO: 8, wherein the cysteine residue at position 156 of SEQ ID NO: 8 has been deleted replaced by another amino acid;

(b) the amino acid sequence of SEQ ID NO: 11, wherein the cysteine residue at position 152 of SEQ ID NO: 11 has been deleted or replaced by another amino acid;

(c) the amino acid sequence of SEQ ID NO: 13, wherein the cysteine residue at position 155 of SEQ ID NO: 13 has been deleted or replaced by another amino acid;

(d) amino-terminal truncations of (a), (b), or (c); and (e) carboxyl-terminal truncations of (a), (b), (c), or (d).

28. A polynucleotide comprising a nucleotide sequence that encodes a polypeptide that binds to human Flt4 receptor tyrosine kinase (VEGFR-3), said polypeptide comprising an amino acid sequence selected from the group consisting of:

(a) the amino acid sequence of SEQ ID NO: 8, wherein the cysteine residue at position 156 of SEQ ID NO: 8 has been deleted or replaced by another amino acid;

(b) the amino acid sequence of SEQ ID NO: 11, wherein the cysteine residue at position 152 of SEQ ID NO: 11 has been deleted or replaced by another amino acid;

(c) the amino acid sequence of SEQ ID NO: 13, wherein the cysteine residue at position 155 of SEQ ID NO: 13 has been deleted or replaced by another amino acid;

(d) amino-terminal truncations of (a), (b), or (c); and (e) carboxyl-terminal truncations of (a), (b), (c), or (d).

29. A polynucleotide according to claim 28, wherein the nucleotide sequence that encodes the peptide comprises a sequence selected from the group consisting of:

(a) the nucleotide sequence set forth in SEQ ID NO: 7 from nucleotide 352 to 1611, wherein the cysteine codon at positions 817–819 has been deleted or replaced by a codon for an amino acid other than cysteine;

(b) the nucleotide sequence set forth in SEQ ID NO: 10 from nucleotide 168 to 1412, wherein the cysteine codon at positions 621–623 has been deleted or replaced by a codon for an amino acid other than cysteine;

(c) the nucleotide sequence set forth in SEQ ID NO: 12 from nucleotide 453 to 1706, wherein the cysteine codon at positions 915–917 has been deleted or replaced by a codon for an amino aid other than cysteine;

(d) 5'-deletion fragments of (a), (b), or (c); and (e) 3'-deletion fragments of (a), (b), (c), or (d).

* * * * *

UNITED STATES PATENT AND TRADEMARK OFFICE
CERTIFICATE OF CORRECTION

PATENT NO. : 6,130,071
APPLICATION NO. : 08/795430
DATED : October 10, 2000
INVENTOR(S) : Kari Alitalo et al.

It is certified that error appears in the above-identified patent and that said Letters Patent is hereby corrected as shown below:

First page, first column, Abstract, line 5 "polypeptide;" should be --polypeptides;--, Column 119, line 13, "continuous portion" should be --a continuous portion--, Column 119, line 21, "continuous portions" should be --(c) continuous portions--, Column 119, line 23, "claim 2," should be --claim 2--, Column 119, line 28, "SEQ ID NO;" should be --SEQ ID NO:--, Column 119, line 44, "nultirner," should be --multimer,--, Column 119, line 56, "polypepude" should be --polypeptide--, Column 119, line 63, "polypeptide," should be --polypeptide--, Column 120, line 14, "kmase" should be --kinase--, Column 120, line 16, "pepro" should be --prepro--, Column 120, line 17-18, "VEGFR3, with the iproviso that, in said polyypeptide" should be --VEGFR-3, with the proviso that, in said polypeptide,--, Column 120, line 28, "Na*PO6" should be --Na•PO4--, Column 120, line 38, "(PIGF-1)," should be --(PIGF-1),--, Column 120, line 60, "trunations" should be --truncations--, Column 120, line 67, "acids;" should be --acid;--, Column 121, line 5, "trosine kiase" should be --tyrosine kinase--, Column 121, lines 17-18, "nucleotides at 352 to 1611" should be --nucleotides 352 to 1611--, Column 121, line 19, "condition: hybridizatin" should be --conditions: hybridization--,

UNITED STATES PATENT AND TRADEMARK OFFICE
CERTIFICATE OF CORRECTION

PATENT NO. : 6,130,071
APPLICATION NO. : 08/795430
DATED : October 10, 2000
INVENTOR(S) : Kari Alitalo et al.

It is certified that error appears in the above-identified patent and that said Letters Patent is hereby corrected as shown below:

Column 121, line 21, "Na.PO" should be --Na•PO4--,

Column 121, line 23, "encoded" should be --encode--,

Column 121, line 30, "A," should be --A--,

Column 121, line 31, "(P1GE-1)" should be --(PIGF-1)--,

Column 121, line 32, "(VEGR-B)," should be --(VEGF-B),--,

Column 122, line 3, "deleted replaced" should be --deleted or replaced--,

Column 122, line 44, "aid" should be --acid--,

Signed and Sealed this

Fifteenth Day of April, 2008

JON W. DUDAS
*Director of the United States Patent and Trademark Office*

SEQUENCE LISTING (1) GENERAL INFORMATION:

(iii) NUMBER OF SEQUENCES: 57

(2) INFORMATION FOR SEQ ID NO:1:

(i) SEQUENCE CHARACTERISTICS:
        (A) LENGTH: 4416 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:1:

```
CCACGCGCAG CGGCCGGAGA TGCAGCGGGG CGCCGCGCTG TGCCTGCGAC TGTGGCTCTG      60

CCTGGGACTC CTGGACGGCC TGGTGAGTGG CTACTCCATG ACCCCCCCGA CCTTGAACAT     120

CACGGAGGAG TCACACGTCA TCGACACCGG TGACAGCCTG TCCATCTCCT GCAGGGGACA     180

GCACCCCCTC GAGTGGGCTT GGCCAGGAGC TCAGGAGGCG CCAGCCACCG GAGACAAGGA     240
```

-continued

| | |
|---|---|
| CAGCGAGGAC ACGGGGGTGG TGCGAGACTG CGAGGGCACA GACGCCAGGC CCTACTGCAA | 300 |
| GGTGTTGCTG CTGCACGAGG TACATGCCAA CGACACAGGC AGCTACGTCT GCTACTACAA | 360 |
| GTACATCAAG GCACGCATCG AGGGCACCAC GGCCGCCAGC TCCTACGTGT TCGTGAGAGA | 420 |
| CTTTGAGCAG CCATTCATCA ACAAGCCTGA CACGCTCTTG GTCAACAGGA AGGACGCCAT | 480 |
| GTGGGTGCCC TGTCTGGTGT CCATCCCCGG CCTCAATGTC ACGCTGCGCT CGCAAAGCTC | 540 |
| GGTGCTGTGG CCAGACGGGC AGGAGGTGGT GTGGGATGAC CGGCGGGGCA TGCTCGTGTC | 600 |
| CACGCCACTG CTGCACGATG CCCTGTACCT GCAGTGCGAG ACCACCTGGG GAGACCAGGA | 660 |
| CTTCCTTTCC AACCCCTTCC TGGTGCACAT CACAGGCAAC GAGCTCTATG ACATCCAGCT | 720 |
| GTTGCCCAGG AAGTCGCTGG AGCTGCTGGT AGGGGAGAAG CTGGTCCTGA ACTGCACCGT | 780 |
| GTGGGCTGAG TTTAACTCAG GTGTCACCTT TGACTGGGAC TACCCAGGGA AGCAGGCAGA | 840 |
| GCGGGGTAAG TGGGTGCCCG AGCGACGCTC CCAGCAGACC CACACAGAAC TCTCCAGCAT | 900 |
| CCTGACCATC CACAACGTCA GCCAGCACGA CCTGGGCTCG TATGTGTGCA AGGCCAACAA | 960 |
| CGGCATCCAG CGATTTCGGG AGAGCACCGA GGTCATTGTG CATGAAAATC CCTTCATCAG | 1020 |
| CGTCGAGTGG CTCAAAGGAC CCATCCTGGA GGCCACGGCA GGAGACGAGC TGGTGAAGCT | 1080 |
| GCCCGTGAAG CTGGCAGCGT ACCCCCCGCC CGAGTTCCAG TGGTACAAGG ATGGAAAGGC | 1140 |
| ACTGTCCGGG CGCCACAGTC CACATGCCCT GGTGCTCAAG GAGGTGACAG AGGCCAGCAC | 1200 |
| AGGCACCTAC ACCCTCGCCC TGTGGAACTC CGCTGCTGGC CTGAGGCGCA ACATCAGCCT | 1260 |
| GGAGCTGGTG GTGAATGTGC CCCCCAGAT ACATGAGAAG GAGGCCTCCT CCCCCAGCAT | 1320 |
| CTACTCGCGT CACAGCCGCC AGGCCCTCAC CTGCACGGCC TACGGGGTGC CCCTGCCTCT | 1380 |
| CAGCATCCAG TGGCACTGGC GGCCCTGGAC ACCCTGCAAG ATGTTTGCCC AGCGTAGTCT | 1440 |
| CCGGCGGCGG CAGCAGCAAG ACCTCATGCC ACAGTGCCGT GACTGGAGGG CGGTGACCAC | 1500 |
| GCAGGATGCC GTGAACCCCA TCGAGAGCCT GGACACCTGG ACCGAGTTTG TGGAGGGAAA | 1560 |
| GAATAAGACT GTGAGCAAGC TGGTGATCCA GAATGCCAAC GTGTCTGCCA TGTACAAGTG | 1620 |
| TGTGGTCTCC AACAAGGTGG GCCAGGATGA GCGGCTCATC TACTTCTATG TGACCACCAT | 1680 |
| CCCCGACGGC TTCACCATCG AATCCAAGCC ATCCGAGGAG CTACTAGAGG CCAGCCGGT | 1740 |
| GCTCCTGAGC TGCCAAGCCG ACAGCTACAA GTACGAGCAT CTGCGCTGGT ACCGCCTCAA | 1800 |
| CCTGTCCACG CTGCACGATG CGCACGGGAA CCCGCTTCTG CTCGACTGCA AGAACGTGCA | 1860 |
| TCTGTTCGCC ACCCCTCTGG CCGCCAGCCT GGAGGAGGTG GCACCTGGGG CGCGCCACGC | 1920 |
| CACGCTCAGC CTGAGTATCC CCCGCGTCGC GCCCGAGCAC GAGGGCCACT ATGTGTGCGA | 1980 |
| AGTGCAAGAC CGGCGCAGCC ATGACAAGCA CTGCCACAAG AAGTACCTGT CGGTGCAGGC | 2040 |
| CCTGGAAGCC CCTCGGCTCA CGCAGAACTT GACCGACCTC CTGGTGAACG TGAGCGACTC | 2100 |
| GCTGGAGATG CAGTGCTTGG TGGCCGGAGC GCACGCGCCC AGCATCGTGT GGTACAAAGA | 2160 |
| CGAGAGGCTG CTGGAGGAAA AGTCTGGAGT CGACTTGGCG GACTCCAACC AGAAGCTGAG | 2220 |
| CATCCAGCGC GTGCGCGAGG AGGATGCGGG ACGCTATCTG TGCAGCGTGT GCAACGCCAA | 2280 |
| GGGCTGCGTC AACTCCTCCG CCAGCGTGGC CGTGGAAGGC TCCGAGGATA AGGGCAGCAT | 2340 |
| GGAGATCGTG ATCCTTGTCG GTACCGGCGT CATCGCTGTC TTCTTCTGGG TCCTCCTCCT | 2400 |
| CCTCATCTTC TGTAACATGA GGAGGCCGGC CCACGCAGAC ATCAAGACGG CTACCTGTC | 2460 |
| CATCATCATG GACCCCGGGG AGGTGCCTCT GGAGGAGCAA TGCGAATACC TGTCCTACGA | 2520 |
| TGCCAGCCAG TGGGAATTCC CCCGAGAGCG GCTGCACCTG GGGAGAGTGC TCGGCTACGG | 2580 |

| | |
|---|---|
| CGCCTTCGGG AAGGTGGTGG AAGCCTCCGC TTTCGGCATC CACAAGGGCA GCAGCTGTGA | 2640 |
| CACCGTGGCC GTGAAAATGC TGAAAGAGGG CGCCACGGCC AGCGAGCACC GCGCGCTGAT | 2700 |
| GTCGGAGCTC AAGATCCTCA TTCACATCGG CAACCACCTC AACGTGGTCA ACCTCCTCGG | 2760 |
| GGCGTGCACC AAGCCGCAGG GCCCCCTCAT GGTGATCGTG GAGTTCTGCA AGTACGGCAA | 2820 |
| CCTCTCCAAC TTCCTGCGCG CCAAGCGGGA CGCCTTCAGC CCCTGCGCGG AGAAGTCTCC | 2880 |
| CGAGCAGCGC GGACGCTTCC GCGCCATGGT GGAGCTCGCC AGGCTGGATC GGAGGCGGCC | 2940 |
| GGGGAGCAGC GACAGGGTCC TCTTCGCGCG GTTCTCGAAG ACCGAGGGCG GAGCGAGGCG | 3000 |
| GGCTTCTCCA GACCAAGAAG CTGAGGACCT GTGGCTGAGC CCGCTGACCA TGGAAGATCT | 3060 |
| TGTCTGCTAC AGCTTCCAGG TGGCCAGAGG GATGGAGTTC CTGGCTTCCC GAAAGTGCAT | 3120 |
| CCACAGAGAC CTGGCTGCTC GGAACATTCT GCTGTCGGAA AGCGACGTGG TGAAGATCTG | 3180 |
| TGACTTTGGC CTTGCCCGGG ACATCTACAA AGACCCTGAC TACGTCCGCA AGGGCAGTGC | 3240 |
| CCGGCTGCCC CTGAAGTGGA TGGCCCCTGA AGCATCTTC GACAAGGTGT ACACCACGCA | 3300 |
| GAGTGACGTG TGGTCCTTTG GGGTGCTTCT CTGGGAGATC TTCTCTCTGG GGGCCTCCCC | 3360 |
| GTACCCTGGG GTGCAGATCA ATGAGGAGTT CTGCCAGCGG CTGAGAGACG GCACAAGGAT | 3420 |
| GAGGGCCCCG GAGCTGGCCA CTCCCGCCAT ACGCCGCATC ATGCTGAACT GCTGGTCCGG | 3480 |
| AGACCCCAAG GCGAGACCTG CATTCTCGGA GCTGGTGGAG ATCCTGGGGG ACCTGCTCCA | 3540 |
| GGGCAGGGGC CTGCAAGAGG AAGAGGAGGT CTGCATGGCC CCGCGCAGCT CTCAGAGCTC | 3600 |
| AGAAGAGGGC AGCTTCTCGC AGGTGTCCAC CATGGCCCTA CACATCGCCC AGGCTGACGC | 3660 |
| TGAGGACAGC CCGCCAAGCC TGCAGCGCCA CAGCCTGGCC GCCAGGTATT ACAACTGGGT | 3720 |
| GTCCTTTCCC GGGTGCCTGG CCAGAGGGGC TGAGACCCGT GGTTCCTCCA GGATGAAGAC | 3780 |
| ATTTGAGGAA TTCCCCATGA CCCCAACGAC CTACAAAGGC TCTGTGGACA ACCAGACAGA | 3840 |
| CAGTGGGATG GTGCTGGCCT CGGAGGAGTT TGAGCAGATA GAGAGCAGGC ATAGACAAGA | 3900 |
| AAGCGGCTTC AGGTAGCTGA AGCAGAGAGA GAGAAGGCAG CATACGTCAG CATTTTCTTC | 3960 |
| TCTGCACTTA TAAGAAAGAT CAAAGACTTT AAGACTTTCG CTATTTCTTC TACTGCTATC | 4020 |
| TACTACAAAC TTCAAAGAGG AACCAGGAGG ACAAGAGGAG CATGAAAGTG GACAAGGAGT | 4080 |
| GTGACCACTG AAGCACCACA GGGAAGGGGT TAGGCCTCCG GATGACTGCG GGCAGGCCTG | 4140 |
| GATAATATCC AGCCTCCCAC AAGAAGCTGG TGGAGCAGAG TGTTCCCTGA CTCCTCCAAG | 4200 |
| GAAAGGGAGA CGCCCTTTCA TGGTCTGCTG AGTAACAGGT GCNTTCCCAG ACACTGGCGT | 4260 |
| TACTGCTTGA CCAAAGAGCC CTCAAGCGGC CCTTATGCCA GCGTGACAGA GGGCTCACCT | 4320 |
| CTTGCCTTCT AGGTCACTTC TCACACAATG TCCCTTCAGC ACCTGACCCT GTGCCCGCCA | 4380 |
| GTTATTCCTT GGTAATATGA GTAATACATC AAAGAG | 4416 |

(2) INFORMATION FOR SEQ ID NO:2:

(i) SEQUENCE CHARACTERISTICS:
        (A) LENGTH: 216 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:2:

| | |
|---|---|
| CAAGAAAGCG GCTTCAGCTG TAAAGGACCT GGCCAGAATG TGGCTGTGAC CAGGGCACAC | 60 |
| CCTGACTCCC AAGGGAGGCG GCGGCGGCCT GAGCGGGGGG CCCGAGGAGG CCAGGTGTTT | 120 |

-continued

| TACAACAGCG AGTATGGGGA GCTGTCGGAG CCAAGCGAGG AGGACCACTG CTCCCCGTCT | 180 |
| GCCCGCGTGA CTTTCTTCAC AGACAACAGC TACTAA | 216 |

(2) INFORMATION FOR SEQ ID NO:3:

(i) SEQUENCE CHARACTERISTICS:
        (A) LENGTH: 4273 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:3:

| AAGCTTATCG ATTTCGAACC CGGGGGTACC GAATTCCTCG AGTCTAGAGG AGCATGCCTG | 60 |
| CAGGTCGACC GGGCTCGATC CCCTCGCGAG TTGGTTCAGC TGCTGCCTGA GGCTGGACGA | 120 |
| CCTCGCGGAG TTCTACCGGC AGTGCAAATC CGTCGGCATC CAGGAAACCA GCAGCGGCTA | 180 |
| TCCGCGCATC CATGCCCCCG AACTGCAGGA GTGGGGAGGC ACGATGGCCG CTTTGGTCCC | 240 |
| GGATCTTTGT GAAGGAACCT TACTTCTGTG GTGTGACATA ATTGGACAAA CTACCTACAG | 300 |
| AGATTTAAAG CTCTAAGGTA AATATAAAAT TTTTAAGTGT ATAATGTGTT AAACTACTGA | 360 |
| TTCTAATTGT TTGTGTATTT TAGATTCCAA CCTATGGAAC TGATGAATGG GAGCAGTGGT | 420 |
| GGAATGCCTT TAATGAGGAA AACCTGTTTT GCTCAGAAGA AATGCCATCT AGTGATGATG | 480 |
| AGGCTACTGC TGACTCTCAA CATTCTACTC CTCCAAAAAA GAAGAGAAAG GTAGAAGACC | 540 |
| CCAAGGACTT TCCTTCAGAA TTGCTAAGTT TTTTGAGTCA TGCTGTGTTT AGTAATAGAA | 600 |
| CTCTTGCTTG CTTTGCTATT TACACCACAA AGGAAAAAGC TGCACTGCTA TACAAGAAAA | 660 |
| TTATGGAAAA ATATTCTGTA ACCTTTATAA GTAGGCATAA CAGTTATAAT CATAACATAC | 720 |
| TGTTTTTTCT TACTCCACAC AGGCATAGAG TGTCTGCTAT TAATAACTAT GCTCAAAAAT | 780 |
| TGTGTACCTT TAGCTTTTTA ATTTGTAAAG GGGTTAATAA GGAATATTTG ATGTATAGTG | 840 |
| CCTTGACTAG AGATCATAAT CAGCCATACC ACATTTGTAG AGGTTTTACT TGCTTTAAAA | 900 |
| AACCTCCCAC ACCTCCCCCT GAACCTGAAA CATAAAATGA ATGCAATTGT TGTTGTTAAC | 960 |
| TTGTTTATTG CAGCTTATAA TGGTTACAAA TAAAGCAATA GCATCACAAA TTTCACAAAT | 1020 |
| AAAGCATTTT TTTCACTGCA TTCTAGTTGT GGTTTGTCCA AACTCATCAA TGTATCTTAT | 1080 |
| CATGTCTGGA TCTGCCGGTC TCCCTATAGT GAGTCGTATT AATTTCGATA AGCCAGGTTA | 1140 |
| ACCTGCATTA ATGAATCGGC CAACGCGCGG GGAGAGGCGG TTTGCGTATT GGGCGCTCTT | 1200 |
| CCGCTTCCTC GCTCACTGAC TCGCTGCGCT CGGTCGTTCG GCTGCGGCGA GCGGTATCAG | 1260 |
| CTCACTCAAA GGCGGTAATA CGGTTATCCA CAGAATCAGG GGATAACGCA GGAAAGAACA | 1320 |
| TGTGAGCAAA AGGCCAGCAA AAGGCCAGGA ACCGTAAAAA GGACGCGTTG CTGGCGTTTT | 1380 |
| TCCATAGGCT CCGCCCCCCT GACGAGCATC ACAAAAATCG ACGCTCAAGT CAGAGGTGGC | 1440 |
| GAAACCCGAC AGGACTATAA AGATACCAGG CGTTTCCCCC TGGAAGCTCC CTCGTGCGCT | 1500 |
| CTCCTGTTCC GACCCTGCCG CTTACCGGAT ACCTGTCCGC CTTTCTCCCT TCGGGAAGCG | 1560 |
| TGGCGCTTTC TCAATGCTCA CGCTGTAGGT ATCTCAGTTC GGTGTAGGTC GTTCGCTCCA | 1620 |
| AGCTGGGCTG TGTGCACGAA CCCCCCGTTC AGCCCGACCC CTGCGCCTTA TCCGGTAACT | 1680 |
| ATCGTCTTGA GTCCAACCCG GTAAGACACG ACTTATCGCC ACTGGCAGCA GCCACTGGTA | 1740 |
| ACAGGATTAG CAGAGCGAGG TATGTAGGCG GTGCTACAGA GTTCTTGAAG TGGTGGCCTA | 1800 |
| ACTACGGCTA CACTAGAAGG ACAGTATTTG GTATCTGCGC TCTGCTGAAG CCAGTTACCT | 1860 |

-continued

```
TCGGAAAAAG AGTTGGTAGC TCTTGATCCG GCAAACAAAC CACCGCTGGT AGCGGTGGTT      1920

TTTTTGTTTG CAAGCAGCAG ATTACGCGCA GAAAAAAGG ATCTCAAGAA GATCCTTTGA       1980

TCTTTTCTAC GGGGTCTGAC GCTCAGTGGA ACGAAAACTC ACGTTAAGGG ATTTTGGTCA      2040

TGAGATTATC AAAAAGGATC TTCACCTAGA TCCTTTTAAA TTAAAAATGA AGTTTTAAAT      2100

CAATCTAAAG TATATATGAG TAAACTTGGT CTGACAGTTA CCAATGCTTA ATCAGTGAGG      2160

CACCTATCTC AGCGATCTGT CTATTTCGTT CATCCATAGT TGCCTGACTC CCCGTCGTGT      2220

AGATAACTAC GATACGGGAG GGCTTACCAT CTGGCCCCAG TGCTGCAATG ATACCGCGAG      2280

ACCCACGCTC ACCGGCTCCA GATTTATCAG CAATAAACCA GCCAGCCGGA AGGGCCGAGC      2340

GCAGAAGTGG TCCTGCAACT TTATCCGCCT CCATCCAGTC TATTAATTGT TGCCGGGAAG      2400

CTAGAGTAAG TAGTTCGCCA GTTAATAGTT TGCGCAACGT TGTTGCCATT GCTACAGGCA      2460

TCGTGGTGTC ACGCTCGTCG TTTGGTATGG CTTCATTCAG CTCCGGTTCC CAACGATCAA      2520

GGCGAGTTAC ATGATCCCCC ATGTTGTGCA AAAAAGCGGT TAGCTCCTTC GGTCCTCCGA      2580

TCGTTGTCAG AAGTAAGTTG GCCGCAGTGT TATCACTCAT GGTTATGGCA GCACTGCATA      2640

ATTCTCTTAC TGTCATGCCA TCCGTAAGAT GCTTTTCTGT GACTGGTGAG TACTCAACCA      2700

AGTCATTCTG AGAATAGTGT ATGCGGCGAC CGAGTTGCTC TTGCCCGGCG TCAATACGGG      2760

ATAATACCGC GCCACATAGC AGAACTTTAA AAGTGCTCAT CATTGGAAAA CGTTCTTCGG      2820

GGCGAAAACT CTCAAGGATC TTACCGCTGT TGAGATCCAG TTCGATGTAA CCCACTCGTG      2880

CACCCAACTG ATCTTCAGCA TCTTTTACTT TCACCAGCGT TTCTGGGTGA GCAAAAACAG      2940

GAAGGCAAAA TGCCGCAAAA AAGGGAATAA GGGCGACACG GAAATGTTGA ATACTCATAC      3000

TCTTCCTTTT TCAATATTAT TGAAGCATTT ATCAGGGTTA TTGTCTCATG AGCGGATACA      3060

TATTTGAATG TATTTAGAAA AATAAACAAA TAGGGGTTCC GCGCACATTT CCCCGAAAAG      3120

TGCCACCTGA CGTCTAAGAA ACCATTATTA TCATGACATT AACCTATAAA AATAGGCGTA      3180

TCACGAGGCC CTTTCGTCTC GCGCGTTTCG GTGATGACGG TGAAAACCTC TGACACATGC      3240

AGCTCCCGGA GACGGTCACA GCTTGTCTGT AAGCGGATGC CGGGAGCAGA CAAGCCCGTC      3300

AGGGCGCGTC AGCGGGTGTT GGCGGGTGTC GGGGCTGGCT TAACTATGCG GCATCAGAGC      3360

AGATTGTACT GAGAGTGCAC CATATGGACA TATTGTCGTT AGAACGCGGC TACAATTAAT      3420

ACATAACCTT ATGTATCATA CACATACGAT TTAGGTGACA CTATAGAACT CGAGCAGAGC      3480

TTCCAAATTG AGAGAGAGGC TTAATCAGAG ACAGAAACTG TTTGAGTCAA CTCAAGGATG      3540

GTTTGAGGGA CTGTTTAACA GATCCCCTTG GTTTACCACC TTGATATCTA CCATTATGGG      3600

ACCCCTCATT GTACTCCTAA TGATTTTGCT CTTCGGACCC TGCATTCTTA ATCGATTAGT      3660

CCAATTTGTT AAAGACAGGA TATCAGTGGT CCAGGCTCTA GTTTTGACTC AACAATATCA      3720

CCAGCTGAAG CCTATAGAGT ACGAGCCATA GATAAAATAA AAGATTTTAT TTAGTCTCCA      3780

GAAAAAGGGG GGAATGAAAG ACCCCACCTG TAGGTTTGGC AAGCTAGCTT AAGTAACGCC      3840

ATTTTGCAAG GCATGGAAAA ATACATAACT GAGAATAGAG AAGTTCAGAT CAAGGTCAGG      3900

AACAGATGGA ACAGCTGAAT ATGGGCCAAA CAGGATATCT GTGGTAAGCA GTTCCTGCCC      3960

CGGCTCAGGG CCAAGAACAG ATGGAACAGC TGAATATGGG CCAAACAGGA TATCTGTGGT      4020

AAGCAGTTCC TGCCCCGGCT CAGGGCCAAG AACAGATGGT CCCCAGATGC GGTCCAGCCC      4080

TCAGCAGTTT CTAGAGAACC ATCAGATGTT TCCAGGGTGC CCCAAGGACC TGAAATGACC      4140

CTGTGCCTTA TTTGAACTAA CCAATCAGTT CGCTTCTCGC TTCTGTTCGC GCGCTTCTGC      4200

TCCCCGAGCT CAATAAAAGA GCCCACAACC CCTCACTCGG GGCGCCAGTC CTCCGATTGA      4260
```

CTGAGTCGCC CGG                                                                 4273

(2) INFORMATION FOR SEQ ID NO:4:

(i) SEQUENCE CHARACTERISTICS:
        (A) LENGTH: 40 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:4:

Pro Met Thr Pro Thr Thr Tyr Lys Gly Ser Val Asp Asn Gln Thr Asp
1               5                   10                  15

Ser Gly Met Val Leu Ala Ser Glu Glu Phe Glu Gln Ile Glu Ser Arg
            20                  25                  30

His Arg Gln Glu Ser Gly Phe Arg
        35                  40

(2) INFORMATION FOR SEQ ID NO:5:

(i) SEQUENCE CHARACTERISTICS:
        (A) LENGTH: 18 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:5:

Xaa Glu Glu Thr Ile Lys Phe Ala Ala Ala His Tyr Asn Thr Glu Ile
1               5                   10                  15

Leu Lys (2) INFORMATION FOR SEQ ID NO:6:

(i) SEQUENCE CHARACTERISTICS:
        (A) LENGTH: 219 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:6:

TCACTATAGG GAGACCCAAG CTTGGTACCG AGCTCGGATC CACTAGTAAC GGCCGCCAGT      60

GTGGTGGAAT TCGACGAACT CATGACTGTA CTCTACCCAG AATATTGGAA AATGTACAAG    120

TGTCAGCTAA GGCAAGGAGG CTGGCAACAT AACAGAGAAC AGGCCAACCT CAACTCAAGG    180

ACAGAAGAGA CTATAAAATT CGCTGCAGCA CACTACAAC                           219

(2) INFORMATION FOR SEQ ID NO:7:

(i) SEQUENCE CHARACTERISTICS:
        (A) LENGTH: 1997 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 352..1608

(xi) SEQUENCE DESCRIPTION: SEQ ID NO:7:

```
CCCGCCCCGC CTCTCCAAAA AGCTACACCG ACGCGGACCG CGGCGGCGTC CTCCCTCGCC      60

CTCGCTTCAC CTCGCGGGCT CCGAATGCGG GGAGCTCGGA TGTCCGGTTT CCTGTGAGGC     120

TTTTACCTGA CACCCGCCGC CTTTCCCCGG CACTGGCTGG GAGGGCGCCC TGCAAAGTTG     180

GGAACGCGGA GCCCCGGACC CGCTCCCGCC GCCTCCGGCT CGCCCAGGGG GGGTCGCCGG     240

GAGGAGCCCG GGGGAGAGGG ACCAGGAGGG GCCCGCGGCC TCGCAGGGGC GCCCGCGCCC     300

CCACCCCTGC CCCCGCCAGC GGACCGGTCC CCCACCCCCG GTCCTTCCAC C ATG CAC     357
                                                         Met His
                                                           1
```

| TTG | CTG | GGC | TTC | TTC | TCT | GTG | GCG | TGT | TCT | CTG | CTC | GCC | GCT | GCG | CTG | 405 |
|---|---|---|---|---|---|---|---|---|---|---|---|---|---|---|---|---|
| Leu | Leu | Gly | Phe | Phe | Ser | Val | Ala | Cys | Ser | Leu | Leu | Ala | Ala | Ala | Leu | |
|  |  | 5 |  |  |  | 10 |  |  |  |  | 15 |  |  |  |  | |

| CTC | CCG | GGT | CCT | CGC | GAG | GCG | CCC | GCC | GCC | GCC | GCC | TTC | GAG | TCC | 453 |
|---|---|---|---|---|---|---|---|---|---|---|---|---|---|---|---|
| Leu | Pro | Gly | Pro | Arg | Glu | Ala | Pro | Ala | Ala | Ala | Ala | Phe | Glu | Ser | |
|  | 20 |  |  |  |  | 25 |  |  |  |  | 30 |  |  |  | |

| GGA | CTC | GAC | CTC | TCG | GAC | GCG | GAG | CCC | GAC | GCG | GGC | GAG | GCC | ACG | GCT | 501 |
|---|---|---|---|---|---|---|---|---|---|---|---|---|---|---|---|---|
| Gly | Leu | Asp | Leu | Ser | Asp | Ala | Glu | Pro | Asp | Ala | Gly | Glu | Ala | Thr | Ala | |
| 35 |  |  |  | 40 |  |  |  |  | 45 |  |  |  |  | 50 |  | |

| TAT | GCA | AGC | AAA | GAT | CTG | GAG | GAG | CAG | TTA | CGG | TCT | GTG | TCC | AGT | GTA | 549 |
|---|---|---|---|---|---|---|---|---|---|---|---|---|---|---|---|---|
| Tyr | Ala | Ser | Lys | Asp | Leu | Glu | Glu | Gln | Leu | Arg | Ser | Val | Ser | Ser | Val | |
|  |  |  |  | 55 |  |  |  |  | 60 |  |  |  |  | 65 |  | |

| GAT | GAA | CTC | ATG | ACT | GTA | CTC | TAC | CCA | GAA | TAT | TGG | AAA | ATG | TAC | AAG | 597 |
|---|---|---|---|---|---|---|---|---|---|---|---|---|---|---|---|---|
| Asp | Glu | Leu | Met | Thr | Val | Leu | Tyr | Pro | Glu | Tyr | Trp | Lys | Met | Tyr | Lys | |
|  |  |  | 70 |  |  |  |  | 75 |  |  |  |  | 80 |  |  | |

| TGT | CAG | CTA | AGG | AAA | GGA | GGC | TGG | CAA | CAT | AAC | AGA | GAA | CAG | GCC | AAC | 645 |
|---|---|---|---|---|---|---|---|---|---|---|---|---|---|---|---|---|
| Cys | Gln | Leu | Arg | Lys | Gly | Gly | Trp | Gln | His | Asn | Arg | Glu | Gln | Ala | Asn | |
|  |  | 85 |  |  |  |  | 90 |  |  |  |  | 95 |  |  |  | |

| CTC | AAC | TCA | AGG | ACA | GAA | GAG | ACT | ATA | AAA | TTT | GCT | GCA | GCA | CAT | TAT | 693 |
|---|---|---|---|---|---|---|---|---|---|---|---|---|---|---|---|---|
| Leu | Asn | Ser | Arg | Thr | Glu | Glu | Thr | Ile | Lys | Phe | Ala | Ala | Ala | His | Tyr | |
| 100 |  |  |  |  | 105 |  |  |  |  | 110 |  |  |  |  |  | |

| AAT | ACA | GAG | ATC | TTG | AAA | AGT | ATT | GAT | AAT | GAG | TGG | AGA | AAG | ACT | CAA | 741 |
|---|---|---|---|---|---|---|---|---|---|---|---|---|---|---|---|---|
| Asn | Thr | Glu | Ile | Leu | Lys | Ser | Ile | Asp | Asn | Glu | Trp | Arg | Lys | Thr | Gln | |
| 115 |  |  |  | 120 |  |  |  |  | 125 |  |  |  |  | 130 | | |

| TGC | ATG | CCA | CGG | GAG | GTG | TGT | ATA | GAT | GTG | GGG | AAG | GAG | TTT | GGA | GTC | 789 |
|---|---|---|---|---|---|---|---|---|---|---|---|---|---|---|---|---|
| Cys | Met | Pro | Arg | Glu | Val | Cys | Ile | Asp | Val | Gly | Lys | Glu | Phe | Gly | Val | |
|  |  |  | 135 |  |  |  |  | 140 |  |  |  |  | 145 |  |  | |

| GCG | ACA | AAC | ACC | TTC | TTT | AAA | CCT | CCA | TGT | GTG | TCC | GTC | TAC | AGA | TGT | 837 |
|---|---|---|---|---|---|---|---|---|---|---|---|---|---|---|---|---|
| Ala | Thr | Asn | Thr | Phe | Phe | Lys | Pro | Pro | Cys | Val | Ser | Val | Tyr | Arg | Cys | |
|  |  |  | 150 |  |  |  |  | 155 |  |  |  |  | 160 |  |  | |

| GGG | GGT | TGC | TGC | AAT | AGT | GAG | GGG | CTG | CAG | TGC | ATG | AAC | ACC | AGC | ACG | 885 |
|---|---|---|---|---|---|---|---|---|---|---|---|---|---|---|---|---|
| Gly | Gly | Cys | Cys | Asn | Ser | Glu | Gly | Leu | Gln | Cys | Met | Asn | Thr | Ser | Thr | |
|  |  | 165 |  |  |  |  | 170 |  |  |  |  | 175 |  |  |  | |

| AGC | TAC | CTC | AGC | AAG | ACG | TTA | TTT | GAA | ATT | ACA | GTG | CCT | CTC | TCT | CAA | 933 |
|---|---|---|---|---|---|---|---|---|---|---|---|---|---|---|---|---|
| Ser | Tyr | Leu | Ser | Lys | Thr | Leu | Phe | Glu | Ile | Thr | Val | Pro | Leu | Ser | Gln | |
|  | 180 |  |  |  |  | 185 |  |  |  |  | 190 |  |  |  |  | |

| GGC | CCC | AAA | CCA | GTA | ACA | ATC | AGT | TTT | GCC | AAT | CAC | ACT | TCC | TGC | CGA | 981 |
|---|---|---|---|---|---|---|---|---|---|---|---|---|---|---|---|---|
| Gly | Pro | Lys | Pro | Val | Thr | Ile | Ser | Phe | Ala | Asn | His | Thr | Ser | Cys | Arg | |
| 195 |  |  |  | 200 |  |  |  |  | 205 |  |  |  |  | 210 |  | |

| TGC | ATG | TCT | AAA | CTG | GAT | GTT | TAC | AGA | CAA | GTT | CAT | TCC | ATT | ATT | AGA | 1029 |
|---|---|---|---|---|---|---|---|---|---|---|---|---|---|---|---|---|
| Cys | Met | Ser | Lys | Leu | Asp | Val | Tyr | Arg | Gln | Val | His | Ser | Ile | Ile | Arg | |
|  |  |  | 215 |  |  |  |  | 220 |  |  |  |  | 225 |  |  | |

| CGT | TCC | CTG | CCA | GCA | ACA | CTA | CCA | CAG | TGT | CAG | GCA | GCG | AAC | AAG | ACC | 1077 |
|---|---|---|---|---|---|---|---|---|---|---|---|---|---|---|---|---|
| Arg | Ser | Leu | Pro | Ala | Thr | Leu | Pro | Gln | Cys | Gln | Ala | Ala | Asn | Lys | Thr | |
|  |  | 230 |  |  |  |  | 235 |  |  |  |  | 240 |  |  |  | |

| TGC | CCC | ACC | AAT | TAC | ATG | TGG | AAT | AAT | CAC | ATC | TGC | AGA | TGC | CTG | GCT | 1125 |
|---|---|---|---|---|---|---|---|---|---|---|---|---|---|---|---|---|
| Cys | Pro | Thr | Asn | Tyr | Met | Trp | Asn | Asn | His | Ile | Cys | Arg | Cys | Leu | Ala | |
|  | 245 |  |  |  |  | 250 |  |  |  |  | 255 |  |  |  |  | |

```
CAG GAA GAT TTT ATG TTT TCC TCG GAT GCT GGA GAT GAC TCA ACA GAT    1173
Gln Glu Asp Phe Met Phe Ser Ser Asp Ala Gly Asp Asp Ser Thr Asp
        260                 265                 270

GGA TTC CAT GAC ATC TGT GGA CCA AAC AAG GAG CTG GAT GAA GAG ACC    1221
Gly Phe His Asp Ile Cys Gly Pro Asn Lys Glu Leu Asp Glu Glu Thr
275                 280                 285                 290

TGT CAG TGT GTC TGC AGA GCG GGG CTT CGG CCT GCC AGC TGT GGA CCC    1269
Cys Gln Cys Val Cys Arg Ala Gly Leu Arg Pro Ala Ser Cys Gly Pro
                295                 300                 305

CAC AAA GAA CTA GAC AGA AAC TCA TGC CAG TGT GTC TGT AAA AAC AAA    1317
His Lys Glu Leu Asp Arg Asn Ser Cys Gln Cys Val Cys Lys Asn Lys
            310                 315                 320

CTC TTC CCC AGC CAA TGT GGG GCC AAC CGA GAA TTT GAT GAA AAC ACA    1365
Leu Phe Pro Ser Gln Cys Gly Ala Asn Arg Glu Phe Asp Glu Asn Thr
        325                 330                 335

TGC CAG TGT GTA TGT AAA AGA ACC TGC CCC AGA AAT CAA CCC CTA AAT    1413
Cys Gln Cys Val Cys Lys Arg Thr Cys Pro Arg Asn Gln Pro Leu Asn
340                 345                 350

CCT GGA AAA TGT GCC TGT GAA TGT ACA GAA AGT CCA CAG AAA TGC TTG    1461
Pro Gly Lys Cys Ala Cys Glu Cys Thr Glu Ser Pro Gln Lys Cys Leu
355                 360                 365                 370

TTA AAA GGA AAG AAG TTC CAC CAC CAA ACA TGC AGC TGT TAC AGA CGG    1509
Leu Lys Gly Lys Lys Phe His His Gln Thr Cys Ser Cys Tyr Arg Arg
                375                 380                 385

CCA TGT ACG AAC CGC CAG AAG GCT TGT GAG CCA GGA TTT TCA TAT AGT    1557
Pro Cys Thr Asn Arg Gln Lys Ala Cys Glu Pro Gly Phe Ser Tyr Ser
            390                 395                 400

GAA GAA GTG TGT CGT TGT GTC CCT TCA TAT TGG AAA AGA CCA CAA ATG    1605
Glu Glu Val Cys Arg Cys Val Pro Ser Tyr Trp Lys Arg Pro Gln Met
        405                 410                 415

AGC TAAGATTGTA CTGTTTTCCA GTTCATCGAT TTTCTATTAT GGAAAACTGT         1658
Ser

GTTGCCACAG TAGAACTGTC TGTGAACAGA GAGACCCTTG TGGGTCCATG CTAACAAAGA  1718

CAAAGTCTG TCTTTCCTGA ACCATGTGGA TAACTTTACA GAAATGGACT GGAGCTCATC   1778

TGCAAAGGC CTCTTGTAAA GACTGGTTTT CTGCCAATGA CCAAACAGCC AAGATTTTCC   1838

TCTTGTGATT TCTTTAAAAG AATGACTATA TAATTTATTT CCACTAAAAA TATTGTTTCT  1898

GCATTCATTT TTATAGCAAC AACAATTGGT AAAACTCACT GTGATCAATA TTTTTATATC  1958

ATGCAAAATA TGTTTAAAAT AAAATGAAAA TTGTATTAT                         1997

(2) INFORMATION FOR SEQ ID NO:8:

(i) SEQUENCE CHARACTERISTICS:
        (A) LENGTH: 419 amino acids
        (B) TYPE: amino acid
        (D) TOPOLOGY: linear (ii) MOLECULE TYPE: protein (xi) SEQUENCE DESCRIPTION: SEQ ID NO:8:

Met His Leu Leu Gly Phe Phe Ser Val Ala Cys Ser Leu Leu Ala Ala
  1               5                  10                  15

Ala Leu Leu Pro Gly Pro Arg Glu Ala Pro Ala Ala Ala Ala Phe
              20                  25                  30

Glu Ser Gly Leu Asp Leu Ser Asp Ala Glu Pro Asp Ala Gly Glu Ala
         35                  40                  45

Thr Ala Tyr Ala Ser Lys Asp Leu Glu Glu Gln Leu Arg Ser Val Ser
     50                  55                  60
```

```
Ser Val Asp Glu Leu Met Thr Val Leu Tyr Pro Glu Tyr Trp Lys Met
 65                  70                  75                  80

Tyr Lys Cys Gln Leu Arg Lys Gly Gly Trp Gln His Asn Arg Glu Gln
                 85                  90                  95

Ala Asn Leu Asn Ser Arg Thr Glu Thr Ile Lys Phe Ala Ala Ala
            100                 105                 110

His Tyr Asn Thr Glu Ile Leu Lys Ser Ile Asp Asn Glu Trp Arg Lys
            115                 120                 125

Thr Gln Cys Met Pro Arg Glu Val Cys Ile Asp Val Gly Lys Glu Phe
        130                 135                 140

Gly Val Ala Thr Asn Thr Phe Phe Lys Pro Pro Cys Val Ser Val Tyr
145                 150                 155                 160

Arg Cys Gly Gly Cys Cys Asn Ser Glu Gly Leu Gln Cys Met Asn Thr
                165                 170                 175

Ser Thr Ser Tyr Leu Ser Lys Thr Leu Phe Glu Ile Thr Val Pro Leu
            180                 185                 190

Ser Gln Gly Pro Lys Pro Val Thr Ile Ser Phe Ala Asn His Thr Ser
            195                 200                 205

Cys Arg Cys Met Ser Lys Leu Asp Val Tyr Arg Gln Val His Ser Ile
        210                 215                 220

Ile Arg Arg Ser Leu Pro Ala Thr Leu Pro Gln Cys Gln Ala Ala Asn
225                 230                 235                 240

Lys Thr Cys Pro Thr Asn Tyr Met Trp Asn Asn His Ile Cys Arg Cys
                245                 250                 255

Leu Ala Gln Glu Asp Phe Met Phe Ser Ser Asp Ala Gly Asp Asp Ser
            260                 265                 270

Thr Asp Gly Phe His Asp Ile Cys Gly Pro Asn Lys Glu Leu Asp Glu
            275                 280                 285

Glu Thr Cys Gln Cys Val Cys Arg Ala Gly Leu Arg Pro Ala Ser Cys
        290                 295                 300

Gly Pro His Lys Glu Leu Asp Arg Asn Ser Cys Gln Cys Val Cys Lys
305                 310                 315                 320

Asn Lys Leu Phe Pro Ser Gln Cys Gly Ala Asn Arg Glu Phe Asp Glu
                325                 330                 335

Asn Thr Cys Gln Cys Val Cys Lys Arg Thr Cys Pro Arg Asn Gln Pro
            340                 345                 350

Leu Asn Pro Gly Lys Cys Ala Cys Glu Cys Thr Glu Ser Pro Gln Lys
            355                 360                 365

Cys Leu Leu Lys Gly Lys Lys Phe His His Gln Thr Cys Ser Cys Tyr
        370                 375                 380

Arg Arg Pro Cys Thr Asn Arg Gln Lys Ala Cys Glu Pro Gly Phe Ser
385                 390                 395                 400

Tyr Ser Glu Glu Val Cys Arg Cys Val Pro Ser Tyr Trp Lys Arg Pro
                405                 410                 415

Gln Met Ser (2) INFORMATION FOR SEQ ID NO:9:

(i) SEQUENCE CHARACTERISTICS:
        (A) LENGTH: 17 amino acids
        (B) TYPE: amino acid
        (C) STRANDEDNESS: Not Relevant
        (D) TOPOLOGY: linear (ii) MOLECULE TYPE: peptide
```

(xi) SEQUENCE DESCRIPTION: SEQ ID NO:9:

```
Glu Glu Thr Ile Lys Phe Ala Ala Ala His Tyr Asn Thr Glu Ile Leu
1               5                   10                  15
Lys
```

(2) INFORMATION FOR SEQ ID NO:10:

(i) SEQUENCE CHARACTERISTICS:
        (A) LENGTH: 1836 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 168..1412

(xi) SEQUENCE DESCRIPTION: SEQ ID NO:10:

```
GCGGCCGCGT CGACGCAAAA GTTGCGAGCC GCCGAGTCCC GGGAGACGCT CGCCCAGGGG        60

GGTCCCCGGG AGGAAACCAC GGGACAGGGA CCAGGAGAGG ACCTCAGCCT CACGCCCCAG       120

CCTGCGCCAG CCAACGGACC GGCCTCCCTG CTCCCGGTCC ATCCACC ATG CAC TTG         176
                                                   Met His Leu
                                                     1

CTG TGC TTC TTG TCT CTG GCG TGT TCC CTG CTC GCC GCT GCG CTG ATC         224
Leu Cys Phe Leu Ser Leu Ala Cys Ser Leu Leu Ala Ala Ala Leu Ile
      5                  10                  15

CCC AGT CCG CGC GAG GCG CCC GCC ACC GTC GCC GCC TTC GAG TCG GGA         272
Pro Ser Pro Arg Glu Ala Pro Ala Thr Val Ala Ala Phe Glu Ser Gly
 20              25                  30                  35

CTG GGC TTC TCG GAA GCG GAG CCC GAC GGG GGC GAG GTC AAG GCT TTT         320
Leu Gly Phe Ser Glu Ala Glu Pro Asp Gly Gly Glu Val Lys Ala Phe
                 40                  45                  50

GAA GGC AAA GAC CTG GAG GAG CAG TTG CGG TCT GTG TCC AGC GTA GAT         368
Glu Gly Lys Asp Leu Glu Glu Gln Leu Arg Ser Val Ser Ser Val Asp
             55                  60                  65

GAG CTG ATG TCT GTC CTG TAC CCA GAC TAC TGG AAA ATG TAC AAG TGC         416
Glu Leu Met Ser Val Leu Tyr Pro Asp Tyr Trp Lys Met Tyr Lys Cys
         70                  75                  80

CAG CTG CGG AAA GGC GGC TGG CAG CAG CCC ACC CTC AAT ACC AGG ACA         464
Gln Leu Arg Lys Gly Gly Trp Gln Gln Pro Thr Leu Asn Thr Arg Thr
 85                  90                  95

GGG GAC AGT GTA AAA TTT GCT GCT GCA CAT TAT AAC ACA GAG ATC CTG         512
Gly Asp Ser Val Lys Phe Ala Ala Ala His Tyr Asn Thr Glu Ile Leu
100                 105                 110                 115

AAA AGT ATT GAT AAT GAG TGG AGA AAG ACT CAA TGC ATG CCA CGT GAG         560
Lys Ser Ile Asp Asn Glu Trp Arg Lys Thr Gln Cys Met Pro Arg Glu
                120                 125                 130

GTG TGT ATA GAT GTG GGG AAG GAG TTT GGA GCA GCC ACA AAC ACC TTC         608
Val Cys Ile Asp Val Gly Lys Glu Phe Gly Ala Ala Thr Asn Thr Phe
            135                 140                 145

TTT AAA CCT CCA TGT GTG TCC GTC TAC AGA TGT GGG GGT TGC TGC AAC         656
Phe Lys Pro Pro Cys Val Ser Val Tyr Arg Cys Gly Gly Cys Cys Asn
        150                 155                 160

AGC GAG GGG CTG CAG TGC ATG AAC ACC AGC ACA GGT TAC CTC AGC AAG         704
Ser Glu Gly Leu Gln Cys Met Asn Thr Ser Thr Gly Tyr Leu Ser Lys
165                 170                 175

ACG TTG TTT GAA ATT ACA GTG CCT CTC TCA CAA GGC CCC AAA CCA GTC         752
Thr Leu Phe Glu Ile Thr Val Pro Leu Ser Gln Gly Pro Lys Pro Val
```

```
         180                 185                 190                 195
ACA ATC AGT TTT GCC AAT CAC ACT TCC TGC CGG TGC ATG TCT AAA CTG        800
Thr Ile Ser Phe Ala Asn His Thr Ser Cys Arg Cys Met Ser Lys Leu
                    200                 205                 210

GAT GTT TAC AGA CAA GTT CAT TCA ATT ATT AGA CGT TCT CTG CCA GCA        848
Asp Val Tyr Arg Gln Val His Ser Ile Ile Arg Arg Ser Leu Pro Ala
                215                 220                 225

ACA TTA CCA CAG TGT CAG GCA GCT AAC AAG ACA TGT CCA ACA AAC TAT        896
Thr Leu Pro Gln Cys Gln Ala Ala Asn Lys Thr Cys Pro Thr Asn Tyr
            230                 235                 240

GTG TGG AAT AAC TAC ATG TGC CGA TGC CTG GCT CAG CAG GAT TTT ATC        944
Val Trp Asn Asn Tyr Met Cys Arg Cys Leu Ala Gln Gln Asp Phe Ile
            245                 250                 255

TTT TAT TCA AAT GTT GAA GAT GAC TCA ACC AAT GGA TTC CAT GAT GTC        992
Phe Tyr Ser Asn Val Glu Asp Asp Ser Thr Asn Gly Phe His Asp Val
260                 265                 270                 275

TGT GGA CCC AAC AAG GAG CTG GAT GAA GAC ACC TGT CAG TGT GTC TGC       1040
Cys Gly Pro Asn Lys Glu Leu Asp Glu Asp Thr Cys Gln Cys Val Cys
                    280                 285                 290

AAG GGG GGG CTT CGG CCA TCT AGT TGT GGA CCC CAC AAA GAA CTA GAT       1088
Lys Gly Gly Leu Arg Pro Ser Ser Cys Gly Pro His Lys Glu Leu Asp
                295                 300                 305

AGA GAC TCA TGT CAG TGT GTC TGT AAA AAC AAA CTT TTC CCT AAT TCA       1136
Arg Asp Ser Cys Gln Cys Val Cys Lys Asn Lys Leu Phe Pro Asn Ser
            310                 315                 320

TGT GGA GCC AAC AGG GAA TTT GAT GAG AAT ACA TGT CAG TGT GTA TGT       1184
Cys Gly Ala Asn Arg Glu Phe Asp Glu Asn Thr Cys Gln Cys Val Cys
            325                 330                 335

AAA AGA ACG TGT CCA AGA AAT CAG CCC CTG AAT CCT GGG AAA TGT GCC       1232
Lys Arg Thr Cys Pro Arg Asn Gln Pro Leu Asn Pro Gly Lys Cys Ala
340                 345                 350                 355

TGT GAA TGT ACA GAA AAC ACA CAG AAG TGC TTC CTT AAA GGG AAG AAG       1280
Cys Glu Cys Thr Glu Asn Thr Gln Lys Cys Phe Leu Lys Gly Lys Lys
                    360                 365                 370

TTC CAC CAT CAA ACA TGC AGT TGT TAC AGA AGA CCG TGT GCG AAT CGA       1328
Phe His His Gln Thr Cys Ser Cys Tyr Arg Arg Pro Cys Ala Asn Arg
                375                 380                 385

CTG AAG CAT TGT GAT CCA GGA CTG TCC TTT AGT GAA GAA GTA TGC CGC       1376
Leu Lys His Cys Asp Pro Gly Leu Ser Phe Ser Glu Glu Val Cys Arg
            390                 395                 400

TGT GTC CCA TCG TAT TGG AAA AGG CCA CAT CTG AAC TAAGATCATA            1422
Cys Val Pro Ser Tyr Trp Lys Arg Pro His Leu Asn
            405                 410                 415

CCAGTTTTCA GTCAGTCACA GTCATTTACT CTCTTGAAGA CTGTTGGAAC AGCACTTAGC     1482

ACTGTCTATG CACAGAAAGA CTCTGTGGGA CCACATGGTA ACAGAGGCCC AAGTCTGTGT     1542

TTATTGAACC ATGTGGATTA CTGCGGGAGA GGACTGGCAC TCATGTGCAA AAAAAACCTC    1602

TTCAAAGACT GGTTTTCTGC CAGGGACCAG ACAGCTGAGG TTTTTCTCTT GTGATTTAAA     1662

AAAGAATGA CTATATAATT TATTTCCACT AAAAATATTG TTCCTGCATT CATTTTTATA      1722

GCAATAACAA TTGGTAAAGC TCACTGTGAT CAGTATTTTT ATAACATGCA AAACTATGTT     1782

TAAAATAAAA TGAAAATTGT ATTATAAAAA AAAAAAAAA AAAAAAAAA GCTT             1836

(2) INFORMATION FOR SEQ ID NO:11:

(i) SEQUENCE CHARACTERISTICS:
        (A) LENGTH: 415 amino acids
        (B) TYPE: amino acid
        (D) TOPOLOGY: linear
```

(ii) MOLECULE TYPE: protein (xi) SEQUENCE DESCRIPTION: SEQ ID NO:11:

| Met | His | Leu | Leu | Cys | Phe | Leu | Ser | Leu | Ala | Cys | Ser | Leu | Leu | Ala | Ala |
| 1 | | | | 5 | | | | | 10 | | | | | 15 | |

| Ala | Leu | Ile | Pro | Ser | Pro | Arg | Glu | Ala | Pro | Ala | Thr | Val | Ala | Ala | Phe |
| | | | 20 | | | | | 25 | | | | | 30 | | |

| Glu | Ser | Gly | Leu | Gly | Phe | Ser | Glu | Ala | Glu | Pro | Asp | Gly | Gly | Glu | Val |
| | | 35 | | | | | | 40 | | | | | 45 | | |

| Lys | Ala | Phe | Glu | Gly | Lys | Asp | Leu | Glu | Glu | Gln | Leu | Arg | Ser | Val | Ser |
| | 50 | | | | | 55 | | | | | 60 | | | | |

| Ser | Val | Asp | Glu | Leu | Met | Ser | Val | Leu | Tyr | Pro | Asp | Tyr | Trp | Lys | Met |
| 65 | | | | | 70 | | | | | 75 | | | | | 80 |

| Tyr | Lys | Cys | Gln | Leu | Arg | Lys | Gly | Gly | Trp | Gln | Gln | Pro | Thr | Leu | Asn |
| | | | | 85 | | | | | 90 | | | | | 95 | |

| Thr | Arg | Thr | Gly | Asp | Ser | Val | Lys | Phe | Ala | Ala | Ala | His | Tyr | Asn | Thr |
| | | | 100 | | | | | 105 | | | | | 110 | | |

| Glu | Ile | Leu | Lys | Ser | Ile | Asp | Asn | Glu | Trp | Arg | Lys | Thr | Gln | Cys | Met |
| | | | 115 | | | | | 120 | | | | | 125 | | |

| Pro | Arg | Glu | Val | Cys | Ile | Asp | Val | Gly | Lys | Glu | Phe | Gly | Ala | Ala | Thr |
| | 130 | | | | | 135 | | | | | 140 | | | | |

| Asn | Thr | Phe | Phe | Lys | Pro | Pro | Cys | Val | Ser | Val | Tyr | Arg | Cys | Gly | Gly |
| 145 | | | | | 150 | | | | | 155 | | | | | 160 |

| Cys | Cys | Asn | Ser | Glu | Gly | Leu | Gln | Cys | Met | Asn | Thr | Ser | Thr | Gly | Tyr |
| | | | | 165 | | | | | 170 | | | | | 175 | |

| Leu | Ser | Lys | Thr | Leu | Phe | Glu | Ile | Thr | Val | Pro | Leu | Ser | Gln | Gly | Pro |
| | | | 180 | | | | | 185 | | | | | 190 | | |

| Lys | Pro | Val | Thr | Ile | Ser | Phe | Ala | Asn | His | Thr | Ser | Cys | Arg | Cys | Met |
| | | | 195 | | | | | 200 | | | | | 205 | | |

| Ser | Lys | Leu | Asp | Val | Tyr | Arg | Gln | Val | His | Ser | Ile | Ile | Arg | Arg | Ser |
| | 210 | | | | | 215 | | | | | 220 | | | | |

| Leu | Pro | Ala | Thr | Leu | Pro | Gln | Cys | Gln | Ala | Ala | Asn | Lys | Thr | Cys | Pro |
| 225 | | | | | 230 | | | | | 235 | | | | | 240 |

| Thr | Asn | Tyr | Val | Trp | Asn | Asn | Tyr | Met | Cys | Arg | Cys | Leu | Ala | Gln | Gln |
| | | | | 245 | | | | | 250 | | | | | 255 | |

| Asp | Phe | Ile | Phe | Tyr | Ser | Asn | Val | Glu | Asp | Asp | Ser | Thr | Asn | Gly | Phe |
| | | | 260 | | | | | 265 | | | | | 270 | | |

| His | Asp | Val | Cys | Gly | Pro | Asn | Lys | Glu | Leu | Asp | Glu | Asp | Thr | Cys | Gln |
| | | | 275 | | | | | 280 | | | | | 285 | | |

| Cys | Val | Cys | Lys | Gly | Gly | Leu | Arg | Pro | Ser | Ser | Cys | Gly | Pro | His | Lys |
| | 290 | | | | | 295 | | | | | 300 | | | | |

| Glu | Leu | Asp | Arg | Asp | Ser | Cys | Gln | Cys | Val | Cys | Lys | Asn | Lys | Leu | Phe |
| 305 | | | | | 310 | | | | | 315 | | | | | 320 |

| Pro | Asn | Ser | Cys | Gly | Ala | Asn | Arg | Glu | Phe | Asp | Glu | Asn | Thr | Cys | Gln |
| | | | | 325 | | | | | 330 | | | | | 335 | |

| Cys | Val | Cys | Lys | Arg | Thr | Cys | Pro | Arg | Asn | Gln | Pro | Leu | Asn | Pro | Gly |
| | | | 340 | | | | | 345 | | | | | 350 | | |

| Lys | Cys | Ala | Cys | Glu | Cys | Thr | Glu | Asn | Thr | Gln | Lys | Cys | Phe | Leu | Lys |
| | | | 355 | | | | | 360 | | | | | 365 | | |

| Gly | Lys | Lys | Phe | His | His | Gln | Thr | Cys | Ser | Cys | Tyr | Arg | Arg | Pro | Cys |
| | 370 | | | | | 375 | | | | | 380 | | | | |

| Ala | Asn | Arg | Leu | Lys | His | Cys | Asp | Pro | Gly | Leu | Ser | Phe | Ser | Glu | Glu |
| 385 | | | | | 390 | | | | | 395 | | | | | 400 |

```
Val Cys Arg Cys Val Pro Ser Tyr Trp Lys Arg Pro His Leu Asn
            405                 410                 415

(2) INFORMATION FOR SEQ ID NO:12:

(i) SEQUENCE CHARACTERISTICS:
        (A) LENGTH: 1741 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 453..1706

(xi) SEQUENCE DESCRIPTION: SEQ ID NO:12:

GCCCCCGCCG AGCGCTCCGC GCGCAGCCGC CGGGCCGGGC CGGCCCGCGG AGGGCGCGCT     60

GCGAGCGGCC ACTGGGTCCT GCTTCCCTCC TTCCTCTCCC TCCTCCTCCT CCTCCTTCTC    120

TCTGCGCTTT CCACCGCTCC CGAGCGAGCG CACGCTCGGA TGTCCGGTTT CCTGGTGGGT    180

TTTTTACCTG GCAAAGTCCG GATAACTTCG GTGAGAATTT GCAAAGAGGC TGGGAGCTCC    240

CCTGCAGGCG TCTGGGAGCT GCTGCCGCCG TCGCATCTTC TCCATCCCGC GGATTTTACT    300

GCCTTGGATA TTGCGAGGGG AGGGAGGGGG GTGAGGACAG CAAAAAGAAA GGGGTGGGGG    360

GGGGGAGAGA AAAGGAAAAG AAGGAGCCTC GGAATTGTGC CCGCATTCCT GCGCTGCCCC    420

GCGGCCCCCC TCCGCTCTGC CATCTCCGCA CA ATG CAC TTG CTG GAG ATG CTC      473
                                    Met His Leu Leu Glu Met Leu
                                     1               5

TCC CTG GGC TGC TGC CTC GCT GCT GGC GCC GTG CTC CTG GGA CCC CGG      521
Ser Leu Gly Cys Cys Leu Ala Ala Gly Ala Val Leu Leu Gly Pro Arg
         10                  15                  20

CAG CCG CCC GTC GCC GCC GCC TAC GAG TCC GGG CAC GGC TAC TAC GAG      569
Gln Pro Pro Val Ala Ala Ala Tyr Glu Ser Gly His Gly Tyr Tyr Glu
     25                  30                  35

GAG GAG CCC GGT GCC GGG GAA CCC AAG GCT CAT GCA AGC AAA GAC CTG      617
Glu Glu Pro Gly Ala Gly Glu Pro Lys Ala His Ala Ser Lys Asp Leu
 40                  45                  50                  55

GAA GAG CAG TTG CGA TCT GTG TCC AGT GTG GAT GAA CTC ATG ACA GTA      665
Glu Glu Gln Leu Arg Ser Val Ser Ser Val Asp Glu Leu Met Thr Val
                 60                  65                  70

CTT TAC CCA GAA TAC TGG AAA ATG TTC AAA TGT CAG TTG AGG AAA GGA      713
Leu Tyr Pro Glu Tyr Trp Lys Met Phe Lys Cys Gln Leu Arg Lys Gly
             75                  80                  85

GGT TGG CAA CAC AAC AGG GAA CAC TCC AGC TCT GAT ACA AGA TCA GAT      761
Gly Trp Gln His Asn Arg Glu His Ser Ser Ser Asp Thr Arg Ser Asp
         90                  95                 100

GAT TCA TTG AAA TTT GCC GCA GCA CAT TAT AAT GCA GAG ATC CTG AAA      809
Asp Ser Leu Lys Phe Ala Ala Ala His Tyr Asn Ala Glu Ile Leu Lys
     105                 110                 115

AGT ATT GAT ACT GAA TGG AGA AAA ACC CAG GGC ATG CCA CGT GAA GTG      857
Ser Ile Asp Thr Glu Trp Arg Lys Thr Gln Gly Met Pro Arg Glu Val
120                 125                 130                 135

TGT GTG GAT TTG GGG AAA GAG TTT GGA GCA ACT ACA AAC ACC TTC TTT      905
Cys Val Asp Leu Gly Lys Glu Phe Gly Ala Thr Thr Asn Thr Phe Phe
                 140                 145                 150

AAA CCC CCG TGT GTA TCC ATC TAC AGA TGT GGA GGT TGC TGC AAT AGT      953
Lys Pro Pro Cys Val Ser Ile Tyr Arg Cys Gly Gly Cys Cys Asn Ser
             155                 160                 165
```

```
GAA GGA CTC CAG TGT ATG AAT ATC AGC ACA AAT TAC ATC AGC AAG ACA      1001
Glu Gly Leu Gln Cys Met Asn Ile Ser Thr Asn Tyr Ile Ser Lys Thr
            170                 175                 180

TTG TTT GAG ATT ACA GTG CCT CTC TCT CAT GGC CCC AAA CCT GTA ACA      1049
Leu Phe Glu Ile Thr Val Pro Leu Ser His Gly Pro Lys Pro Val Thr
    185                 190                 195

GTC AGT TTT GCC AAT CAC ACG TCC TGC CGA TGC ATG TCT AAG TTG GAT      1097
Val Ser Phe Ala Asn His Thr Ser Cys Arg Cys Met Ser Lys Leu Asp
200                 205                 210                 215

GTT TAC AGA CAA GTT CAT TCT ATC ATA AGA CGT TCC TTG CCA GCA ACA      1145
Val Tyr Arg Gln Val His Ser Ile Ile Arg Arg Ser Leu Pro Ala Thr
                220                 225                 230

CAA ACT CAG TGT CAT GTG GCA AAC AAG ACC TGT CCA AAA AAT CAT GTC      1193
Gln Thr Gln Cys His Val Ala Asn Lys Thr Cys Pro Lys Asn His Val
            235                 240                 245

TGG AAT AAT CAG ATT TGC AGA TGC TTA GCA CAG CAC GAT TTT GGT TTC      1241
Trp Asn Asn Gln Ile Cys Arg Cys Leu Ala Gln His Asp Phe Gly Phe
        250                 255                 260

TCT TCT CAC CTT GGA GAT TCT GAC ACA TCT GAA GGA TTC CAT ATT TGT      1289
Ser Ser His Leu Gly Asp Ser Asp Thr Ser Glu Gly Phe His Ile Cys
    265                 270                 275

GGG CCC AAC AAA GAG CTG GAT GAA GAA ACC TGT CAA TGC GTC TGC AAA      1337
Gly Pro Asn Lys Glu Leu Asp Glu Glu Thr Cys Gln Cys Val Cys Lys
280                 285                 290                 295

GGA GGT GTG CGG CCC ATA AGC TGT GGC CCT CAC AAA GAA CTA GAC AGG      1385
Gly Gly Val Arg Pro Ile Ser Cys Gly Pro His Lys Glu Leu Asp Arg
                300                 305                 310

GCA TCA TGT CAG TGC ATG TGC AAA AAC AAA CTG CTC CCC AGT TCC TGT      1433
Ala Ser Cys Gln Cys Met Cys Lys Asn Lys Leu Leu Pro Ser Ser Cys
            315                 320                 325

GGG CCT AAC AAA GAA TTT GAT GAA GAA AAG TGC CAG TGT GTA TGT AAA      1481
Gly Pro Asn Lys Glu Phe Asp Glu Glu Lys Cys Gln Cys Val Cys Lys
        330                 335                 340

AAG ACC TGT CCC AAA CAT CAT CCA CTA AAT CCT GCA AAA TGC ATC TGC      1529
Lys Thr Cys Pro Lys His His Pro Leu Asn Pro Ala Lys Cys Ile Cys
    345                 350                 355

GAA TGT ACA GAA TCT CCC AAT AAA TGT TTC TTA AAA GGA AAA AGA TTT      1577
Glu Cys Thr Glu Ser Pro Asn Lys Cys Phe Leu Lys Gly Lys Arg Phe
360                 365                 370                 375

CAT CAC CAG ACA TGC AGT TGT TAC AGA CCA CCA TGT ACA GTC CGA ACG      1625
His His Gln Thr Cys Ser Cys Tyr Arg Pro Pro Cys Thr Val Arg Thr
                380                 385                 390

AAA CGC TGT GAT GCT GGA TTT CTG TTA GCT GAA GAA GTG TGC CGC TGT      1673
Lys Arg Cys Asp Ala Gly Phe Leu Leu Ala Glu Glu Val Cys Arg Cys
            395                 400                 405

GTA CGC ACA TCT TGG AAA AGA CCA CTT ATG AAT TAAGCGAAGA AAGCACTACT    1726
Val Arg Thr Ser Trp Lys Arg Pro Leu Met Asn
        410                 415

CGCTATATAG TGTCG                                                     1741
```

(2) INFORMATION FOR SEQ ID NO:13:

(i) SEQUENCE CHARACTERISTICS:
        (A) LENGTH: 418 amino acids
        (B) TYPE: amino acid
        (D) TOPOLOGY: linear (ii) MOLECULE TYPE: protein (xi) SEQUENCE DESCRIPTION: SEQ ID NO:13:

Met His Leu Leu Glu Met Leu Ser Leu Gly Cys Cys Leu Ala Ala Gly

-continued

```
  1               5                  10                 15
Ala Val Leu Leu Gly Pro Arg Gln Pro Val Ala Ala Tyr Glu
             20                  25              30

Ser Gly His Gly Tyr Tyr Glu Glu Pro Gly Ala Gly Glu Pro Lys
             35                  40              45

Ala His Ala Ser Lys Asp Leu Glu Glu Gln Leu Arg Ser Val Ser Ser
 50                  55                  60

Val Asp Glu Leu Met Thr Val Leu Tyr Pro Glu Tyr Trp Lys Met Phe
 65                  70                  75                  80

Lys Cys Gln Leu Arg Lys Gly Gly Trp Gln His Asn Arg Glu His Ser
                     85                  90                  95

Ser Ser Asp Thr Arg Ser Asp Asp Ser Leu Lys Phe Ala Ala Ala His
                    100                 105             110

Tyr Asn Ala Glu Ile Leu Lys Ser Ile Asp Thr Glu Trp Arg Lys Thr
            115                 120                 125

Gln Gly Met Pro Arg Glu Val Cys Val Asp Leu Gly Lys Glu Phe Gly
        130                 135             140

Ala Thr Thr Asn Thr Phe Phe Lys Pro Pro Cys Val Ser Ile Tyr Arg
145                 150                 155                 160

Cys Gly Gly Cys Cys Asn Ser Glu Gly Leu Gln Cys Met Asn Ile Ser
                    165                 170                 175

Thr Asn Tyr Ile Ser Lys Thr Leu Phe Glu Ile Thr Val Pro Leu Ser
                180                 185                 190

His Gly Pro Lys Pro Val Thr Val Ser Phe Ala Asn His Thr Ser Cys
            195                 200                 205

Arg Cys Met Ser Lys Leu Asp Val Tyr Arg Gln Val His Ser Ile Ile
210                 215                 220

Arg Arg Ser Leu Pro Ala Thr Gln Thr Gln Cys His Val Ala Asn Lys
225                 230                 235             240

Thr Cys Pro Lys Asn His Val Trp Asn Asn Gln Ile Cys Arg Cys Leu
                245                 250                 255

Ala Gln His Asp Phe Gly Phe Ser Ser His Leu Gly Asp Ser Asp Thr
            260                 265                 270

Ser Glu Gly Phe His Ile Cys Gly Pro Asn Lys Glu Leu Asp Glu Glu
        275                 280                 285

Thr Cys Gln Cys Val Cys Lys Gly Gly Val Arg Pro Ile Ser Cys Gly
    290                 295                 300

Pro His Lys Glu Leu Asp Arg Ala Ser Cys Gln Cys Met Cys Lys Asn
305                 310                 315                 320

Lys Leu Leu Pro Ser Ser Cys Gly Pro Asn Lys Glu Phe Asp Glu Glu
                325                 330                 335

Lys Cys Gln Cys Val Cys Lys Lys Thr Cys Pro Lys His His Pro Leu
            340                 345                 350

Asn Pro Ala Lys Cys Ile Cys Glu Cys Thr Glu Ser Pro Asn Lys Cys
        355                 360                 365

Phe Leu Lys Gly Lys Arg Phe His His Gln Thr Cys Ser Cys Tyr Arg
    370                 375                 380

Pro Pro Cys Thr Val Arg Thr Leu Arg Cys Asp Ala Gly Phe Leu Leu
385                 390                 395                 400

Ala Glu Glu Val Cys Arg Cys Val Arg Thr Ser Trp Lys Arg Pro Leu
                405                 410                 415

Met Asn
```

(2) INFORMATION FOR SEQ ID NO:14:

(i) SEQUENCE CHARACTERISTICS:
        (A) LENGTH: 10 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:14:

Ala Val Val Met Thr Gln Thr Pro Ala Ser
1            5                10

(2) INFORMATION FOR SEQ ID NO:15:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:15:

TCTCTTCTGT GCTTGAGTTG AG                                    22

(2) INFORMATION FOR SEQ ID NO:16:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:16:

TCTCTTCTGT CCCTGAGTTG AG                                    22

(2) INFORMATION FOR SEQ ID NO:17:

(i) SEQUENCE CHARACTERISTICS:
        (A) LENGTH: 65 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:17:

TGTGCTGCAG CAAATTTTAT AGTCTCTTCT GTGGCGGCGG CGGCGGCGGG CGCCTCGCGA      60

GGACC                                                                          65

(2) INFORMATION FOR SEQ ID NO:18:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:18:

CTGGCAGGGA ACTGCTAATA ATGGAATGAA                                  30

(2) INFORMATION FOR SEQ ID NO:19:

(i) SEQUENCE CHARACTERISTICS:
        (A) LENGTH: 84 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:19:

```
GGGCTCCGCG TCCGAGAGGT CGAGTCCGGA CTCGTGATGG TGATGGTGAT GGGCGGCGGC      60

GGCGGCGGGC GCCTCGCGAG GACC                                            84
```

(2) INFORMATION FOR SEQ ID NO:20:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:20:

```
GTATTATAAT GTCCTCCACC AAATTTTATA G                                    31
```

(2) INFORMATION FOR SEQ ID NO:21:

(i) SEQUENCE CHARACTERISTICS:
        (A) LENGTH: 93 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:21:

```
GTTCGCTGCC TGACACTGTG GTAGTGTTGC TGGCGGCCGC TAGTGATGGT GATGGTGATG      60

AATAATGGAA TGAACTTGTC TGTAAACATC CAG                                  93
```

(2) INFORMATION FOR SEQ ID NO:22:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:22:

```
CATGTACGAA CCGCCAGG                                                   18
```

(2) INFORMATION FOR SEQ ID NO:23:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:23:

```
AATGACCAGA GAGAGGCGAG                                                 20
```

(2) INFORMATION FOR SEQ ID NO:24:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:24:

GCCACGGTAG GTCTGCGT                                                      18

(2) INFORMATION FOR SEQ ID NO:25:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:25:

TTTCTTTGAC AGGCTTAT                                                      18

(2) INFORMATION FOR SEQ ID NO:26:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:26:

ATCTTGAAAA GTAAGTATGG G                                               21

(2) INFORMATION FOR SEQ ID NO:27:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:27:

ATGACTTGAC AGGTATTGAT                                               20

(2) INFORMATION FOR SEQ ID NO:28:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:28:

AGCAAGACGG TGGGTATTGT                                               20

(2) INFORMATION FOR SEQ ID NO:29:

(i) SEQUENCE CHARACTERISTICS:
        (A) LENGTH: 22 base pairs (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:29:

CCCTTCTTTG TAGTTATTTG AA                                              22

(2) INFORMATION FOR SEQ ID NO:30:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:30:

CCACAGTGAG TATGAATTAA                                                 20

(2) INFORMATION FOR SEQ ID NO:31:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:31:

TTCTTCCAAA GGTGTCAG                                                   18

(2) INFORMATION FOR SEQ ID NO:32:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:32:

GGAGATGGTA GCAGAATG                                                   18

(2) INFORMATION FOR SEQ ID NO:33:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:33:

CTATTTGTCT AGACTCAACA GAT                                             23

(2) INFORMATION FOR SEQ ID NO:34:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:34:

CAAACATGCA GGTAAGAGAT CC 22

(2) INFORMATION FOR SEQ ID NO:35:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:35:

TGTTCTCCTA GCTGTTACAG A 21

(2) INFORMATION FOR SEQ ID NO:36:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:36:

GGCGAGGTCA AGGTAGGTGC AAGG 24

(2) INFORMATION FOR SEQ ID NO:37:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:37:

ATTGTCTTTG ACAGGCTTTT TGAAGG 26

(2) INFORMATION FOR SEQ ID NO:38:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:38:

GAGATCCTGA AAAGTAAGTA G 21

(2) INFORMATION FOR SEQ ID NO:39:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:39:

```
TGTGACTCGA CAGGTATTGA TAAT                                              24

(2) INFORMATION FOR SEQ ID NO:40:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:40:

CTCAGCAAGA CGGTAGGTAT                                                   20

(2) INFORMATION FOR SEQ ID NO:41:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:41:

TTGTCCCTTG TAGTTGTTTG AAATT                                             25

(2) INFORMATION FOR SEQ ID NO:42:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:42:

ACATTACCAC AGTGAGTATG                                                   20

(2) INFORMATION FOR SEQ ID NO:43:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:43:

GTCTCCCCAA AAGGTGTCAG GCAGCT                                            26

(2) INFORMATION FOR SEQ ID NO:44:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:44:

AATGTTGAAG ATGGTAAGTA AAA                                               23

(2) INFORMATION FOR SEQ ID NO:45:
```

(i) SEQUENCE CHARACTERISTICS:
            (A) LENGTH: 16 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:45:

TCTAGACTCA ACCAAT                                                          16

(2) INFORMATION FOR SEQ ID NO:46:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:46:

CAAACATGCA GGTAAGGAGT GT                                                   22

(2) INFORMATION FOR SEQ ID NO:47:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:47:

TTTTCCCCTA GTTGTTACAG AAGA                                                 24

(2) INFORMATION FOR SEQ ID NO:48:

(i) SEQUENCE CHARACTERISTICS:
            (A) LENGTH: 2991 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:48:

GTTTTAAGTA GAGACGGGGT TTCACCAACG GTTGAAAATA TTTATCATGG TCTCCCTAAG       60

ATGGACGGTG TTAGCTAGGA TGGTCTCGAT CTCCTGACCT CATGATCCAC CCGCCTCGGC      120

CTCCCAAAGT GCTGGGATTA CAGGCGTGAG CCACCGTGTC CGACCAACCT TAAGACAAAC      180

AACTACTGCA TGATTGTTTT TGGAGACCTT TTTTTTATTC AAATAAATTT TTGCCAGCAT      240

TTTCTGACTC AAAGTATAGC AGCAGGAAGA TAACACTTTT GTGAGAAAAA AGTTTGAATA      300

CAGCTTACTG CTGTATTTAA ATGAAACAGT AGTTAATATG ATATTAATAT ATTTTGGATA      360

TATTTTGAGT TTGTTGATTT TCCAGTCTTC ACCCGCTGCT AGGCCTGTGG GTGTTGGAAA      420

TGCCTGTGTT TCTCAATTTT GTTTGCCTAT TAGAATCCTG ATGTCCAAGC CTTACTCCAG      480

TTAGACCAGT TAAGCCAGAA AGGCAGAAGG TGTACTCAAG CATCTGTTTT TTCAAAATCT      540

CCTTTTGTGA TGCCAAGTGC AATCAAAGTT TAGAATCATT GTAATAGCAA ATGGTTGAAT      600

GGAAACTCCA CCTTCTATTC AAATCCTACC CCAGTCTGCC CTTAGCTGTT CTCTTTTCAC      660

AGATCTATCA ATGTCTGAAG ATAACTATGG CAGGCTGATC AAATATGCAT AGAGCAGGAA      720

```
GACAGCAAGA GAGTGATACA CTGACCATGT TCCAAATCAC AAAACATCTC AACAGGCTAG    780

ATCATGGACC GAGTCTGATG GGATGGAATT TCATAAAGAT ACATAAAAAA GCATCTTGGA    840

TACAGTAAAC TTAACTCCAC AAATACAGGG GAATTTAGAC GTGACTAAGT AGCAGTACAT    900

ATGAAAAATT ATTGAGGAAT TTTGTTGACT TTAAGGGTAG TGTGAGTCAA CACTGTGATT    960

TGGCTGCCAG AAAATAAACT CAATCCAAGG CTGTATCAAC AAAGGCATAC TGTCCATTCT   1020

GCATGCTCAT TACAGCACTA AGTACCGAGC CATGTTCTCA ACCGCATACT TCATGAACAT   1080

GGAAAGCTAA CAGTATGGTT AAGGGGGGAA ACTGGAACTG TCATCTTGGG GAATAAAAGG   1140

GATATTTAGC CAGGAGTAAA GTTAGCTTAG GGAGACCATG ATAAATATTT TCAAAATATT   1200

TGAAGGACTC AGTTGTGGAA GTGAGATTAG ATTTATTGTG TAAAACTCCA GGAGTCAAAA   1260

GCAATAGAGA GATAGAAGGA AATGCTTTTC AGCAGTGTTG CTCATCAATA AAGGGAGTGA   1320

ACAGCCACAC AGAATGGAAG GTTCCCTGTC CTTTGAGATA TTTAAGCCTT CAAGTAAATT   1380

ATGGGTGAGG AGTTTCAAAT CTAGAGTTGA ACCAGATAAG AAAGTCTCTT CTTCCGGTAA   1440

GATATTATGG ACCTATAACA TCTGTGTACT TAAAAGTAGA TTGGGAGTGA AAGGCAGACT   1500

TTTGATGTTC TGTACACTGT TGAAACCCCT TAGCGTGGTC CTCTGTAACC TGCTCACCCT   1560

GCCCCAAGGA GGCAGCTAGC CAATGCCACC AGCCCAACGG AAACCCCAGT GCTTTTCCAA   1620

TGGGGAAATG CAGTCACTTT TCTTTGGATG CTACACATCC TTTCTGGAAT ATGTCTCACA   1680

CACATCTCTC TTTATCACCC CCTTTTTCAA GTAAACCAAC TTCTTGCAGA AGCTGACAAT   1740

GTGTCTCTTT ACTCTCCACG AAGATTCTGG CCCTTCTCTT CACCTGTCAG AAGTTTAGGA   1800

TTCCAAAGGG ATCATTAGCA TCCATCCCAA CAGCCTGCAC TGCATCCTGA GAACTGCGGT   1860

TCTTGGATCA TCAGGCAACT TTCAACTACA CAGACCAAGG GAGAGAGGGG ACCCCTCCGA   1920

GGTCCCATAG GGTTCTCTGA CATAGTGATG ACCTTTTTCC AAACTTTGAG CAGGGCGCTG   1980

GGGGCCAGGC GTGCGGGAGG GAGGACAAGA ACTCGGGAGT GGCCGAGGAT AAAGCGGGGG   2040

CTCCCTCCAC CCCACGGTGC CCAGTTTCTC CCCGCTGCAC GTGGTCCAGG GTGGTCGCAT   2100

CACCTCTAAA GCCGGTCCCG CCAACCGCCA GCCCCGGGAC TGAACTTGCC CCTCCGGCCG   2160

CCCGCTCCCC GCAGGGGACA GGGGCGGGGA GGGAGAGATC CAGAGGGGGG CTGGGGGAGG   2220

TGGGGCCGCC GGGGAGGAGG CGAGGGAAAC GGGGAGCTCC AGGGAGACGG CTTCCGAGGG   2280

AGAGTGAGAG GGGAGGGCAG CCCGGGCTCG GCACGCTCCC TCCCTCGGCC GCTTTCTCTC   2340

ACATAAGCGC AGGCAGAGGG CGCGTCAGTC ATGCCCTGCC CCTGCGCCCG CCGCCGCCGC   2400

CGCCGCCGCT CAGCCCGGCG CGCTCTGGAG GATCCTGCGC CGCGGCGCTC CCGGGCCCCG   2460

CCGCCGCCAG CCGCCCCGGC GGCCCTCCTC CCGCCCCCGG CACCGCCGCC AGCGCCCCCG   2520

CCGCAGCGCC CGCGGCCCGG CTCCTCTCAC TTCGGGGAAG GGGAGGGAGG AGGGGACGA    2580

GGGCTCTGGC GGGTTTGGAG GGGCTGAACA TCGCGGGGTG TTCTGGTGTC CCCGCCCCG    2640

CCTCTCCAAA AAGCTACACC GACGCGGACC GCGGCGGCGT CCTCCCTCGC CCTCGCTTCA   2700

CCTCGCGGGC TCCGAATGCG GGGAGCTCGG ATGTCCGGTT TCCTGTGAGG CTTTTACCTG   2760

ACACCCGCCG CCTTTCCCCG GCACTGGCTG GGAGGGCGCC CTGCAAAGTT GGGAACGCGG   2820

AGCCCCGGAC CCGCTCCCGC CGCCTCCGGC TCGCCCAGGG GGGTCGCCG GGAGGAGCCC    2880

GGGGGAGAGG GACCAGGAGG GGCCCGCGGC CTCGCAGGGG CGCCCGCGCC CCCACCCCTG   2940

CCCCCGCCAG CGGACCGGTC CCCCACCCCC GGTCCTTCCA CCATGCACTT G            2991

(2) INFORMATION FOR SEQ ID NO:49:
```

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:49:

CACGGCTTAT GCAAGCAAAG                                               20

(2) INFORMATION FOR SEQ ID NO:50:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE:  cDNA (xi) SEQUENCE DESCRIPTION: SEQ ID NO:50:

AACACAGTTT TCCATAATAG                                               20

(2) INFORMATION FOR SEQ ID NO:51:

(i) SEQUENCE CHARACTERISTICS:
        (A) LENGTH: 19 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:51:

Leu Ser Lys Thr Val Ser Gly Ser Glu Gln Asp Leu Pro His Glu Leu
1               5                   10                  15

His Val Glu (2) INFORMATION FOR SEQ ID NO:52:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:52:

GACGGACACA GATGGAGGTT TAAAG                                         25

(2) INFORMATION FOR SEQ ID NO:53:

(i) SEQUENCE CHARACTERISTICS:
        (A) LENGTH: 196 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:53:

Met Arg Thr Leu Ala Cys Leu Leu Leu Gly Cys Gly Tyr Leu Ala
1               5                   10                  15

His Val Leu Ala Glu Glu Ala Glu Ile Pro Arg Glu Val Ile Glu Arg
            20                  25                  30

-continued

```
Leu Ala Arg Ser Gln Ile His Ser Ile Arg Asp Leu Gln Arg Leu Leu
            35                  40                  45

Glu Ile Asp Ser Val Gly Ser Glu Asp Ser Leu Asp Thr Ser Leu Arg
 50                  55                  60

Ala His Gly Val His Ala Thr Lys His Val Pro Glu Lys Arg Pro Leu
 65                  70                  75                  80

Pro Ile Arg Arg Lys Arg Ser Ile Glu Glu Ala Val Pro Ala Val Cys
                 85                  90                  95

Lys Thr Arg Thr Val Ile Tyr Glu Ile Pro Arg Ser Gln Val Asp Pro
                100                 105                 110

Thr Ser Ala Asn Phe Leu Ile Trp Pro Pro Cys Val Glu Val Lys Arg
            115                 120                 125

Cys Thr Gly Cys Cys Asn Thr Ser Ser Val Lys Cys Gln Pro Ser Arg
            130                 135                 140

Val His His Arg Ser Val Lys Val Ala Lys Val Glu Tyr Val Arg Lys
145                 150                 155                 160

Lys Pro Lys Leu Lys Glu Val Gln Val Arg Leu Glu Glu His Leu Glu
                165                 170                 175

Cys Ala Cys Ala Thr Thr Ser Leu Asn Pro Asp Tyr Arg Glu Glu Asp
            180                 185                 190

Thr Asp Val Arg
            195

(2) INFORMATION FOR SEQ ID NO:54:

(i) SEQUENCE CHARACTERISTICS:
        (A) LENGTH: 241 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:54:

Met Asn Arg Cys Trp Ala Leu Phe Leu Ser Leu Cys Cys Tyr Leu Arg
 1               5                  10                  15

Leu Val Ser Ala Glu Gly Asp Pro Ile Pro Glu Glu Leu Tyr Glu Met
             20                  25                  30

Leu Ser Asp His Ser Ile Arg Ser Phe Asp Asp Leu Gln Arg Leu Leu
            35                  40                  45

His Gly Asp Pro Gly Glu Glu Asp Gly Ala Glu Leu Asp Leu Asn Met
 50                  55                  60

Thr Arg Ser His Ser Gly Gly Glu Leu Glu Ser Leu Ala Arg Gly Arg
 65                  70                  75                  80

Arg Ser Leu Gly Ser Leu Thr Ile Ala Glu Pro Ala Met Ile Ala Glu
                 85                  90                  95

Cys Lys Thr Arg Thr Glu Val Phe Glu Ile Ser Arg Arg Leu Ile Asp
                100                 105                 110

Arg Thr Asn Ala Asn Phe Leu Val Trp Pro Pro Cys Val Glu Val Gln
            115                 120                 125

Arg Cys Ser Gly Cys Cys Asn Asn Arg Asn Val Gln Cys Arg Pro Thr
            130                 135                 140

Gln Val Gln Leu Arg Pro Val Gln Val Arg Lys Ile Glu Ile Val Arg
145                 150                 155                 160

Lys Lys Pro Ile Phe Lys Lys Ala Thr Val Thr Leu Glu Asp His Leu
                165                 170                 175
```

```
Ala Cys Lys Cys Glu Thr Val Ala Ala Ala Arg Pro Val Thr Arg Ser
            180                 185                 190

Pro Gly Gly Ser Gln Glu Gln Arg Ala Lys Thr Pro Gln Thr Arg Val
            195                 200                 205

Thr Ile Arg Thr Val Arg Val Arg Arg Pro Lys Gly Lys His Arg
            210                 215                 220

Lys Phe Lys His Thr His Asp Lys Thr Ala Leu Lys Glu Thr Leu Gly
225             230                 235                 240

Ala
```

(2) INFORMATION FOR SEQ ID NO:55:

(i) SEQUENCE CHARACTERISTICS:
        (A) LENGTH: 149 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:55:

```
Met Pro Val Met Arg Leu Phe Pro Cys Phe Leu Gln Leu Leu Ala Gly
1               5                   10                  15

Leu Ala Leu Pro Ala Val Pro Pro Gln Gln Trp Ala Leu Ser Ala Gly
            20                  25                  30

Asn Gly Ser Ser Glu Val Glu Val Val Pro Phe Gln Glu Val Trp Gly
            35                  40                  45

Arg Ser Tyr Cys Arg Ala Leu Glu Arg Leu Val Asp Val Val Ser Glu
            50                  55                  60

Tyr Pro Ser Glu Val Glu His Met Phe Ser Pro Ser Cys Val Ser Leu
65              70                  75                  80

Leu Arg Cys Thr Gly Cys Cys Gly Asp Glu Asn Leu His Cys Val Pro
            85                  90                  95

Val Glu Thr Ala Asn Val Thr Met Gln Leu Leu Lys Ile Arg Ser Gly
            100                 105                 110

Asp Arg Pro Ser Tyr Val Glu Leu Thr Phe Ser Gln His Val Arg Cys
            115                 120                 125

Glu Cys Arg Pro Leu Arg Glu Lys Met Lys Pro Glu Arg Cys Gly Asp
            130                 135                 140

Ala Val Pro Arg Arg
145
```

(2) INFORMATION FOR SEQ ID NO:56:

(i) SEQUENCE CHARACTERISTICS:
        (A) LENGTH: 191 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:56:

```
Met Asn Phe Leu Leu Ser Trp Val His Trp Ser Leu Ala Leu Leu Leu
1               5                   10                  15

Tyr Leu His His Ala Lys Trp Ser Gln Ala Ala Pro Met Ala Glu Gly
            20                  25                  30

Gly Gly Gln Asn His His Glu Val Val Lys Phe Met Asp Val Tyr Gln
            35                  40                  45
```

```
Arg Ser Tyr Cys His Pro Ile Glu Thr Leu Val Asp Ile Phe Gln Glu
    50                  55                  60

Tyr Pro Asp Glu Ile Glu Tyr Ile Phe Lys Pro Ser Cys Val Pro Leu
65                  70                  75                  80

Met Arg Cys Gly Gly Cys Cys Asn Asp Glu Gly Leu Glu Cys Val Pro
                85                  90                  95

Thr Glu Glu Ser Asn Ile Thr Met Gln Ile Met Arg Ile Lys Pro His
                100                 105                 110

Gln Gly Gln His Ile Gly Glu Met Ser Phe Leu Gln His Asn Lys Cys
            115                 120                 125

Glu Cys Arg Pro Lys Lys Asp Arg Ala Arg Gln Glu Asn Pro Cys Gly
        130                 135                 140

Pro Cys Ser Glu Arg Arg Lys His Leu Phe Val Gln Asp Pro Gln Thr
145                 150                 155                 160

Cys Lys Cys Ser Cys Lys Asn Thr Asp Ser Arg Cys Lys Ala Arg Gln
                165                 170                 175

Leu Glu Leu Asn Glu Arg Thr Cys Arg Cys Asp Lys Pro Arg Arg
                180                 185                 190

(2) INFORMATION FOR SEQ ID NO:57:

(i) SEQUENCE CHARACTERISTICS:
        (A) LENGTH: 188 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:57:

Met Ser Pro Leu Leu Arg Arg Leu Leu Leu Ala Ala Leu Leu Gln Leu
1               5                   10                  15

Ala Pro Ala Gln Ala Pro Val Ser Gln Pro Asp Ala Pro Gly His Gln
                20                  25                  30

Arg Lys Val Val Ser Trp Ile Asp Val Tyr Thr Arg Ala Thr Cys Gln
            35                  40                  45

Pro Arg Glu Val Val Val Pro Leu Thr Val Glu Leu Met Gly Thr Val
    50                  55                  60

Ala Lys Gln Leu Val Pro Ser Cys Val Thr Val Gln Arg Cys Gly Gly
65                  70                  75                  80

Cys Cys Pro Asp Asp Gly Leu Glu Cys Val Pro Thr Gly Gln His Gln
                85                  90                  95

Val Arg Met Gln Ile Leu Met Ile Arg Tyr Pro Ser Ser Gln Leu Gly
                100                 105                 110

Glu Met Ser Leu Glu Glu His Ser Gln Cys Glu Cys Arg Pro Lys Lys
            115                 120                 125

Lys Asp Ser Ala Val Lys Pro Asp Ser Pro Arg Pro Leu Cys Pro Arg
        130                 135                 140

Cys Thr Gln His His Gln Arg Pro Asp Pro Arg Thr Cys Arg Cys Arg
145                 150                 155                 160

Cys Arg Arg Arg Ser Phe Leu Arg Cys Gln Gly Arg Gly Leu Glu Leu
                165                 170                 175

Asn Pro Asp Thr Cys Arg Cys Arg Lys Leu Arg Arg
                180                 185
```